(12) United States Patent
D'Amour et al.

(10) Patent No.: US 7,989,204 B2
(45) Date of Patent: Aug. 2, 2011

(54) HEPATOCYTE LINEAGE CELLS

(75) Inventors: Kevin D'Amour, San Diego, CA (US); Emmanuel E. Baetge, Encinitas, CA (US)

(73) Assignee: Viacyte, Inc., San Diego, CA (US)

( * ) Notice: Subject to any disclaimer, the term of this patent is extended or adjusted under 35 U.S.C. 154(b) by 25 days.

(21) Appl. No.: 12/298,898

(22) PCT Filed: Apr. 27, 2007

(86) PCT No.: PCT/US2007/010380
§ 371 (c)(1),
(2), (4) Date: Jun. 16, 2009

(87) PCT Pub. No.: WO2007/127454
PCT Pub. Date: Nov. 8, 2007

(65) Prior Publication Data
US 2009/0298170 A1  Dec. 3, 2009

Related U.S. Application Data

(60) Provisional application No. 60/795,853, filed on Apr. 28, 2006.

(51) Int. Cl.
*C12N 5/00* (2006.01)
*C12N 5/02* (2006.01)
*C12P 21/04* (2006.01)

(52) U.S. Cl. ...................................... 435/377; 435/70.1
(58) Field of Classification Search .................. 435/70.1, 435/377
See application file for complete search history.

(56) References Cited

U.S. PATENT DOCUMENTS

| | | | |
|---|---|---|---|
| 5,260,203 A | 11/1993 | Ladner et al. | |
| 5,453,357 A | 9/1995 | Hogan | |
| 5,670,372 A | 9/1997 | Hogan | |
| 5,690,622 A | 11/1997 | Smith et al. | |
| 5,690,926 A | 11/1997 | Hogan | |
| 5,817,637 A | 10/1998 | Weiner et al. | |
| 5,830,876 A | 11/1998 | Weiner et al. | |
| 5,843,780 A | 12/1998 | Thomson | |
| 5,866,366 A | 2/1999 | Kallender | |
| 5,869,620 A | 2/1999 | Whitlow et al. | |
| 6,090,622 A | 7/2000 | Gearhart et al. | |
| 6,117,635 A | 9/2000 | Nazarenko et al. | |
| 6,117,986 A | 9/2000 | Nardone et al. | |
| 6,165,993 A | 12/2000 | Herrmann et al. | |
| 6,200,806 B1 | 3/2001 | Thomson | |
| 6,251,671 B1 | 6/2001 | Hogan et al. | |
| 7,045,353 B2 * | 5/2006 | Benvenisty | 435/377 |
| 7,153,684 B1 | 12/2006 | Hogan | |
| 7,510,876 B2 | 3/2009 | D'Amour et al. | |
| 7,534,608 B2 | 5/2009 | Martinson et al. | |
| 7,541,185 B2 | 6/2009 | D'Amour et al. | |
| 2002/0072117 A1 | 6/2002 | Xu et al. | |
| 2003/0175956 A1 | 9/2003 | Bodnar et al. | |
| 2003/0190748 A1 | 10/2003 | Thomson | |
| 2004/0107453 A1 * | 6/2004 | Furcht et al. | 800/18 |
| 2004/0229350 A1 | 11/2004 | Strelchenko et al. | |
| 2006/0019387 A1 | 1/2006 | Faris | |

FOREIGN PATENT DOCUMENTS

| | | |
|---|---|---|
| EP | 0 543 942 | 6/1993 |
| WO | WO 98/18943 | 5/1998 |
| WO | WO 99/13915 | 3/1999 |
| WO | WO 00/29442 | 5/2000 |
| WO | WO 2005/097980 | 10/2005 |
| WO | WO 2005/116073 | 12/2005 |
| WO | WO 2006/034873 | 4/2006 |

OTHER PUBLICATIONS

Deutsch et al., 2001, Development, vol. 128, pp. 871-881.*
Gouon-Evans et al., 2006, Nature Biotechnology, vol. 24(11), pp. 1402-1411.*
Valdimarsdottir et al., 2005, APMIS, vol. 113, pp. 773-789.*
Inami et al., 2010, Immunology and Cell Biology, pp. 1-8.*
McLean et al., 2007, Stem Cells, vol. 25, pp. 29-38.*
Alexander et al., "A molecular pathway leading to endoderm formation in zebrafish", *Curr Biol*, (2009) 9: 1147-1157.
Alexander et al., "Casanova plays an early and essential role in endoderm formation in zebrafish," *Dev Biol*, (1999) 215:343-357.
Aoki et al., Regulation of nodal signalling and mesendoderm formation by TARAM-A, a TGFbeta-related type I receptor. *Dev Biol* 241, 273-288, 2002.
Barringer et al., "Blunt-end and single-strand ligations by *Escherichia coli* ligase: influence on an in vitro amplification scheme," *Gene*, (1990) 89(1):117-22.
Barry et al., "Production of monoclonal antibodies by genetic immunization." *Biotechniques* 16 : 616-620. (1994).
Beck et al., "Extra-embryonic proteases regulate Nodal signaling during gastrulation," *Nat Cell Biol* (2002) 4, 981-985.
Beddington et al., "Brachyury—a gene affecting mouse gastrulation and easly organogenesis," *Dev Suppl*, (1992) 157-165.
Bongso et al., "Isolation and culture of inner cell mass cells from human blastocysts," *Hum Reprod* (1994) 9:2110-2117.
Burke et al., "Prox1 is an early specific marker for the developing liver and pancreas in the mammalian foregut endoderm," *Mech. Dev.*, (2002) 118(1-2):147-55.
Chang et al., "Genetic analysis of the mammalian transforming growth factor-beta superfamily", *Endocr Rev* (2002) 23:787-823.
Clackson et al., "Making antibody fragments using phage display libraries," *Nature*, (1991) 352(6336):624-8.
Collins et al., "Asialoglycoprotein receptor expression in murine pregnancy and development," *Hepatology*, (1984) 1:80-83.
Conlon et al., A primary requirement for nodal in the formation and maintenance of the primitive streak in the mouse. *Development* (1994) 120:1919-1928.

(Continued)

*Primary Examiner* — Peter Paras, Jr.
*Assistant Examiner* — David A Montanari
(74) *Attorney, Agent, or Firm* — Knobbe, Martens, Olson & Bear LLP

(57) ABSTRACT

Disclosed herein are methods for producing liver precursor cells as well as hepatocyte cells form pluripotent and/or multipotent cells. Also disclosed herein are methods of enriching isolating and/or purifying liver precursor cells and/or hepatocyte cells. Further disclosed are compositions comprising cell cultures and cell populations that are enriched for liver precursor cells or hepatocyte cells.

39 Claims, 86 Drawing Sheets

OTHER PUBLICATIONS

Costaglia et al., "Genetic immunization against the human thyrotropin receptor causes thyroiditis and allows production of monoclonal antibodies recognizing the native receptor", *J. Immunol.* (1998) 160:1458-1465.

D'Amour et al., "Efficient differentiation of human embryonic stem cells to definitive endoderm." *Nature Biotechnology*, Dec. 2005, vol. 23, No. 12, pp. 1534-1541.

Dougan et al., "The role of the zebrafish nodal-related genes squint and Cyclops in patterning of mesendoderm", *Development* (2003) 130:1837-1851.

Elghanian et al., "Selective colorimetric detection of polynucleotides based on the distance-dependent optical properties of gold nanoparticles," *Science*, (1997) 577(5329):1078-81.

Evans et al., "The potential supply of organ donors. An assessment of the efficacy of organ procurement efforts in the United States," *JAMA*, (1992) 267(2):239-46.

Feldman et al., "Zebrafish organizer development and germ-layer formation require nodal-related signals", *Nature* (1998) 395:181-185.

Feng et al., "HIV-1 entry cofactor: functional cDNA cloning of a seven-transmembrane G protein-coupled receptor", *Science* (1996) 272:872-877.

Futaki et al., "Molecular basis of constitutive production of basement membrane components: Gene expression profiles of engelbreth-holm-swarm tumor and F9 embryonal carcinoma cells", *J Biol. Chem.*, (2003) 50691-701.

Gordon et al., "Temporal analysis of hepatocyte differentiation by small hepatocyte-like progenitor cells during liver regeneration in retrorsine-exposed rats," *Am. J. Pathol.*, (2000) 157(3):771-86.

Grapin-Botton et al., "Endoderm development: from patterning to organogenesis", *Trends Genet* (2000) 16:124-130.

Guatelli et al., "Isothermal, in vitro amplification of nucleic acids by a multienzyme reaction modeled after retroviral replication", *Proc. Natl. Acad. Sci. USA*, (1990), 87(5):1874-8.

Harris et al., Global gene expression patterns during differentiation of F9 embryonal carcinoma cells into parietal endoderm *Funct Integr Geneomics* 2:105-119, 2002.

Hogan, "Bone morphogenetic proteins in development", *Curr Opin Genet Dev*, (1996) 6:432-438.

Howe et al., "Expression of SPARC/osteonectin transcript in murine embryos and gonads", *Differentiation*, (1988) 37:20-25.

Hudson et al., "Xsox17alpha and -beta mediate endoderm formation in Xenopus", *Cell*, (1997) 91:397-405.

Imada et al., "Fetomodulin: Marker surface protein of fetal development which is modulatable by cyclic AMP", *Dev Biol*, (1987) 122:483-491.

Ise et al., "Low asiaglycoprotein receptor expression as markers for highly proliferative potential hepatocytes," *Biochem. Biophys. Res. Commun.*, (2001) 285:172-182.

Kanai-Azuma et al., "Depletion of definitive gut endoderm in Sox17-null mutant mice", *Development*, (2002) 129:2367-2379.

Katoh, "Expression of human SOX7 in normal tissues and tumors", *Int J Mol Med*, (2001) 9:363-368.

Kikuchi et al., "Casanova encodes a novel Sox-related protein necessary and sufficient for early endoderm formation in zebrafish", *Genes Dev*, (2001) 15:1493-1505.

Kilpatrick et al., "Gene gun delivered DNA-based immunizations mediate rapid production of murine monoclonal antibodies to the Flt-3 receptor", *Hybridoma*, (1998) 17: 569-576.

Kim et al., "Chemokines: signal lamps for trafficking of T and B cells for development and effector function", *J Leukoc Biol*, (1999) 65:6-15.

Kimelman et al., "Vertebrae mesendoderm induction and patterning", *Curr Opin Genet Dev*, (2000) 10:350-356.

Kimmel et al., "Preparation of cDNA and the Generation of cDNA Libraries: Overview," *Methods in Enzymol.*, (1987) 152:307-316.

Köhler et al., "Continuous cultures of fused cells secreting antibody of predefined specificity," *Nature*, (1975) 256(5517):495-7.

Krasemann et al., "Generation of monoclonal antibodies against proteins with an unconventional nucleic acid-based immunization strategy", *J. Biotechnol.*, (1999) 73:119-129.

Kubo et al., "Development of definitive endoderm from embryonic stem cells in culture", *Development*, (2004) 131:1651-1652.

Kumar et al., "Nodal signaling uses activin and transforming growth factor-beta receptor-regulated Smads", *J Biol Chem*, (2001) 276: 656-661.

Kuo et al., "Roles of histone acetyltransferases and deacetylases", *BioEssays*, (1998) 20:615-626.

Kwoh et al., "Transcription-based amplification system and detection of amplified human immunodeficiency virus type 1 with a bead-based sandwich hybridization format," *Proc. Natl. Acad. Sci USA*, 86(4):1173-7, 1989.

Labosky et al., "Embryonic germ cell lines and their derivation from mouse primordial germ cells", *Ciba Found Symp*, (1994) 182:157-168; discussion 168-178.

Labosky et al., "Mouse embryonic germ (EG) cell lines: transmission through the germline and differences in the methylation imprint of insulin-like growth factor 2 receptor (Igf2r) gene compared with embryonic stem (ES) cell lines", *Development*, (1994) 120:3197-3204.

Landegren et al., "A ligase-mediated gene detection technique," *Science*, (1988) 241(4869):1077-80.

Lickert et al., "Formation of multiple hearts in mice following deletion of beta-catenin in the embryonic endoderm", *Dev Cell* (2002) 3:171-181.

Lodish, "Recognition of complex oligosaccharides by the multi-subunit asialoglycoprotein receptor," *Trends Biochem Sci.*, (1991) 16(10):374-7.

Lomeli et al., "Quantitative assays based on the use of replicatable hybridization probes," *Clin. Chem.*, (1989) 35(9):1826-31.

Lu et al., "From fertilization to gastrulation: axis formation in the mouse embryo", *Curr Opin Genet Dev*, (2001) 11:384-392.

Ma et al., "The chemokine receptor CXCR4 is required for the retention of B lineage and granulocytic precursors within the bone marrow microenvironment, *Immunity*", (1999) 10:463-471.

Marks et al., "By-passing immunization. Human antibodies from V-gene libraries displayed on phage," *J. Mol. Biol.*, (1991) 222(3):581-97.

McGrath et al., "Embryonic expression and function of the chemokine SDF-1 and its receptor, CXCR4", *Dev Biol.* (1999) 213:442-456.

Menthena et al., "Bone marrow progenitors are not the source of expanding oval cells in injured liver," *Stem Cells*, (2004) 22(6):1049-61.

Michalopoulos et al., "Transdifferentiation of rat hepatocytes into biliary cells after bile duct ligation and toxic biliary injury," *Hepatology*, (2005) 41(3):535-44.

Miyazono et al., "Divergence and convergenence of TGF-beta/BMP signaling", *J Cell Physiol* (2001) 187:265-276.

Monroe et al., "The major form of the murine asiaglycoprotein receptor: cDNA sequence and expression in liver, testis and epididymis," *Gene*, (1994) 148:237-244.

Mu et al., "Asialoglycoprotein receptor mRNAs are expressed in most extrahepatic rat tissues during development," *Am. J. Physiol.*, (1993) 264(4 Pt. 1):G752-62.

Nagasawa et al., "Defects of B-cell lymphopoiesis and bone-marrow myelopoiesis in mice lacking the CXC chemokine PBSF/SDF-1", *Nature* (1996) 382:635-638.

Niwa "Molecular mechanisum to maintain stem cell renewal of ES cells", (2001) *Cell Struct Funct* 26:137-148.

Ogura et al., "Behavioral abnormalities of Zic1 and Zic2 mutant mice: implications as models for human neurological disorders", (2001) *Behav Genet* 31:317-324.

Pacifico et al., "Differential expression of the asyaloglycoprotein receptor in discrete brain areas, in kidney and thyroid," *Biochem. Biophys. Res. Comm.*, (1995) 210(1):138-144.

Parker, et al., "Altered Cell Strains in Continuous Culture: A General Survey" *N.Y. Academy of Sciences* (1957) 5: 303-313.

Rambhatla et al., "Generation of hepatocyte-like celll s from human embryonic stem cells," *Cell Transplantation* (2003) 12:1-11.

Reubinoff et al., "Embryonic stem cell lines from human blastocysts: somatic differentiation in vitro", (2000) *Nat Biotechnol* 18:399-404.

Rodaway et al., "Mesendoderm, an ancient germ layer?", (2001) *Cell* 105:169-172.

Rodaway et al., "Induction of the mesendoderm in the zebrafish germ ring by yolk cell-derived TGF-beta family signals and discrimination of mesoderm and endoderm by FGF", (1999) *Development* 126:3067-3078.

Rohr et al., "Zebrafish zic1 expression in brain and somites is affected by BMP and hedgehog signaling", *Mech Dev*, (1999) 85:147-159.

Schier, "Nodal signaling in vertebrae development", *Annu Rev Cell Dev Biol*, (2003) 19:589-621.

Schmolke et al., "Identification of hepatitis G virus particles in human serum by E2-specific monoclonal antibodies generated by DNA immunization", (1998) *J. Virol.* 72: 4541-4545.

Schoenwolf et al., "Gastrulation and early mesodermal patterning in vertebrates", *Methods Mol Biol*, (2000) 135:113-125.

Schwartz et al. "Defined Conditions for Development of Functional Hepatic Cells from Human Embryonic Stem Cells" Stem Cells and *Development* (2005) 14(6): 643-655.

Shamblott et al., "Derivation of pluripotent stem cells from cultured human primordial germ cells", *Proc Natl Acad Sci USA* (1998) 95:13726-13731.

Shapiro et al., "Islet transplantation in seven patients with type 1 diabetes mellitus using a glucocorticoid-free immunosuppressive regimen", *N Engl J Med*, (2000) 343:230-238.

Shapiro et al., "Pancreatic islet transplantation in the treatment of diabetes mellitus", *Best Pract Res Clin Endocrinol Metab* (2001) 15:241-264.

Shapiro et al., "Could fewer islet cells be transplanted in type 1 diabetes? Insulin independence should be dominant force in islet transplantation", *Bmj* (2001) 322:861.

Shiozawa et al., "Cloning and characterization of *Xenopus laevis* xSox 7 xDNA", *Biochim Biophys Acta* (1996) 1309:73-76.

Shirahashi et al., "Differentiation of Human and Mouse Embyonic Stem Cells Along a Hepatocyte Lineage" *Cell Transplantation* (2004) 13:197-211.

Smith, "Brachyury and the T-box genes", *Curr. Opin. Genet. Dev.* (1997) 7:474-480.

Smith et al., "Upstream and downstream from Brachyury, a gene required for vertebrae mesoderm formation", *Cold Springs Harb Symp Quant Biol* (1997) 62:337-346.

Sooknanan et al., "NASBA: a detection and amplification system uniquely suited for RNA," *Nature Biotechnology*, (1995) 13:563-564.

Takash et al., "SOX7 transcription factor: sequence, chromosomal localization, expression, transactivation and interference with Wnt signaling", *Nucleic Acids Res*, (2001) 29:4274-4283.

Taniguchi et al., "Isolation and characterization of a mouse SRY-related cDNA, mSox7", *Biochim Biophys Act*, (1999) 1445:225-231.

Technau, "Brachyury, the blastopore and the evolution of the mesoderm", *Bioessays*, (2001) 23:788-794.

International Search Report and Written Opinion issued in PCT/US2007/010380 dated Feb. 20, 2008.

* cited by examiner

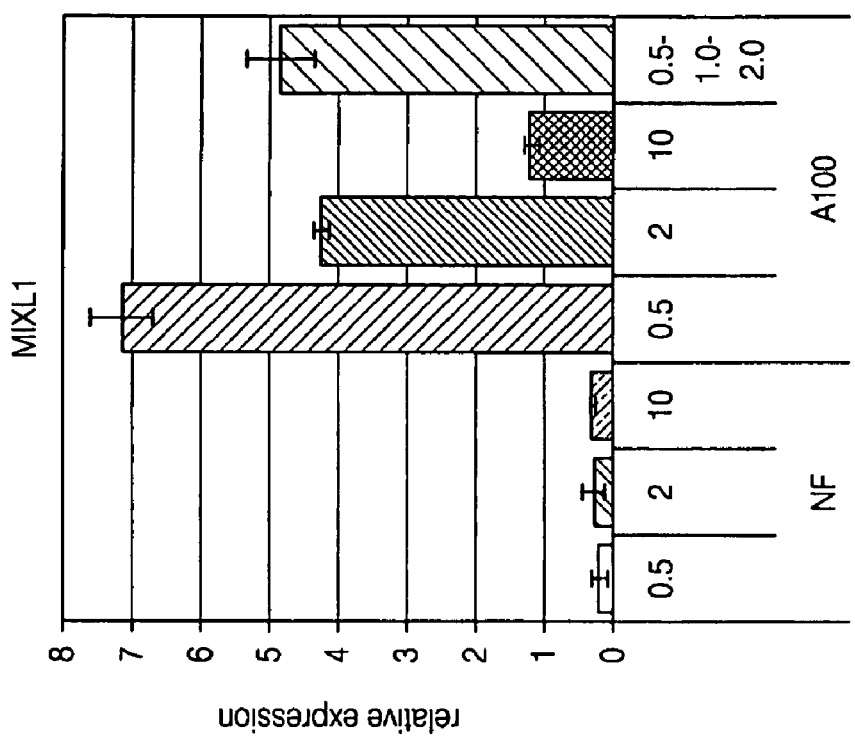
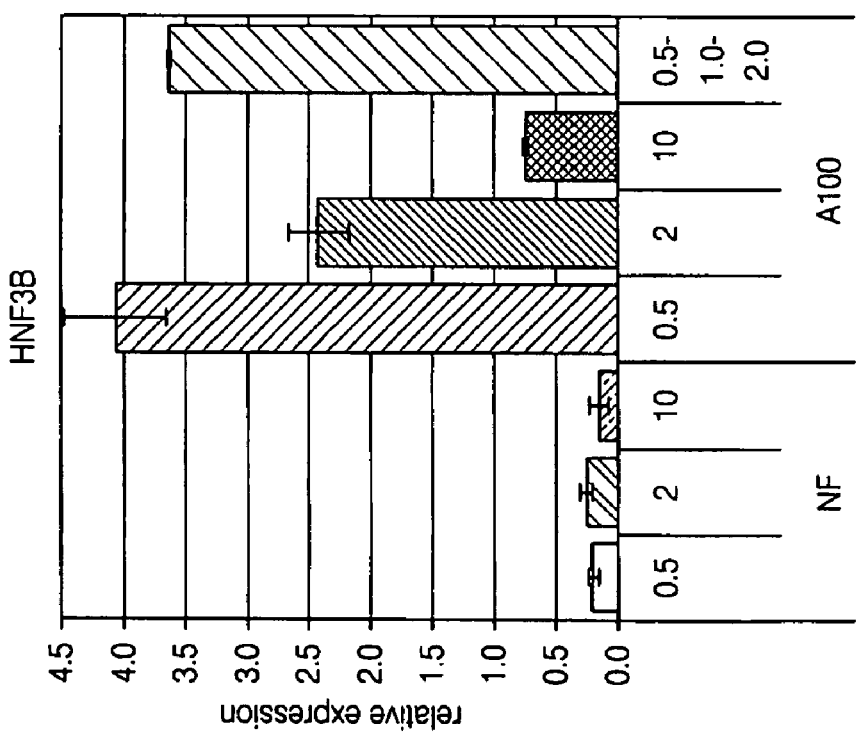
FIG. 27D
FIG. 27C

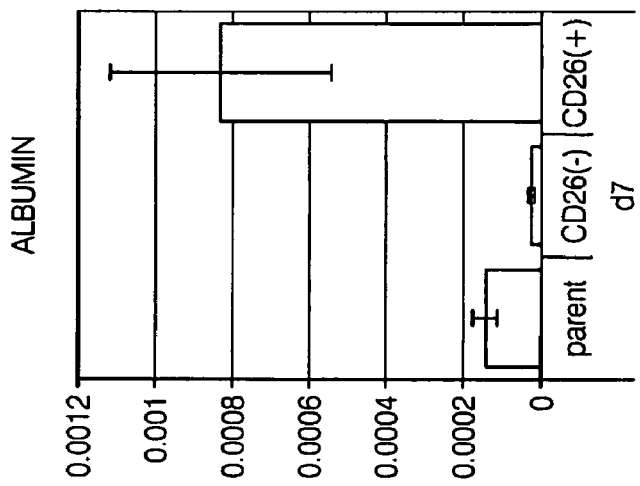
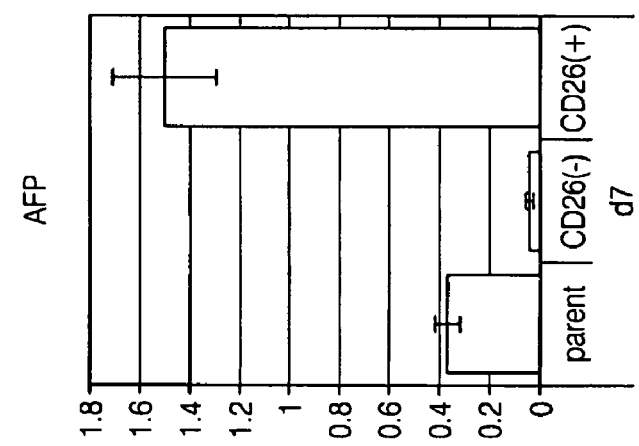
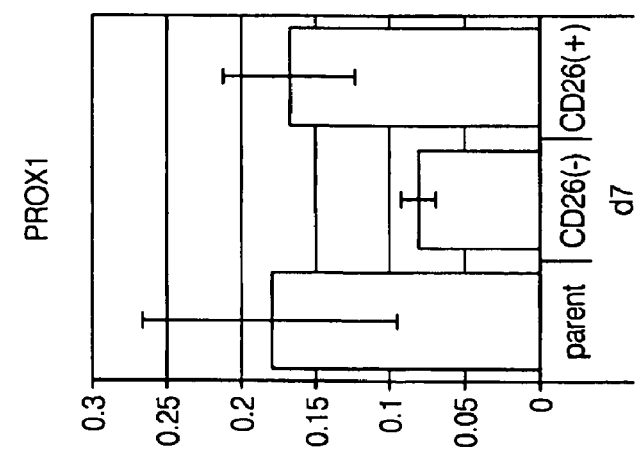
FIG. 37A
FIG. 37B
FIG. 37C

HEPATOCYTE LINEAGE CELLS

RELATED APPLICATIONS

This application is a U.S. national phase application under 35 U.S.C. §371 of International Application No. PCT/US2007/010380, filed Apr. 27, 2007 designating the United States and published in English on Nov. 8, 2007 as WO2007/127454, which claims priority under 35 U.S.C. §119(e) to U.S. Provisional Patent Application No. 60/795,853, entitled HEPATOCYTE LINEAGE CELLS, filed Apr. 28, 2006, the disclosure of which is incorporated herein by reference in its entirety.

REFERENCE TO SEQUENCE LISTING

The present application is being filed along with a Sequence Listing in electronic format. The Sequence Listing provided is a file entitled CYTHERA.053NP, created Oct. 28, 2008, which is 5.20 KB in size. The information in the electronic format of the Sequence Listing is incorporated herein by reference in its entirety.

FIELD OF THE INVENTION

The present invention relates to the fields of medicine and cell biology. In particular, the present invention relates to compositions comprising various hepatocyte lineage cells and methods of making and isolating such cells.

BACKGROUND

Human pluripotent stem cells, such as embryonic stem (ES) cells and embryonic germ (EG) cells, were first isolated in culture without fibroblast feeders in 1994 (Bongso et al., 1994) and with fibroblast feeders (Hogan, 1997). Later, Thomson, Reubinoff and Shamblott established continuous cultures of human ES and EG cells using mitotically inactivated mouse feeder layers (Reubinoff et al., 2000; Shamblott et al., 1998; Thomson et al., 1998).

Human ES and EG cells (hESCs) offer unique opportunities for investigating early stages of human development as well as for therapeutic intervention in several disease states, such as liver disease and others. The use of hepatocyte cells, as well as liver precursor cells derived from hESCs for therapeutic liver regeneration, would offer a vast improvement over current cell therapy procedures that utilize cells from donor livers for the treatment of liver disease. Further, the ability to derive hepatocyte cells and liver precursor cells would be beneficial in providing cells for investigating properties of drugs, such as ADME/tox (absorption, distribution, metabolism, excretion/toxicity) studies. However, presently it is not known how to generate liver precursor cells and differentiated liver cells (e.g., mature hepatocyte cells) from hESCs. As such, current cell therapy treatments for liver disease, which utilize liver cells from donor livers, are limited by the scarcity of high quality liver cells needed for transplant. As few as 5 percent of the organs needed for transplant in the United States alone ever become available to a recipient (Evans, et al., (1992). J. Am. Med Assoc., 267:239-246). For example, the American Liver Foundation reports that there are fewer than 3,000 donors for the nearly 30,000 patients who die each year from liver failure. Human embryonic stem cells offer a source of starting material from which to develop substantial quantities of high quality differentiated cells for drug studies as well as human cell therapies.

Two properties that make hESCs uniquely suited to cell therapy applications are pluripoietence and the ability to maintain these cells in culture for prolonged periods. Pluripoietency is defined by the ability of hESCs to differentiate to derivatives of all 3 primary germ layers (endoderm, mesoderm, ectoderm) which, in turn, form all somatic cell types of the mature organism in addition to extraembryonic tissues (e.g. placenta) and germ cells. Although pluripoietency imparts extraordinary utility upon hESCs, this property also poses unique challenges for the study and manipulation of these cells and their derivatives. Owing to the large variety of cell types that may arise in differentiating hESC cultures, the vast majority of cell types are produced at very low efficiencies. Additionally, success in evaluating production of any given cell type depends critically on defining appropriate markers. Achieving efficient, directed differentiation is of great importance for therapeutic application of hESCs.

In order to use hESCs as a starting material to generate cells that are useful in cell therapy applications, it would be advantageous to overcome the foregoing problems. For example, it would be useful to identify and isolate cell types, such as liver precursor cells that can later differentiate into liver cells, as well as other useful cell types.

In addition to efficient direction of the differentiation process, it would also be beneficial to isolate and characterize intermediate cell types along the differentiation pathway towards the hepatocyte cell lineage and to use such cells as appropriate lineage precursors for further steps in the differentiation to mature liver cells.

SUMMARY OF THE INVENTION

Some embodiments of the present invention relate to cell cultures comprising human cells that can differentiate into mature liver cells. In accordance with certain embodiments, the human cells express or fail to significantly express certain markers. In some embodiments, the cells are liver precursor cells that express DPP4 and APOA1, APOA2, HNF4A, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, or CUBN, and do not substantially express CYP3A7, Transferrin, HBGZ, ASGR1, SLC17A8, PCDHGB7, OCT4, PDX1, or SLC10A1.

Additional embodiments of the present invention relate to enriched, isolated, and/or purified cell populations comprising DPP4-positive human cells that can differentiate into mature liver cells. In accordance with certain embodiments, the DPP4-positive cells express APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, or CUBN, and do not substantially express CYP3A7, Transferrin, HBGZ, ASGR1, SLC17A8, PCDHGB7, OCT4, PDX1, or SLC10A1.

Yet other embodiments of the present invention relate to methods or processes for production of human cells that can differentiate into mature liver cells. Such methods include providing definitive endoderm cells with BMP and/or FGF10. In some embodiments, the definitive endoderm cells are provided with BMP and/or FGF10 in the presence of one or more growth factors that are members of the TGF-β superfamily, such as activin A. In other embodiments, the definitive endoderm cells are provided with BMP and/or FGF-10 in the absence of a growth factor that is a member of the TGF-β superfamily of growth factors such as activin A. In some embodiments, the definitive endoderm cells are derived from stem cells. Preferably, the stem cells are embryonic stem cells.

Still other embodiments relate to methods of producing a cell population enriched in liver precursor cells. Such methods include the steps of contacting definitive endoderm cells with activin A, BMP and FGF10, contacting said population of cells with a reagent that binds to a marker or a fusion protein to a marker, and separating cells bound to the reagent from cells that are not bound to the reagent. In some embodiments, the marker is selected from the group consisting of DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN. In a preferred embodiment, the population of cells is contacted with a reagent that binds to a marker selected from the group consisting of DPP4, DGKB, DOK4, SLC35D1, PCDH17, FN1, HLA-B, HLA-C, CYP4X1, EPHA6 and PP1057, and the cells bound to the reagent are separated from cells that are not bound to the reagent. In some embodiments, the cells are derived from definitive endoderm cells. In some embodiments, the definitive endoderm cells are derived from hESCs.

Additional embodiments relate to methods of isolating hepatocyte cells. Such methods include the steps of obtaining a population of pluripotent cells, contacting the cells with activin A, BMP and FGF10, contacting said population of cells with a reagent that binds to a marker or a fusion protein to a marker, and separating cells bound to the reagent from cells that are not bound to the reagent. In some embodiments, the marker is selected from the group consisting of DPP4, ASGR1, CYP3A7, Transferrin, HBGZ, SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD. In a preferred embodiment, the marker is selected from the group consisting of SLC5A12, TM4SF4, MUSK, TM4SF1, and OLR1. In some embodiments, the cells are derived from definitive endoderm cells. In some embodiments, the definitive endoderm cells are derived from hESCs.

In certain jurisdictions, there may not be any generally accepted definition of the term "comprising." As used herein, the term "comprising" is intended to represent "open" language which permits the inclusion of any additional elements. With this in mind, additional embodiments of the present invention are described with reference to the numbered paragraphs below:

1. A cell culture comprising human cells, wherein at least about 10% of said human cells are liver precursor cells that express DPP4 and a marker selected from the group consisting of APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1 and CUBN and which do not substantially express a marker selected from the group consisting of CYP3A7, Transferrin, HBGZ, ASGR1, SLC17A8, PCDHGB7, OCT4, PDX1 and SLC10A1, and wherein said liver precursor cells can differentiate into mature liver cells.

2. The cell culture of paragraph 1, wherein at least about 20% of said human cells are liver precursor cells that express DPP4 and a marker selected from the group consisting of APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1 and CUBN and which do not substantially express a marker selected from the group consisting of CYP3A7, Transferrin, HBGZ, ASGR1, SLC17A8, PCDHGB7, OCT4, PDX1 and SLC10A1, and wherein said liver precursor cells can differentiate into mature liver cells.

3. The cell culture of paragraph 1, wherein at least about 30% of said human cells are liver precursor cells that express DPP4 and a marker selected from the group consisting of APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1 and CUBN and which do not substantially express a marker selected from the group consisting of CYP3A7, Transferrin, HBGZ, ASGR1, SLC17A8, PCDHGB7, OCT4, PDX1 and SLC10A1, and wherein said liver precursor cells can differentiate into mature liver cells.

4. The cell culture of paragraph 1, wherein at least about 40% of said human cells are liver precursor cells that express DPP4 and a marker selected from the group consisting of APOA1, APOA2, HNF4A, PROX1, ALBUMIN, APP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1 and CUBN and which do not substantially express a marker selected from the group consisting of CYP3A7, Transferrin, HBGZ, ASGR1, SLC17A8, PCDHGB7, OCT4, PDX1 and SLC10A1, and wherein said liver precursor cells can differentiate into mature liver cells.

5. The cell culture of paragraph 1, wherein at least about 50% of said human cells are liver precursor cells that express DPP4 and a marker selected from the group consisting of APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1 and CUBN and which do not substantially express a marker selected from the group consisting of CYP3A7, Transferrin, HBGZ, ASGR1, SLC17A8, PCDHGB7, OCT4, PDX1 and SLC10A1, and wherein said liver precursor cells can differentiate into mature liver cells.

6. The cell culture of paragraph 1, wherein at least about 60% of said human cells are liver precursor cells that express DPP4 and a marker selected from the group consisting of APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1 and CUBN and which do not substantially express a marker selected from the group consisting of CYP3A7, Transferrin, HBGZ, ASGR1, SLC17A8, PCDHGB7, OCT4, PDX1 and SLC10A1, and wherein said liver precursor cells can differentiate into mature liver cells.

7. The cell culture of paragraph 1, wherein at least about 70% of said human cells are liver precursor cells that express DPP4 and a marker selected from the group consisting of APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1 and CUBN and which do not substantially express a marker selected from the group consisting of CYP3A7, Transferrin, HBGZ, ASGR1, SLC17A8, PCDHGB7, OCT4, PDX1 and SLC10A1, and wherein said liver precursor cells can differentiate into mature liver cells.

8. The cell culture of paragraph 1, wherein at least about 80% of said human cells are liver precursor cells that express DPP4 and a marker selected from the group consisting of APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1 and CUBN and which do not substantially express a marker selected from the group consisting of CYP3A7, Transferrin, HBGZ, ASGR1, SLC17A8, PCDHGB7, OCT4, PDX1 and SLC10A1, and wherein said liver precursor cells can differentiate into mature liver cells.

9. The cell culture of paragraph 1, wherein at least about 85% of said human cells are liver precursor cells that express DPP4 and a marker selected from the group consisting of APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1 and CUBN and which do not substantially express a marker selected from the group consisting of CYP3A7, Transferrin, HBGZ, ASGR1, SLC17A8, PCDHGB7, OCT4, PDX1 and SLC10A1, and wherein said liver precursor cells can differentiate into mature liver cells.

10. A cell culture comprising human liver precursor cells, said human liver precursor cells expressing a marker selected from the group consisting of DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1 and CUBN, prior to substantially expressing a marker selected from the group consisting of CYP3A7, Transferrin, HBGZ, ASGR1, SLC17A8, PCDHGB7 and SLC10A1, wherein said human liver precursor cells can differentiate into mature liver cells.

11. An enriched cell population comprising human cells wherein at least about 90% of said human cells are liver precursor cells that express a first marker selected from the group consisting of DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1 and CUBN, and which do not substantially express a second marker from the group consisting of CYP3A7, Transferrin, HBGZ, ASGR1, SLC17A8, PCDHGB7, OCT4, PDX1 and SLC10A1, and wherein said liver precursor cells can differentiate into mature liver cells.

12. The enriched cell population of paragraph 11, wherein at least about 95% of said human cells are liver precursor cells that express a first marker selected from the group consisting of DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1 and CUBN, and which do not substantially express a second marker from the group consisting of CYP3A7, Transferrin, HBGZ, ASGR1, SLC17A8, PCDHGB7, OCT4, PDX1 and SLC10A1, and wherein said liver precursor cells can differentiate into mature liver cells.

13. The enriched cell population of paragraph 11, wherein at least about 98% of said human cells are liver precursor cells that express a first marker selected from the group consisting of DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1 and CUBN, and which do not substantially express a second marker from the group consisting of CYP3A7, Transferrin, HBGZ, ASGR1, SLC17A8, PCDHGB7, OCT4, PDX1 and SLC10A1, and wherein said liver precursor cells can differentiate into mature liver cells.

14. The enriched cell population of paragraph 11, wherein at least about 99% of said human cells are liver precursor cells that express a first marker selected from the group consisting of DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1 and CUBN, and which do not substantially express a second marker from the group consisting of CYP3A7, Transferrin, HBGZ, ASGR1, SLC17A8, PCDHGB7, OCT4, PDX1 and SLC10A1, and wherein said liver precursor cells can differentiate into mature liver cells.

15. A method of producing liver precursor cells, said method comprising the steps of obtaining a cell population comprising definitive endoderm cells and providing said cell population with a BMP family growth factor and an FGF family growth factor for a time sufficient to allow the differentiation of liver precursor cells from said definitive endoderm cells.

16. The method of paragraph 15, wherein said BMP family growth factor is provided to said cell population for about 1 day to about 8 days.

17. The method of paragraph 15, wherein said BMP family growth factor is provided to said cell population for about 1 day to about 5 days.

18. The method of paragraph 15, wherein said BMP family growth factor is provided to said cell population for about 1 day to about 3 days.

19. The method of paragraph 15, wherein said FGF family growth factor is provided to said cell population for about 1 day to about 8 days.

20. The method of paragraph 15, wherein said FGF family growth factor is provided to said cell population for about 1 day to about 5 days.

21. The method of paragraph 15, wherein said FGF family growth factor is provided to said cell population for about 1 day to about 3 days.

22. The method of paragraph 15, wherein said FGF family growth factor is provided to said cell population for about 1 day to about 2 days.

23. The method of paragraph 15, wherein said BMP family growth factor is BMP4.

24. The method of paragraph 23, wherein BMP4 is provided to said cell population at a concentration ranging from about 0.1 ng/ml to about 100 ng/ml.

25. The method of paragraph 23, wherein BMP4 is provided to said cell population at a concentration ranging from about 1 ng/ml to about 5 ng/ml.

26. The method of paragraph 23, wherein BMP4 is provided to said cell population at a concentration of about 3 ng/ml.

27. The method of paragraph 15, wherein said FGF growth factor is FGF10.

28. The method of paragraph 27, wherein FGF10 is provided to said cell population at a concentration ranging from about 1 ng/ml to about 1000 ng/ml.

29. The method of paragraph 27, wherein FGF10 is provided to said cell population at a concentration ranging from about 5 ng/ml to about 500 ng/ml.

30. The method of paragraph 27, wherein said FGF10 is provided to said cell population at a concentration ranging from about 20 ng/ml to about 200 ng/ml.

31. The method of paragraph 27, wherein FGF10 is provided to said cell population at a concentration of about 50 ng/ml.

32. The method of paragraph 15, further comprising providing B27 to said cell population.

33. The method of paragraph 32, wherein said B27 is provided to said cell population at a concentration ranging from about 0.1% to about 20% of the total medium.

34. The method of paragraph 32, wherein said B27 is provided to said cell population at a concentration ranging from about 0.2% to about 2% of the total medium.

35. The method of paragraph 32, wherein said B27 is provided to said cell population at a concentration of about 0.5% of the total medium.

36. The method of paragraph 32, wherein said B27 is provided to said cell population for about 1 day to about 8 days.

37. The method of paragraph 32, wherein said B27 is provided to said cell population for about 2 days to about 6 days.

38. The method of paragraph 32, wherein said B27 is provided to said cell population for about 5 days.

39. The method of paragraph 15, wherein activin A is present in said cell population.

40. The method of paragraph 15, wherein activin A is not substantially present in said cell population.

41. The method of paragraph 15, wherein said definitive endoderm cells are differentiated in vitro from human embryonic stem cells (hESCs).

42. The method of paragraph 41, wherein the method of differentiation of said hESCs to definitive endoderm cells comprises providing said hESCs with activin A.

43. The method of paragraph 42, wherein said hESCs are provided with activin A for about 1 day to about 8 days.

44. The method of paragraph 42, wherein said hESCs are provided with activin A for about 1 day to about 6 days.

45. The method of paragraph 42, wherein said hESCs are provided with activin A for about 1 day to about 5 days.

46. The method of paragraph 42, wherein said hESCs are provided with activin A for about 3 days.

47. The method of paragraph 42, wherein activin A is provided to said hESCs at a concentration ranging from about 0.1 ng/ml to about 1000 ng/ml.

48. The method of paragraph 42, wherein activin A is provided to said hESCs at a concentration ranging from about 1 ng/ml to about 500 ng/ml.

49. The method of paragraph 42, wherein activin A is provided to said hESCs at a concentration ranging from about 20 ng/ml to about 200 ng/ml.

50. The method of paragraph 42, wherein activin A is provided to said hESCs at a concentration of about 100 ng/ml.

51. A method of producing an enriched population of liver precursor cells, said method comprising providing a cell population comprising liver precursor cells with a reagent that binds to a marker selected from the group consisting of DPP4, NOSTRIN, DOK4, SLC35D1, OCDH17, FN1, HLA-C, HLA-B, CYP4X1, CPHA6 and PP1057, and separating cells bound to said reagent from cells that are not bound to said reagent, thereby producing an enriched population of liver precursor cells.

52. The method of paragraph 51, wherein said marker is DPP4.

53. The method of paragraph 51, wherein said marker is a cell surface marker.

54. The method of paragraph 51, wherein said reagent comprises an antibody.

55. The method of paragraph 51, wherein said reagent comprises a ligand that binds to said marker.

56. The method of paragraph 51, wherein said liver precursor cells are differentiated from definitive endoderm cells.

57. The method of paragraph 56, wherein a BMP family growth factor and an FGF family growth factor are provided to said definitive endoderm cells.

58. The method of paragraph 57, wherein said BMP family growth factor is BMP4.

59. The method of paragraph 57, wherein said FGF family growth factor is FGF10.

60. The method of paragraph 57, wherein said definitive endoderm cells are provided with said BMP family growth factor and said FGF family growth factor for about 1 day to about 8 days.

61. The method of paragraph 57, wherein said definitive endoderm cells are provided with said BMP family growth factor and said FGF family growth factor for about 4 days.

62. An enriched cell population comprising human cells wherein at least about 90% of said human cells are hepatocytes that express a marker selected from the group consisting of DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A and UBD.

63. The enriched cell population of paragraph 62, wherein at least about 95% of said human cells are hepatocyte cells that express a marker selected from the group consisting of DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A and UBD.

64. The enriched cell population of paragraph 62, wherein at least about 99% of said human cells are hepatocyte cells that express a first marker selected from the group consisting of DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A and UBD.

65. A method of producing a population of hepatocyte cells, said method comprising the steps of obtaining a cell population comprising definitive endoderm cells and providing said cell population with a BMP family growth factor and an FGF family growth factor for a time sufficient to permit cells in said cell population to substantially express at least one marker selected from the group consisting of ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A and UBD.

66. The method of paragraph 65, wherein said BMP family growth factor is provided to said cell population for about 2 days to about 14 days.

67. The method of paragraph 65, wherein said BMP family growth factor is provided to said cell population for about 3 days to about 9 days.

68. The method of paragraph 65, wherein said BMP family growth factor is provided to said cell population for about 6 days.

69. The method of paragraph 65, wherein said FGF family growth factor is provided to said cell population for about 2 days to about 14 days.

70. The method of paragraph 65, wherein said FGF family growth factor is provided to said cell population for about 3 days to about 9 days.

71. The method of paragraph 65, wherein said FGF family growth factor is provided to said cell population for about 6 days.

72. The method of paragraph 65, wherein said BMP family growth factor is BMP4.

73. The method of paragraph 72, wherein BMP4 is provided to said cell population at a concentration ranging from about 0.1 ng/ml to about 100 ng/ml.

74. The method of paragraph 72, wherein BMP4 is provided to said cell population at a concentration ranging from about 1 ng/ml to about 5 ng/ml.

75. The method of paragraph 72, wherein BMP4 is provided to said cell population at a concentration of about 3 ng/ml.

76. The method of paragraph 65, wherein said FGF growth factor is FGF10.

77. The method of paragraph 76, wherein FGF10 is provided to said cell population at a concentration ranging from about 1 ng/ml to about 1000 ng/ml.

78. The method of paragraph 76, wherein FGF10 is provided to said cell population at a concentration ranging from about 5 ng/ml to about 500 ng/ml.

79. The method of paragraph 76, wherein FGF10 is provided to said cell population at a concentration ranging from about 20 ng/ml to about 200 ng/ml.

80. The method of paragraph 76, wherein FGF10 is provided to said cell population at a concentration of about 50 ng/ml.

81. The method of paragraph 65, further comprising providing B27 to said cell population.

82. The method of paragraph 81, wherein said B27 is provided to said cell population in a concentration ranging from about 0.1% to about 20% of the total medium.

83. The method of paragraph 81, wherein said B27 is provided to said cell population in a concentration ranging from about 0.2% to about 2% of the total medium.

84. The method of paragraph 81, wherein said B27 is provided to said cell population in a concentration of about 0.5% of the total medium.

85. The method of paragraph 81, wherein said B27 is provided to said cell population for about 2 days to about 14 days.

86. The method of paragraph 81, wherein said B27 is provided to said cell population for about 3 days to about 9 days.

87. The method of paragraph 81, wherein said B27 is provided to said cell population for about 6 days.

88. The method of paragraph 65, wherein activin A is present in said cell population.

89. The method of paragraph 65, wherein activin A is not substantially present in said cell population.

90. The method of paragraph 65, wherein said definitive endoderm cells are differentiated in vitro from human embryonic stem cells (hESCs).

91. The method of paragraph 90, wherein the method of differentiation of said hESCs to definitive endoderm cells comprises providing said hESCs with activin A.

92. The method of paragraph 91, wherein said hESCs are provided with activin A for about 1 day to about 8 days.

93. The method of paragraph 91, wherein said hESCs are provided with activin A for about 1 day to about 6 days.

94. The method of paragraph 91, wherein said hESCs are provided with activin A for about 1 day to about 5 days.

95. The method of paragraph 91, wherein said hESCs are provided with activin A for about 3 days.

96. The method of paragraph 91, wherein activin A is provided to said hESCs at a concentration ranging from about 0.1 ng/ml to about 1000 ng/ml.

97. The method of paragraph 91, wherein activin A is provided to said hESCs at a concentration ranging from about 1 ng/ml to about 500 ng/ml.

98. The method of paragraph 91, wherein activin A is provided to said hESCs at a concentration ranging from about 20 ng/ml to about 200 ng/ml.

99. The method of paragraph 91, wherein activin A is provided to said hESCs at a concentration of about 100 ng/ml.

100. A method of producing an enriched population of hepatocyte cells, said method comprising contacting a cell population comprising hepatocyte cells with a reagent that binds to a marker selected from the group consisting of DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A and UBD, and separating cells bound to said reagent from cells that are not bound to said reagent, thereby producing an enriched population of hepatocyte cells.

101. The method of paragraph 100, wherein said marker is DPP4.

102. The method of paragraph 100, wherein said marker is a cell surface marker.

103. The method of paragraph 100, wherein said reagent is an antibody.

104. The method of paragraph 100, wherein said reagent is a ligand that binds to said marker.

105. The method of paragraph 100, wherein said hepatocyte cells are differentiated from definitive endoderm cells.

106. The method of paragraph 105, wherein a BMP family growth factor and an FGF family growth factor are provided to said definitive endoderm cells.

107. The method of paragraph 106, wherein said BMP family growth factor is BMP4.

108. The method of paragraph 106, wherein said FGF family growth factor is FGF10.

109. The method of paragraph 106, wherein said definitive endoderm cells are provided with said BMP family growth factor and said FGF family growth factor for about 1 day to about 8 days.

110. The method of paragraph 106, wherein said definitive endoderm cells are provided with said BMP family growth factor and said FGF family growth factor for about 4 days.

111. A method of producing an enriched population of liver precursor cells, said method comprising the steps of obtaining a population of pluripotent cells, providing said cell population with a growth factor of the TGFβ superfamily and a growth factor of the fibroblast growth factor family, allowing sufficient time for at least a portion of said pluripotent cell population to differentiate into liver precursor cells, contacting said liver precursor cells with a reagent that binds to a marker selected from the group consisting of DPP4, NOSTRIN, DOK4, SLC35D1, OCDH17, FN1, HLA-C, HLA-B, CYP4X1, CPHA6 and PP1057, and separating cells bound to said reagent from cells that are not bound to said reagent, thereby producing an enriched population of liver precursor cells.

112. The method of paragraph 111, wherein growth factor of the TGFβ superfamily is selected from activin A and BMP4.

113. The method of paragraph 111, wherein growth factor of the fibroblast growth factor family is FGF10.

114. The method of paragraph 111, wherein said reagent is selected from the group consisting of an antibody and a ligand.

115. The method of paragraph 111, wherein said liver precursor cells do not substantially express a second marker from the group consisting of CYP3A7, Transferrin, HBGZ, ASGR1, SLC17A8, PCDHGB7, OCT4, PDX1 and SLC10A1, and wherein said liver precursor cells can differentiate into mature liver cells.

116. A method of producing an enriched population of hepatocyte cells, said method comprising the steps of obtaining a population of pluripotent cells, providing said cell population with a growth factor of the TGFβ superfamily and a growth factor of the fibroblast growth factor family, allowing sufficient time for at least a portion of said pluripotent cell population to differentiate into hepatocyte cells, contacting said hepatocyte cells with a reagent that binds to a marker selected from the group consisting of DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A and UBD, and separating cells bound to said reagent from cells that are not bound to said reagent, thereby producing an enriched population of hepatocyte cells.

117. The method of paragraph 116, wherein said hepatocyte cells are terminally differentiated cells.

118. The method of paragraph 116, wherein growth factor of the TGFβ superfamily is selected from activin A and BMP4.

119. The method of paragraph 116, wherein growth factor of the fibroblast growth factor family is FGF10.

120. The method of paragraph 116, wherein said reagent is selected from the group consisting of an antibody and a ligand.

121. The method of any one of paragraphs 15-50 and 65-99, wherein said cell population comprises human definitive endoderm cells.

122. The method of paragraph 121, wherein said cell population comprises at least about 10% human definitive endoderm cells.

123. The method of paragraph 121, wherein said cell population comprises at least about 20% human definitive endoderm cells.

124. The method of paragraph 121, wherein said cell population comprises at least about 30% human definitive endoderm cells.

125. The method of paragraph 121, wherein said cell population comprises at least about 40% human definitive endoderm cells.

126. The method of paragraph 121, wherein said cell population comprises at least about 50% human definitive endoderm cells.

127. The method of paragraph 121, wherein said cell population comprises at least about 60% human definitive endoderm cells.

128. The method of paragraph 121, wherein said cell population comprises at least about 70% human definitive endoderm cells.

129. The method of paragraph 121, wherein said cell population comprises at least about 80% human definitive endoderm cells.

130. The method of paragraph 121, wherein said cell population comprises at least about 90% human definitive endoderm cells.

131. The method of paragraph 121, wherein said cell population comprises at least about 95% human definitive endoderm cells.

132. The method of any one of paragraphs 111-120, wherein said population comprises human pluripotent cells.

133. The method of any one of paragraphs 15-61 and 65-132, wherein said method is performed in vitro.

Additional embodiments of the present invention may also be found in U.S. Provisional Patent Application No. 60/532,004, entitled DEFINITIVE ENDODERM, filed Dec. 23, 2003; U.S. Provisional Patent Application No. 60/566,293, entitled PDX1 EXPRESSING ENDODERM, filed Apr. 27, 2004; U.S. Provisional Patent Application No. 60/586,566, entitled CHEMOKINE CELL SURFACE RECEPTOR FOR THE ISOLATION OF DEFINITIVE ENDODERM, filed Jul. 9, 2004; U.S. Provisional Patent Application No. 60/587,942, entitled CHEMOKINE CELL SURFACE RECEPTOR FOR THE ISOLATION OF DEFINITIVE ENDODERM, filed Jul. 14, 2004; U.S. patent application Ser. No. 11/021,618, entitled DEFINITIVE ENDODERM, filed Dec. 23, 2004, U.S. patent application Ser. No. 11/115,868, entitled PDX1 EXPRESSING ENDODERM, filed Apr. 26, 2005, U.S. patent application Ser. No. 11/165,305, entitled METHODS FOR IDENTIFYING FACTORS FOR DIFFERENTIATING DEFINITIVE ENDODERM, filed Jun. 23, 2005, and U.S. Provisional Patent Application No. 60/736,598, entitled MARKERS OF DEFINITIVE ENDODERM, FILED Nov. 14, 2005, the disclosures of which are hereby expressly incorporated by reference in their entireties.

BRIEF DESCRIPTION OF THE DRAWINGS

FIGS. 27A-D are bar charts that show how a panel of definitive endoderm markers share a very similar pattern of expression to CXCR4 across the same differentiation treatments displayed in FIG. 26.

FIG. 36 demonstrates that the DPP4$^+$ cells contain much of the APOA1 (panel A), APOA2 (panel B), and HNF4α (panel C) gene expression present in each parent population, whereas the DPP4$^-$ populations contain very little or no APOA1, APOA2, and HNF4α gene expression. Furthermore, the DPP4$^-$ cells contain much of the OCT4 (panel E), and PDX1 panel E) gene expression present in each parent population.

FIGS. 37A-C are bar charts depicting gene expression patterns from DPP4$^+$ and DPP4$^-$ cells isolated using fluorescence-activated cell sorting (FACS) after 7 days of growth in defined medium described in Example 12 and Example 13, as well as gene expression in the parent populations. These figures demonstrate that DPP4$^+$ cells contain essentially all the AFP (panel B) and Albumin gene (panel C) expression present in each parent population, whereas the DPP4$^-$ populations contain very little or no AFP and Albumin gene expression.

DETAILED DESCRIPTION

Figure 1:
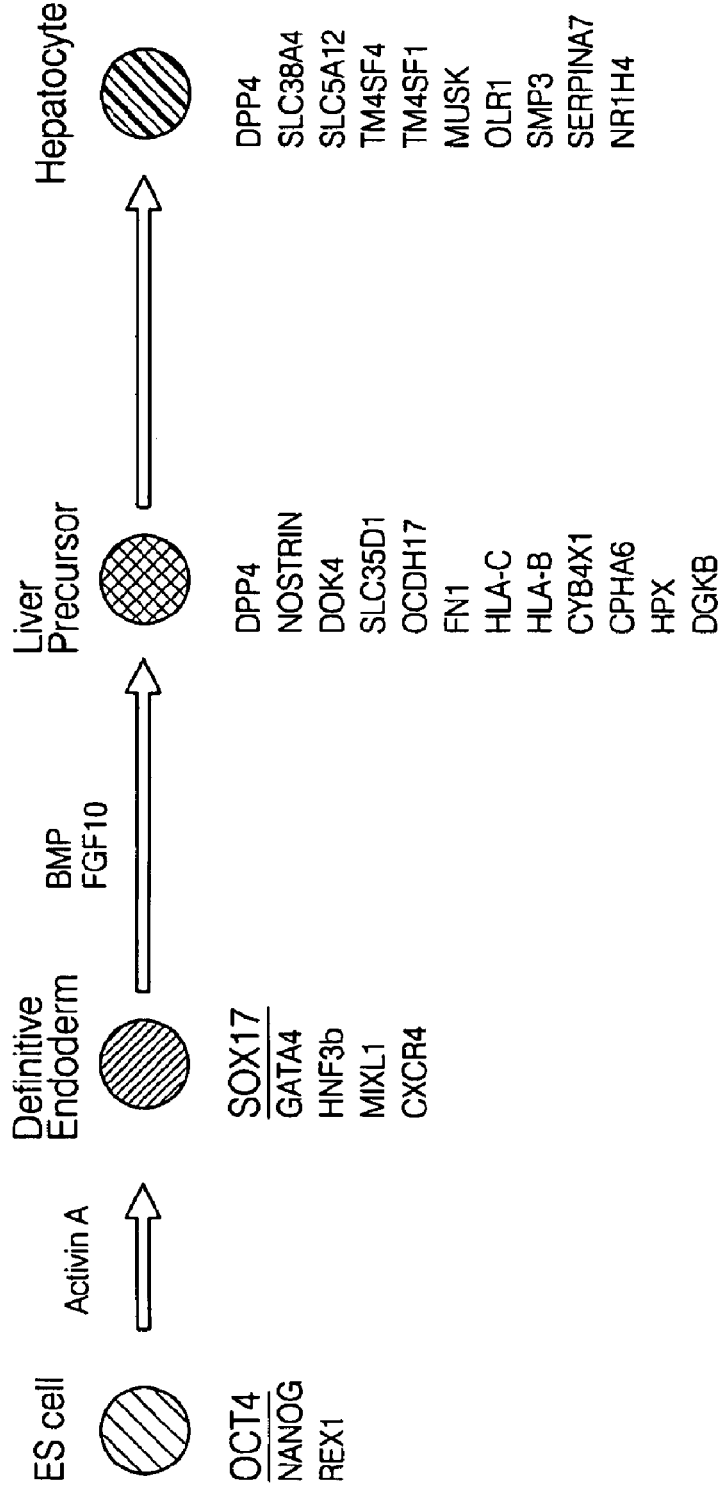
FIG. 1 is a schematic of a proposed differentiation pathway for the production of hepatocytes from hESCs. The first step in the pathway shows the differentiation of an the ES cell to a cell of definitive endoderm lineage. This represents an early step, prior to further differentiation events to liver precursor cells and ultimately mature hepatocytes. The next step in the pathway shows the conversion of SOX17-positive definitive endoderm to DPP4-positive liver precursor cells. Finally, differentiation proceeds to mature hepatocyte cells. Some factors useful for mediating these transitions are italicized. Relevant markers for defining the target cells are underlined.

A crucial stage in early human development termed gastrulation occurs 2-3 weeks after fertilization. Gastrulation is extremely significant because it is at this time that the three primary germ layers are first specified and organized (Lu et al., 2001; Schoenwolf and Smith, 2000). The ectoderm is responsible for the eventual formation of the outer coverings of the body and the entire nervous system whereas the heart, blood, bone, skeletal muscle and other connective tissues are derived from the mesoderm. Definitive endoderm is defined as the germ layer that is responsible for formation of the entire gut tube which includes the esophagus, stomach and small and large intestines, and the organs which derive from the gut tube such as the lungs, liver, thymus, parathyroid and thyroid glands, gall bladder and pancreas (Grapin-Botton and Melton, 2000; Kimelman and Griffin, 2000; Tremblay et al., 2000; Wells and Melton, 1999; Wells and Melton, 2000). A very important distinction should be made between the definitive endoderm and the completely separate lineage of cells termed primitive endoderm. The primitive endoderm is primarily responsible for formation of extra-embryonic tissues, mainly the parietal and visceral endoderm portions of the placental yolk sac and the extracellular matrix material of Reichert's membrane.

During gastrulation, the process of definitive endoderm formation begins with a cellular migration event in which mesendoderm cells (cells competent to form mesoderm or endoderm) migrate through a structure called the primitive streak. Definitive endoderm is derived from cells, which migrate through the anterior portion of the streak and through the node (a specialized structure at the anterior-most region of the streak). As migration occurs, definitive endoderm populates first the most anterior gut tube and culminates with the formation of the posterior end of the gut tube.

In vivo analyses of the formation of definitive endoderm, such as the studies in Zebrafish and Xenopus by Conlon et al., 1994; Feldman et al., 1998; Zhou et al., 1993; Aoki et al., 2002; Dougan et al., 2003; Tremblay et al., 2000; Vincent et al., 2003; Alexander et al., 1999; Alexander and Stainier, 1999; Kikuchi et al., 2001; Hudson et al., 1997 and in mouse by Kanai-Azuma et al., 2002 lay a foundation for how one might attempt to approach the development of a specific germ layer cell type in the culture dish using human embryonic stem cells. There are two aspects associated with in vitro ESC culture that pose major obstacles in the attempt to recapitulate development in the culture dish. First, organized germ layer or organ structures are not produced. The majority of germ layer and organ specific genetic markers will be expressed in a heterogeneous fashion in the differentiating hESC culture system. Therefore it is difficult to evaluate formation of a specific tissue or cell type due to this lack of organ specific boundaries. Almost all genes expressed in one cell type within a particular germ layer or tissue type are expressed in other cells of different germ layer or tissue types as well. Without specific boundaries there is considerably less means to assign gene expression specificity with a small sample of 1-3 genes. Therefore one must examine considerably more genes, some of which should be present as well as some that should not be expressed in the particular cell type of the organ or tissue of interest. Second, the timing of gene expression patterns is crucial to movement down a specific developmental pathway.

To further complicate matters, it should be noted that stem cell differentiation in vitro is rather asynchronous, likely considerably more so than in vivo. As such, one group of cells may be expressing genes associated with gastrulation, while another group may be starting final differentiation. Furthermore, manipulation of hESC monolayers or embryoid bodies (EBs) with or without exogenous factor application may result in profound differences with respect to overall gene expression pattern and state of differentiation. For these reasons, the application of exogenous factors must be timed according to gene expression patterns within a heterogeneous cell mixture in order to efficiently move the culture down a specific differentiation pathway. It is also beneficial to consider the morphological association of the cells in the culture vessel. The ability to uniformly influence hESCs when formed into so called embryoid bodies may be less optimal than hESCs grown and differentiated as monolayers and or hESC colonies in the culture vessel.

As an effective way to ameliorate the special boundary and timing problems, some embodiments of the present invention contemplate methods for differentiating hESCs and definitive endoderm cells to produce liver precursor cells and mature hepatocytes. Additional embodiments relate to the identification of intermediate cell types in the hepatocyte differentiation pathway. Yet other embodiments relate to enrichment, isolation and/or purification of liver precursor cells as well as mature hepatocytes.

Definitions

Certain terms and phrases as used throughout this application have the meanings provided as follows:

As used herein, "embryonic" refers to a range of developmental stages of an organism beginning with a single zygote and ending with a multicellular structure that no longer comprises pluripotent or totipotent cells other than developed gametic cells. In addition to embryos derived by gamete fusion, the term "embryonic" refers to embryos derived by somatic cell nuclear transfer.

As used herein, "multipotent" or "multipotent cell" refers to a cell type that can give rise to a limited number of other particular cell types.

As used herein, "expression" refers to the production of a material or substance as well as the level or amount of production of a material or substance. Thus, determining the expression of a specific marker refers to detecting either the relative or absolute amount of the marker that is expressed or simply detecting the presence or absence of the marker.

The phrase "does not substantially express" as used in connection with the expression of cell markers means that the cell expresses an indicated marker at less than about 25% of the expression level of the same marker in a mature hepatocyte.

As used herein, "marker" refers to any molecule that can be observed or detected. For example, a marker can include, but is not limited to, a nucleic acid, such as a transcript of a specific gene, a polypeptide product of a gene, a non-gene product polypeptide, a glycoprotein, a carbohydrate, a glycolipd, a lipid, a lipoprotein or a small molecule (for example, molecules having a molecular weight of less than 10,000 amu).

When used in connection with cell cultures and/or cell populations, the term "portion" means any non-zero amount of the cell culture or cell population, which ranges from a single cell to the entirety of the cell culture or cells population.

With respect to cells in cell cultures or in cell populations, the phrase "substantially free of" means that the specified cell type of which the cell culture or cell population is free, is present in an amount of less than about 5% of the total number of cells present in the cell culture or cell population.

"Stringency" of hybridization reactions is readily determinable by those skilled in the art, and generally is an empirical calculation based upon oligonucleotide length and composition, washing temperature, sand salt concentration. In general, longer oligonucleotides may anneal at relatively high temperatures, while shorter oligonucleotides generally anneal at lower temperatures. Hybridization generally depends on the ability of denatured nucleic acid to reanneal when complementary strands are present in an environment below their melting temperature. The higher the degree of desired homology between the oligonucleotide and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions," as used herein, are identified by those that: (1) employ low ionic strength and high temperature for washing, for example 0.015M sodium chloride/0.0015M sodium citrate/0.1% SDS at 50° C.; (2) employ during hybridization a denaturing agent, such as formamide, for example 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C., or (3) for example, employ 50% formamide, 5×SSC (0.75M NaCl, 0.075 M sodium citrate) 50 mM sodium phosphate (pH 6.8), 0.1% sodium pyrophosphate, 5×Denhardt's solution, sonicated salmon sperm DNA (50 µg/mL) 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1× SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the fitters in 1×SSC at about 37-50°C. The skilled artisan will recognize how to adjust the temperature, ionic strength, etc. as necessary to accommodate factors such as probe length and the like.

As used herein, the term "label" refers to, for example, radioactive, fluorescent, biological or enzymatic tags or labels of standard use in the art. A label can be conjugated, or otherwise bound, to nucleic acids, polypeptides, such as antibodies, or small molecules. For example, oligonucleotides of the present invention can be labeled subsequent to synthesis, by incorporating biotinylated dNTPs or rNTP, or some similar means (e.g., photo-cross-linking a psoralen derivative of biotin to RNAS), followed by addition of labeled streptavidin (e.g., phycoerythrin-conjugated streptavidin) or the equivalent. Alternatively, when fluorescently-labeled oligonucleotide probes are used, fluorescein, lissamine, phycoerythirin, rhodamine (Perkin Elmer Cetus), Cy2, Cy3, Cy3.5, Cy5, Cy5.5, Cy7, FluorX (Amersham) and others, can be attached to nucleic acids. Non-limiting examples of detectable labels that may be conjugated to polypeptides such as antibodies include but are not limited to radioactive labels, such as $^{3}$H, $^{11}$C, $^{14}$C, $^{18}$F, $^{32}$P, $^{35}$S, $^{64}$Cu, $^{76}$Br, $^{86}$Y, $^{99}$Tc, $^{111}$In, $^{123}$I, $^{125}$I, or $^{177}$Lu, enzymes, such as horseradish peroxidase, fluorophores, chromophores, chemiluminescent agents, chelating complexes, dyes, colloidal gold or latex particles.

Cells of Hepatocytic Lineage and Process Related Thereto

There are three cell types in the liver that have been identified as potential progenitor cells for regenerating liver: hepatocytes, oval cells, and small hepatocyte progenitor cells (SHPC's). Hepatocytes are considered unipotential progenitors for the generation of additional hepatocytes lost through partial hepatectomy or toxic injury. Michalopoulos, G. K., et al. *Hepatology*, 41, 535-544 2005. Oval cells are liver epithelial (ductular) stemlike cells which regenerate liver during toxic insults that functionally impair hepatocyte replicative capacity. SHPCs resemble fully differentiated, small hepatocytes. When compared to differentiated hepatocytes and oval cells, however, SHPCs are resistant to more severe liver toxic events which impair the replicative capacity of both hepatocytes and oval cells. Gene expression in SHPCs differs from hepatocytes as well. For example, in contrast to mature hepatocytes, SHPCs express oval cell/duct/fetal cell markers OC.2, OC.5 as well as α-fetoprotein (AFP), and p-glycoprotein. SHPCs also express certain markers to a much lower degree than mature hepatocytes (e.g., tyrosine amino transferase (TAT) and α-1 antitrypsin (α-1AT)) (Gordon, G. J. et al. *Amer. J. Pathology*, 157, 771-786).

Disclosed herein are data demonstrating that human embryonic stem cell (hESC)-generated definitive endoderm can give rise to the earliest hepatic progenitors (e.g., oval cells & SHPCs) as well as differentiated liver cells (e.g., hepatocytes). Since hESC cells are functionally immortal, they have the potential to generate an unlimited number of early and late liver precursor cells.

Liver precursor cells and hepatocyte cells have several useful applications, such as absorption, distribution, ADME-tox studies and therapeutic liver regeneration. Methods of differentiating liver precursor cells and hepatocyte cells from hESCs in vitro as well as methods for the enrichment, isolation, and/or purification of such cells have not been previously described. In view of the desirability of efficient differentiation of pluripotent cells to liver precursor cells and hepatocyte cells, some aspects of the differentiation processes described herein relate to in vitro methodology that results in approximately 50-80% conversion of pluripotent cells to liver precursor cells or hepatocyte cells. Typically, such methods encompass the application of culture and growth factor conditions in a defined and temporally specified fashion. Further direction of the cell population to liver precursor cell or hepatocyte cell types can be achieved by enrichment, isolation and/or purification of the liver precursor or hepatocyte cells from other cells in the population by using a reagent that specifically binds to liver precursor cells or hepatocyte cells, respectively. As such, some embodiments described herein relate to liver precursor or hepatocyte cells, as well as methods for producing and enriching, isolating and/or purifying such cells.

In order to determine the amount of liver precursor or hepatocyte cells are present in a cell culture or cell population, methods of distinguishing these cell types from the other cells in the culture is desirable. Accordingly, certain embodiments described herein relate to cell markers whose presence, absence, and/or relative expression levels are specific for liver precursor cells and methods for detecting and determining the expression of such markers. Other embodiments described herein relate to cell markers whose presence, absence, and/or relative expression levels are specific for hepatocyte cells and methods for detecting and determining the expression of such markers.

In some embodiments, a marker useful for such purification is DPP4. DPP4 is serine exopeptidase that cleaves X-proline dipeptides from the N terminus of polypeptides. It is an intrinsic membrane glycoprotein anchored into the cell membrane by its N-terminal end. High levels of DPP4 exopeptidase are found in the brush-border membranes of the kidney proximal tubule and of the small intestine. DPP4 exopeptidase is found in several other tissues including the liver and lung at moderate levels compared to the kidney and small intestine. In liver cells, DPP4 (CD26) is expressed in all epithelia cells of the liver including oval cells and SHPCs (Menthena, A., et al., *Stem Cells*, 22, 1049-1061). DPP4 can be employed as a marker for each of the cells that can regenerate the liver (e.g., liver precursor cells such as oval cells and SHPCs). Definitive endoderm is the lineage responsible for generation of the hepatic lineage. According to some embodiments of the present invention, definitive endoderm can be directed to differentiate to the hepatic lineage in a time dependent sequential manner providing the opportunity to purify early to, late time dependent hepatic lineage cells.

In some embodiments described herein, the presence, absence, and/or relative levels of expression of a marker can be determined by quantitative PCR (Q-PCR). For example, as discussed in further detail below, the relative amount of transcript produced by certain genetic markers, such as DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN can be used to identify liver precursor cells. Further, the relative amount of transcript produced by DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD can be used to identify hepatocyte cells. In other embodiments, immunohistochemistry can be used to detect the proteins expressed by the above-mentioned genes. Accordingly, in a preferred embodiment, immunohistochemistry is used to detect one or more markers selected from the group consisting of: APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN. In another preferred embodiment, immunohistochemistry is used to detect one or more markers selected from the group consisting of: DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD. In still other embodiments, Q-PCR and immunohistochemical techniques are both used to identify and determine the amount or relative proportions of markers, such as those mentioned above.

By using methods, such as those described above, to determine the expression of one or more appropriate markers, it is possible to identify liver precursor cells and hepatocyte cells, as well as determine the proportion of these cells in a cell culture or cell population. For example, in some embodiments of the present invention, the liver precursor cells or cell populations that are produced express one or more markers selected from DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN at a level of about 2 orders of magnitude greater than definitive endoderm cells, or other definitive endoderm-derived cells. In other embodiments, the liver precursor cells or cell populations that are produced express one or more markers selected from the group consisting of DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN at a level of about 2 orders of magnitude greater than hESCs or other non-definitive endoderm derived cells or cell populations, or non-definitive endoderm cells or cell populations. In some embodiments, the liver precursor cells do not substantially express one or more markers selected from the group consisting of CYP3A7, Transferrin, HBGZ, ASGR1, SLC17A8, PCDHGB7, OCT4, PDX1, and SLC10A1. In still other embodiments, the hepatocyte cells or cell populations that are produced express one or more markers selected from DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD at a level of more than 2 orders of magnitude greater than definitive endoderm, or other definitive endoderm derived cells. In other embodiments, the hepatocyte cells or cell populations that are produced express one or more markers selected from the group consisting of DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD at a level of more than 2 orders of magnitude greater than hESCs or other non-definitive endoderm derived cells or cell populations. In certain preferred embodiments of the present invention, the mature hepatocyte cells or cell populations that are produced express one or more markers selected from DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD at a level of about 2 orders of magnitude greater than liver precursor cells or cell populations.

Embodiments described herein also relate to compositions comprising liver precursor cells. For example, some embodiments relate to cell cultures comprising liver precursor cells, whereas others relate to cell populations enriched in liver precursor cells. Some preferred embodiments relate to cell cultures which comprise liver precursor cells, wherein at least about 50-80% of the cells in culture are liver precursor cells. An especially preferred embodiment relates to cells cultures comprising human cells, wherein at least about 50-80% of the human cells in culture are liver precursor cells. Because the efficiency of the differentiation procedure can be adjusted by modifying certain parameters, which include but are not limited to, cell growth conditions, growth factor concentrations and the timing of culture steps, the differentiation procedures described herein can result in about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or greater than about 95% conversion of pluripotent cells to liver precursor cells. In other preferred embodiments, conversion of a pluripotent cell population, such as a stem cell population, to substantially pure liver precursor cell population is contemplated.

Embodiments described herein also relate to hepatocyte cell compositions. For example, some embodiments relate to cell cultures comprising hepatocyte cells, whereas others relate to cell populations enriched in hepatocyte cells. Some preferred embodiments relate to cell cultures which comprise hepatocyte cells, wherein at least about 50-80% of the cells in culture are hepatocyte cells. An especially preferred embodiment relates to cell cultures comprising human cells, wherein at least about 50-80% of the human cells in culture are hepatocyte cells. Because the efficiency of the differentiation procedure can be adjusted by modifying certain parameters, which include but are not limited to, cell growth conditions, growth factor concentrations and the timing of culture steps, the differentiation procedures described herein can result in about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or greater than about 95% conversion of pluripotent cells to hepatocyte cells. In other preferred embodiments, conversion of a pluripotent cell population, such as a stem cell population, to substantially pure hepatocyte cell population is contemplated.

The compositions and methods described herein have several useful features. For example, the cell cultures and cell populations comprising liver precursor cells or hepatocyte cells as well as the methods for producing such cell cultures and cell populations are useful for modeling the early stages of human development. Furthermore, the compositions and methods described herein can also serve for therapeutic intervention in disease states, such as liver disease. Further, the liver precursor cells and hepatocyte cells have enormous value as reagents to investigate the properties of drugs (e.g., absorption, distribution, metabolism, excretion and toxicity).

In preferred embodiments, the liver precursor cells and cell populations and the hepatocyte cells are derived from definitive endoderm cells or cell populations. In more preferred embodiments, the definitive endoderm cells are derived starting from pluripotent stem cells, such as hESCs. In some preferred embodiments, pluripotent stem cells, such as hESCs, are first differentiated to definitive endoderm cells. The definitive endoderm cells are then enriched, isolated, or purified using one or more of the methods described in U.S. patent application Ser. No. 11/021,618 entitled DEFINITIVE ENDODERM, filed Dec. 23, 2004, the disclosure of which is expressly incorporated by reference in its entirety. The enriched, isolated and/or purified definitive endoderm cell population is then differentiated to form liver precursor cells and/or mature hepatocytes.

Materials and Methods for the Production of Liver Precursor Cells and Mature Hepatocytes Some of the embodiments described herein relate to processes for producing liver precursor cells and/or mature hepatocytes from pluripotent cells. Certain preferred embodiments, which are set forth in detail below, relate to differentiating liver precursor cells and/or mature hepatocytes from human embryonic stem cells.

Human Embryonic Stem Cells

A preferred method for deriving definitive endoderm cells and ultimately liver precursor cells and/or mature hepatocytes utilizes human embryonic stem cells as the starting material. Such pluripotent cells can be cells that originate from the morula, embryonic inner cell mass or those obtained from embryonic gonadal ridges. Human embryonic stem cells can be maintained in culture in a pluripotent state without substantial differentiation using methods that are known in the art. Such methods are described, for example, in U.S. Pat. Nos. 5,453,357, 5,670,372, 5,690,926 5,843,780, 6,200,806 and 6,251,671 the disclosures of which are incorporated herein by reference in their entireties.

In some processes, hESCs are maintained on a feeder layer. In such processes, any feeder layer which allows hESCs to be maintained in a pluripotent state can be used. One commonly used feeder layer for the cultivation of human embryonic stem cells is a layer of mouse fibroblasts. More recently, human fibroblast feeder layers have been developed for use in the cultivation of hESCs (see US Patent Application No. 2002/0072117, the disclosure of which is incorporated herein by reference in its entirety). Alternative processes permit the maintenance of pluripotent hESC without the use of a feeder layer. Methods of maintaining pluripotent hESCs under feeder-free conditions have been described in US Patent Application No. 2003/0175956, the disclosure of which is incorporated herein by reference in its entirety.

The human embryonic stem cells used herein can be maintained in culture either with or without serum. In some embryonic stem cell maintenance procedures, serum replacement is used. In others, serum free culture techniques, such as those described in US Patent Application No. 2003/0190748, the disclosure of which is incorporated herein by reference in its entirety, are used.

Stem cells are maintained in culture in a pluripotent state by routine passage until it is desired that they be differentiated into definitive endoderm then ultimately to liver precursor cells and/or mature hepatocytes.

Production of Definitive Endoderm

In preferred embodiments, differentiation of liver precursor cells and mature hepatocytes from hESCs proceeds through a definitive endoderm intermediate. Detailed procedures for producing and monitoring the production of definitive endoderm cells from pluripotent cells is described in U.S. patent application Ser. No. 11/021,618, entitled DEFINITIVE ENDODERM, filed Dec. 23, 2004, the disclosure of which is incorporated herein by reference in its entirety. Such processes are briefly described below.

In some processes, differentiation of hESCs to definitive endoderm is achieved by providing to the stem cell culture a growth factor of the TGFβ superfamily in an amount sufficient to promote differentiation to definitive endoderm. Growth factors of the TGFβ superfamily which are useful for the production of definitive endoderm are selected from the Nodal/Activin or BMP subgroups. In some preferred differentiation processes, the growth factor is selected from the group consisting of Nodal, activin A, activin B and BMP4. Additionally, the growth factor Wnt3a and other Wnt family members are useful for the production of definitive endoderm cells. In certain differentiation processes, combinations of any of the above-mentioned growth factors can be used.

With respect to some of the processes for the differentiation of pluripotent stem cells to definitive endoderm cells, the above-mentioned growth factors are provided to the cells so that the growth factors are present in the cultures at concentrations sufficient to promote differentiation of at least a portion of the stem cells to definitive endoderm cells. In some processes, the above-mentioned growth factors are present in the cell culture at a concentration of at least about 5 ng/ml, at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, at least about 1000 ng/ml, at least about 2000 ng/ml, at least about 3000 ng/ml, at least about 4000 ng/ml, at least about 5000 ng/ml or more than about 5000 ng/ml.

In certain processes for the differentiation of pluripotent stem cells to definitive endoderm cells, the above-mentioned growth factors are removed from the cell culture subsequent to their addition. For example, the growth factors can be removed within about one day, about two days, about three days, about four days, about five days, about six days, about seven days, about eight days, about nine days or about ten days after their addition. In a preferred processes, the growth factors are removed about four days after their addition.

Cultures of definitive endoderm cells can be grown in medium containing reduced serum or no serum. Under certain culture conditions, serum concentrations can range from about 0.05% v/v to about 20% v/v. For example, in some differentiation processes, the serum concentration of the medium can be less than about 0.05% (v/v), less than about 0.1% (v/v), less than about 0.2% (v/v), less than about 0.3% (v/v), less than about 0.4% (v/v), less than about 0.5% (v/v), less than about 0.6% (v/v), less than about 0.7% (v/v), less than about 0.8% (v/v), less than about 0.9% (v/v), less than about 1% (v/v), less than about 2% (v/v), less than about 3% (v/v), less than about 4% (v/v), less than about 5% (v/v), less than about 6% (v/v), less than about 7% (v/v), less than about 8% (v/v), less than about 9% (v/v), less than about 10% (v/v), less than about 15% (v/v) or less than about 20% (v/v). In some processes, definitive endoderm cells are grown without serum or with serum replacement. In still other processes, definitive endoderm cells are grown in the presence of B27. In such processes, the concentration of B27 supplement can range from about 0.1% v/v to about 20% v/v.

Enrichment, Isolation and/or Purification of Definitive Endoderm

In some embodiments of the present invention, definitive endoderm cells are enriched, isolated and/or purified prior to differentiation to liver precursor and/or mature hepatocytes. In such embodiments, definitive endoderm cells can be enriched, isolated and/or purified using any known method. In preferred embodiments, the definitive endoderm cells are enriched, isolated and/or purified using one or more of the methods described in U.S. patent application Ser. No. 11/021,618, entitled DEFINITIVE ENDODERM, filed Dec. 23, 2004, and U.S. Provisional Patent Application No. 60/736,598, entitled MARKERS OF DEFINITIVE ENDODERM, filed Nov. 14, 2005, the disclosures of which are incorporated herein by reference in their entireties.

Production of Liver Precursor Cells and Hepatocyte Cells from Pluripotent Cells

In certain processes, liver precursor cell cultures and enriched liver precursor cell populations, or the mature hepatocyte cells are derived from definitive endoderm cells, which can be produced from embryonic stem cells. (FIG. 1) Preferred methods for producing liver precursor cells and hepatocyte cells utilize human embryonic stem cells that can be differentiated into definitive endoderm cells as described herein. The definitive endoderm cells can be the starting material for liver precursor cell production or hepatocyte cell production. It will be appreciated that the liver precursor cells and/or mature hepatocyte cells can be differentiated from any pluripotent or multipotent cell type that is capable of differentiation into definitive endoderm. For example, liver precursor cells and/or mature hepatocyte cells can be differentiated from hESCs, primitive ectoderm cells, pre-primative streak cells, mesendoderm cells and definitive endoderm cells. Methods for producing these cell types can be found in PCT Application No. PCT/US2005/024161, entitled PREPRIMATIVE STREAK AND MESENDODERM CELLS, filed Jul. 8, 2005, published as WO 06/017134, and U.S. patent application Ser. No. 11/021,618, entitled DEFINITIVE ENDODERM, filed Dec. 23, 2004, the disclosures of which are hereby expressly incorporated by reference in their entireties.

In some processes, differentiation to definitive endoderm cells and the on to liver precursor cells or hepatocyte cells is achieved by providing to the stem cell culture a growth factor of the TGFβ superfamily in an amount sufficient to promote differentiation to definitive endoderm cells. Further application of differentiation factors, such as the FGF family growth factors as well as continued application of TGFβ superfamily growth factors, such as BMP4, promotes the differentiation of definitive endoderm cells to liver precursor cells and hepatocytes. Growth factors of the TGFβ superfamily which are useful for the production of definitive endoderm are selected from the Nodal/Activin or BMP subgroups. In some preferred differentiation processes, the growth factor is selected from the group consisting of Nodal, activin A, activin B and BMP4. In most preferred embodiments, the growth factor is activin A. Additionally, the growth factor Wnt3a and other Wnt family members are useful for the production of liver precursor cells or hepatocyte cells by way of definitive endoderm cells. In certain differentiation processes, combinations of any of the above-mentioned growth factors can be used.

With respect to some of the processes for the differentiation of pluripotent stem cells to liver precursor cells, the above-mentioned growth factors are provided to the cells so that the growth factors are present in the cultures at concentrations sufficient to promote differentiation of at least a portion of the stem cells to liver precursor cells. In some processes, the above-mentioned growth factors are present in the cell culture at a concentration of at least about 0.01 ng/ml, at least about 0.1 ng/ml, at least about 0.2 ng/ml, at least about 0.3 ng/ml, at least about 0.4 ng/ml, at least about 0.5 ng/ml, at least about 1 ng/ml, at least about 1.5 ng/ml, at least about 2 ng/ml, at least about 2.5 ng/ml, at least about 3 ng/ml, at least about 3.5 ng/ml, at least about 4 ng/ml, at least about 5 ng/ml, at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, at least about 1000 ng/ml, at least about 2000 ng/ml, at least about 3000 ng/ml, at least about 4000 ng/ml, at least about 5000 ng/ml or more than about 5000 ng/ml.

In certain processes for the differentiation of pluripotent stem cells to liver precursor cells or hepatocyte cells, combinations of the above-mentioned growth factors are provided in a temporal fashion. For example, in some embodiments, activin A is provided prior to the addition of BMP4 and/or FGF10. Accordingly, some embodiments provide for the differentiation of pluripotent stem cells to liver precursor cells by contacting the cells with activin A for at least about 2 days, at least about 3 days, at least about 4 days, at least about 5 days, at least about 6 days, at least about 7 days, at least about 8 days, or at least about 9 days. The cells can subsequently be contacted with BMP4 and/or FGF10 in combination with activin A for at least about 1 day, at least about 2 days, at least about 3 days, at least about 4 days, at least about 5 days, or at least about 6 days. Preferably, for the differentiation of pluripotent stem cells to liver precursor cells, the pluripotent cells are contacted with activin A for about 3 days, followed by contact with BMP4 and FGF10 for about 2 days to about 4 days.

In embodiments that provide for the differentiation of pluripotent stem cells to hepatocyte cells, liver precursor cells are produced using the methods as described previously and elsewhere herein. The liver precursor cells or cell populations can be maintained in the presence of BMP4, FGF10 and, in some embodiments, B27 supplement for at least 3 days, at least 4 days, at least 5 days, at least 6 days at least 7 days or at least 9 days, thereby producing mature hepatocytes.

In certain processes for the differentiation of pluripotent stem cells to liver precursor cells or hepatocyte cells, the above-mentioned growth factors are removed from the cell culture subsequent to their addition. For example, the growth factors can be removed within about one day, about two days, about three days, about four days, about five days, about six days, about seven days, about eight days, about nine days or about ten days after their addition. In preferred embodiments, activin A is removed from about 3 to 5 days after its addition. In other embodiments, the growth factors are not removed after their addition.

Cultures of liver precursor cells can be grown in medium containing reduced serum or no serum. Under certain culture conditions, serum concentrations can range from about 0.05% v/v to about 20% v/v. For example, in some differentiation processes, the serum concentration of the medium can be less than about 0.05% (v/v), less than about 0.1% (v/v), less than about 0.2% (v/v), less than about 0.3% (v/v), less than about 0.4% (v/v), less than about 0.5% (v/v), less than about 0.6% (v/v), less than about 0.7% (v/v), less than about 0.8% (v/v), less than about 0.9% (v/v), less than about 1% (v/v), less than about 2% (v/v), less than about 3% (v/v), less than about 4% (v/v), less than about 5% (v/v), less than about 6% (v/v), less than about 7% (v/v), less than about 8% (v/v), less than about 9% (v/v), less than about 10% (v/v), less than about 15% (v/v) or less than about 20% (v/v). In some processes, liver precursor cells are grown without serum or with serum replacement. In still other processes, liver precursor cells are grown in the presence of B27. In such processes, the concentration of B27 supplement can range from about 0.1% v/v to about 20% v/v. In some embodiments, the cultures can be grown in medium containing reduced serum or no serum, and subsequently transferred to a medium containing a different concentration of serum, or vice versa. Likewise, cultures of hepatocyte cells can be grown in medium containing reduced serum or no serum and the presence or absence of B27 supplement.

Monitoring the Differentiation of Pluripotent Cells to Definitive Endoderm, Liver Precursor Cells, and Mature Hepatocyte Cells The progression of the hESC culture to definitive endoderm, liver precursor cells, or mature hepatocytes can be monitored by determining the expression of markers characteristic of definitive endoderm, liver precursor cells, or mature hepatocytes. In some processes, the expression of certain markers is determined by detecting the presence or absence of the marker. Alternatively, the expression of certain markers can be determined by measuring the level at which the marker is present in the cells of the cell culture or cell population. In such processes, the measurement of marker expression can be qualitative or quantitative. One method of quantitating the expression of markers that are produced by marker genes is through the use of quantitative PCR (Q-PCR). Methods of performing Q-PCR are well known in the art. Other methods which are known in the art can also be used to quantitate marker gene expression. For example, the expression of a marker gene product can be detected by using antibodies specific for the marker gene product of interest. In certain processes, the expression of marker genes characteristic of definitive endoderm as well as the lack of significant expression of marker genes characteristic of hESCs and other cell types is determined. In other processes, the expression of marker genes characteristic of liver precursor cells, or mature hepatocyte cells as well as the lack of significant expression of marker genes characteristic of hESC and other cell types is determined.

a. Monitoring the Differentiation of Pluripotent Cells to Definitive Endoderm

As described further in the Examples below, reliable markers of definitive endoderm are the SOX17 and CXCR4 genes. As such, the definitive endoderm cells produced by the processes described herein express the SOX17 and CXCR4 marker genes, thereby producing the SOX17 and CXCR4 gene products. Other markers of definitive endoderm are described in U.S. patent application Ser. No. 11/021,618, entitled DEFINITIVE ENDODERM, filed Dec. 23, 2004 and U.S. Provisional Patent Application No. 60/736,598, entitled MARKERS OF DEFINITIVE ENDODERM, filed Nov. 14, 2005, the disclosures of which are incorporated herein by reference in their entireties. Since definitive endoderm cells express the SOX17 and/or CXCR4 marker genes at a level higher than that of the SOX7 marker gene, which is characteristic of primitive and visceral endoderm (see Table 1), in some processes, the expression of SOX17 and/or CXCR4 as well as SOX7 is monitored. In other processes, expression of the SOX17 and/or CXCR4 marker genes as well as the OCT4 marker gene, which is characteristic of hESCs, is monitored. Additionally, because definitive endoderm cells express the SOX17 and/or CXCR4 marker genes at a level higher than that of the AFP, SPARC or Thrombomodulin (TM) markers, the expression of these markers can also be monitored.

Further details describing methods of monitoring definitive endoderm cell production via marker expression is provided in U.S. patent application Ser. No. 11/021,618, entitled DEFINITIVE ENDODERM, filed Dec. 23, 2004 and U.S. Provisional Patent Application No. 60/736,598, entitled MARKERS OF DEFINITIVE ENDODERM, filed Nov. 14, 2005, the disclosures of which are incorporated herein by reference in their entireties.

b. Monitoring the Differentiation of Pluripotent Cells to Liver Precursor Cells and Hepatocyte Cells As described further in the Examples below, reliable markers of liver precursor cells include the following genes: DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1 and CUBN. As such, the liver precursor cells produced by the processes described herein express the DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN marker genes, thereby producing the DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN, gene products. Since the relative levels of expression of the marker genes DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN are enhanced in liver precursor cells compared to hESCs, and the relative level of ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD, are decreased in liver precursor cells and hESCs compared to fully differentiated hepatocyte cells, in some processes, the expression of at least one marker selected from DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN and at least one marker selected from DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD is monitored.

Described in the Examples below are data demonstrating that the following genes are reliable markers of hepatocyte cells: DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD. As such, the hepatocyte cells produced by some of the processes described herein express the DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD marker genes, thereby producing the DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD gene products. Since the relative levels of expression of the marker genes DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD are enhanced in hepatocyte cells compared to hESCs and liver precursor cells, the expression of at least one marker selected from DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD can be monitored in order to track the production of hepatocyte cells.

It will be appreciated that expression of any one of DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, or CUBN markers in liver precursor cells does not preclude the expression of other markers in that group in liver precursor cells. As such, liver precursor cells produced by certain processes described herein can substantially express DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN, but will not substantially express CYP3A7, Transferrin, HBGZ, ASGR1, SLC17A8, PCDHGB7, OCT4, PDX1, and SLC10A1. Likewise, it will be appreciated that the expression of any one of DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, or UBD markers in hepatocyte cells does not preclude the expression of other markers in the group in hepatocyte cells. As such, hepatocyte cells produced by certain processes described herein can substantially express DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD.

It will be appreciated that the expression of DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN is induced over a range of different levels in liver precursor cells depending on the differentiation conditions. As such, in some embodiments described herein, the expression of DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN in liver precursor cells or liver precursor cell populations is at least about 2-fold higher to at least about 10,000-fold higher than the expression of those markers in pluripotent stem cells (e.g., hESCs) and/or definitive endoderm cells. In other embodiments, the expression of DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN in liver precursor cells or liver precursor cell populations is at least about 4-fold higher, at least about 6-fold higher, at least about 8-fold higher, at least about 10-fold higher, at least about 15-fold higher, at least about 20-fold higher, at least about 40-fold higher, at least about 80-fold higher, at least about 100-fold higher, at least about 150-fold higher, at least about 200-fold higher, at least about 500-fold higher, at least about 750-fold higher, at least about 1000-fold higher, at least about 2500-fold higher, at least about 5000-fold higher, at least about 7500-fold higher or at least about 10,000-fold higher than the expression of those markers pluripotent stem cells (e.g., hESCs) and/or definitive endoderm cells. In some embodiments, the expression of DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN in liver precursor cells or liver precursor cell populations is infinitely higher than the expression of DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN in pluripotent stem cells or pluripotent cell populations (e.g., hESCs) and/or definitive endoderm cells.

It will also be appreciated that the expression of DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD is induced over a range of different levels in hepatocyte cells depending on the differentiation conditions. As such, in some embodiments described herein, the expression of DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD in hepatocyte cells or hepatocyte cell populations is at least about 2-fold higher to at least about 10,000-fold higher than the expression of those markers in pluripotent stem cells definitive endoderm cells and/or in liver precursor cells or liver precursor cell populations. In other embodiments, the expression of DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD in hepatocyte cells or hepatocyte cell populations is at least about 4-fold higher, at least about 6-fold higher, at least about 8-fold higher, at least about 10-fold higher, at least about 15-fold higher, at least about 20-fold higher, at least about 40-fold higher, at least about 80-fold higher, at least about 100-fold higher, at least about 150-fold higher, at least about 200-fold higher, at least about 500-fold higher, at least about 750-fold higher, at least about 1000-fold higher, at least about 2500-fold higher, at least about 5000-fold higher, at least about 7500-fold higher or at least about 10,000-fold higher than the expression of those markers in pluripotent stem cells, definitive endoderm cells and/or in liver precursor cell populations. In some embodiments, the expression of DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD in hepatocyte cells or hepatocyte cell populations is infinitely higher than the expression of DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SERPINA7, KNG1, HAL, ORM1, ORM2, NR1H4, SLC5A12, TM4SF4, MUSK, TM4SF1, OLR1, MEP1A, and UBD in pluripotent stem cells definitive endoderm cells and/or liver precursor cells or liver precursor cell populations.

Enrichment, Isolation and/or Purification of Liver Precursor Cells and Hepatocyte Cells With respect to aspects of the present invention, liver precursor cells can be enriched, isolated and/or purified by contacting a cell population that includes liver precursor cells with a reagent that binds to a marker which is expressed in liver precursor cells but not substantially expressed in one or more non-liver precursor cell types, in the cell population, and separating cells bound by the reagent from cells that are not bound by the reagent.

Likewise, hepatocyte cells can be enriched, isolated and/or purified by contacting a cell population that includes hepatocyte cells with a reagent that binds to a marker which is expressed in hepatocyte cells but not substantially expressed in one or more non-hepatocyte cell types in the cell population, and separating cells bound by the reagent from cells that are not bound by the reagent.

In some embodiments for the enrichment, isolation and/or purification of liver precursor cells, the marker can be any marker that is expressed in liver precursor cells but not substantially expressed in one or more non-definitive endoderm cell types. Such markers include, but are not limited to, markers that are more highly expressed in liver precursor cells than hESCs, mesoderm cells, ectoderm cells, and/or extra-embryonic endoderm cells. Non-limiting examples of useful markers expressed in liver precursor cells, but not substantially expressed in one or more non-definitive endoderm cell types, include: DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN. Additionally, in preferred embodiments, the marker used for enrichment, isolation and/or purification can be a marker that is not substantially expressed in definitive endoderm cells. In more preferred embodiments, the marker is not substantially expressed in either definitive endoderm cells or mature hepatocytes.

In other embodiments for the enrichment, isolation and/or purification of hepatocyte cells, the marker can be any marker that is expressed in hepatocyte cells but not substantially expressed in one or more non-definitive endoderm cell types. Such markers include, but are not limited to, markers that are more highly expressed in hepatocyte cells than hESCs, mesoderm cells, ectoderm cells, and/or extra-embryonic endoderm cells. Non-limiting examples of useful markers expressed in hepatocyte cells, but not substantially expressed in one or more non-definitive endoderm cell types, include: DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD. In further embodiments, the markers can include markers that are more highly expressed in hepatocyte cells compared to definitive endoderm cells and/or liver precursor cells. Non-limiting examples of useful markers expressed more highly in hepatocyte cells compared to definitive endoderm cells and/or liver precursor cells include DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD.

In some embodiments for the enrichment, isolation, and/or purification of liver precursor cells, the reagent can be any type of affinity tag that is specific, or at least partially specific, for liver precursor cells, such as antibodies, ligands or other binding agents that are specific, or at least partially specific, to a marker molecule, such as a polypeptide, that is present in liver precursor cells but which is not substantially present in other cell types that are found in a cell culture produced by the methods for the production of liver precursor cells such as the methods described herein. Accordingly, in some embodiments, the reagent can be an antibody, ligand, or other binding agent specific or at least partially specific to one of the following markers: DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN.

In some embodiments for the enrichment, isolation and/or purification of hepatocyte cells, the reagent can be any type of affinity tag that is specific, or at least partially specific, for hepatocyte cells, such as antibodies, ligands or other binding agents that are specific, or at least partially specific, to a marker molecule, such as a polypeptide, that is present in hepatocyte cells but which is not substantially present in other cell types that are found in a cell culture produced by the methods for the production of hepatocyte cells described herein. Accordingly, in some embodiments, the reagent can be an antibody, ligand, or other binding agent specific or at least partially specific to one of the following markers: DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD.

In preferred embodiments, an antibody which binds to one of the cell surface markers selected from the group consisting of DPP4, NOSTRIN, DOK4, SLC35D1, OCDH17, FN1, HLA-C, HLA-B, CYP4X1, CPHA6 and PP1057 is attached to a magnetic bead and then allowed to bind to liver precursor cells in a cell culture, as described in more detail below. In some embodiments, antibodies which bind to DPP4, NOSTRIN, DOK4, SLC35D1, OCDH17, FN1, HLA-C, HLA-B, CYP4X1, CPHA6 and PP1057 are used to form reagent-liver precursor cell complexes, and subsequently treated with a secondary antibody to facilitate FACS-based enrichment of cells, as described in more detail below. Similarly, the skilled artisan will appreciate that ligands that bind to DPP4, NOSTRIN, DOK4, SLC35D1, OCDH17, FN1, HLA-C, HLA-B, CYP4X1, CPHA6 and PP1057 can be used to for ligand-liver precursor cell complexes, to facilitate purification of enrichment or purification of liver precursor cells. Unbound reagent can be removed from the composition by washing, stirring, and/or filtering.

In other preferred embodiments, an antibody which binds to one of the cell surface markers selected from the group consisting of DPP4, SLC5A12, TM4SF4, MUSK, TM4SF1, or OLR1 is attached to a magnetic bead and then allowed to bind to hepatocyte cells in a cell culture. In some embodiments, antibodies which bind to DPP4, SLC5A12, TM4SF4, MUSK, TM4SF1, or OLR1 are used to form reagent-hepatocyte cell complexes, and subsequently treated with a secondary antibody to facilitate FACS-based enrichment of hepatocyte cells. The skilled artisan will appreciate that ligands that bind to DPP4, SLC5A12, TM4SF4, MUSK, TM4SF1, or OLR1 can be used to for ligand-hepatocyte cell complexes, to facilitate purification of enrichment or purification of hepatocyte cells. Unbound reagent can be removed from the composition by washing, stirring, and/or filtering.

Methods that utilize recombinant expression of fluorescently labeled polypeptides or fragments thereof in liver precursor cells or hepatocyte cells are also contemplated, as described in more detail below. For example, in some embodiments a marker selected from the group consisting of DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN is used to create a fluorescent tag which can be used to separate or enrich liver precursor cells from other cell types in a cell culture. In other embodiments, a marker selected from the group consisting of ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD is used to create a fluorescent tag which can be used to separate or enrich hepatocyte cells from other cell types in a cell culture.

In some embodiments, subsequent to providing a cell population with a reagent that binds to a marker, unbound reagent can be removed from the composition by washing, stirring, and/or filtering. One example of reagent-cell complex is an antibody-antigen complex. In preferred embodiments of such complexes, the antigen marker can be localized to the cell surface. Another example of a reagent-cell complex is a receptor-ligand complex, wherein the receptor is expressed in liver precursor cells or mature hepatocyte cells but not substantially expressed in one or more non-liver precursor or non-hepatocyte cell types. In preferred embodiments, the ligand can bind to the receptor-binding domain without appreciably affecting the receptor activity. In still other preferred embodiments, the ligand is attached to another molecule so as to facilitate easy manipulation of the reagent cell complex. For example, in cases where the ligand is a small molecule, the ligand can be linked to a macromolecule, such as a carbohydrate, a protein or a synthetic polymer. In some embodiments, the macromolecules can be coupled to, for example, labels, particles, such as magnetic particles, or surfaces, such as a solid support. Examples of cell surface molecules expressed by liver precursor cells include, but are not limited to DPP4, NOSTRIN, DOK4, SLC35D1, OCDH17, FN1, HLA-C, HLA-B, CYP4X1, CPHA6 and PP1057. Examples of cell surface molecules expressed by hepatocyte cells include, but are not limited to SLC38A4, SLC10A1, SLC5A12, TM4SF4, MUSK, TM4SF1, OLR1, SMP3, SERPINA7, and NR1H4.

In some embodiments of the present invention, an antibody is prepared for use as an affinity tag for the enrichment, isolation and/or purification of liver precursor cells or hepatocyte cells. Methods for making antibodies, for example, the methods described in Kohler, G., and C. Milstein. 1975. Continuous cultures of fused cells secreting antibody of pre-defined specificity. *Nature* 256:495-497, the disclosure of which is incorporated herein by reference in its entirety, are well known in the art. Additionally, antibodies and fragments can be made by other standardized methods (See, for example, E. Harlow et al., Antibodies, A Laboratory Manual, Cold Spring Harbor Laboratory, Cold Spring Harbor, N.Y., 1988). The isolation, identification, and molecular construction of antibodies has been developed to such an extent that the choices are almost inexhaustible. Therefore, examples of methods for making various antibodies, antibody fragments and/or antibody complexes will be provided with the understanding that this only represents a sampling of what is known to those of ordinary skill in the art.

Antibodies can be whole immunoglobulin (IgG) of any class, e.g., IgG, IgM, IgA, IgD, IgE, chimeric antibodies or hybrid antibodies with dual or multiple antigen or epitope specificities, or fragments, such as F(ab')$_2$, Fab', Fab and the like, including hybrid fragments. It will be understood that any immunoglobulin or any natural, synthetic, or genetically engineered protein that acts like an antibody by binding to marker of liver precursor cells or hepatocyte cells can be used.

Preparations of polyclonal antibodies can be made using standard methods which are well known in the art. Antibodies can include antiserum preparations from a variety of commonly used animals, e.g., goats, primates, donkeys, swine, rabbits, horses, hens, guinea pigs, rats, or mice, and even human antisera after appropriate selection and purification. Animal antisera are raised by inoculating the animals with immunogenic epitopes from one or more recombinantly-expressed polypeptide markers described herein. The animals are then bled and the serum or an immunoglobulin-containing serum fraction is recovered.

Hybridoma-derived monoclonal antibodies (human, monkey, rat, mouse, or the like) are also suitable for use in the present invention. Monoclonal antibodies typically display a high degree of specificity. Such antibodies are readily prepared by conventional procedures for the immunization of mammals with preparations such as, the immunogenic epitopes of one or more markers selected from the group consisting of DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, CUBN, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD, fusion of immune lymph or spleen cells with an immortal myeloma cell line, and isolation of specific hybridoma clones. In addition to the foregoing procedure, alternate methods of preparing monoclonal antibodies are also useful. Such methods can include interspecies fusions and genetic engineering manipulations of hypervariable regions. In preferred embodiments, the marker is selected from the group consisting of DPP4, NOSTRIN, DOK4, SLC35D1, OCDH17, FN1, HLA-C, HLA-B, CYP4X1, CPHA6, PP1057 SLC38A4, SCL10A1, SLC5A12, TM4SF4, MUSK, TM4SF1, OLR1, SMP3, SERPINA7, and NR1H4, In one embodiment of the present invention, the antibody is a single chain Fv region. Antibody molecules have two generally recognized regions, in each of the heavy and light chains. These regions are the so-called "variable" region which is responsible for binding to the specific antigen in question, and the so-called "constant" region which is responsible for biological effector responses such as complement binding, binding to neutrophils and macrophages, etc. The constant regions have been separated from the antibody molecule and variable binding regions have been obtained. Fragments containing the variable region, but lacking the constant region, are sufficient for antigen binding.

The variable regions of an antibody are composed of a light chain and a heavy chain. Light and heavy chain variable regions have been cloned and expressed in foreign hosts, while maintaining their binding ability. Therefore, it is possible to generate a single chain structure from the multiple chain aggregate (the antibody), such that the single chain structure will retain the three-dimensional architecture of the multiple chain aggregate.

In some embodiments, single polypeptide chain Fv fragments having the characteristic binding ability of multi-chain variable regions of antibody molecules can be used to bind one or more markers selected from the group consisting of DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, CUBN, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD. In preferred embodiments, Fv fragments that bind to one or more markers selected from the group consisting of DPP4, NOSTRIN, DOK4, SLC35D1, OCDH17, FN1, HLA-C, HLA-B, CYP4X1, CPHA6, PP1057 SLC38A4, SCL10A1, SLC5A12, TM4SF4, MUSK, TM4SF1, OLR1, SMP3, SERPINA7, and NR1H4 are used to bind those markers. Such single chain fragments can be produced, for example, following the methods described in U.S. Pat. No. 5,260,203, the disclosure of which is incorporated herein by reference in its entirety, using a computer based system and method to determine chemical structures. These chemical structures are used for converting two naturally aggregated but chemically separated light and heavy polypeptide chains from an antibody variable region into a single polypeptide chain which will fold into a three dimensional structure very similar to the original structure of the two polypeptide chains. The two regions may be linked using an amino acid sequence as a bridge.

The single polypeptide chain obtained from this method can then be used to prepare a genetic sequence that encodes it. The genetic sequence can then be replicated in appropriate hosts, further linked to control regions, and transformed into expression hosts, where it is expressed. The resulting single polypeptide chain binding protein, upon refolding, has the binding characteristics of the aggregate of the original two (heavy and light) polypeptide chains of the variable region of the antibody.

In a further embodiment, the antibodies used herein can multivalent forms of single-chain antigen-binding proteins. Multivalent forms of single-chain antigen-binding proteins have additional utility beyond that of the monovalent single-chain antigen-binding proteins. In particular, a multivalent antigen-binding protein has more than one antigen-binding site which results in an enhanced binding affinity. The multivalent antibodies can be produced using the method disclosed in U.S. Pat. No. 5,869,620, the disclosure of which is incorporated herein by reference in its entirety. The method involves producing a multivalent antigen-binding protein by linking at least two single-chain molecules, each single chain molecule having two binding portions of the variable region of an antibody heavy or light chain linked into a single chain protein. In this way the antibodies can have binding sites for different parts of an antigen or have binding sites for multiple antigens.

In another embodiment, the antibody can be an oligomer. The oligomer is produced as in WO98/18943, the disclosure of which is incorporated herein by reference in its entirety, by first isolating a specific ligand from a phage-display library. Oligomers overcome the problem of the isolation of mostly low affinity ligands from these libraries, by oligomerizing the low-affinity ligands to produce high affinity oligomers. The oligomers are constructed by producing a fusion protein with the ligand fused to a semi-rigid hinge and a coiled coil domain from, for example, Cartilage Oligomeric Matrix Protein (COMP). When the fusion protein is expressed in a host cell, it self assembles into oligomers.

Preferably, the oligomers are peptabodies (Terskikh et al., Biochemistry 94:1663-1668 (1997)). Peptabodies can be exemplified as IgM antibodies which are pentameric with each binding site having low-affinity binding, but able to bind in a high affinity manner as a complex. Peptabodies are made using phage-display random peptide libraries. A short peptide ligand from the library is fused via a semi-rigid hinge at the N-terminus of a COMP pentamerization domain. The fusion protein is expressed in bacteria where it assembles into a pentameric antibody which shows high affinity for its target. Depending on the affinity of the ligand, an antibody with very high affinity can be produced.

Several generally applicable methods for using antibodies in affinity-based isolation and purification methods are known in the art. Such methods can be implemented for use with the antibodies and cells described herein. In preferred embodiments, an antibody which binds to one of the cell surface markers selected from the group consisting of selected from the group consisting of DPP4, NOSTRIN, DOK4, SLC35D1, OCDH17, FN1, HLA-C, HLA-B, CYP4X1, CPHA6, PP1057 SLC38A4, SCL10A1, SLC5A12, TM4SF4, MUSK, TM4SF1, OLR1, SMP3, SERPINA7, and NR1H4 is attached to a magnetic bead then allowed to bind to liver precursor cells or hepatocyte cells in a cell culture which has been enzymatically treated to reduce intercellular and substrate adhesion, to form reagent-cell complexes. The reagent-cell complexes are then exposed to a movable magnetic field which is used to separate reagent-bound definitive endoderm cells from unbound cells. Once the liver precursor cells or hepatocyte cells are physically separated from other cells in culture, the antibody binding is disrupted and the cells are replated in appropriate tissue culture medium, thereby producing a population of cells enriched for liver precursor cells or hepatocyte cells.

Other methods of enrichment, isolation and/or purification using antibodies to form antibody-cell complexes are contemplated. For example, in some embodiments, a primary antibody which binds to a marker expressed in liver precursor cells or hepatocyte cells, but not substantially expressed in one or more non-liver precursor cell types or non-hepatocyte cell types, is incubated with a liver precursor or hepatocyte-containing cell culture that has been treated to reduce intercellular and substrate adhesion, to form antibody-cell complexes. In preferred embodiments, the primary antibody comprises one or more antibodies that bind to a cell surface polypeptide selected from the group consisting of selected from the group consisting of DPP4, NOSTRIN, DOK4, SLC35D1, OCDH17, FN1, HLA-C, HLA-B, CYP4X1, CPHA6, PP1057 SLC38A4, SCL10A1, SLC5A12, TM4SF4, MUSK, TM4SF1, OLR1, SMP3, SERPINA7, and NR1H4. The cells are then washed, centrifuged and resuspended. The cell suspension is then incubated with a secondary antibody, such as an FITC-conjugated antibody that is capable of binding to the primary antibody of the reagent-cell complex. The cells are then washed, centrifuged and resuspended in buffer. The cell suspension is then analyzed and sorted using a fluorescence activated cell sorter (FACS). Antibody-bound cells are collected separately from cells that are not bound by the antibody, thereby resulting in the isolation of such cell types. If desired, the enriched cell compositions can be further purified by using an alternate affinity-based method or by additional rounds of sorting using the same or different markers that are specific for liver precursor or hepatocyte cells.

Additional methods of enrichment, isolation and/or purification related to using a ligand-based reagent to form ligand-cell complexes. For example, ligand-cell complexes can include a ligand-based reagent and receptor that is expressed on liver precursor cells or hepatocyte cells but not substantially expressed in one or more non-liver precursor cell types or non-hepatocyte cell types. In such embodiments, ligand-based reagents are used as an affinity tag for the enrichment, isolation and/or purification of definitive endoderm cells. By way of example, lactate, which is a ligand for SLC5A12, or other molecules based on lactate is a useful reagent in the enrichment, isolation and/or purification methods described herein. Likewise, lactate fusions or lactate mimetics that retain the ability to form reagent-cell complexes are useful in the enrichment, isolation and/or purification methods described herein. In some embodiments, the ligand is a ligand that binds to one of the cell surface markers selected from the group consisting of DPP4, NOSTRIN, DOK4, SLC35D1, OCDH17, FN1, HLA-C, HLA-B, CYP4X1, CPHA6, PP1057 SLC38A4, SCL10A1, SLC5A12, TM4SF4, MUSK, TM4SF1, OLR1, SMP3, SERPINA7, and NR1H4. In preferred embodiments, a ligand that binds to one of the cell surface markers selected from the group consisting of DPP4, NOSTRIN, DOK4, SLC35D1, OCDH17, FN1, HLA-C, HLA-B, CYP4X1, CPHA6, PP1057 SLC38A4, SLC10A1, SLC5A12, TM4SF4, MUSK, TM4SF1, OLR1, SMP3, SERPINA7, and NR1H4 is attached directly to a macromolecule or a solid support. In other preferred embodiments, a ligand that binds to one of the cell surface markers selected from the group consisting of DPP4, NOSTRIN, DOK4, SLC35D1, OCDH17, FN1, HLA-C, HLA-B, CYP4X1, CPHA6, PP1057 SLC38A4, SCL10A1, SLC5A12, TM4SF4, MUSK, TM4SF1, OLR1, SMP3, SERPINA7, and NR1H4 is attached via a linker to a macromolecule or a solid support. In such embodiments, non-bound cells can be removed from the ligand-cell complexes by washing.

Alternatively, in some embodiments of the processes described herein, liver precursor cells or hepatocyte cells are fluorescently labeled by recombinant expression of a fluorescent polypeptide or fragment thereof in definitive endoderm cells. For example, a nucleic acid encoding green fluorescent protein (GFP) or a nucleic acid encoding a different expressible fluorescent marker gene is used to label liver precursor cells or hepatocyte cells. Various fluorescent marker genes are known in the art, such as luciferase, enhanced green fluorescent protein (EGFP), DS-Red monomer fluorescent protein (Clontech) and others. Any such markers can be used with the enrichment, isolation and/or purification methods described herein. For example, in some embodiments, at least one copy of a nucleic acid encoding GFP or a biologically active fragment thereof is introduced into a pluripotent cell, preferably a human embryonic stem cell, downstream of the promoter of any of the marker genes described herein that are expressed in liver precursor cells or hepatocyte cells, but not substantially expressed in one or more non-liver precursor cell types or non-hepatocyte cell types, such that the expression of the GFP gene product or biologically active fragment thereof is under control of the marker gene's promoter. In some embodiments, the entire coding region of the nucleic acid, which encodes the marker, is replaced by a nucleic acid encoding GFP or a biologically active fragment thereof. In other embodiments, the nucleic acid encoding GFP or a biologically active fragment thereof is fused in frame with at least a portion of the nucleic acid encoding the marker, thereby generating a fusion protein. In such embodiments, the fusion protein retains a fluorescent activity similar to GFP.

The fluorescently-tagged cells produced by the above-described methods are then differentiated to liver precursor cells or hepatocyte cells using the differentiation methods described herein Depending on whether the fluorescently-tagged cells are differentiated into liver precursor cells or hepatocyte cells, liver precursor cells or hepatocyte cells express the fluorescent marker gene, whereas non-liver precursor cell types or non-hepatocyte cell types, respectively do not, these two cell types can be separated. In some embodiments, cell suspensions comprising a mixture of fluorescently-labeled liver precursor cells or hepatocyte cells and unlabeled non-liver precursor cells or non-hepatocyte cells are sorted using a FACS. Liver precursor cells or hepatocyte cells are collected separately from non-liver precursor cells or non-hepatocyte cells, thereby resulting in the isolation of such cell types. If desired, the isolated cell compositions can be further purified by additional rounds of sorting using the same or different markers that are specific for liver precursor cells or hepatocyte cells.

Using the methods and compositions described herein, enriched, isolated and/or purified populations of liver precursor and hepatocyte cells and/or tissues can be produced in vitro from hESC cultures or cell populations which have undergone differentiation for from about 1 hour to greater than about 400 hours. In some embodiments, the cells undergo random differentiation. In a preferred embodiment, however, the cells are directed to differentiate primarily into liver precursor cells or hepatocyte cells. Some preferred enrichment, isolation and/or purification methods relate to the in vitro production of liver precursor cells or hepatocyte cells from human embryonic stem cells or definitive endoderm cells. In preferred embodiments, pluripotent cells (e.g. hESCs) are directed to differentiate primarily into either liver precursor cells, or hepatocyte cells as described herein. Some preferred enrichment, isolation and/or purification methods relate to the in vitro production of liver precursor or hepatocyte cells from hESCs.

Using the methods described herein, cell populations or cell cultures can be enriched in liver precursor cell content by at least about 2- to about 1000-fold as compared to untreated or unenriched cell populations or cell cultures. In some embodiments, liver precursor cells can be enriched by at least about 5- to about 500-fold as compared to untreated or unenriched cell populations or cell cultures. In other embodiments, liver precursor cells can be enriched from at least about 10- to about 200-fold as compared to untreated or unenriched cell populations or cell cultures. In still other embodiments, liver precursor cells can be enriched from at least about 20- to about 100-fold as compared to untreated or unenriched cell populations or cell cultures. In yet other embodiments, liver precursor cells can be enriched from at least about 40- to about 80-fold as compared to untreated or unenriched cell populations or cell cultures. In certain embodiments, liver precursor cells can be enriched from at least about 2- to about 20-fold as compared to untreated or unenriched cell populations or cell cultures.

Also using the methods described herein, cell populations or cell cultures can be enriched in hepatocyte cell content by at least about 2- to about 1000-fold as compared to untreated or unenriched cell populations or cell cultures. In some embodiments, hepatocyte cells can be enriched by at least about 5- to about 500-fold as compared to untreated or unenriched cell populations or cell cultures. In other embodiments, hepatocyte cells can be enriched from at least about 10- to about 200-fold as compared to untreated or unenriched cell populations or cell cultures. In still other embodiments, hepatocyte cells can be enriched from at least about 20- to about 100-fold as compared to untreated or unenriched cell populations or cell cultures. In yet other embodiments, hepatocyte cells can be enriched from at least about 40- to about 80-fold as compared to untreated or unenriched cell populations or cell cultures. In certain embodiments, hepatocyte cells can be enriched from at least about 2- to about 20-fold as compared to untreated or unenriched cell populations or cell cultures.

In preferred embodiments, liver precursor cells or hepatocyte cells are enriched, isolated and/or purified from other non-liver precursor cells or non-hepatocyte cells, respectively, after the stem cell cultures or definitive endoderm cultures are induced to differentiate towards the liver precursor or hepatocyte lineage, respectively. It will be appreciated that the above-described enrichment, isolation and purification procedures can be used with such cultures at any stage of differentiation.

In addition to the procedures just described, liver precursor cells or hepatocyte cells may also be isolated by other techniques for cell isolation. Additionally, liver precursor cells or hepatocyte cells may also be enriched or isolated by methods of serial subculture in growth conditions which promote the selective survival or selective expansion of said liver precursor cells or hepatocyte cells.

Compositions Comprising Liver Precursor Cells or Hepatocyte Cells

Cell compositions produced by the above-described methods include cell cultures comprising liver precursor cells and/or hepatocyte cells and cell populations enriched in liver precursor cells and/or hepatocyte cells. For example, cell cultures which comprise liver precursor cells or hepatocyte cells, wherein at least about 50-80% of the cells in culture are liver precursor cells or hepatocyte cells, respectively, can be produced. Because the efficiency of the differentiation process can be adjusted by modifying certain parameters, which include but are not limited to, cell growth conditions, growth factor concentrations and the timing of culture steps, the differentiation procedures described herein can result in about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or greater than about 95% conversion of pluripotent cells to liver precursor cells or hepatocyte cells. In processes in which isolation of liver precursor cells is employed, for example, by using an affinity reagent that binds to a marker selected from the group consisting of DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN, a substantially pure liver precursor cell population can be recovered. In processes in which isolation of hepatocyte cells is employed, for example, by using an affinity reagent that binds to a marker selected from the group consisting of DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD, a substantially pure hepatocyte can be recovered.

Some embodiments described herein relate to compositions, such as cell populations and cell cultures, that comprise pluripotent cells, such as stem cells, definitive endoderm cells, and liver precursor cells and/or hepatocyte cells. For example, using the methods described herein, compositions comprising mixtures of hESCs, definitive endoderm cells, and liver precursor cells and/or hepatocyte cells can be produced. In some embodiments, compositions comprising at least about 5 liver precursor cells for about every 95 pluripotent cells or definitive endoderm cells are produced. In other embodiments, compositions comprising at least about 95 liver precursor cells for about every 5 pluripotent cells or definitive endoderm are produced. Additionally, compositions comprising other ratios of liver precursor cells to pluripotent or definitive endoderm cells are contemplated. For example, compositions comprising at least about 1 liver precursor cell for about every 1,000,000 pluripotent cells or definitive endoderm cells, at least about 1 liver precursor cell for about every 100,000 pluripotent cells or definitive endoderm cells, at least about 1 liver precursor cell for about every 10,000 pluripotent cells or definitive endoderm cells, at least about 1 liver precursor cell for about every 1000 pluripotent cells or definitive endoderm cells, at least about 1 liver precursor cell for about every 500 pluripotent cells or definitive endoderm cells, at least about 1 liver precursor cell for about every 100 pluripotent cells or definitive endoderm cells, at least about 1 liver precursor cell for about every 10 pluripotent cells or definitive endoderm cells, at least about 1 liver precursor cell for about every 5 pluripotent cells or definitive endoderm cells, at least about 1 liver precursor cell for about every 2 pluripotent cells or definitive endoderm cells, at least about 2 liver precursor cells for about every 1 pluripotent cell or definitive endoderm cell, at least about 5 liver precursor cells for about every 1 pluripotent cell or definitive endoderm cell, at least about 10 liver precursor cells for about every 1 pluripotent cell or definitive endoderm cell, at least about 20 liver precursor cells for about every 1 pluripotent cell or definitive endoderm cell, at least about 50 liver precursor cells for about every 1 pluripotent cell or definitive endoderm cell, at least about 100 liver precursor cells for about every 1 pluripotent cell or definitive endoderm cell, at least about 1000 liver precursor cells for about every 1 pluripotent cell or definitive endoderm cell, at least about 10,000 liver precursor cells for about every 1 pluripotent cell or definitive endoderm cell, at least about 100,000 liver precursor cells for about every 1 pluripotent cell or definitive endoderm cell and at least about 1,000,000 liver precursor cells for about every 1 pluripotent cell or definitive endoderm cell are contemplated. In some embodiments, the pluripotent cells are human pluripotent stem cells. In certain embodiments the stem cells are derived from a morula, the inner cell mass of an embryo or the gonadal ridges of an embryo. In certain other embodiments, the pluripotent cells are derived from the gondal or germ tissues of a multicellular structure that has developed past the embryonic stage.

In other embodiments, compositions comprising at least about 5 hepatocyte cells for about every 95 pluripotent cells or definitive endoderm cells are produced. In other embodiments, compositions comprising at least about 95 hepatocyte cells for about every 5 pluripotent cells, definitive endoderm cells, or liver precursor cells are produced. Additionally, compositions comprising other ratios of hepatocyte cells to pluripotent cells, definitive endoderm cells, or liver precursor cells are contemplated. For example, compositions comprising at least about 1 hepatocyte cell for about every 1,000,000 pluripotent cells, definitive endoderm cells, or liver precursor cells, at least about 1 hepatocyte cell for about every 100,000 pluripotent cells, definitive endoderm cells, or liver precursor cells, at least about 1 hepatocyte cell for about every 10,000 pluripotent cells, definitive endoderm cells, or liver precursor cells, at least about 1 hepatocyte cell for about every 1000 pluripotent cells, definitive endoderm cells, or liver precursor cells, at least about 1 hepatocyte cell for about every 500 pluripotent cells, definitive endoderm cells, or liver precursor cells, at least about 1 hepatocyte cell for about every 100 pluripotent cells, definitive endoderm cells, or liver precursor cells, at least about 1 hepatocyte cell for about every 10 pluripotent cells, definitive endoderm cells, or liver precursor cells, at least about 1 hepatocyte cell for about every 5 pluripotent cells, definitive endoderm cells, or liver precursor cells, at least about 1 hepatocyte cell for about every 2 pluripotent cells, definitive endoderm cells, or liver precursor cells, at least about 2 hepatocyte cells for about every 1 pluripotent cell, definitive endoderm cell, or liver precursor cell, at least about 5 hepatocyte cells for about every 1 pluripotent cell, definitive endoderm cell, or liver precursor cell, at least about 10 hepatocyte cells for about every 1 pluripotent cell, definitive endoderm cell, or liver precursor cell, at least about 20 hepatocyte cells for about every 1 pluripotent cell, definitive endoderm cell, or liver precursor cell, at least about 50 hepatocyte cells for about every 1 pluripotent cell, definitive endoderm cell, or liver precursor cell, at least about 100 hepatocyte cells for about every 1 pluripotent cell, definitive endoderm cell, or liver precursor cell, at least about 1000 hepatocyte cells for about every 1 pluripotent cell, definitive endoderm cell, or liver precursor cell, at least about 10,000 hepatocyte cells for about every 1 pluripotent cell, definitive endoderm cell, or liver precursor cell, at least about 100,000 hepatocyte cells for about every 1 pluripotent cell, definitive endoderm cell, or liver precursor cell and at least about 1,000,000 hepatocyte cells for about every 1 pluripotent cell, definitive endoderm cell, or liver precursor cell are contemplated. In some embodiments, the pluripotent cells are human pluripotent stem cells. In certain embodiments the stem cells are derived from a morula, the inner cell mass of an embryo or the gonadal ridges of an embryo. In certain other embodiments, the pluripotent cells are derived from the gondal or germ tissues of a multicellular structure that has developed past the embryonic stage.

Some embodiments described herein relate to cell cultures or cell populations comprising from at least about 5% liver precursor cells to at least about 95% liver precursor cells. In some embodiments the cell cultures or cell populations comprise mammalian cells. In preferred embodiments, the cell cultures or cell populations comprise human cells. For example, certain specific embodiments relate to cell cultures comprising human cells, wherein from at least about 5% to at least about 95% of the human cells are liver precursor cells. Other embodiments relate to cell cultures comprising human cells, wherein at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or greater than 90% of the human cells are liver precursor cells. In embodiments where the cell cultures or cell populations comprise human feeder cells, the above percentages are calculated without respect to the human feeder cells in the cell cultures or cell populations.

Other embodiments relate to cell cultures or cell populations comprising from at least about 5% hepatocyte cells to at least about 95% hepatocyte cells. In some embodiments the cell cultures or cell populations comprise mammalian cells. In preferred embodiments, the cell cultures or cell populations comprise human cells. For example, certain specific embodiments relate to cell cultures comprising human cells, wherein from at least about 5% to at least about 95% of the human cells are hepatocyte cells. Other embodiments relate to cell cultures comprising human cells, wherein at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or greater than 90% of the human cells are hepatocyte cells. In embodiments where the cell cultures or cell populations comprise human feeder cells, the above percentages are calculated without respect to the human feeder cells in the cell cultures or cell populations.

Further embodiments described herein relate to compositions, such as cell cultures or cell populations, comprising human cells, such as human liver precursor cells, wherein the relative expression of DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN is enhanced, compared to the expression of the CYP3A7, Transferrin, HBGZ, ASGR1, SLC17A8, PCDHGB7, OCT4, PDX1, or SLC10A1 markers in at least about 5% of the human cells. In other embodiments, the expression of DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN markers is enhanced, compared to the expression of the CYP3A7, Transferrin, HBGZ, ASGR1, SLC17A8, PCDHGB7, OCT4, PDX1, or SLC10A1 markers in at least about 10% of the human cells, in at least about 15% of the human cells, in at least about 20% of the human cells, in at least about 25% of the human cells, in at least about 30% of the human cells, in at least about 35% of the human cells, in at least about 40% of the human cells, in at least about 45% of the human cells, in at least about 50% of the human cells, in at least about 55% of the human cells, in at least about 60% of the human cells, in at least about 65% of the human cells) in at least about 70% of the human cells, in at least about 75% of the human cells, in at least about 80% of the human cells, in at least about 85% of the human cells, in at least about 90% of the human cells, in at least about 95% of the human cells or in greater than 95% of the human cells. In embodiments where the cell cultures or cell populations comprise human feeder cells, the above percentages are calculated without respect to the human feeder cells in the cell cultures or cell populations. In certain embodiments, the liver precursor cells expressing DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN do not express significant levels or amounts of CYP3A7, Transferrin, HBGZ, ASGR1, SLC17A8, PCDHGB7, OCT4, PDX1, or SLC10A1.

Using the methods described herein, compositions comprising liver precursor cells substantially free of other cell types can be produced. In some embodiments described herein, the liver precursor cell populations or cell cultures produced by the methods described herein are substantially free of cells that significantly express the CYP3A7, Transferrin, HBGZ, ASGR1, SLC17A8, PCDHGB7, OCT4, PDX1, or SLC10A1 marker genes.

In some embodiments, compositions, such as cell cultures or cell populations, that are substantially free of cells other than hepatocyte cells are contemplated. In addition, compositions, such as cell cultures or cell populations that are enriched, isolated and/or purified for hepatocyte cells are contemplated. In some such embodiments, the enriched, isolated and/or purified hepatocyte cell cultures or cell population comprise hepatocyte cells that express one or more markers selected from the group consisting of DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD.

Reagent-Cell Complexes

Aspects of the present invention relate to compositions, such as cell cultures and/or cell populations, that comprise complexes of one or more liver precursor cells bound to one or more reagents (reagent-cell complexes). For example, cell cultures and/or cell populations comprising reagent-cell complexes, wherein at least about 5 to at least about 100% of the liver precursor cells in culture are in the form of reagent-cell complexes, can be produced. In other embodiments, cell cultures and/or cell populations can be produced which comprise at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99% or at least about 100% reagent-cell complexes. In some embodiments, the reagent cell complexes comprise one or more liver precursor cells bound to one or more antibodies that bind to a marker selected from the group consisting of DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057; PFTK1, and CUBN. In still other embodiments, the reagent cell complexes comprise one or more liver precursor cells bound to one or more ligands that bind to a marker selected from the group consisting of DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN.

Other aspects of the present invention relate to compositions, such as cell cultures and/or cell populations that comprise complexes of one or more hepatocyte cells bound to one or more reagents (reagent-cell complexes). For example, cell cultures and/or cell populations comprising reagent-cell complexes, wherein at least about 5 to at least about 100% of the hepatocyte cells in culture are in the form of reagent-cell complexes, can be produced. In other embodiments, cell cultures and/or cell populations can be produced which comprise at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99% or at least about 100% reagent-cell complexes. In some embodiments, the reagent cell complexes comprise one or more hepatocyte cells bound to one or more antibodies that bind to a marker selected from the group consisting of DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SER-PINA7, KNG1, HAL, ORM1, ORM2, NR1H4, SLC5A12, TM4SF4, MUSK, TM4SF1, OLR1, MEP1A, and UBD. In still other embodiments, the reagent cell complexes comprise one or more hepatocyte cells bound to one or more ligands that bind to a marker selected from the group consisting of DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD.

Some embodiments described herein relate to cell cultures and/or cell populations comprising from at least about 5% reagent cell complexes to at least about 95% reagent-cell complexes. In some embodiments the cell cultures or cell populations comprise mammalian cells. In preferred embodiments, the cell cultures or cell populations comprise human cells. For example, certain specific embodiments relate to cell cultures comprising human cells, wherein from at least about 5% to at least about 95% of the human cells are liver precursor cells. Other embodiments relate to cell cultures comprising human cells, wherein from at least about 5% to at least about 95% of the human cells are hepatocyte cells. Other embodiments relate to cell cultures comprising human cells, wherein at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or greater than 90% of the human cells are reagent cell complexes. In embodiments where the cell cultures or cell populations comprise human feeder cells, the above percentages are calculated without respect to the human feeder cells in the cell cultures or cell populations. In some embodiments, the reagent cell complexes comprise one or more liver precursor cells bound to one or more antibodies that bind to a marker selected from the group consisting of DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN. In other embodiments, the reagent cell complexes comprise one or more hepatocyte cells bound to one or more antibodies that bind to a marker selected from the group consisting of: DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD.

In some embodiments, the expression of DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN is enhanced in liver precursor cells present in the reagent-cell complexes that have been described above compared to the expression of CYP3A7, Transferrin, HBGZ, ASGR1, SLC17A8, PCDHGB7, OCT4, PDX1, and SLC10A1. In preferred embodiments, the liver precursor cells expressing DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN do not express significant levels or amounts of CYP3A7, Transferrin, HBGZ, ASGR1, SLC17A8, PCDHGB7, OCT4, PDX1, or SLC10A1.

Additional embodiments described herein relate to compositions, such as cell cultures and/or cell populations that comprise both pluripotent cells, such as stem cells, and reagent-cell complexes. In some embodiments, the compositions also comprise mutlipotent cells, such as definitive endoderm cells. For example, using the methods described herein, compositions comprising mixtures of hESCs and/or definitive endoderm cells and reagent-cell complexes of liver precursor cells can be produced. Further, using the methods described herein, compositions comprising mixtures of hESCs and/or definitive endoderm cells and reagent-cell complexes of hepatocyte cells can be produced. In some embodiments, compositions comprising at least about 5 reagent-cell complexes for about every 95 pluripotent and/or definitive endoderm cells are provided. In other embodiments, compositions comprising at least about 95 reagent-cell complexes for about every 5 pluripotent cells and/or definitive endoderm cells are provided. Additionally, compositions comprising other ratios of reagent-cell complexes cells to pluripotent cells and/or definitive endoderm cells are contemplated. For example, compositions comprising at least about 1 reagent-cell complex for about every 1,000,000 pluripotent cells and/or definitive endoderm cells, at least about 1 reagent-cell complex for about every 100,000 pluripotent cells and/or definitive endoderm cells, at least about 1 reagent-cell complex cell for about every 10,000 pluripotent cells and/or definitive endoderm cells, at least about 1 reagent-cell complex for about every 1000 pluripotent cells and/or definitive endoderm cells, at least about 1 reagent-cell complex for about every 500 pluripotent cells and/or definitive endoderm cells, at least about 1 reagent-cell complex for about every 100 pluripotent cells and/or definitive endoderm cells, at least about 1 reagent-cell complex for about every 10 pluripotent cells and/or definitive endoderm cells, at least about 1 reagent-cell complex for about every 5 pluripotent cells and/or definitive endoderm cells, at least about 1 reagent-cell complex for about every 2 pluripotent cells and/or definitive endoderm cells, at least about reagent-cell complexes for about every 1 pluripotent cell and/or definitive endoderm cell, at least about 5 reagent-cell complexes for about every 1 pluripotent cell and/or definitive endoderm cell, at least about 10 definitive endoderm cells for about every 1 pluripotent cell and/or definitive endoderm cells at least about 20 reagent-cell complexes for about every 1 pluripotent cell and/or definitive endoderm cell, at least about 50 reagent-cell complexes for about every 1 pluripotent cell and/or definitive endoderm cell, at least about reagent-cell complexes for about every 1 pluripotent cell and/or definitive endoderm cell, at least about 1000 reagent-cell complexes for about every 1 pluripotent cell and/or definitive endoderm cell, at least about 10,000 reagent-cell complexes for about every 1 pluripotent cell, at least about 100,000 reagent-cell complexes for about every 1 pluripotent cell and/or definitive endoderm cell and at least about 1,000,000 reagent-cell complexes for about every 1 pluripotent cell and/or definitive endoderm cell are contemplated. In some embodiments of the present invention, the pluripotent cells are human pluripotent stem cells. In certain embodiments the stem cells are derived from a morula, the inner cell mass of an embryo or the gonadal ridges of an embryo. In certain other embodiments, the pluripotent cells are derived from the gonadal or germ tissues of a multicellular structure that has developed past the embryonic stage.

Identification and Quantitation of Definitive Endoderm Cells, Liver Precursor Cells, and Hepatocyte Cells The desirability of detecting or determining the amount of liver precursor cells, and/or hepatocyte cells in a cell culture or cell population, and methods of distinguishing these cell types from each other and other cells in the culture or in the population is readily apparent. Accordingly, certain embodiments described herein relate to reagents and methods for the detection, identification, and quantitation of cell markers whose presence, absence and/or relative expression levels are indicative for liver precursor cells, or hepatocyte cells.

Some embodiments set forth herein provide a method for detecting liver precursor cells in a cell population that includes the steps of detecting the expression of at least one of the markers selected from the group consisting of DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN. In some embodiments, the method also includes the step of detecting the expression of at least one marker selected from the group consisting of CYP3A7, Transferrin, HBGZ, ASGR1, SLC17A8, PCDHGB7, OCT4, PDX1, or SLC10A1. In certain embodiments, the expression of one or more of the markers selected from the group consisting of DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN is enhanced compared to the level of expression of CYP3A7, Transferrin, HBGZ, ASGR1, SLC17A8, PCDHGB7, OCT4, PDX1, or SLC10A1. In some embodiments, the expression of CYP3A7 and/or Transferring is not significantly detected in cells that express one or more markers selected from DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN.

Other embodiments provide a method for detecting hepatocyte cells in a cell population that includes the steps of detecting the expression of at least one of the markers selected from the group consisting of DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD.

As discussed below, expression levels of the markers may be determined by any method known to those skilled in the art, including but not limited to immunocytochemistry or quantitative PCR (Q-PCR). Embodiments of the present invention relate to compositions useful in the detection and quantitation of definitive endoderm cells.

Immunodetection of Liver Precursor Cells and Mature Hepatocyte Cells

In some embodiments, immunochemistry is used to detect the presence, absence, and/or level of expression of proteins encoded by the above-mentioned markers expressed in liver precursor cells, and mature hepatocyte cells. In preferred embodiments, immunochemistry is used to detect the presence, absence, and/or level of expression of proteins including DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, CUBN ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD.

In preferred embodiments, immunochemistry is used to detect the presence, absence, and/or level of expression of proteins indicative of liver precursor cells, including: DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN. In still other embodiments, immunochemistry is used to detect the presence, absence, and/or level of expression of proteins indicative of mature hepatocyte cells, including DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD.

The term "antibody" is used in the broadest sense and unless specified specifically covers single monoclonal antibodies (including agonist and antagonist antibodies) and antibody compositions with polyepitopic specificity. The term "antibody" also includes obvious variants, derivatives, analogs, fragments, mimetics, all of which substantially retain the binding characteristics and other properties of the stated antibody.

Monoclonal antibodies (moAbs) refer to antibodies obtained from a population of substantially homogeneous antibodies, i.e., the individual antibodies comprising the population are identical except for possible naturally occurring mutations that may be present in minor amounts. In some embodiments, monoclonal antibodies may be highly specific, being directed against a single epitopic region of an antigen. Furthermore, in contrast to conventional (polyclonal) antibody preparations that typically include different antibodies directed against different determinants (epitopes), each moAb is directed against a single determinant on the antigen. In addition to their specificity, monoclonal antibodies are advantageous in that they can be synthesized by hybridoma culture, uncontaminated by other immunoglobulins.

The modifier "monoclonal" indicates the character of the antibody as being obtained from a substantially homogeneous population of antibodies, and is not to be construed as requiring production of the antibody by any particular method. As described above, the monoclonal antibodies to be used in accordance with the invention may be made by the hybridoma method first described by Kohler et al., Nature, 256:495 (1975), or may be made by recombinant DNA methods (see, e.g., U.S. Pat. No. 4,816,567 to Cabilly et al.). The "monoclonal antibodies" also include clones of antigen-recognition and binding-site containing antibody fragments (Fv clones) isolated from phage antibody libraries using the techniques described in Clackson et al., Nature, 352:624-628 (1991) and Marks et al., J. Mol. Biol., 222:581-597 (1991), for example.

Furthermore, as described above, in some embodiments, the antibodies can be "antibody fragments," which refer to a portion of an intact antibody comprising the antigen binding site or variable region of the intact antibody, wherein the portion is free of the constant heavy chain domains of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules; (2) single chain polypeptides containing only one light chain variable domain, or a fragment thereof that contains the three CDRs of the light chain variable domain, without an associated heavy chain moiety; and (3) single chain polypeptides containing only one heavy chain variable region, or a fragment thereof containing the three CDRs of the heavy chain variable region, without an associated light chain moiety. In some embodiments, antibody fragments further encompass multispecific or multivalent structures formed from the aforementioned antibody fragments.

It will be appreciated that a wide variety of techniques are useful for the immunodetection of molecules including the markers described herein. For example, flow cytometry, immunomicroscopy, Western blotting, direct and indirect sandwich assays, such as ELISA, Western blotting, and the like. These techniques are described, herein and, for example in Malik and Lillehoj (1994), herein incorporated by reference in its entirety.

Nucleic Acid-Based Detection of Liver Precursor Cells and Mature Hepatocyte Cells In other embodiments, nucleic acid hybridization and/or amplification techniques are used to detect the presence, absence and/or level of expression of one or more markers associated with liver precursor cells and/or hepatocyte cells. For example, the amount of transcript produced by certain genetic markers, such as DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, CUBN, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD can be determined by nucleic acid hybridization techniques, such as, for example, Northern blots, slot blots, RNase protection, in situ hybridization, and the like. Techniques for the detection and quantitation of specific nucleic acids are well-known to those skilled in the art and are described in, for example, Ausubel et al., (1997), Current Protocols of Molecular Biology, John Wiley and Sons (1997); *Gene transcription: RNA analysis: essential techniques.* 1996. K. Docherty (ed.), Chichester; and Reue, K, *mRNA Quantitation Techniques Considerations for Experimental Design and Application*, (1998), J. Nutr., 128(11):2038-2044, each of which is herein incorporated by reference in their entirety. Several sophisticated techniques exist for the sensitive and specific detection nucleic acids.

In some embodiments, nucleic acid detection techniques such as those described herein are used in combination with nucleic acid amplification techniques. Several nucleic acid amplification techniques are also useful in detection of the presence/absence and/or level of expression markers. The skilled artisan will appreciate that any nucleic acid amplification method that can be adapted to detect expression levels of genes, such as ligase chain reaction (LCR) (See, Wu (1989) *Genomics* 4:560; Landegren (1988) *Science* 241:1077; Barringer (1990) *Gene* 89:117), nucleic acid sequence-based amplification (NASBA), self-sustained sequence replication (3SR) (See, Guatelli (1990) *Proc. Natl. Acad. Sci. USA*, 87:1874), strand displacement amplification (SDA), transcription-mediated amplification (TMA) (See, Kwoh (1989) *Proc. Natl. Acad. Sci. USA* 86:1173), cycling probe technology (CPT), solid phase amplification (SPA), nuclease dependent signal amplification (NDSA), rolling circle amplification technology (RCA), Anchored strand displacement amplification, solid-phase (immobilized) rolling circle amplification, Q Beta replicase amplification and other RNA polymerase mediated techniques (e.g., NASBA, Cangene, Mississauga, Ontario) are useful in the methods described herein. These and other techniques are also described in Berger (1987) *Methods Enzymol.* 152:307-316; Sambrook, Ausubel, Mullis (1987) U.S. Pat. Nos. 4,683,195 and 4,683,202; Arnheim (1990) *C&EN* 36-47; Lomell *J. Clin. Chem.*, 35:1826 (1989); Van Brunt, *Biotechnology*, 8:291-294 (1990); Wu (1989) *Gene* 4:560; Sooknanan (1995) *Biotechnology* 13:563-564. For example, several real-time reverse-transcription-PCR (RT-PCR) based techniques are available that enable mRNA detection and quantitation.

Detection and quantitation of nucleic acids is also known to those skilled in the art. Non-limiting examples of amplification and detection techniques include, for example, TaqMan probe technology (See, European Patent EP 0 543 942), molecular beacon probe technology (See, Tyagi et al., (1996) *Nat. Biotech.* 14:303-308.), Scorpion probe technology (See, Thewell (2000), *Nucl. Acids Res.* 28:3752), nanoparticle probe technology (See, Elghanian, et al. (1997) *Science* 277: 1078-1081.) and Amplifluor probe technology (See, U.S. Pat. Nos. 5,866,366; 6,090,592; 6,117,635; and 6,117,986), fluorescence resonance energy transfer (FRET)-based methods such as adjacent hybridization of probes (including probe-probe and probe-primer methods) (See, J. R. Lakowicz, "Principles of Fluorescence Spectroscopy," Kluwer Academic/Plenum Publishers, New York, 1999).

Accordingly, some embodiments of the present invention relate to compositions useful in nucleic acid based techniques for the detection, identification and/or quantitation of liver precursor cells and/or hepatocyte cells in a cell population. Some embodiments relate to composition that include a first oligonucleotide that hybridizes to a first marker, such as those described herein, and a second oligonucleotide that hybridizes to a second marker other than the first marker, such as those described herein. By way of example, the first and second oligonucleotides can hybridize to different markers selected from DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, and CUBN. In still other preferred embodiments, the first and second oligonucleotides can hybridize to different markers selected from the group consisting of DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD. In preferred embodiments, the oligonucleotides hybridize to the above markers under stringent conditions.

As used herein, oligonucleotides refer to polynucleotides that are generally at least about 10 nucleotides in length, at least about 12 nucleotides in length, at least about 14 nucleotides in length, at least about 16 nucleotides in length, at least about 18 nucleotides in length, at least about 20 nucleotides in length, at least about 22 nucleotides in length, at least about 24 nucleotides in length, at least about 26 nucleotides in length, at least about 28 nucleotides in length, at least about 30 nucleotides in length, at least about 35 nucleotides in length, at least about 40 nucleotides in length, at least about 45 nucleotides in length, at least about 50 nucleotides in length or greater than 50 nucleotides in length.

It will be appreciated by one skilled in the art that hybridization of the oligonucleotides to marker sequence is achieved by selecting sequences which are at least substantially complementary to the target or reference nucleic acid sequence. In some embodiments, this includes base-pairing of the oligonucleotide target nucleic acid sequence over the entire length of the oligonucleotide sequence. Such sequences can be referred to as "fully complementary" with respect to each other. Where an oligonucleotide is referred to as "substantially complementary" with respect to a nucleic acid sequence herein, the two sequences can be fully complementary, or they may form mismatches upon hybridization, but retain the ability to hybridize under the conditions used to detect the presence marker.

As set forth above, oligonucleotides of the embodiments described herein may be used in an amplification reaction. Accordingly, the compositions may include a polymerase, such as an RNA-dependent DNA polymerase. In some embodiments, the RNA-dependent DNA polymerase is a reverse transcriptase. Moloney Murine Leukemia Virus reverse transcriptase and Avian Myeloblastosis Virus (AMV) reverse transcriptase are non-limiting examples of reverse transcriptase enzymes commonly used by those skilled in the art and which are useful in the embodiments described herein. Further embodiments may also include DNA-dependent DNA polymerases, such as Taq polymerase and the like.

Advantageously, the oligonucleotides described herein can include a label, such as a radioactive label, a fluorescent label, or any other type of label that facilitates the detection and/or quantitation of nucleic acid markers, such as those described herein.

In still other embodiments, Q-PCR and immunohistochemical techniques are both used to identify and determine the amount or relative proportions of such markers.
Identification of Factors Capable of Promoting the Differentiation of hESCs and/or Definitive Endoderm Cells to Liver Precursor Cells and/or Hepatocyte Cells Certain screening methods described herein relate to methods for identifying at least one differentiation factor that is capable of promoting the differentiation of hESCs and/or definitive endoderm cells to liver precursor cells. Other screening methods described herein relate to methods for identifying at least one differentiation factor that is capable of promoting the differentiation of hESCs and/or definitive endoderm cells to hepatocyte cells. For each of these methods the starting cell culture or cell population is contacted with one or more candidate differentiation factors as set forth below.

In some embodiments of these differentiation screening methods, cell populations comprising hESCs and/or definitive endoderm cells are obtained. The cell population is then provided with a candidate differentiation factor. At a first time point, which is prior to or at approximately the same time as providing the candidate differentiation factor, expression of a marker indicative of liver precursor cells is determined. In some embodiments, the marker is selected from the group consisting of DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1 and CUBN. Alternatively, expression of the marker can be determined after providing the candidate differentiation factor. At a second time point, which is subsequent to the first time point and subsequent to the step of providing the candidate differentiation factor to the cell population, expression of the same marker is again determined. Whether the candidate differentiation factor is capable of promoting the differentiation of the hESCs and/or definitive endoderm cells to liver precursor cells is determined by comparing expression of the marker at the first time point with the expression of the marker at the second time point. If expression of the marker at the second time point is increased as compared to expression of the marker at the first time point, then the candidate differentiation factor is capable of promoting the differentiation of hESCs and/or definitive endoderm cells to liver precursor cells.

In similar embodiments, hESCs and/or definitive endoderm cells can be screened to determine whether a candidate factor can promote differentiation of the cells to hepatocyte cells. In such embodiments, cell populations comprising hESCs and/or definitive endoderm cells are obtained. The cell population is then provided with a candidate differentiation factor. At a first time point, which is prior to or at approximately the same time as providing the candidate differentiation factor, expression of a marker indicative of hepatocyte cells is determined. In some embodiments, the marker is selected from the group consisting of DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A and UBD. Alternatively, expression of the marker can be determined after providing the candidate differentiation factor. At a second time point, which is subsequent to the first time point and subsequent to the step of providing the candidate differentiation factor to the cell population, expression of the same marker is again determined. Whether the candidate differentiation factor is capable of promoting the differentiation of the hESCs and/or definitive endoderm cells to hepatocyte cells is determined by comparing expression of the marker at the first time point with the expression of the marker at the second time point. If expression of the marker at the second time point is increased as compared to expression of the marker at the first time point, then the candidate differentiation factor is capable of promoting the differentiation of hESCs and/or hepatocyte cells to liver precursor cells. In some embodiments, the capability of a candidate differentiation factor to promote the differentiation of hESCs and/or definitive endoderm cells to hepatocyte cells is also evaluated by determining the decrease in expression of a marker that is characteristic of liver precursor cells.

Some embodiments of the screening methods described herein utilize enriched cell populations or cell cultures which comprise hESCs and/or definitive endoderm cells. For example, the cell population can be a substantially purified population of hESCs or a substantially purified population of definitive endoderm cells. Alternatively, the cell population can be an enriched population of hESCs or definitive endoderm cells, wherein at least about 90%, at least about 91%, at least about 92%, at least about 93%, at least about 94%, at least about 95%, at least about 96%, at least about 97% or greater than at least about 97% of the human cells in the cell population are hESCs or definitive endoderm cells. In other embodiments described herein, the cell population comprises human cells wherein at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85% or greater than at least about 85% of the human cells are hESCs, definitive endoderm cells or mixtures thereof. In some embodiments, the cell population includes non-human cells such as non-human feeder cells. In other embodiments, the cell population includes human feeder cells. In such embodiments, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95% or greater than at least about 95% of the human cells, other than said feeder cells, are hESCs, definitive endoderm cells or mixtures thereof.

In embodiments of the screening methods described herein, the cell population is contacted or otherwise provided with a candidate (test) differentiation factor. The candidate differentiation factor can comprise any molecule that may have the potential to promote the differentiation of hESCs and/or definitive endoderm cells. In some embodiments described herein, the candidate differentiation factor comprises a molecule that is known to be a differentiation factor for one or more types of cells. In alternate embodiments, the candidate differentiation factor comprises a molecule that in not known to promote cell differentiation. In preferred embodiments, the candidate differentiation factor comprises a molecule that is not known to promote the differentiation of hESCs. In other preferred embodiments, the candidate differentiation factor comprises a molecule that is not known to promote the differentiation of human definitive endoderm cells.

In some embodiments of the screening methods described herein, the candidate differentiation factor comprises a small molecule. In preferred embodiments, a small molecule is a molecule having a molecular mass of about 10,000 amu or less. In some embodiments, the small molecule comprises a retinoid.

In other embodiments described herein, the candidate differentiation factor comprises a polypeptide. The polypeptide can be any polypeptide including, but not limited to, a glycoprotein, a lipoprotein, an extracellular matrix protein, a cytokine, a chemokine, a peptide hormone, an interleukin or a growth factor. Preferred polypeptides include growth factors. In some embodiments, the candidate differentiation factors comprises one or more growth factors selected from the group consisting of BMP4, FGF10, FGF4, FGF2, Wnt3A and Wnt3B.

In some embodiments of the screening methods described herein, the candidate differentiation factors comprise one or more growth factors selected from the group consisting of Amphiregulin, B-lymphocyte stimulator, IL-16, Thymopoietin, TRAIL/Apo-2, Pre B cell colony enhancing factor, Endothelial differentiation-related factor 1 (EDF1), Endothelial monocyte activating polypeptide II, Macrophage migration inhibitory factor (MIF), Natural killer cell enhancing factor (NKEFA), Bone mophogenetic protein 2, Bone mophogenetic protein 8 (osteogeneic protein 2), Bone morphogenic protein 6, Bone morphogenic protein 7, Connective tissue growth factor (CTGF), CGI-149 protein (neuroendocrine differentiation factor), Cytokine A3 (macrophage inflammatory protein 1-alpha), Gliablastoma cell differentiation-related protein (GBDR1), Hepatoma-derived growth factor, Neuromedin U-25 precursor, Vascular endothelial growth factor (VEGF), Vascular endothelial growth factor B (VEGF-B), T-cell specific RANTES precursor, thymic dendritic cell-derived factor 1, Transferrin, Interleukin-1 (IL 1), Interleukin-2 (IL 2), Interleukin-3 (IL 3), Interleukin-4 (IL 4), Interleukin-5 (IL 5), Interleukin-6 (IL 6), Interleukin-7 (IL 7), Interleukin-8 (IL 8), Interleukin-9 (IL 9), Interleukin-10 (IL 10), Interleukin-11 (IL 11), Interleukin-12 (IL 12), Interleukin-13 (IL 13), Granulocyte-colony stimulating factor (G-CSF), Granulocyte macrophage colony stimulating factor (GM-CSF), Macrophage colony stimulating factor (M-CSF), Erythropoietin, Thrombopoietin, Vitamin $D_3$, Epidermal growth factor (EGF), Brain-derived neurotrophic factor, Leukemia inhibitory factor, Thyroid hormone, Basic fibroblast growth factor (bFGF), aFGF, FGF-4, FGF-6, Keratinocyte growth factor (KGF), Platelet-derived growth factor (PDGF), Platelet-derived growth factor-BB, beta nerve growth factor, activin A, Transforming growth factor beta 1 (TGF-$\beta$1), Interferon-$\alpha$, Interferon-$\beta$, Interferon-$\gamma$, Tumor necrosis factor-$\alpha$, Tumor necrosis factor-$\beta$, Burst promoting activity (BPA), Erythroid promoting activity (EPA), $PGE_2$, insulin growth factor-1 (IGF-1), IGF-II, Neutrophin growth factor (NGF), Neutrophin-3, Neutrophin 4/5, Ciliary neurotrophic factor, Glial-derived nexin, Dexamethasone, $\beta$-mercaptoethanol, Retinoic acid, Butylated hydroxyanisole, 5-azacytidine, Amphotericin B, Ascorbic acid, Ascrorbate, isobutylxanthine, indomethacin, $\beta$-glycerolphosphate, nicotinamide, DMSO, Thiazolidinediones, TWS119, oxytocin, vasopressin, melanocyte-stimulating hormone, corticortropin, lipotropin, thyrotropin, growth hormone, prolactin, luteinizing hormone, human chorionic gonadotropin, follicle stimulating hormone, corticotropin-releasing factor, gonadotropin-releasing factor, prolactin-releasing factor, prolactin-inhibiting factor, growth-hormone releasing factor, somatostatin, thyrotropin-releasing factor, calcitonin gene-related peptide, parathyroid hormone, glucagon-like peptide 1, glucose-dependent insulinotropic polypeptide, gastrin, secretin, cholecystokinin, motilin, vasoactive intestinal peptide, substance P, pancreatic polypeptide, peptide tyrosine tyrosine, neuropeptide tyrosine, insulin, glucagon, placental lactogen, relaxin, angiotensin II, calctriol, atrial natriuretic peptide, and melatonin, thyroxine, triiodothyronine, calcitonin, estradiol, estrone, progesterone, testosterone, cortisol, corticosterone, aldosterone, epinephrine, norepinepherine, androstiene, calcitriol, collagen, Dexamethasone, $\beta$-mercaptoethanol, Retinoic acid, Butylated hydroxyanisole, 5-azacytidine, Amphotericin B, Ascorbic acid, Ascrorbate, isobutylxanthine, indomethacin, $\beta$-glycerolphosphate, nicotinamide, DMSO, Thiazolidinediones, and TWS119.

In some embodiments of the screening methods described herein, the candidate differentiation factor is provided to the cell population in one or more concentrations. In some embodiments, the candidate differentiation factor is provided to the cell population so that the concentration of the candidate differentiation factor in the medium surrounding the cells ranges from about 0.1 ng/ml to about 10 mg/ml. In some embodiments, the concentration of the candidate differentiation factor in the medium surrounding the cells ranges from about 1 ng/ml to about 1 mg/ml. In other embodiments, the concentration of the candidate differentiation factor in the medium surrounding the cells ranges from about 10 ng/ml to about 100 µg/ml. In still other embodiments, the concentration of the candidate differentiation factor in the medium surrounding the cells ranges from about 100 ng/ml to about 10 µg/ml. In preferred embodiments, the concentration of the candidate differentiation factor in the medium surrounding the cells is about 5 ng/ml, about 25 ng/ml, about 50 ng/ml, about 75 ng/ml, about 100 ng/ml, about 125 ng/ml, about 150 ng/ml, about 175 ng/ml, about 200 ng/ml, about 225 ng/ml, about 250 ng/ml, about 275 ng/ml, about 300 ng/ml, about 325 ng/ml, about 350 ng/ml, about 375 ng/ml, about 400 ng/ml, about 425 ng/ml, about 450 ng/ml, about 475 ng/ml, about 500 ng/ml, about 525 ng/ml, about 550 ng/ml, about 575 ng/ml, about 600 ng/ml, about 625 ng/ml, about 650 ng/ml, about 675 ng/ml, about 700 ng/ml, about 725 ng/ml, about 750 ng/ml, about 775 ng/ml, about 800 ng/ml, about 825 ng/ml, about 850 ng/ml, about 875 ng/ml, about 900 ng/ml, about 925 ng/ml, about 950 ng/ml, about 975 ng/ml, about 1 µg/ml, about 2 µg/ml, about 3 µg/ml, about 4 µg/ml, about 5 µg/ml, about 6 µg/ml, about 7 µg/ml, about 8 µg/ml, about 9 µg/ml, about 10 µg/ml, about 11 µg/ml, about 12 µg/ml, about 13 µg/ml, about 14 µg/ml, about 15 µg/ml, about 16 µg/ml, about 17 µg/ml, about 18 µg/ml, about 19 µg/ml, about 20 µg/ml, about 25 µg/ml, about 50 µg/ml, about 75 µg/ml, about 100 µg/ml, about 125 µg/ml, about 150 µg/ml, about 175 µg/ml, about 200 µg/ml, about 250 µg/ml, about 300 µg/ml, about 350 µg/ml, about 400 µg/ml, about 450 µg/ml, about 500 µg/ml, about 550 µg/ml, about 600 µg/ml, about 650 µg/ml, about 700 µg/ml, about 750 µg/ml, about 800 µg/ml, about 850 µg/ml, about 900 µg/ml, about 950 µg/ml, about 1000 µg/ml or greater than about 1000 µg/ml.

In certain embodiments of the screening methods described herein, the cell population is provided with a candidate differentiation factor which comprises any molecule other than foregut differentiation factor. For example, in some embodiments, the cell population is provided with a candidate differentiation factor which comprises any molecule other than a retinoid, a member of the TGF$\beta$ superfamily of growth factors, FGF10 or FGF4. In some embodiments, the cell population is provided with a candidate differentiation factor which comprises any molecule other than retinoic acid.

In some embodiments, steps of the screening methods described herein comprise determining expression of at least one marker at a first time point and a second time point. In some of these embodiments, the first time point can be prior to or at approximately the same time as providing the cell population with the candidate differentiation factor. Alternatively, in some embodiments, the first time point is subsequent to providing the cell population with the candidate differentiation factor. In some embodiments, expression of a plurality of markers is determined at a first time point.

In addition to determining expression of at least one marker at a first time point, some embodiments of the screening methods described herein contemplate determining expression of at least one marker at a second time point, which is subsequent to the first time point and which is subsequent to providing the cell population with the candidate differentiation factor. In such embodiments, expression of the same marker is determined at both the first and second time points. In some embodiments, expression of a plurality of markers is determined at both the first and second time points. In such embodiments, expression of the same plurality of markers is determined at both the first and second time points. In some embodiments, marker expression is determined at a plurality of time points, each of which is subsequent to the first time point, and each of which is subsequent to providing the cell population with the candidate differentiation factor. In certain embodiments, marker expression is determined by Q-PCR. In other embodiments, marker expression is determined by immunocytochemistry.

In some embodiments of the screening methods described herein, sufficient time is allowed to pass between providing the cell population with the candidate differentiation factor and determining marker expression at the second time point. Sufficient time between providing the cell population with the candidate differentiation factor and determining expression of the marker at the second time point can be as little as from about 1 hour to as much as about 10 days. In some embodiments, the expression of at least one marker is determined multiple times subsequent to providing the cell population with the candidate differentiation factor. In some embodiments, sufficient time is at least about 1 hour, at least about 6 hours, at least about 12 hours, at least about 18 hours, at least about 24 hours, at least about 30 hours, at least about 36 hours, at least about 42 hours, at least about 48 hours, at least about 54 hours, at least about 60 hours, at least about 66 hours, at least about 72 hours, at least about 78 hours, at least about 84 hours, at least about 90 hours, at least about 96 hours, at least about 102 hours, at least about 108 hours, at least about 114 hours, at least about 120 hours, at least about 126 hours, at least about 132 hours, at least about 138 hours, at least about 144 hours, at least about 150 hours, at least about 156 hours, at least about 162 hours, at least about 168 hours, at least about 174 hours, at least about 180 hours, at least about 186 hours, at least about 192 hours, at least about 198 hours, at least about 204 hours, at least about 210 hours, at least about 216 hours, at least about 222 hours, at least about 228 hours, at least about 234 hours, at least about 240 hours, at least about 246 hours, at least about 252 hours, at least about 258 hours, at least about 264 hours, or at least about 270 hours.

In some embodiments of the methods described herein, it is further determined whether the expression of the marker at the second time point has increased or decreased as compared to the expression of this marker at the first time point. Similarly, if expression of a plurality of markers is determined, it is further determined whether the expression of the plurality of markers at the second time point has increased or decreased as compared to the expression of this plurality of markers at the first time point. An increase or decrease in marker expression can be determined by measuring or otherwise evaluating the amount, level or activity of the marker in the cell population at the first and second time points. Such determination can be relative to other markers, for example housekeeping gene expression, or absolute. In certain embodiments, wherein marker expression is increased at the second time point as compared with the first time point, the amount of increase is at least about 2-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold or more than at least about 100-fold. In some embodiments, the amount of increase is less than 2-fold. In embodiments where marker expression is decreased at the second time point as compared with the first time point, the amount of decrease is at least about 2-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold or more than at least about 100-fold. In some embodiments, the amount of decrease is less than 2-fold.

Identification of Factors Capable of Promoting the Differentiation of Liver Precursor Cells, and Hepatocyte Cells Certain screening methods described herein relate to methods for identifying at least one differentiation factor that is capable of promoting the differentiation of liver precursor cells. Other screening methods described herein relate to methods for identifying at least one differentiation factor that is capable of promoting the differentiation of hepatocyte cells that are not yet terminally differentiated. As such, it will be appreciated that the methods described below for liver precursor cells can also be applied to hepatocyte cells that are not terminally differentiated.

In some embodiments of these differentiation screening methods, cell populations comprising liver precursor cells, such as human liver precursor cells, are obtained. The cell population is then provided with a candidate differentiation factor. At a first time point, which is prior to or at approximately the same time as providing the candidate differentiation factor, expression of a marker is determined. Alternatively, expression of the marker can be determined after providing the candidate differentiation factor. At a second time point, which is subsequent to the first time point and subsequent to the step of providing the candidate differentiation factor to the cell population, expression of the same marker is again determined. Whether the candidate differentiation factor is capable of promoting the differentiation of the liver precursor cells is determined by comparing expression of the marker at the first time point with the expression of the marker at the second time point. If expression of the marker at the second time point is increased or decreased as compared to expression of the marker at the first time point, then the candidate differentiation factor is capable of promoting the differentiation of liver precursor cells.

Some embodiments of the screening methods described herein utilize cell populations or cell cultures which comprise human liver precursor cells. For example, the cell population can be a substantially purified population of liver precursor cells. Alternatively, the cell population can be an enriched population of human liver precursor cells, wherein at least about 90%, at least about 91%, at least about 92%, at least about 93%, at least about 94%, at least about 95%, at least about 96%, at least about 97% or greater than at least about 97% of the human cells in the cell population are human liver precursor cells. In other embodiments described herein, the cell population comprises human cells wherein at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85% or greater than at least about 85% of the human cells are human liver precursor cells. In some embodiments, the cell population includes non-human cells such as non-human feeder cells. In other embodiments, the cell population includes human feeder cells. In such embodiments, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95% or greater than at least about 95% of the human cells, other than said feeder cells, are human liver precursor cells.

In embodiments of the screening methods described herein, the cell population is contacted or otherwise provided with a candidate (test) differentiation factor. The candidate differentiation factor can comprise any molecule that may have the potential to promote the differentiation of human liver precursor cells. In some embodiments described herein, the candidate differentiation factor comprises a molecule that is known to be a differentiation factor for one or more types of cells. In alternate embodiments, the candidate differentiation factor comprises a molecule that in not known to promote cell differentiation. In preferred embodiments, the candidate differentiation factor comprises a molecule that is not known to promote the differentiation of human liver precursor cells. In other preferred embodiments, the candidate differentiation factor comprises a molecule that is not known to promote the differentiation of human hepatocytes.

In some embodiments of the screening methods described herein, the candidate differentiation factor comprises a small molecule. In preferred embodiments, a small molecule is a molecule having a molecular mass of about 10,000 amu or less. In some embodiments, the small molecule comprises a retinoid.

In other embodiments described herein, the candidate differentiation factor comprises a polypeptide. The polypeptide can be any polypeptide including, but not limited to, a glycoprotein, a lipoprotein, an extracellular matrix protein, a cytokine, a chemokine, a peptide hormone, an interleukin or a growth factor. Preferred polypeptides include growth factors. In some embodiments, the candidate differentiation factors comprises one or more growth factors selected from the group consisting of FGF10, FGF4, FGF2, Wnt3A and Wnt3B.

In some embodiments of the screening methods described herein, the candidate differentiation factors comprise one or more growth factors selected from the group consisting of Amphiregulin, B-lymphocyte stimulator, IL-16, Thymopoietin, TRAIL/Apo-2, Pre B cell colony enhancing factor, Endothelial differentiation-related factor 1 (EDF1), Endothelial monocyte activating polypeptide II, Macrophage migration inhibitory factor (MIF), Natural killer cell enhancing factor (NKEFA), Bone mophogenetic protein 2, Bone mophogenetic protein 8 (osteogeneic protein 2), Bone morphogenic protein 6, Bone morphogenic protein 7, Connective tissue growth factor (CTGF), CGI-149 protein (neuroendocrine differentiation factor), Cytokine A3 (macrophage inflammatory protein 1-alpha), Gliablastoma cell differentiation-related protein (GBDR1), Hepatoma-derived growth factor, Neuromedin U-25 precursor, Vascular endothelial growth factor (VEGF), Vascular endothelial growth factor B (VEGF-B), T-cell specific RANTES precursor, thymic dendritic cell-derived factor 1, Transferrin, Interleukin-1 (IL 1), Interleukin-2 (IL 2), Interleukin-3 (IL 3), Interleukin-4 (IL 4), Interleukin-5 (IL 5), Interleukin-6 (IL 6), Interleukin-7 (IL 7), Interleukin-8 (IL 8), Interleukin-9 (IL 9), Interleukin-10 (IL 10), Interleukin-11 (IL 11), Interleukin-12 (IL 12), Interleukin-13 (IL 13), Granulocyte-colony stimulating factor (G-CSF), Granulocyte macrophage colony stimulating factor (GM-CSF), Macrophage colony stimulating factor (M-CSF), Erythropoietin, Thrombopoietin, Vitamin $D_3$, Epidermal growth factor (EGF), Brain-derived neurotrophic factor, Leukemia inhibitory factor, Thyroid hormone, Basic fibroblast growth factor (bFGF), aFGF, FGF-4, FGF-6, Keratinocyte growth factor (KGF), Platelet-derived growth factor (PDGF), Platelet-derived growth factor-BB, beta nerve growth factor, activin A, Transforming growth factor beta 1 (TGF-β1), Interferon-α, Interferon-β, Interferon-γ, Tumor necrosis factor-α, Tumor necrosis factor-β, Burst promoting activity (BPA), Erythroid promoting activity (EPA), $PGE_2$, insulin growth factor-1 (IGF-1), IGF-II, Neutrophin growth factor (NGF), Neutrophin-3, Neutrophin 4/5, Ciliary neurotrophic factor, Glial-derived nexin, Dexamethasone, β-mercaptoethanol, Retinoic acid, Butylated hydroxyanisole, 5-azacytidine, Amphotericin B, Ascorbic acid, Ascrorbate, isobutylxanthine, indomethacin, β-glycerolphosphate, nicotinamide, DMSO, Thiazolidinediones, TWS119, oxytocin, vasopressin, melanocyte-stimulating hormone, corticortropin, lipotropin, thyrotropin, growth hormone, prolactin, luteinizing hormone, human chorionic gonadotropin, follicle stimulating hormone, corticotropin-releasing factor, gonadotropin-releasing factor, prolactin-releasing factor, prolactin-inhibiting factor, growth-hormone releasing factor, somatostatin, thyrotropin-releasing factor, calcitonin gene-related peptide, parathyroid hormone, glucagon-like peptide 1, glucose-dependent insulinotropic polypeptide, gastrin, secretin, cholecystokinin, motilin, vasoactive intestinal peptide, substance P, pancreatic polypeptide, peptide tyrosine tyrosine, neuropeptide tyrosine, insulin, glucagon, placental lactogen, relaxin, angiotensin II, calctriol, atrial natriuretic peptide, and melatonin, thyroxine, triiodothyronine, calcitonin, estradiol, estrone, progesterone, testosterone, cortisol, corticosterone, aldosterone, epinephrine, norepinepherine, androstiene, calcitriol, collagen, Dexamethasone, β-mercaptoethanol, Retinoic acid, Butylated hydroxyanisole, 5-azacytidine, Amphotericin B, Ascorbic acid, Ascrorbate, isobutylxanthine, indomethacin, β-glycerolphosphate, nicotinamide, DMSO, Thiazolidinediones, and TWS119.

In some embodiments of the screening methods described herein, the candidate differentiation factor is provided to the cell population in one or more concentrations. In some embodiments, the candidate differentiation factor is provided to the cell population so that the concentration of the candidate differentiation factor in the medium surrounding the cells ranges from about 0.1 ng/ml to about 10 mg/ml. In some embodiments, the concentration of the candidate differentiation factor in the medium surrounding the cells ranges from about 1 ng/ml to about 1 mg/ml. In other embodiments, the concentration of the candidate differentiation factor in the medium surrounding the cells ranges from about 10 ng/ml to about 100 µg/ml. In still other embodiments, the concentration of the candidate differentiation factor in the medium surrounding the cells ranges from about 100 ng/ml to about 10 µg/ml. In preferred embodiments, the concentration of the candidate differentiation factor in the medium surrounding the cells is about 5 ng/ml, about 25 ng/ml, about 50 ng/ml, about 75 ng/ml, about 100 ng/ml, about 125 ng/ml, about 150 ng/ml, about 175 ng/ml, about 200 ng/ml, about 225 ng/ml, about 250 ng/ml, about 275 ng/ml, about 300 ng/ml, about 325 ng/ml, about 350 ng/ml, about 375 ng/ml, about 400 ng/ml, about 425 ng/ml, about 450 ng/ml, about 475 ng/ml, about 500 ng/ml, about 525 ng/ml, about 550 ng/ml, about 575 ng/ml, about 600 ng/ml, about 625 ng/ml, about 650 ng/ml, about 675 ng/ml, about 700 ng/ml, about 725 ng/ml, about 750 ng/ml, about 775 ng/ml, about 800 ng/ml, about 825 ng/ml, about 850 ng/ml, about 875 ng/ml, about 900 ng/ml, about 925 ng/ml, about 950 ng/ml, about 975 ng/ml, about 1 µg/ml, about 2 µg/ml, about 3 µg/ml, about 4 µg/ml, about 5 µg/ml, about 6 µg/ml, about 7 µg/ml, about 8 µg/ml, about 9 µg/ml, about 10 µg/ml, about 11 µg/ml, about 12 µg/ml, about 13 µg/ml, about 14 µg/ml, about 15 µg/ml, about 16 µg/ml, about 17 µg/ml, about 18 µg/ml, about 19 µg/ml, about 20 µg/ml, about 25 µg/ml, about 50 µg/ml, about 75 µg/ml, about 100 µg/ml, about 125 µg/ml, about 150 µg/ml, about 175 µg/ml, about 200 µg/ml, about 250 µg/ml, about 300 µg/ml, about 350 µg/ml, about 400 µg/ml, about 450 µg/ml, about 500 µg/ml, about 550 µg/ml, about 600 µg/ml, about 650 µg/ml, about 700 µg/ml, about 750 µg/ml, about 800 µg/ml, about 850 µg/ml, about 900 µg/ml, about 950 µg/ml, about 1000 µg/ml or greater than about 1000 µg/ml.

In certain embodiments of the screening methods described herein, the cell population is provided with a candidate differentiation factor which comprises any molecule other than foregut differentiation factor. For example, in some embodiments, the cell population is provided with a candidate differentiation factor which comprises any molecule other than a retinoid, a member of the TGFβ superfamily of growth factors, FGF10 or FGF4. In some embodiments, the cell population is provided with a candidate differentiation factor which comprises any molecule other than retinoic acid.

In some embodiments, steps of the screening methods described herein comprise determining expression of at least one marker at a first time point and a second time point. In some of these embodiments, the first time point can be prior to or at approximately the same time as providing the cell population with the candidate differentiation factor. Alternatively, in some embodiments, the first time point is subsequent to providing the cell population with the candidate differentiation factor. In some embodiments, expression of a plurality of markers is determined at a first time point.

Some preferred markers for use in the above embodiments include one or more markers selected from the group consisting of DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1, CUBN, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, and UBD.

In addition to determining expression of at least one marker at a first time point, some embodiments of the screening methods described herein contemplate determining expression of at least one marker at a second time point, which is subsequent to the first time point and which is subsequent to providing the cell population with the candidate differentiation factor. In such embodiments, expression of the same marker is determined at both the first and second time points. In some embodiments, expression of a plurality of markers is determined at both the first and second time points. In such embodiments, expression of the same plurality of markers is determined at both the first and second time points. In some embodiments, marker expression is determined at a plurality of time points, each of which is subsequent to the first time point, and each of which is subsequent to providing the cell population with the candidate differentiation factor. In certain embodiments, marker expression is determined by Q-PCR. In other embodiments, marker expression is determined by immunocytochemistry.

In certain embodiments of the screening methods described herein, the marker having its expression is determined at the first and second time points is a marker that is associated with the differentiation of liver precursor cells to cells which are the precursors of terminally differentiated cells which make up liver tissues. In some embodiments, the marker is indicative of liver precursor cells. In preferred embodiments the marker is DPP4, APOA1, APOA2, HNF4A, PROX1, ALBUMIN, AFP, NOSTRIN, DGKB, DOK4, HPX, LOC440450, SLC35D1, PCDH17, LOC286167, C3orf15, GLUD1, GLUD2, GSN, FN1, LOC286167, EVI1, SP8, ALDH2, HLA-B, HLA-C, Hs.570199, PLA2G12B, SYTL5, FKBP7, CYP4X1, LOC130576, MUSTN1, EPHA6, PP1057, PFTK1 or CUBN. In certain preferred embodiments, the marker is albumin, hepatocyte specific antigen (HSA) or prospero-related homeobox 1 (PROX1). In other embodiments, the marker is indicative of mature hepatocyte cells. In preferred embodiments, the marker is DPP4, ASGR1, CYP3A7, Transferrin, HBGZ SLC17A8, PCDHGB7, SLC10A1, TF, CYP3A5, SL2A2, CYP3A4, ADH6, CYP2C9, SLC38A4, SMP3, SERPINA7, KNG1, HAL, ORM1, ORM2, NR1H4, SLC5A12, TM4SF4, MUSK, TM4SF1, OLR1, MEP1A, or UBD.

In some embodiments of the screening methods described herein, sufficient time is allowed to pass between providing the cell population with the candidate differentiation factor and determining marker expression at the second time point. Sufficient time between providing the cell population with the candidate differentiation factor and determining expression of the marker at the second time point can be as little as from about 1 hour to as much as about 10 days. In some embodiments, the expression of at least one marker is determined multiple times subsequent to providing the cell population with the candidate differentiation factor. In some embodiments, sufficient time is at least about 1 hour, at least about 6 hours, at least about 12 hours, at least about 18 hours, at least about 24 hours, at least about 30 hours, at least about 36 hours, at least about 42 hours, at least about 48 hours, at least about 54 hours, at least about 60 hours, at least about 66 hours, at least about 72 hours, at least about 78 hours, at least about 84 hours, at least about 90 hours, at least about 96 hours, at least about 102 hours, at least about 108 hours, at least about 114 hours, at least about 120 hours, at least about 126 hours, at least about 132 hours, at least about 138 hours, at least about 144 hours, at least about 150 hours, at least about 156 hours, at least about 162 hours, at least about 168 hours, at least about 174 hours, at least about 180 hours, at least about 186 hours, at least about 192 hours, at least about 198 hours, at least about 204 hours, at least about 210 hours, at least about 216 hours, at least about 222 hours, at least about 228 hours, at least about 234 hours, at least about 240 hours, at least about 246 hours, at least about 252 hours, at least about 258 hours, at least about 264 hours, or at least about 270 hours.

In some embodiments of the methods described herein, it is further determined whether the expression of the marker at the second time point has increased or decreased as compared to the expression of this marker at the first time point. An increase or decrease in the expression of the at least one marker indicates that the candidate differentiation factor is capable of promoting the differentiation of the liver precursor cells. Similarly, if expression of a plurality of markers is determined, it is further determined whether the expression of the plurality of markers at the second time point has increased or decreased as compared to the expression of this plurality of markers at the first time point. An increase or decrease in marker expression can be determined by measuring or otherwise evaluating the amount, level or activity of the marker in the cell population at the first and second time points. Such determination can be relative to other markers, for example housekeeping gene expression, or absolute. In certain embodiments, wherein marker expression is increased at the second time point as compared with the first time point, the amount of increase is at least about 2-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold or more than at least about 100-fold. In some embodiments, the amount of increase is less than 2-fold. In embodiments where marker expression is decreased at the second time point as compared with the first time point, the amount of decrease is at least about 2-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold or more than at least about 100-fold. In some embodiments, the amount of decrease is less than 2-fold.

Having generally described this invention, a further understanding can be obtained by reference to certain specific examples which are provided herein for purposes of illustration only, and are not intended to be limiting.

EXAMPLES

Many of the examples below describe the use of pluripotent human cells. Methods of producing pluripotent human cells are well known in the art and have been described in numerous scientific publications, including U.S. Pat. Nos. 5,453,357, 5,670,372, 5,690,622, 5,690.926, 6,200,806, and 6,251,671, as well as U.S. Patent Application Publication No. 2004/0229350, the disclosures of which are hereby expressly incorporated by reference in their entireties.

Example 1

Human ES Cells

For our studies of endoderm development we employed human embryonic stem cells, which are pluripotent and can divide seemingly indefinitely in culture while maintaining a normal karyotype. ES cells were derived from the 5-day-old embryo inner cell mass using either immunological or mechanical methods for isolation. In particular, the human embryonic stem cell line hESCyt-25 was derived from a supernumerary frozen embryo from an in vitro fertilization cycle following informed consent by the patient. Upon thawing the hatched blastocyst was plated on mouse embryonic fibroblasts (MEF), in ES medium (DMEM, 20% FBS, non essential amino acids, beta-mercaptoethanol, FGF-2). The embryo adhered to the culture dish and after approximately two weeks, regions of undifferentiated hESCs were transferred to new dishes with MEFs. Transfer was accomplished with mechanical cutting and a brief digestion with dispase, followed by mechanical removal of the cell clusters, washing and re-plating. Since derivation, hESCyt-25 has been serially passaged over 100 times. We employed the hESCyt-25 human embryonic stem cell line as our starting material for the production of definitive endoderm.

It will be appreciated by those of skill in the art that stem cells or other pluripotent cells can also be used as starting material for the differentiation procedures described herein. For example, cells obtained from embryonic gonadal ridges, which can be isolated by methods known in the art, can be used as pluripotent cellular starting material.

Example 2 hESCyt-25 Characterization

The human embryonic stem cell line, hESCyt-25 has maintained a normal morphology, karyotype, growth and self-renewal properties over 18 months in culture. This cell line displays strong immunoreactivity for the OCT4, SSEA-4 and TRA-1-60 antigens, all of which, are characteristic of undifferentiated hESCs and displays alkaline phosphatase activity as well as a morphology identical to other established hESC lines. Furthermore, the human stem cell line, hESCyt-25, also readily forms embryoid bodies (EBs) when cultured in suspension. As a demonstration of its pluripotent nature, hESCyT-25 differentiates into various cell types that represent the three principal germ layers. Ectoderm production was demonstrated by Q-PCR for ZIC1 as well as immunocytochemistry (ICC) for nestin and more mature neuronal markers. Immunocytochemical staining for β-III tubulin was observed in clusters of elongated cells, characteristic of early neurons. Previously, we treated EBs in suspension with retinoic acid, to induce differentiation of pluripotent stem cells to visceral endoderm (VE), an extra-embryonic lineage. Treated cells expressed high levels of α-fetoprotein (AFP) and SOX7, two markers of VE, by 54 hours of treatment. Cells differentiated in monolayer expressed AFP in sporadic patches as demonstrated by immunocytochemical staining. As will be described below, the hESCyT-25 cell line was also capable of forming definitive endoderm, as validated by real-time quantitative polymerase chain reaction (Q-PCR) and immunocytochemistry for SOX17, in the absence of AFP expression. To demonstrate differentiation to mesoderm, differentiating EBs were analyzed for Brachyury gene expression at several time points. Brachyury expression increased progressively over the course of the experiment. In view of the foregoing, the hESCyT-25 line is pluripotent as shown by the ability to form cells representing the three germ layers.

Example 3

Production of SOX17 Antibody

A primary obstacle to the identification of definitive endoderm in hESC cultures is the lack of appropriate tools. We therefore undertook the production of an antibody raised against human SOX17 protein.

The marker SOX17 is expressed throughout the definitive endoderm as it forms during gastrulation and its expression is maintained in the gut tube (although levels of expression vary along the A-P axis) until around the onset of organogenesis. SOX17 is also expressed in a subset of extra-embryonic endoderm cells. No expression of this protein has been observed in mesoderm or ectoderm. It has now been discovered that SOX17 is an appropriate marker for the definitive endoderm lineage when used in conjunction with markers to exclude extra-embryonic lineages.

As described in detail herein, the SOX17 antibody was utilized to specifically examine effects of various treatments and differentiation procedures aimed at the production of SOX17 positive definitive endoderm cells. Other antibodies reactive to AFP, SPARC and Thrombomodulin were also employed to rule out the production of visceral and parietal endoderm (extra-embryonic endoderm).

Figure 2:
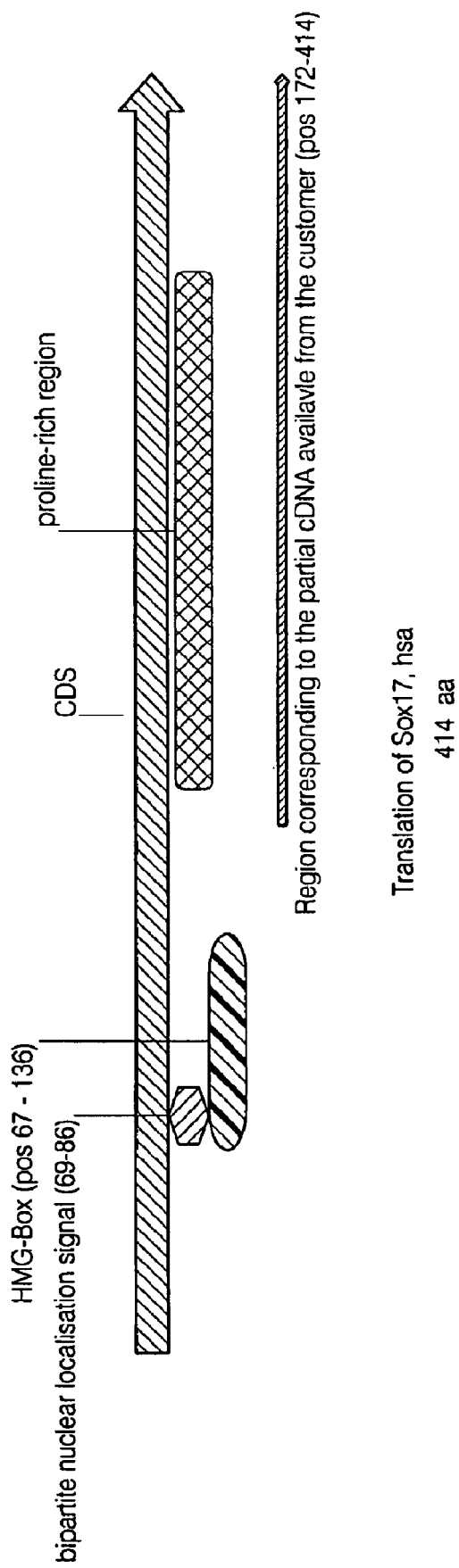
FIG. 2 is a diagram of the human SOX17 cDNA which displays the positions of conserved motifs and highlights the region used for the immunization procedure by GENOVAC.

In order to produce an antibody against SOX17, a portion of the human SOX17 cDNA (SEQ ID NO: 1) corresponding to amino acids 172-414 (SEQ ID NO: 2) in the carboxyterminal end of the SOX17 protein (FIG. 2) was used for genetic immunization in rats at the antibody production company, GENOVAC (Freiburg, Germany), according to procedures developed there. Procedures for genetic immunization can be found in U.S. Pat. Nos. 5,830,876, 5,817,637, 6,165,993 and 6,261,281 as well as International Patent Application Publication Nos. WO00/29442 and WO99/13915, the disclosures of which are incorporated herein by reference in their entireties.

Other suitable methods for genetic immunization are also described in the non-patent literature. For example, Barry et al. describe the production of monoclonal antibodies by genetic immunization in *Biotechniques* 16: 616-620, 1994, the disclosure of which is incorporated herein by reference in its entirety. Specific examples of genetic immunization methods to produce antibodies against specific proteins can be found, for example, in Costaglia et al., (1998) Genetic immunization against the human thyrotropin receptor causes thyroiditis and allows production of monoclonal antibodies recognizing the native receptor, *J. Immunol.* 160: 1458-1465; Kilpatrick et al (1998) Gene gun delivered DNA-based immunizations mediate rapid production of murine monoclonal antibodies to the Flt-3 receptor, *Hybridoma* 17: 569-576; Schmolke et al., (1998) Identification of hepatitis G virus particles in human serum by E2-specific monoclonal antibodies generated by DNA immunization, *J. Virol.* 72: 4541-4545; Krasemann et al., (1999) Generation of monoclonal antibodies against proteins with an unconventional nucleic acid-based immunization strategy, *J. Biotechnol.* 73: 119-129; and Ulivieri et al., (1996) Generation of a monoclonal antibody to a defined portion of the *Heliobacter pylori* vacuolating cytotoxin by DNA immunization, *J. Biotechnol.* 51: 191-194, the disclosures of which are incorporated herein by reference in their entireties.

Figure 3:
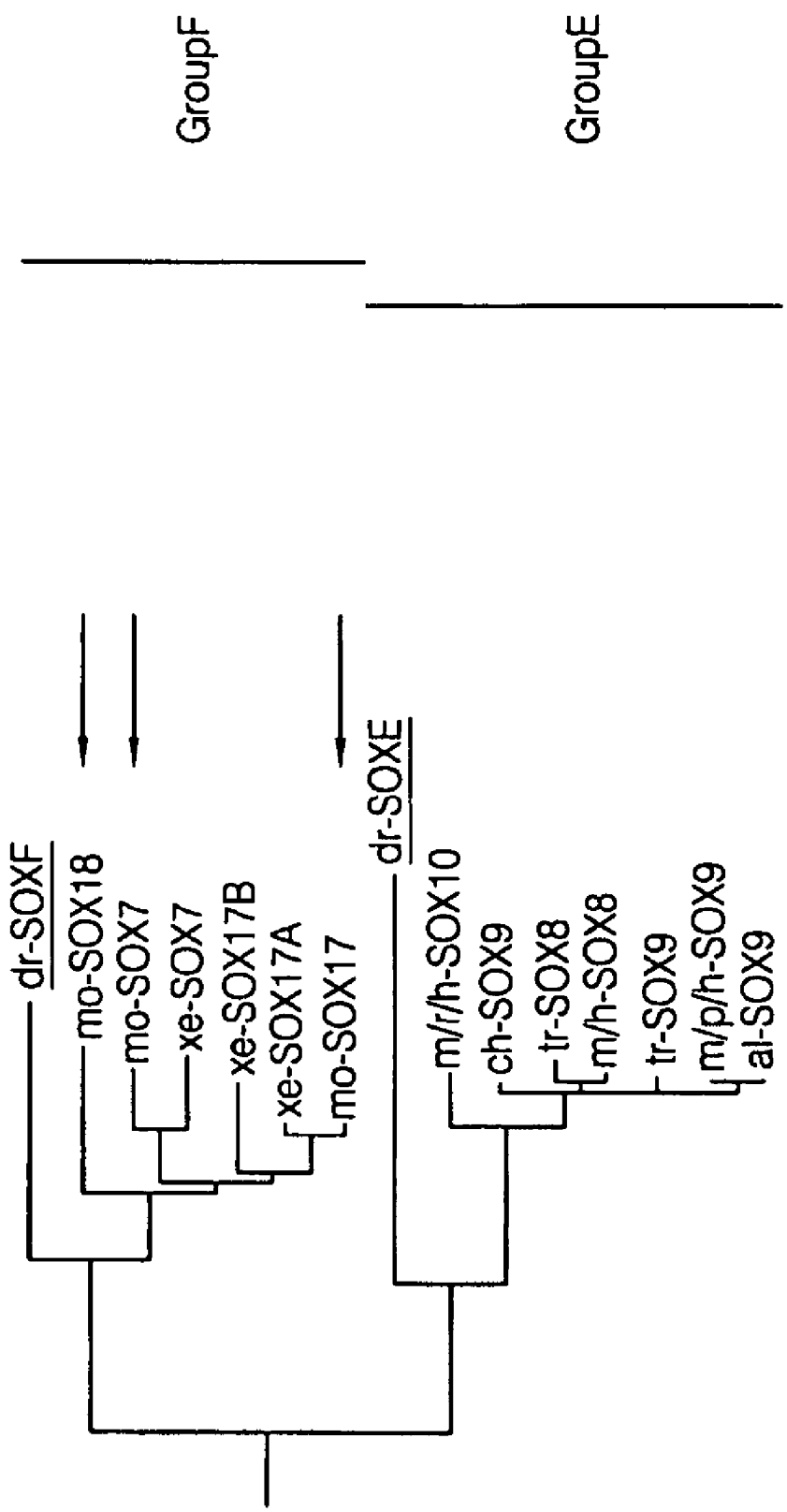
FIG. 3 is a relational dendrogram illustrating that SOX17 is most closely related to SOX7 and somewhat less to SOX18. The SOX17 proteins are more closely related among species homologs than to other members of the SOX group F subfamily within the same species.

SOX7 and SOX18 are the closest Sox family relatives to SOX17 as depicted in the relational dendrogram shown in FIG. 3. We employed the human SOX7 polypeptide as a negative control to demonstrate that the SOX17 antibody produced by genetic immunization is specific for SOX17 and does not react with its closest family member. In particular, SOX7 and other proteins were expressed in human fibroblasts, and then, analyzed for cross reactivity with the SOX17 antibody by Western blot and ICC. For example, the following methods were utilized for the production of the SOX17, SOX7 and EGFP expression vectors, their transfection into human fibroblasts and analysis by Western blot. Expression vectors employed for the production of SOX17, SOX7, and EGFP were pCMV6 (OriGene Technologies, Inc., Rockville, Md.), pCMV-SPORT6 (Invitrogen, Carlsbad, Calif.) and pEGFP-N1 (Clonetech, Palo Alto, Calif.), respectively. For protein production, telomerase immortalized MDX human fibroblasts were transiently transfected with supercoiled DNA in the presence of Lipofectamine 2000 (Invitrogen, Carlsbad, Calif.). Total cellular lysates were collected 36 hours post-transfection in 50 mM TRIS-HCl (pH 8), 150 mM NaCl, 0.1% SDS, 0.5% deoxycholate, containing a cocktail of protease inhibitors (Roche Diagnostics Corporation, Indianapolis, Ind.). Western blot analysis of 100 µg of cellular proteins, separated by SDS-PAGE on NuPAGE (4-12% gradient polyacrylamide, Invitrogen, Carlsbad, Calif.), and transferred by electro-blotting onto PDVF membranes (Hercules, Calif.), were probed with a 1/1000 dilution of the rat SOX17 anti-serum in 10 mM TRIS-HCl (pH 8), 150 mM NaCl, 10% BSA, 0.05% Tween-20 (Sigma, St. Louis, Mo.), followed by Alkaline Phosphatase conjugated anti-rat IgG (Jackson ImmunoResearch Laboratories, West Grove, Pa.), and revealed through Vector Black Alkaline Phosphatase staining (Vector Laboratories, Burlingame, Calif.). The proteins size standard used was wide range color markers (Sigma, St. Louis, Mo.).

Figure 4:
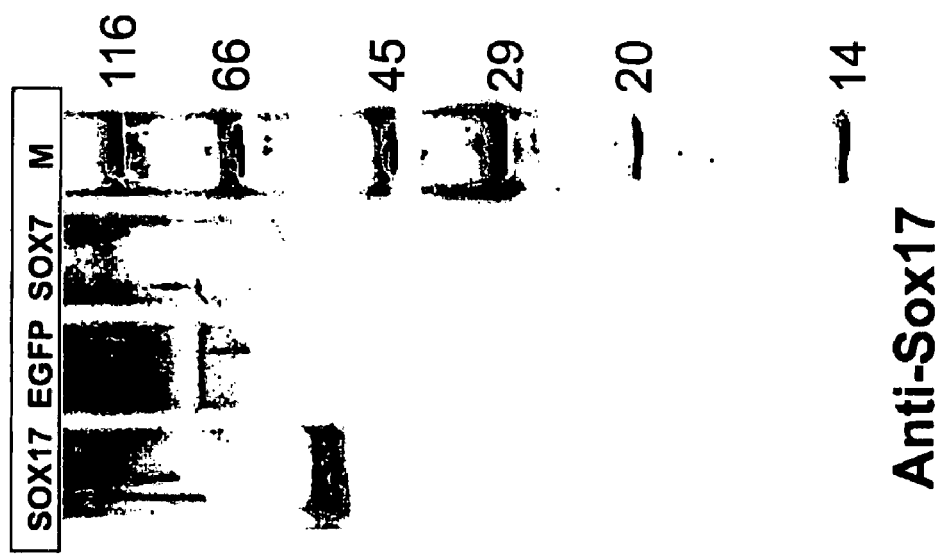
FIG. 4 is a Western blot probed with the rat anti-SOX17 antibody. This blot demonstrates the specificity of this antibody for human SOX17 protein over-expressed in fibroblasts (lane 1) and a lack of immunoreactivity with EGFP (lane 2) or the most closely related SOX family member, SOX7 (lane 3).

In FIG. 4, protein extracts made from human fibroblast cells that were transiently transfected with SOX17, SOX7 or EGFP cDNA's were probed on Western blots with the SOX17 antibody. Only the protein extract from hSOX17 transfected cells produced a band of ~51Kda which closely matched the predicted 46Kda molecular weight of the human SOX17 protein. There was no reactivity of the SOX17 antibody to extracts made from either human SOX7 or EGFP transfected cells. Furthermore, the SOX17 antibody clearly labeled the nuclei of human fibroblast cells transfected with the hSOX17 expression construct but did not label cells transfected with EGFP alone. As such, the SOX17 antibody exhibits specificity by ICC.

Example 4

Validation of SOX17 Antibody as a Marker of Definitive Endoderm

Figure 5:
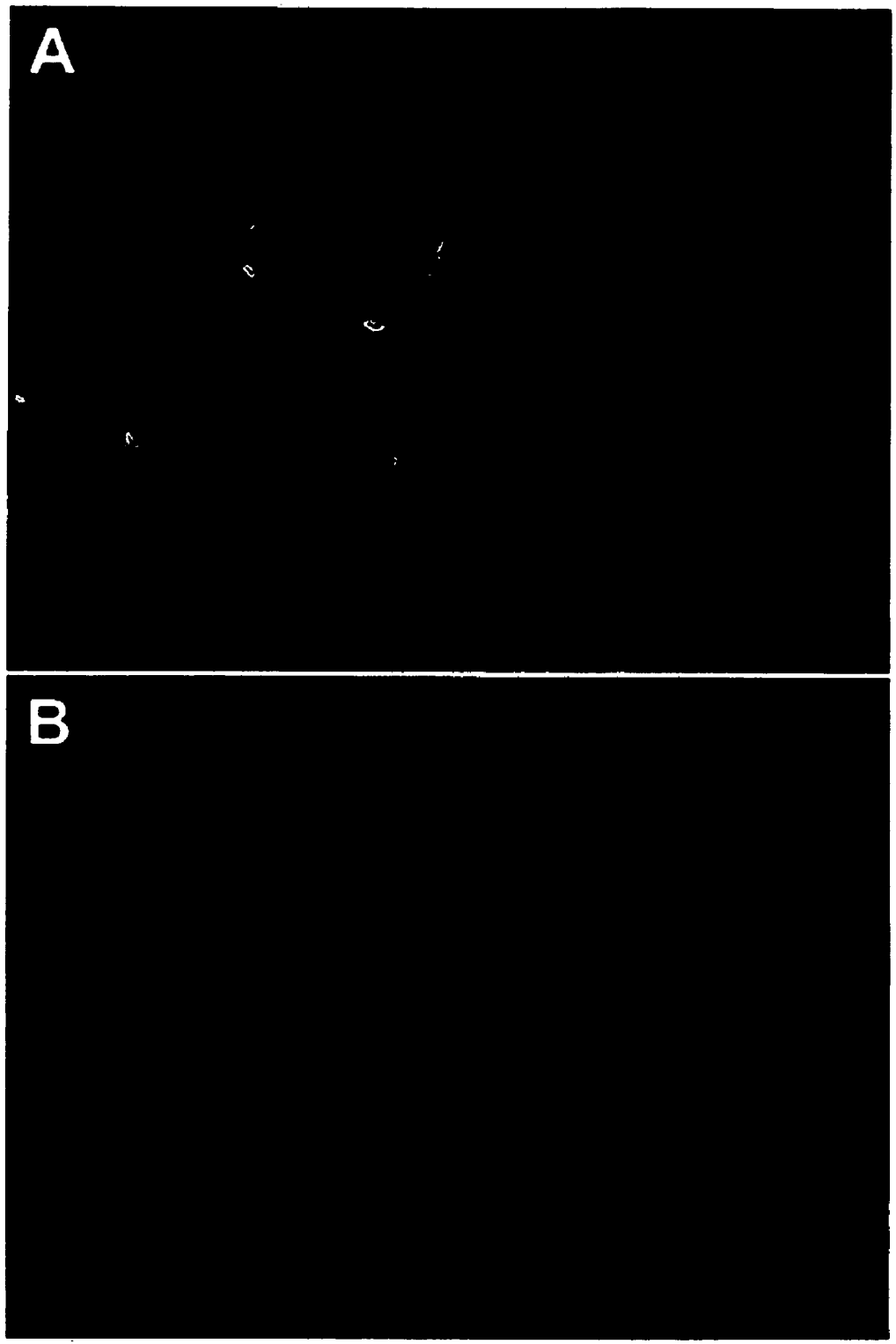
FIGS. 5A-B are micrographs showing a cluster of SOX17$^+$ cells that display a significant number of AFP$^+$ co-labeled cells (A). This is in striking contrast to other SOX17$^+$ clusters (B) where little or no AFP$^+$ cells are observed.
Figure 6:
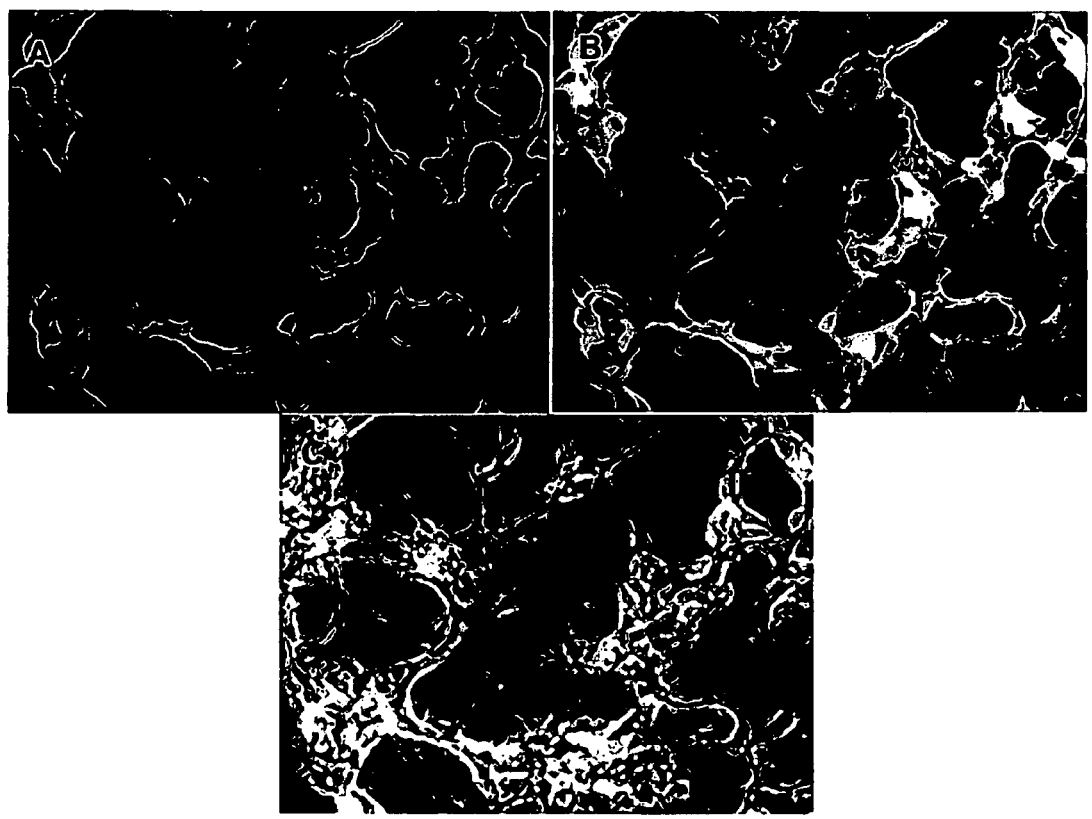
FIGS. 6A-C are micrographs showing parietal endoderm and SOX17. Panel A shows immunocytochemistry for human Thrombomodulin (TM) protein located on the cell surface of parietal endoderm cells in randomly differentiated cultures of hES cells. Panel B is the identical field shown in A double-labeled for TM and SOX17. Panel C is the phase contrast image of the same field with DAPI labeled nuclei. Note the complete correlation of DAPI labeled nuclei and SOX17 labeling.

Partially differentiated hESCs were co-labeled with SOX17 and AFP antibodies to demonstrate that the SOX17 antibody is specific for human SOX17 protein and furthermore marks definitive endoderm. It has been demonstrated that SOX17, SOX7 (which is a closely related member of the SOX gene family subgroup F (FIG. 3)) and AFP are each expressed in visceral endoderm. However, AFP and SOX7 are not expressed in definitive endoderm cells at levels detectable by ICC, and thus, they can be employed as negative markers for bonifide definitive endoderm cells. It was shown that SOX17 antibody labels populations of cells that exist as discrete groupings of cells or are intermingled with AFP positive cells. In particular, FIG. 5A shows that small numbers of SOX17 cells were co-labeled with AFP; however, regions were also found where there were little or no AFP$^+$ cells in the field of SOX17$^+$ cells (FIG. 5B). Similarly, since parietal endoderm has been reported to express SOX17, antibody co-labeling with SOX17 together with the parietal markers SPARC and/or Thrombomodulin (TM) can be used to identify the SOX17$^+$ cells that are parietal endoderm. As shown in FIGS. 6A-C, Thrombomodulin and SOX17 co-labeled parietal endoderm cells were produced by random differentiation of hES cells.

In view of the above cell labeling experiments, the identity of a definitive endoderm cell can be established by the marker profile SOX17$^{hi}$/AFP$^{lo}$/[TM$^{lo}$ or SPARC$^{lo}$]. In other words, the expression of the SOX17 marker is greater than the expression of the AFP marker, which is characteristic of visceral endoderm, and the TM or SPARC markers, which are characteristic of parietal endoderm. Accordingly, those cells positive for SOX17 but negative for AFP and negative for TM or SPARC are definitive endoderm.

Figure 7B:
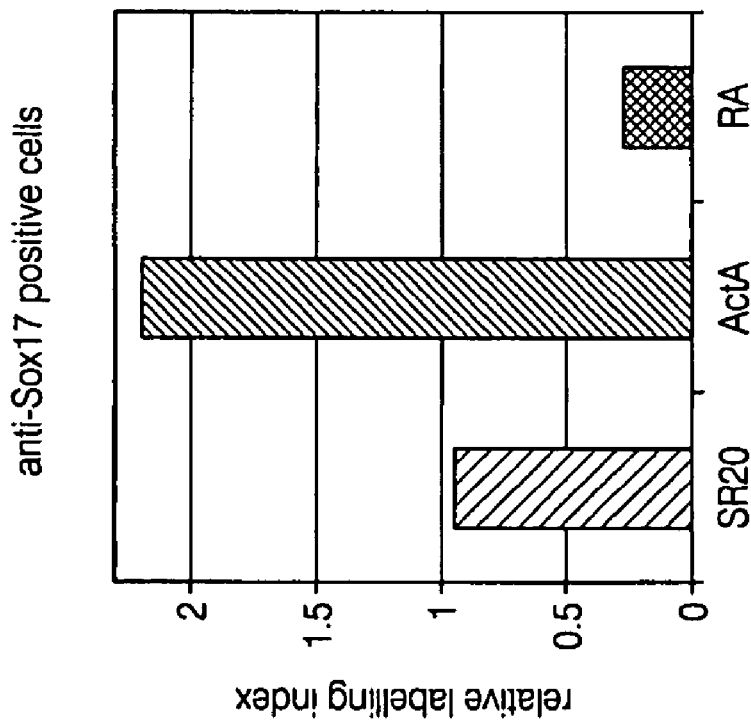
FIGS. 7A-B are bar charts showing SOX17 gene expression by quantitative PCR (Q-PCR) and anti-SOX17 positive cells by SOX17-specific antibody. Panel A shows that activin A increases SOX17 gene expression while retinoic acid (RA) strongly suppresses SOX17 expression relative to the undifferentiated control media (SR20). Panel B shows the identical pattern as well as a similar magnitude of these changes is reflected in SOX17$^+$ cell number, indicating that Q-PCR measurement of SOX17 gene expression is very reflective of changes at the single cell level.
Figure 7A:
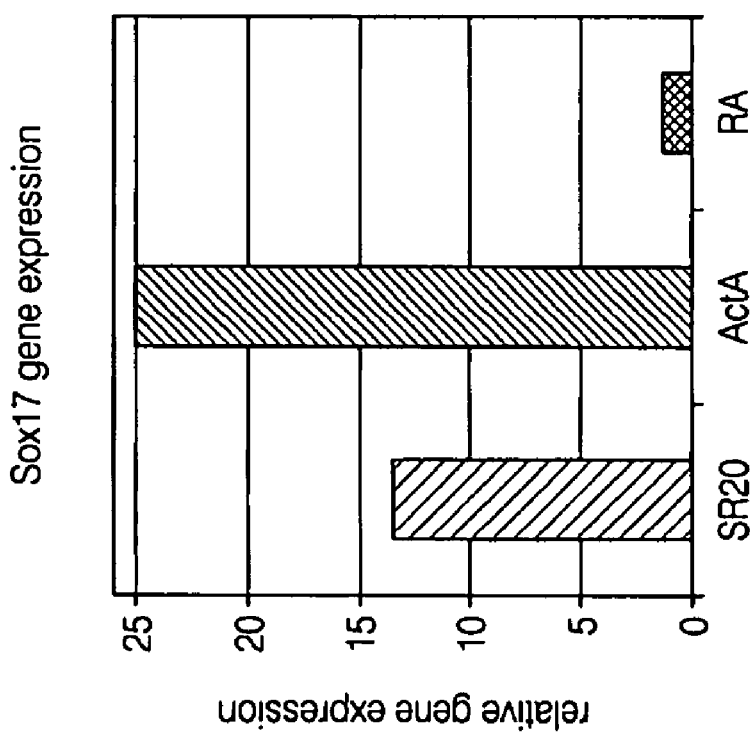
Figure 8A:
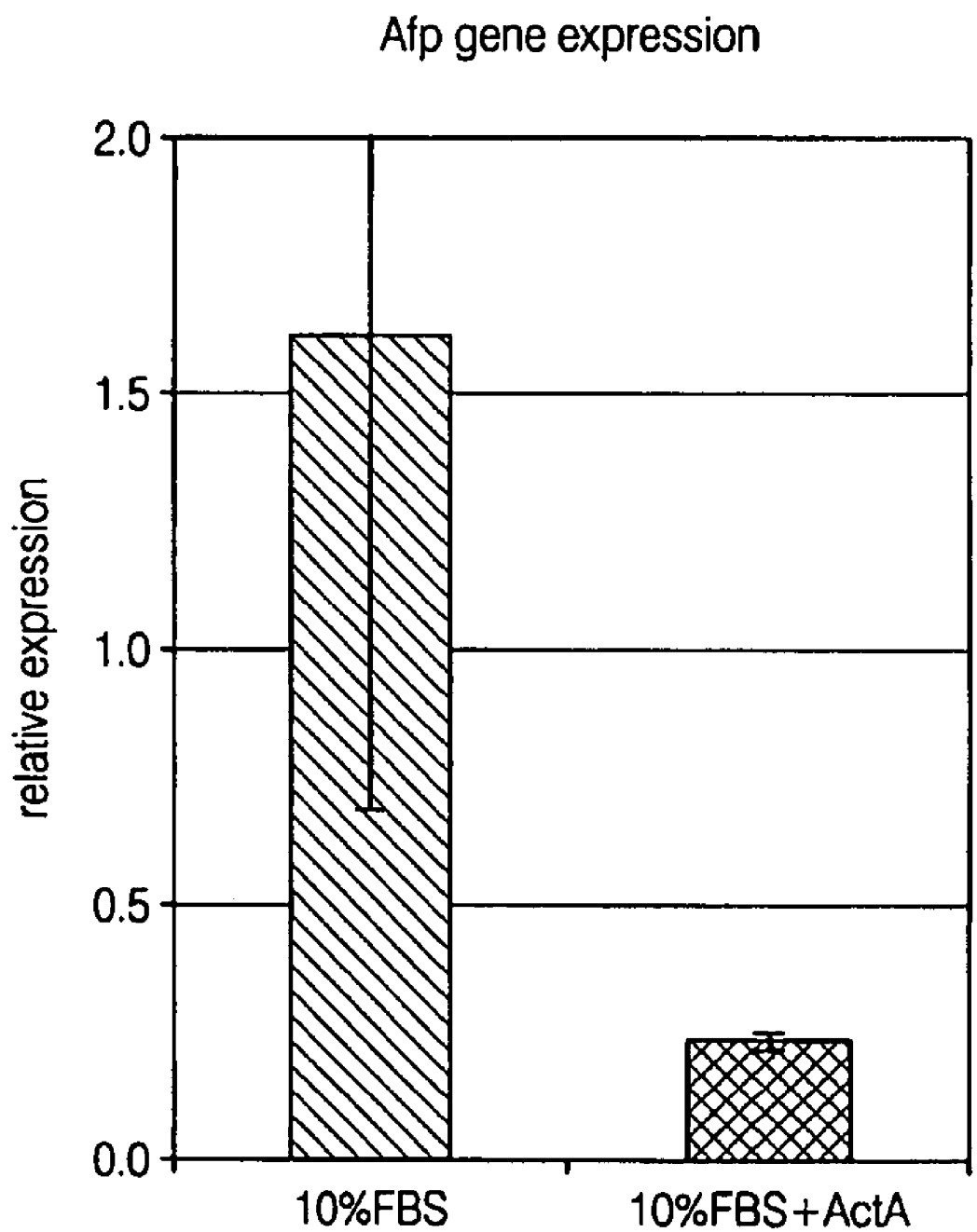
FIG. 8A is a bar chart which shows that a culture of differentiating hESCs in the presence of activin A maintains a low level of AFP gene expression while cells allowed to randomly differentiate in 10% fetal bovine serum (FBS) exhibit a strong upregulation of AFP. The difference in expression levels is approximately 7-fold.
Figure 8:
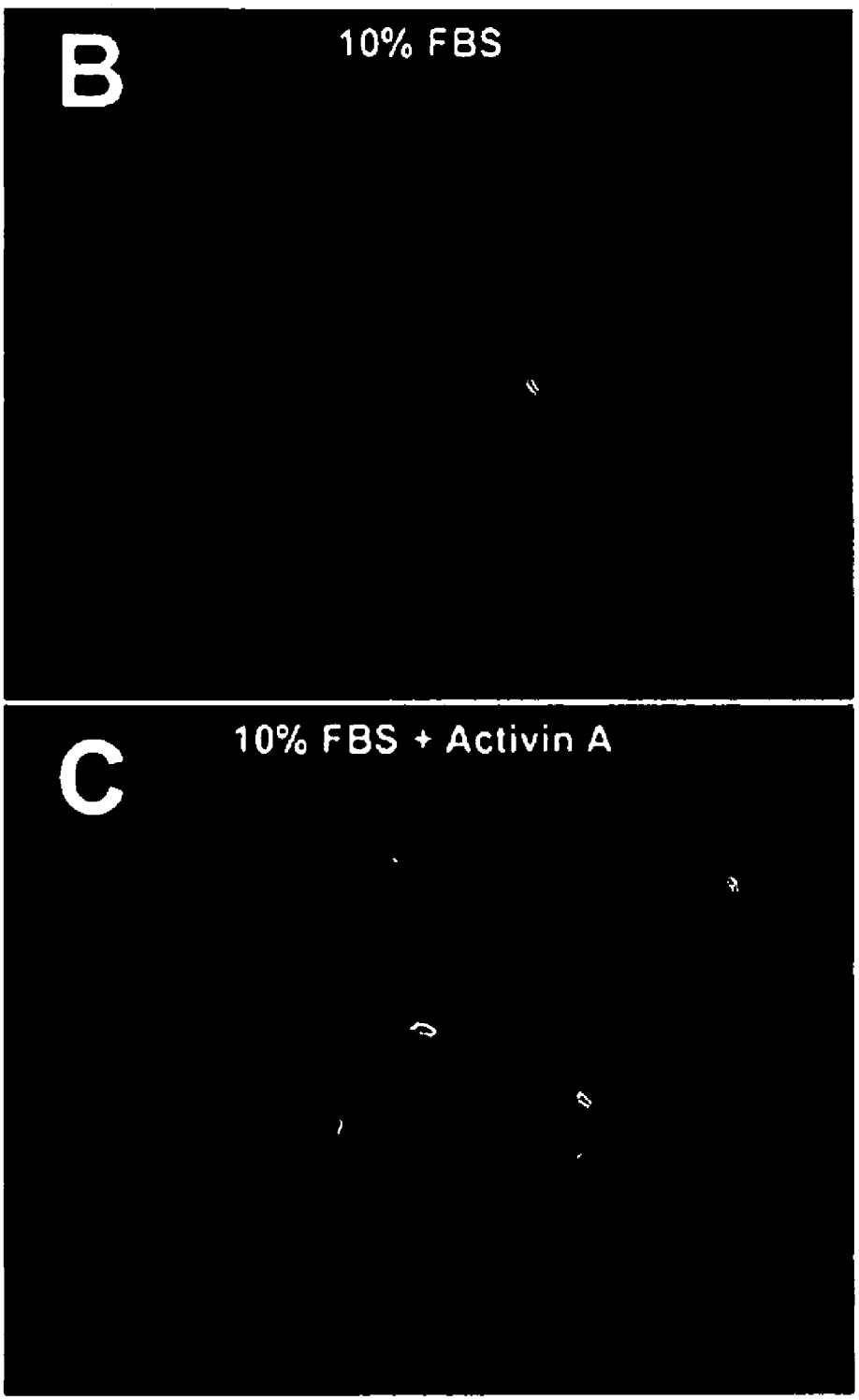
FIGS. 8B-C are images of two micrographs showing that the suppression of AFP expression by activin A is also evident at the single cell level as indicated by the very rare and small clusters of AFP$^+$ cells observed in activin A treatment conditions (bottom) relative to 10% FBS alone (top).
Figure 9:
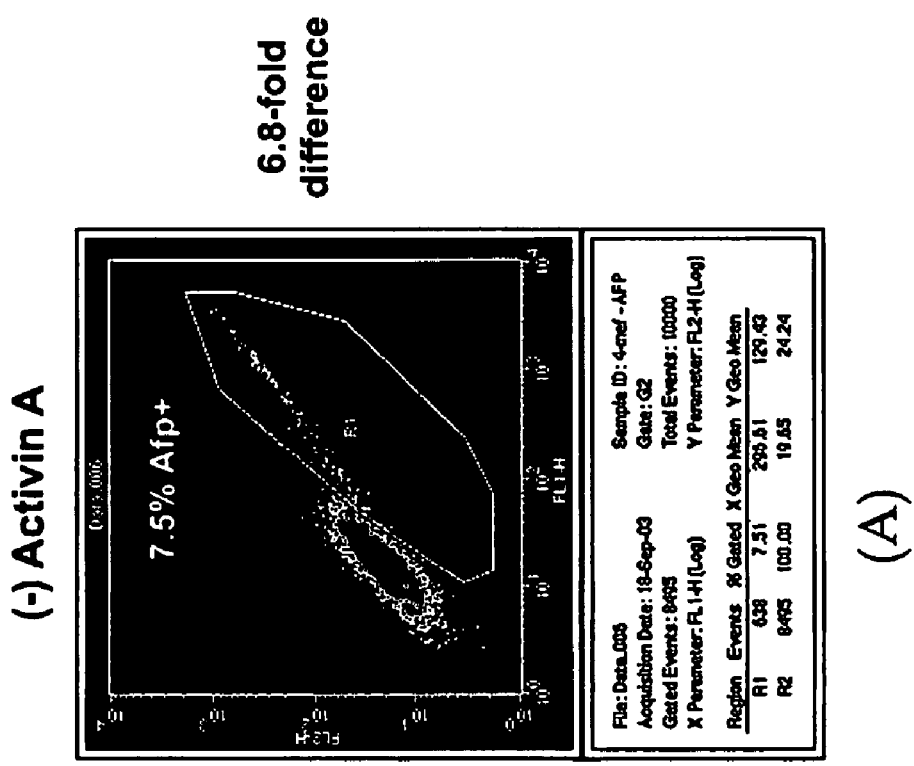
FIGS. 9A-B are comparative images showing the quantitation of the AFP$^+$ cell number using flow cytometry. This figure demonstrates that the magnitude of change in AFP gene expression (FIG. 8A) in the presence (right panel) and absence (left panel) of activin A exactly corresponds to the number of AFP$^+$ cells, further supporting the utility of Q-PCR analyses to indicate changes occurring at the individual cell level.
Figure 10:
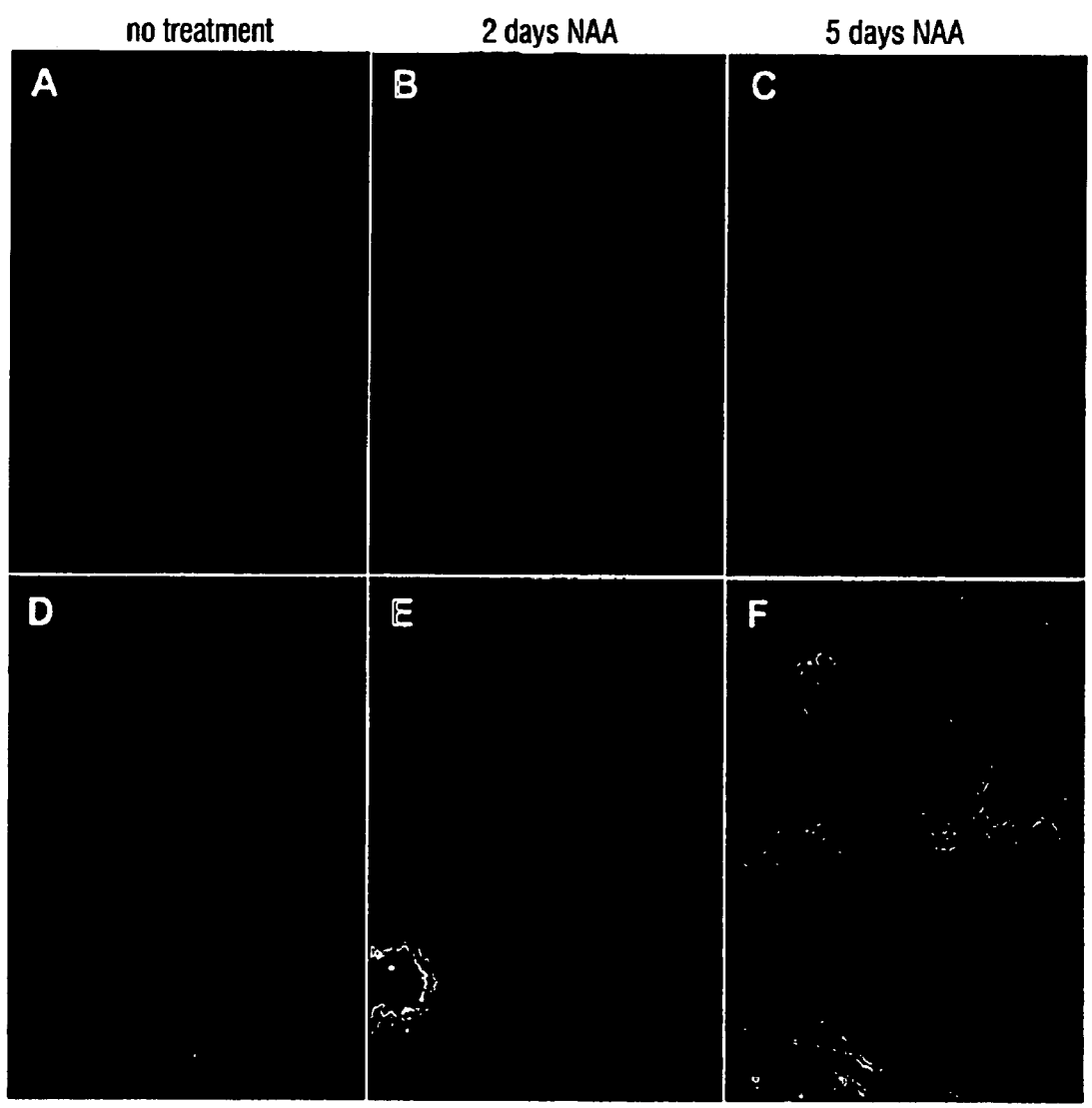
FIGS. 10A-F are micrographs which show that exposure of hESCs to nodal, activin A and activin B (NAA) yields a striking increase in the number of SOX17$^+$ cells over the period of 5 days (A-C). By comparing to the relative abundance of SOX17$^+$ cells to the total number of cells present in each field, as indicated by DAPI stained nuclei (D-F), it can be seen that approximately 30-50% of all cells are immunoreactive for SOX17 after five days treatment with NAA.
Figure 11:
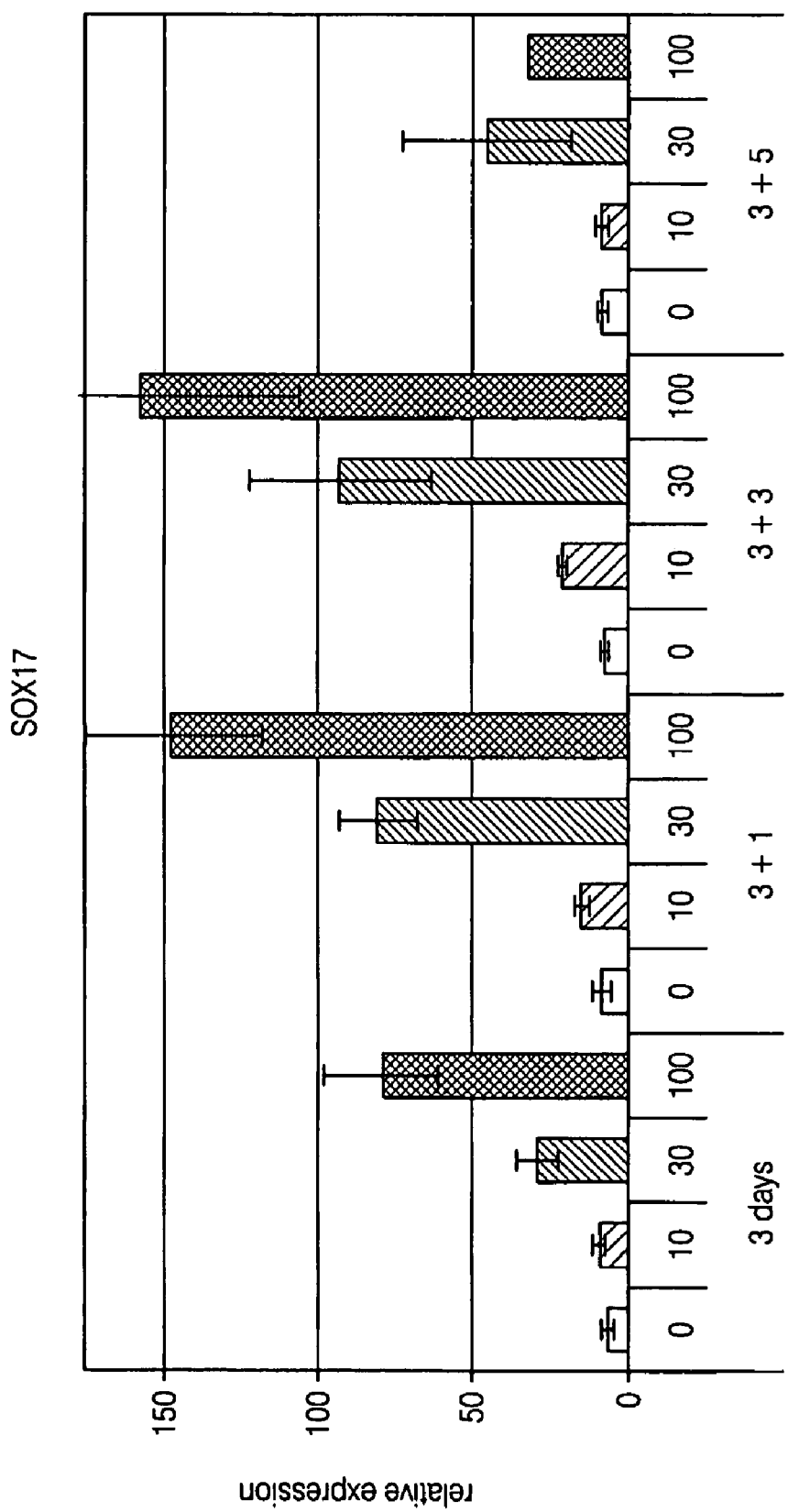
FIG. 11 is a bar chart which demonstrates that activin A (0, 10, 30 or 100 ng/ml) dose-dependently increases SOX17 gene expression in differentiating hESCs. Increased expression is already robust after 3 days of treatment on adherent cultures and continues through subsequent 1, 3 and 5 days of suspension culture as well.
Figure 12A:
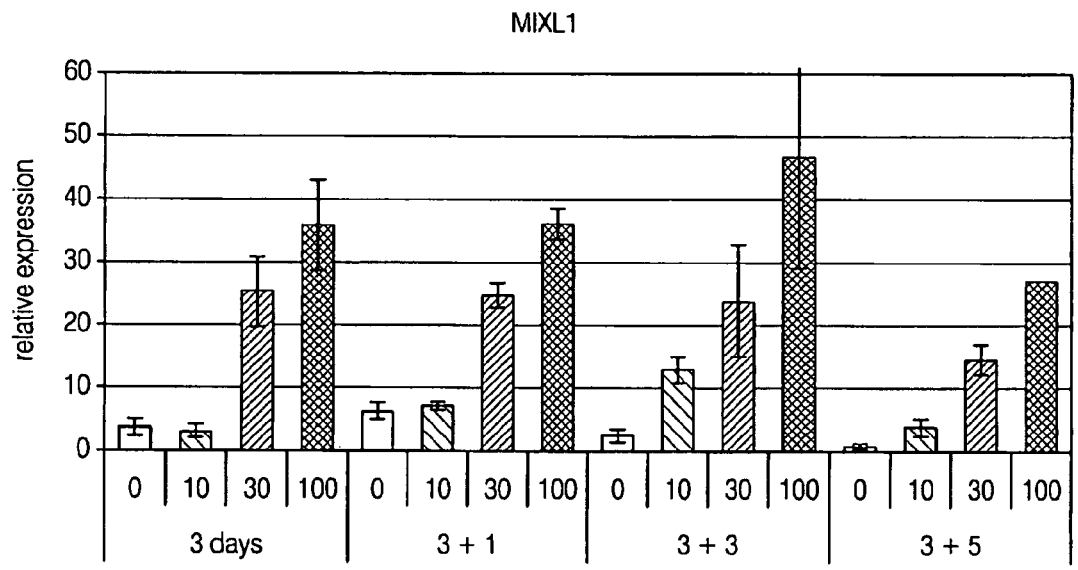
FIGS. 12A-C are bar charts which demonstrate the effect of activin A on the expression of MIXL1 (panel A), GATA4 (panel B) and HNF3b (panel C). Activin A dose-dependent increases are also observed for three other markers of definitive endoderm; MIXL1, GATA4 and HNF3b. The magnitudes of increased expression in response to activin dose are strikingly similar to those observed for SOX17, strongly indicating that activin A is specifying a population of cells that co-express all four genes (SOX17$^+$, MIXL1$^+$, GATA4$^+$ and HNF3b$^+$).
Figure 12B:
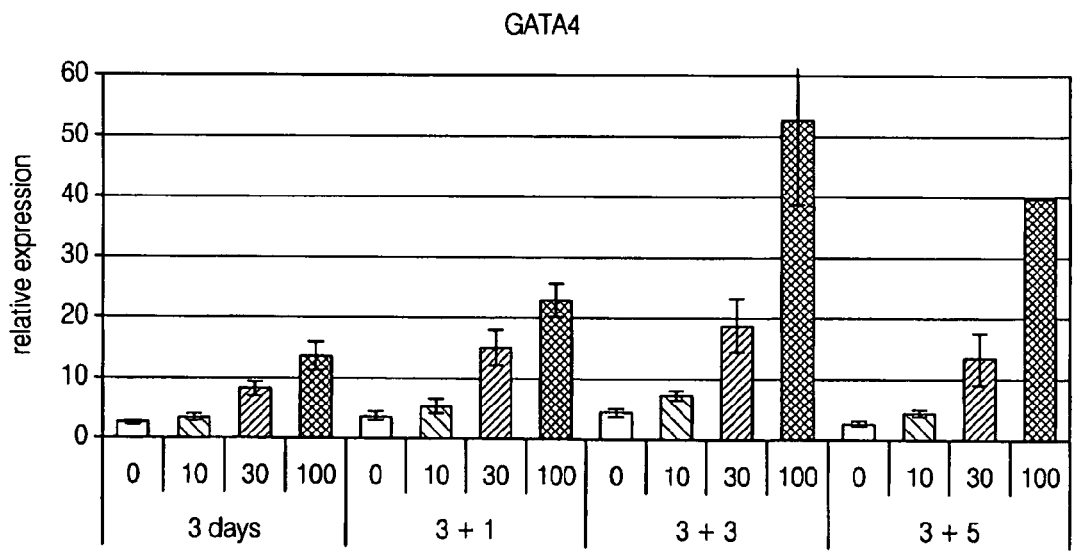
Figure 12C:
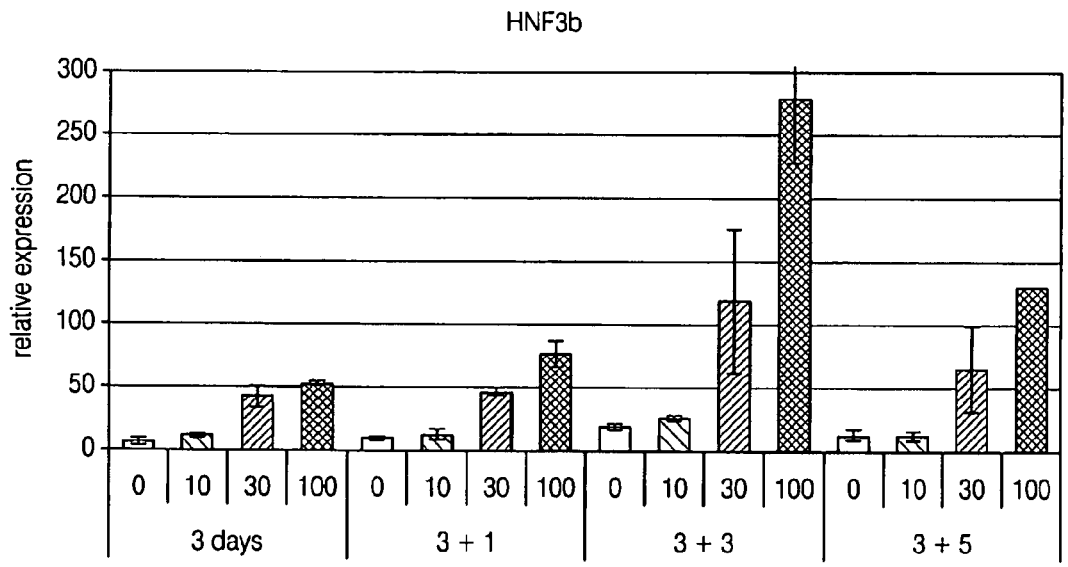
Figure 13A:
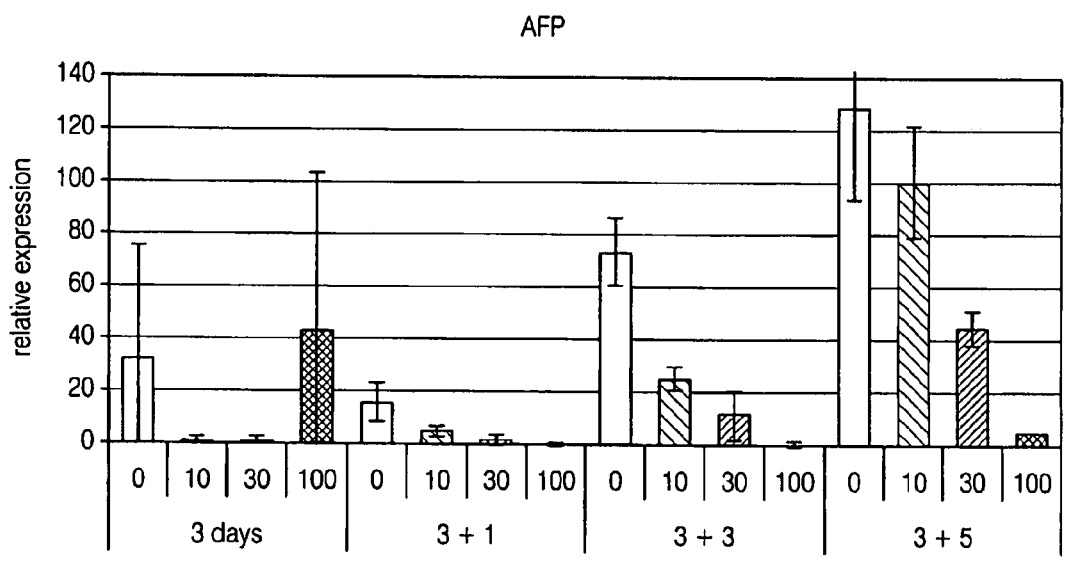
FIGS. 13A-C are bar charts which demonstrate the effect of activin A on the expression of AFP (panel A), SOX7 (panel B) and SPARC (panel C). There is an activin A dose-dependent decrease in expression of the visceral endoderm marker AFP. Markers of primitive endoderm (SOX7) and parietal endoderm (SPARC) remain either unchanged or exhibit suppression at some time points indicating that activin A does not act to specify these extra-embryonic endoderm cell types. This further supports the fact that the increased expression of SOX17, MIXL1, GATA4, and HNF3b are due to an increase in the number of definitive endoderm cells in response to activin A.
Figure 13B:
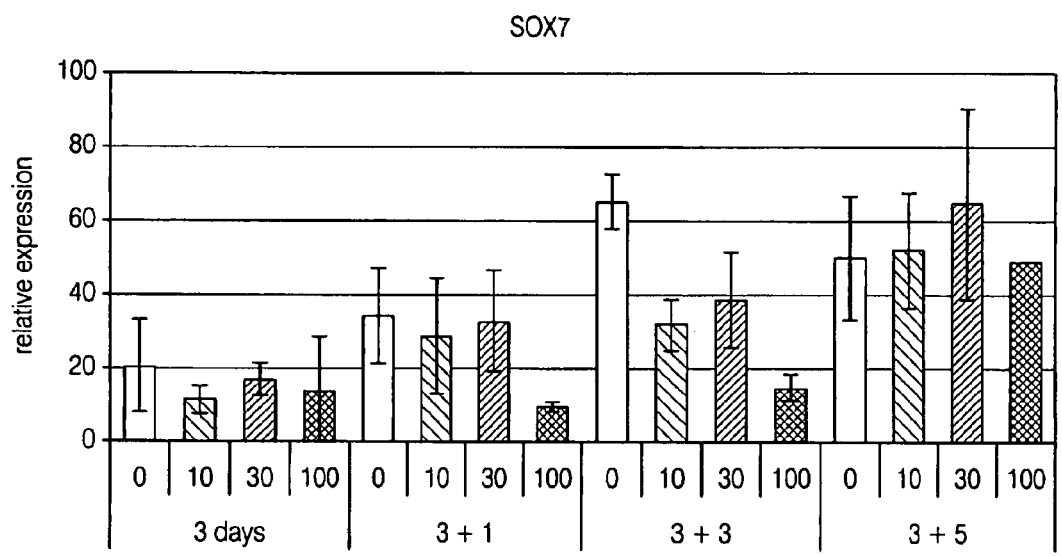
Figure 13C:
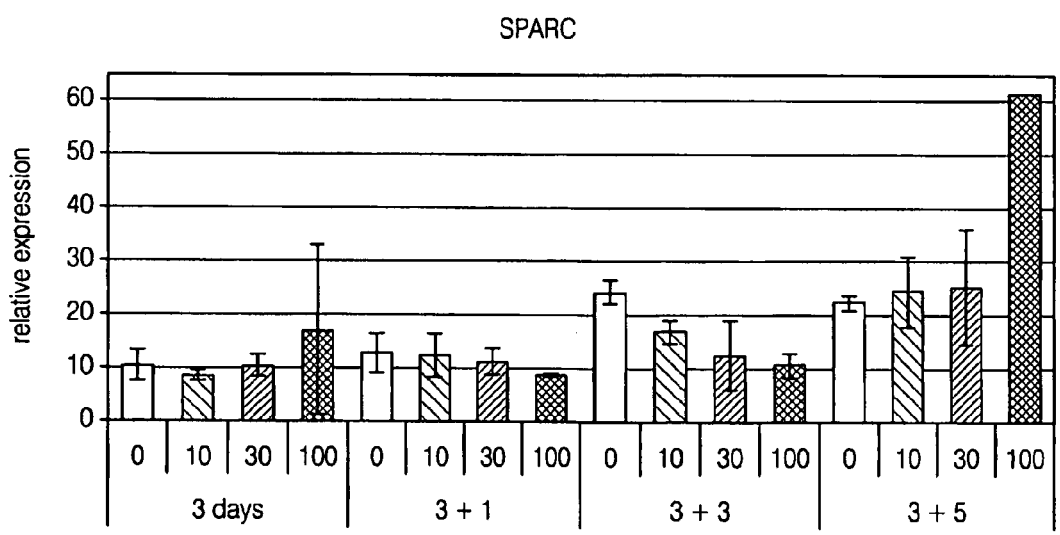
Figure 14A:
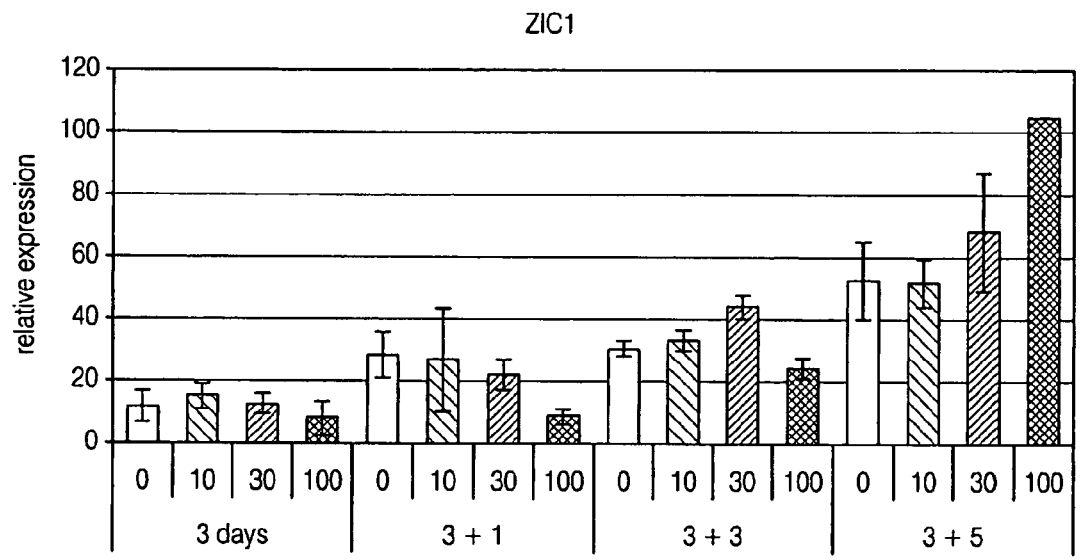
FIGS. 14A-B are bar charts showing the effect of activin A on ZIC1 (panel A) and Brachyury expression (panel B) Consistent expression of the neural marker ZIC1 demonstrates that there is not a dose-dependent effect of activin A on neural differentiation. There is a notable suppression of mesoderm differentiation mediated by 100 ng/ml of activin A treatment as indicated by the decreased expression of brachyury. This is likely the result of the increased specification of definitive endoderm from the mesendoderm precursors. Lower levels of activin A treatment (10 and 30 ng/ml) maintain the expression of brachyury at later time points of differentiation relative to untreated control cultures.
Figure 14B:
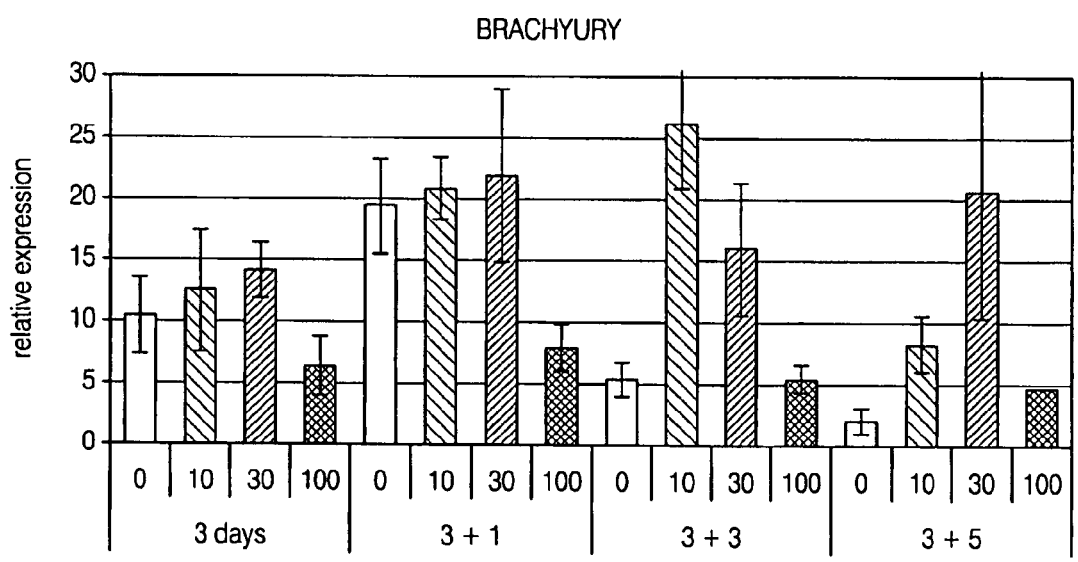

As a further evidence of the specificity of the SOX17$^{hi}$/AFP$^{lo}$/TM$^{lo}$/SPARC$^{lo}$ marker profile as predictive of definitive endoderm, SOX17 and AFP gene expression was quantitatively compared to the relative number of antibody labeled cells. As shown in FIG. 7A, hESCs treated with retinoic acid (visceral endoderm inducer), or activin A (definitive endoderm inducer), resulted in a 10-fold difference in the level of SOX17 mRNA expression. This result mirrored the 10-fold difference in SOX17 antibody-labeled cell number (FIG. 7B). Furthermore, as shown in FIG. 8A, activin A treatment of hESCs suppressed AFP gene expression by 6.8-fold in comparison to no treatment. This was visually reflected by a dramatic decrease in the number of AFP labeled cells in these cultures as shown in FIGS. 8B-C. To quantify this further, it was demonstrated that this approximately 7-fold decrease in AFP gene expression was the result of a similar 7-fold decrease in AFP antibody-labeled cell number as measured by flow cytometry (FIGS. 9A-B). This result is extremely significant in that it indicates that quantitative changes in gene expression as seen by Q-PCR mirror changes in cell type specification as observed by antibody staining.

Incubation of hESCs in the presence of Nodal family members (Nodal, activin A and activin B—NAA) resulted in a significant increase in SOX17 antibody-labeled cells over time. By 5 days of continuous activin treatment greater than 50% of the cells were labeled with SOX17 (FIGS. 10A-F). There were few or no cells labeled with AFP after 5 days of activin treatment.

In summary, the antibody produced against the carboxy-terminal 242 amino acids of the human SOX17 protein identified human SOX17 protein on Western blots but did not recognize SOX7, it's closest Sox family relative. The SOX17 antibody recognized a subset of cells in differentiating hESC cultures that were primarily SOX17$^+$/AFP$^{lo/-}$ (greater than 95% of labeled cells) as well as a small percentage (<5%) of cells that co-label for SOX17 and AFP (visceral endoderm). Treatment of hESC cultures with activins resulted in a marked elevation of SOX17 gene expression as well as SOX17 labeled cells and dramatically suppressed the expression of AFP mRNA and the number of cells labeled with AFP antibody.

Example 5

Q-PCR Gene Expression Assay

In the following experiments, real-time quantitative RT-PCR (Q-PCR) was the primary assay used for screening the effects of various treatments on hESC differentiation. In particular, real-time measurements of gene expression were analyzed for multiple marker genes at multiple time points by Q-PCR. Marker genes characteristic of the desired as well as undesired cell types were evaluated to gain a better understanding of the overall dynamics of the cellular populations. The strength of Q-PCR analysis includes its extreme sensitivity and relative ease of developing the necessary markers, as the genome sequence is readily available. Furthermore, the extremely high sensitivity of Q-PCR permits detection of gene expression from a relatively small number of cells within a much larger population. In addition, the ability to detect very low levels of gene expression provides indications for "differentiation bias" within the population. The bias towards a particular differentiation pathway, prior to the overt differentiation of those cellular phenotypes, is unrecognizable using immunocytochemical techniques. For this reason, Q-PCR provides a method of analysis that is at least complementary and potentially much superior to immunocytochemical techniques for screening the success of differentiation treatments. Additionally, Q-PCR provides a mechanism by which to evaluate the success of a differentiation protocol in a quantitative format at semi-high throughput scales of analysis.

The approach taken here was to perform relative quantitation using SYBR Green chemistry on a Rotor Gene 3000 instrument (Corbett Research) and a two-step RT-PCR format. Such an approach allowed for the banking of cDNA samples for analysis of additional marker genes in the future, thus avoiding variability in the reverse transcription efficiency between samples.

Primers were designed to lie over exon-exon boundaries or span introns of at least 800 bp when possible, as this has been empirically determined to eliminate amplification from contaminating genomic DNA. When marker genes were employed that do not contain introns or they possess pseudo-genes, DNase I treatment of RNA samples was performed.

We routinely used Q-PCR to measure the gene expression of multiple markers of target and non-target cell types in order to provide a broad profile description of gene expression in cell samples. The markers relevant for the early phases of hESC differentiation (specifically ectoderm, mesoderm, definitive endoderm and extra-embryonic endoderm) and for which validated primer sets are available are provided below in Table 1. The human specificity of these primer sets has also been demonstrated. This is an important fact since the hESCs were often grown on mouse feeder layers. Most typically, triplicate samples were taken for each condition and independently analyzed in duplicate to assess the biological variability associated with each quantitative determination.

To generate PCR template, total RNA was isolated using RNeasy (Qiagen) and quantitated using RiboGreen (Molecular Probes). Reverse transcription from 350-500 ng of total RNA was carried out using the iScript reverse transcriptase kit (BioRad), which contains a mix of oligo-dT and random primers. Each 20 µL reaction was subsequently diluted up to 100 µL total volume and 3 µL was used in each 10 µL Q-PCR reaction containing 400 nM forward and reverse primers and 5 µL 2×SYBR Green master mix (Qiagen). Two step cycling parameters were used employing a 5 second denature at 85-94° C. (specifically selected according to the melting temp of the amplicon for each primer set) followed by a 45 second anneal/extend at 60° C. Fluorescence data was collected during the last 15 seconds of each extension phase. A three point, 10-fold dilution series was used to generate the standard curve for each run and cycle thresholds (Ct's) were converted to quantitative values based on this standard curve. The quantitated values for each sample were normalized to housekeeping gene performance and then average and standard deviations were calculated for triplicate samples. At the conclusion of PCR cycling, a melt curve analysis was performed to ascertain the specificity of the reaction. A single specific product was indicated by a single peak at the $T_m$ appropriate for that PCR amplicon. In addition, reactions performed without reverse transcriptase served as the negative control and do not amplify.

A first step in establishing the Q-PCR methodology was validation of appropriate housekeeping genes (HGs) in the experimental system. Since the HG was used to normalize across samples for the RNA input, RNA integrity and RT efficiency, it was of value that the HG exhibited a constant level of expression over time in all sample types in order for the normalization to be meaningful. We measured the expression levels of Cyclophilin G, hypoxanthine phosphoribosyltransferase I (HPRT), beta-2-microglobulin, hydroxymethylbiane synthase (HMBS), TATA-binding protein TBP), and glucoronidase beta (GUS) in differentiating hESCs. Our results indicated that beta-2-microglobulin expression levels increased over the course of differentiation and therefore we excluded the use of this gene for normalization. The other genes exhibited consistent expression levels over time as well as across treatments. We routinely used both Cyclophilin G and GUS to calculate a normalization factor for all samples. The use of multiple HGs simultaneously reduces the variability inherent to the normalization process and increases the reliability of the relative gene expression values.

After obtaining genes for use in normalization, Q-PCR was then utilized to determine the relative gene expression levels of many marker genes across samples receiving different experimental treatments. The marker genes employed have been chosen because they exhibit enrichment in specific populations representative of the early germ layers and in particular have focused on sets of genes that are differentially expressed in definitive endoderm and extra-embryonic endoderm. These genes as well as their relative enrichment profiles are highlighted in Table 1.

TABLE 1

| Germ Layer | Gene | Expression Domains |
|---|---|---|
| Endoderm | SOX17 | definitive, visceral and parietal endoderm |
| | MIXL1 | endoderm and mesoderm |
| | GATA4 | definitive and primitive endoderm |
| | HNF3b | definitive endoderm and primitive endoderm, mesoderm, neural plate |
| | GSC | endoderm and mesoderm |
| Extra-embryonic | SOX7 | visceral endoderm |
| | AFP | visceral endoderm, liver |
| | SPARC | parietal endoderm |
| | TM | parietal endoderm/trophectoderm |
| Ectoderm | ZIC1 | neural tube, neural progenitors |
| Mesoderm | BRACH | nascent mesoderm |

Since many genes are expressed in more than one germ layer it is useful to quantitatively compare expression levels of many genes within the same experiment. SOX17 is expressed in definitive endoderm and to a smaller extent in visceral and parietal endoderm, SOX7 and AFP are expressed in visceral endoderm at this early developmental time point. SPARC and TM are expressed in parietal endoderm and Brachyury is expressed in early mesoderm.

Definitive endoderm cells were predicted to express high levels of SOX17 mRNA and low levels of AFP and SOX7 (visceral endoderm), SPARC (parietal endoderm) and Brachyury (mesoderm). In addition, ZIC1 was used here to further rule out induction of early ectoderm. Finally, GATA4 and HNF3b were expressed in both definitive and extra-embryonic endoderm, and thus, correlate with SOX17 expression in definitive endoderm (Table 1). A representative experiment is shown in FIGS. 11-14 which demonstrates how the marker genes described in Table 1 correlate with each other among the various samples, thus highlighting specific patterns of differentiation to definitive endoderm and extra-embryonic endoderm as well as to mesodermal and neural cell types.

In view of the above data it is clear that increasing doses of activin resulted in increasing SOX17 gene expression. Further this SOX17 expression predominantly represented definitive endoderm as opposed to extra-embryonic endoderm. This conclusion stems from the observation that SOX17 gene expression was inversely correlated with AFP, SOX7, and SPARC gene expression.

Example 6

Directed Differentiation of Human ES Cells to Definitive Endoderm

Human ES cell cultures randomly differentiate if cultured under conditions that do not actively maintain their undifferentiated state. This heterogeneous differentiation results in production of extra-embryonic endoderm cells comprised of both parietal and visceral endoderm (AFP, SPARC and SOX7 expression) as well as early ectodermal and mesodermal derivatives as marked by ZIC1 and Nestin (ectoderm) and Brachyury (mesoderm) expression. Definitive endoderm cell appearance has not been examined or specified for lack of specific antibody markers in ES cell cultures. As such, and by default, early definitive endoderm production in ES cell cultures has not been well studied. Since satisfactory antibody reagents for definitive endoderm cells have been unavailable, most of the characterization has focused on ectoderm and extra-embryonic endoderm. Overall, there are significantly greater numbers of extra-embryonic and neuroectodermal cell types in comparison to SOX17$^{hi}$ definitive endoderm cells in randomly differentiated ES cell cultures.

As undifferentiated hESC colonies expand on a bed of fibroblast feeders, the cells at the edges of the colony take on alternative morphologies that are distinct from those cells residing within the interior of the colony. Many of these outer edge cells can be distinguished by their less uniform, larger cell body morphology and by the expression of higher levels of OCT4. It has been described that as ES cells begin to differentiate they alter the levels of OCT4 expression up or down relative to undifferentiated ES cells. Alteration of OCT4 levels above or below the undifferentiated threshold may signify the initial stages of differentiation away from the pluripotent state.

When undifferentiated colonies were examined by SOX17 immunocytochemistry, occasionally small 10-15-cell clusters of SOX17-positive cells were detected at random locations on the periphery and at the junctions between undifferentiated hESC colonies. As noted above, these scattered pockets of outer colony edges appeared to be some of the first cells to differentiate away from the classical ES cell morphology as the colony expanded in size and became more crowded. Younger, smaller fully undifferentiated colonies (<1 mm; 4-5 days old) showed no SOX17 positive cells within or at the edges of the colonies while older, larger colonies (1-2 mm diameter, >5 days old) had sporadic isolated patches of SOX17 positive, AFP negative cells at the periphery of some colonies or in regions interior to the edge that did not display the classical hESC morphology described previously. Given that this was the first development of an effective SOX17 antibody, definitive endoderm cells generated in such early "undifferentiated" ES cell cultures have never been previously demonstrated.

Figure 15:
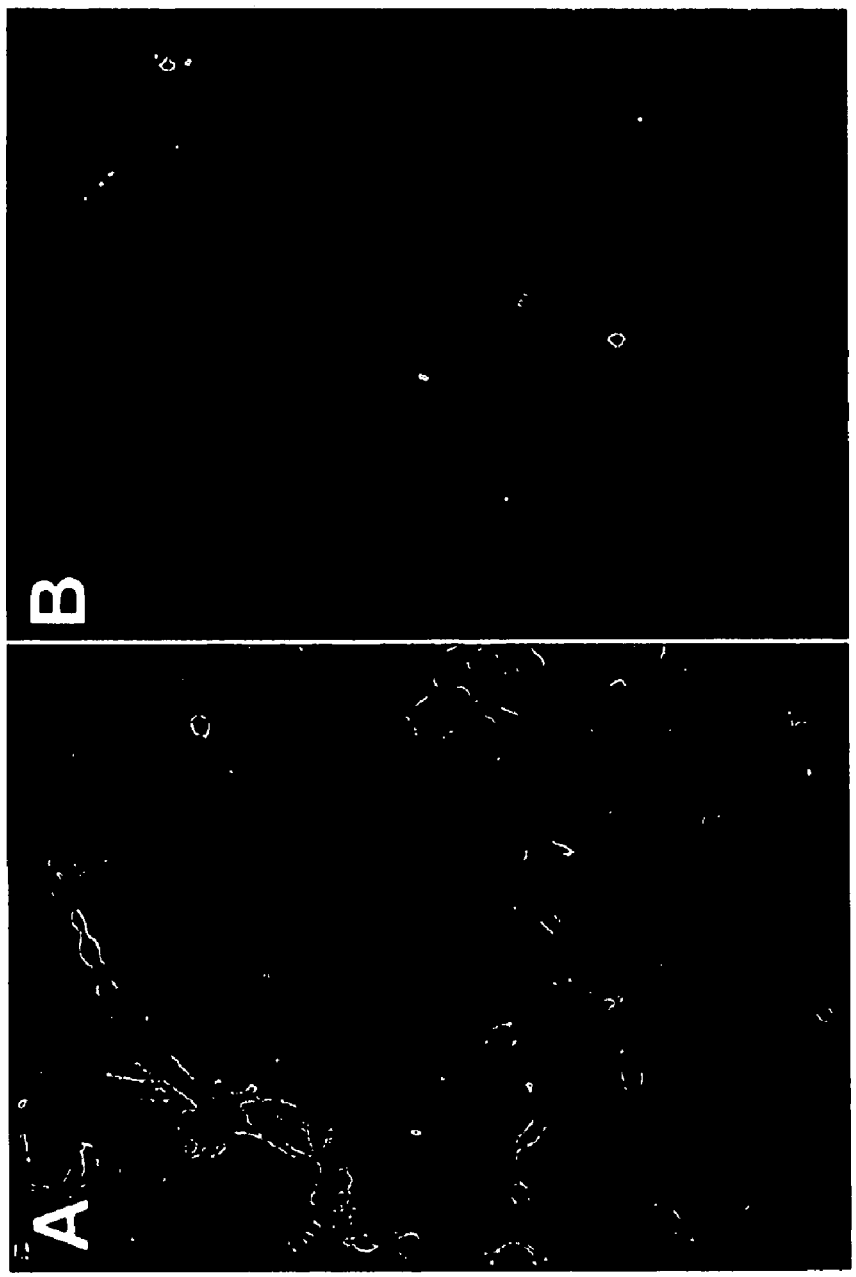
FIGS. 15A-B are micrographs showing decreased parietal endoderm differentiation in response to treatment with activins. Regions of TM$^{hi}$ parietal endoderm are found through the culture (A) when differentiated in serum alone, while differentiation to TM$^+$ cells is scarce when activins are included (B) and overall intensity of TM immunoreactivity is lower.
Figure 16:
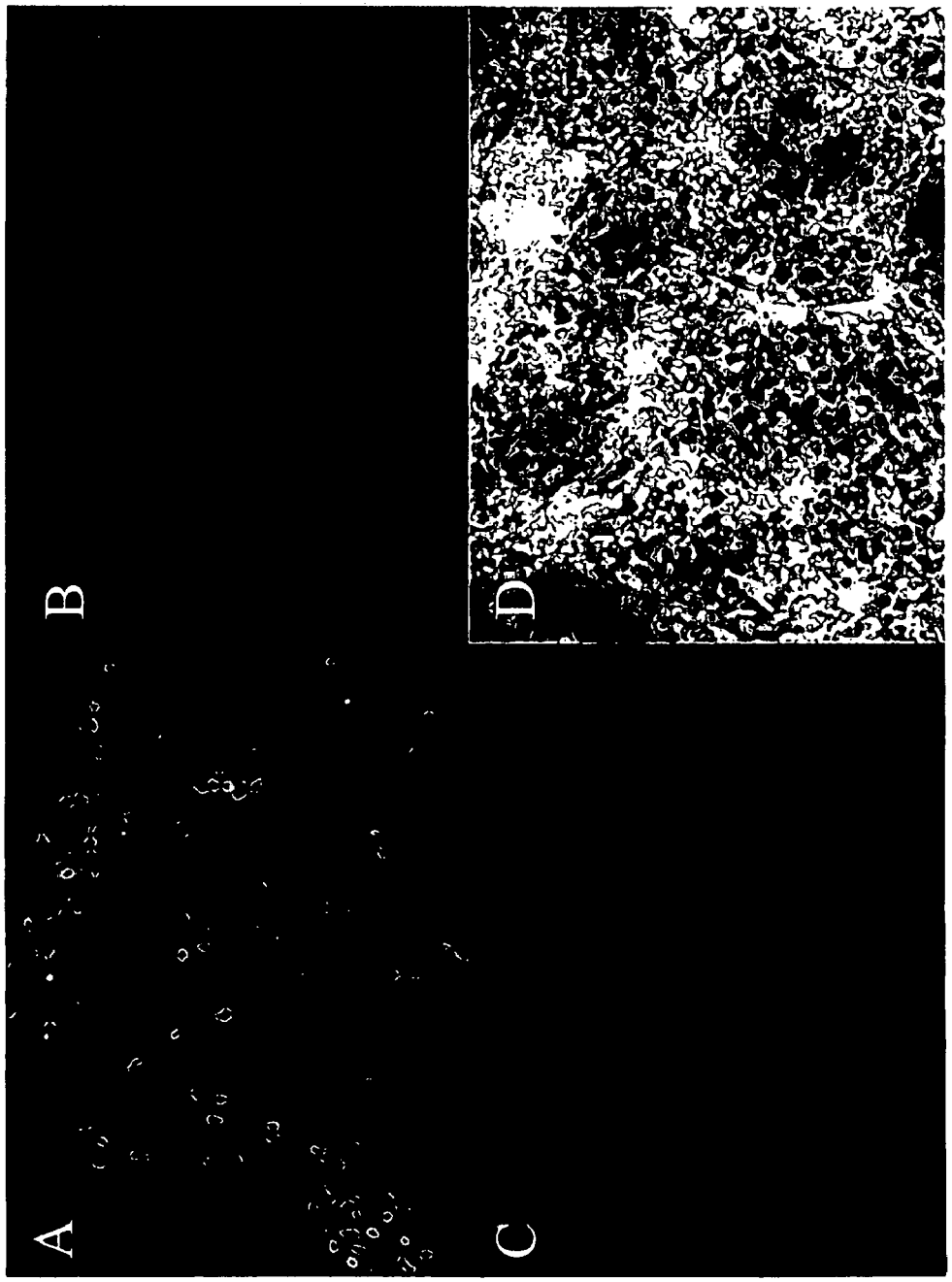
FIGS. 16A-D are micrographs which show marker expression in response to treatment with activin A and activin B. hESCs were treated for four consecutive days with activin A and activin B and triple labeled with SOX17, AFP and TM antibodies. Panel A—SOX17; Panel B—AFP; Panel C—TM; and Panel D—Phase/DAPI. Notice the numerous SOX17 positive cells (A) associated with the complete absence of AFP (B) and TM (C) immunoreactivity.
Figure 17:
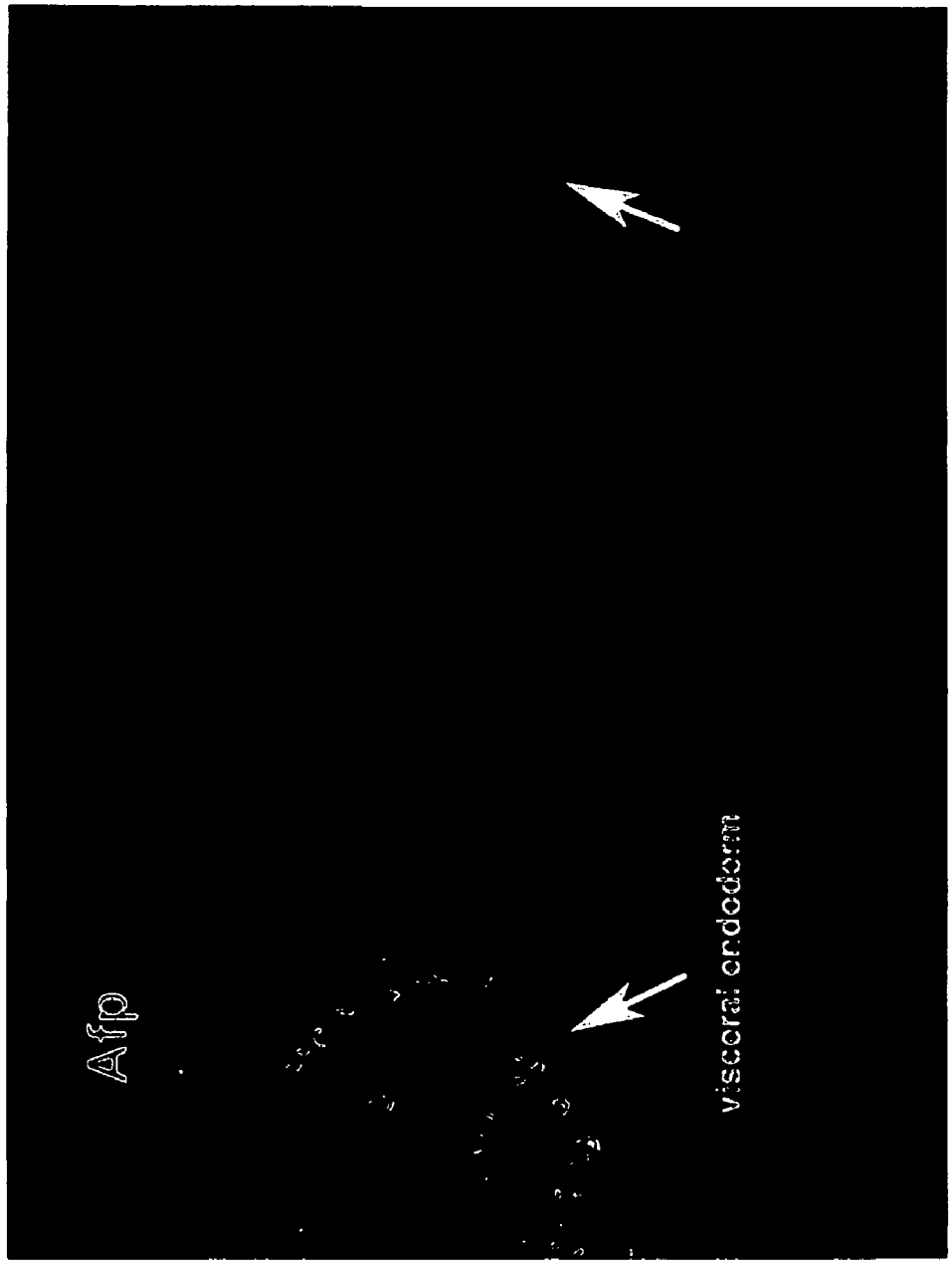
FIG. 17 is a micrograph showing the appearance of definitive endoderm and visceral endoderm in vitro from hESCs. The regions of visceral endoderm are identified by AFP$^{hi}$/SOX17$^{lo/-}$ while definitive endoderm displays the complete opposite profile, SOX17$^{hi}$/AFP$^{lo/-}$. This field was selectively chosen due to the proximity of these two regions to each other. However, there are numerous times when SOX17$^{hi}$/AFP$^{lo/-}$ regions are observed in absolute isolation from any regions of AFP$^{hi}$ cells, suggesting the separate origination of the definitive endoderm cells from visceral endoderm cells.
Figure 18:
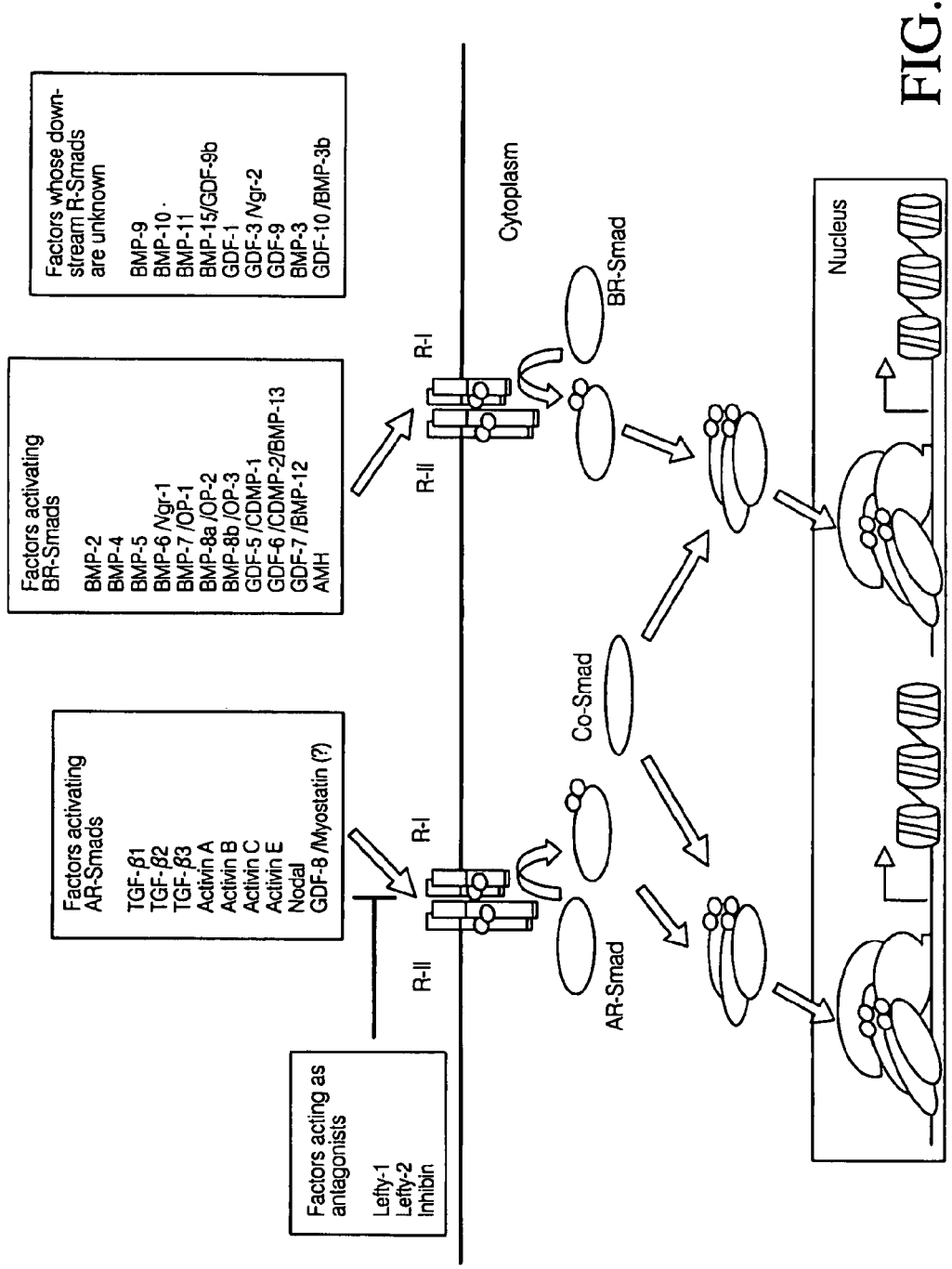
FIG. 18 is a diagram depicting the TGFβ family of ligands and receptors. Factors activating AR Smads and BR Smads are useful in the production of definitive endoderm from human embryonic stem cells (see, *J Cell Physiol.* 187:265-76).

Based on negative correlations of SOX17 and SPARC gene expression levels by Q-PCR, the vast majority of these SOX17 positive, AFP negative cells will be negative for parietal endoderm markers by antibody co-labeling. This was specifically demonstrated for TM-expressing parietal endoderm cells as shown in FIGS. 15A-B. Exposure to Nodal factors activin A and B resulted in a dramatic decrease in the intensity of TM expression and the number of TM positive cells. By triple labeling using SOX17, AFP and TM antibodies on an activin treated culture, clusters of SOX17 positive cells that were also negative for AFP and TM were observed (FIGS. 16A-D). These are the first cellular demonstrations of SOX17 positive definitive endoderm cells in differentiating hESC cultures (FIGS. 16A-D and 17).

With the SOX17 antibody and Q-PCR tools described above we have explored a number of procedures capable of efficiently programming hESCs to become SOX17$^{hi}$/AFP$^{lo}$/SPARC/TM$^{lo}$ definitive endoderm cells. We applied a variety of differentiation protocols aimed at increasing the number and proliferative capacity of these cells as measured at the population level by Q-PCR for SOX17 gene expression and at the level of individual cells by antibody labeling of SOX17 protein.

We were the first to analyze and describe the effect of TGFβ family growth factors, such as Nodal/activin/BMP, for use in creating definitive endoderm cells from embryonic stem cells in vitro cell cultures. In typical experiments, activin A, activin B, BMP or combinations of these growth factors were added to cultures of undifferentiated human stem cell line hESCyt-25 to begin the differentiation process.

Figure 19:
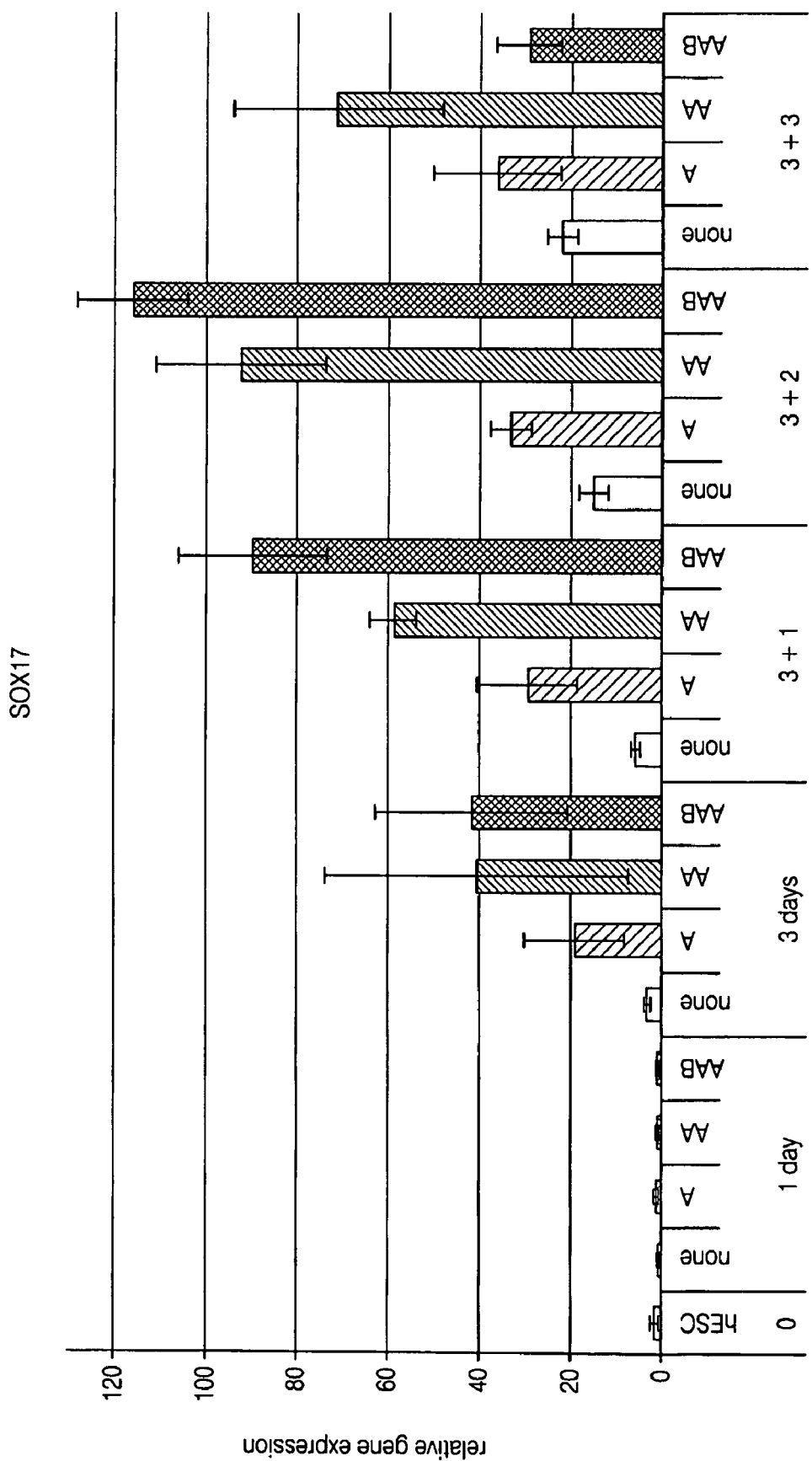
FIG. 19 is a bar chart showing the induction of SOX17 expression over time as a result of treatment with individual and combinations of TGFβ factors.

As shown in FIG. 19, addition of activin A at 100 ng/ml resulted in a 19-fold induction of SOX17 gene expression vs. undifferentiated hESCs by day 4 of differentiation. Adding activin B, a second member of the activin family, together with activin A, resulted in a 37-fold induction over undifferentiated hESCs by day 4 of combined activin treatment. Finally, adding a third member of the TGFβ family from the Nodal/Activin and BMP subgroups, BMP4, together with activin A and activin B, increased the fold induction to 57 times that of undifferentiated hESCs (FIG. 19). When SOX17 induction with activins and BMP was compared to no factor medium controls 5-, 10-, and 15-fold inductions resulted at the 4-day time point. By five days of triple treatment with activins A, B and BMP, SOX17 was induced more than 70 times higher than hESCs. These data indicate that higher doses and longer treatment times of the Nodal/activin TGFβ family members results in increased expression of SOX17.

Nodal and related molecules activin A, B and BMP facilitate the expression of SOX17 and definitive endoderm formation in vivo or in vitro. Furthermore, addition of BMP results in an improved SOX17 induction possibly through the further induction of Cripto, the Nodal co-receptor.

We have demonstrated that the combination of activins A and B together with BMP4 result in additive increases in SOX17 induction and hence definitive endoderm formation. BMP4 addition for prolonged periods (>4 days), in combination with activin A and B may induce SOX17 in parietal and visceral endoderm as well as definitive endoderm. In some embodiments of the present invention, it is therefore valuable to remove BMP4 from the treatment within 4 days of addition.

Figure 20:
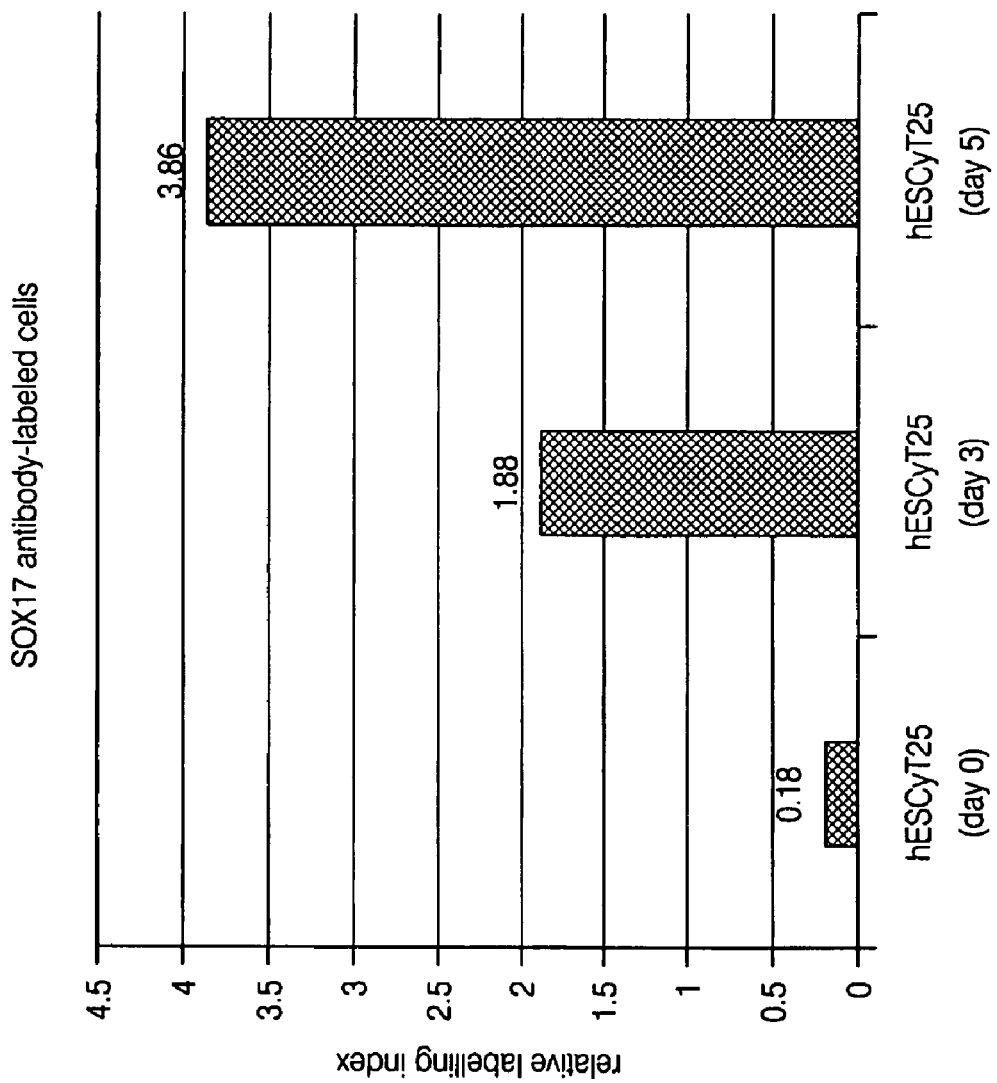
FIG. 20 is a bar chart showing the increase in SOX17$^+$ cell number with time as a result of treatment with combinations of TGFβ factors.
Figure 21:
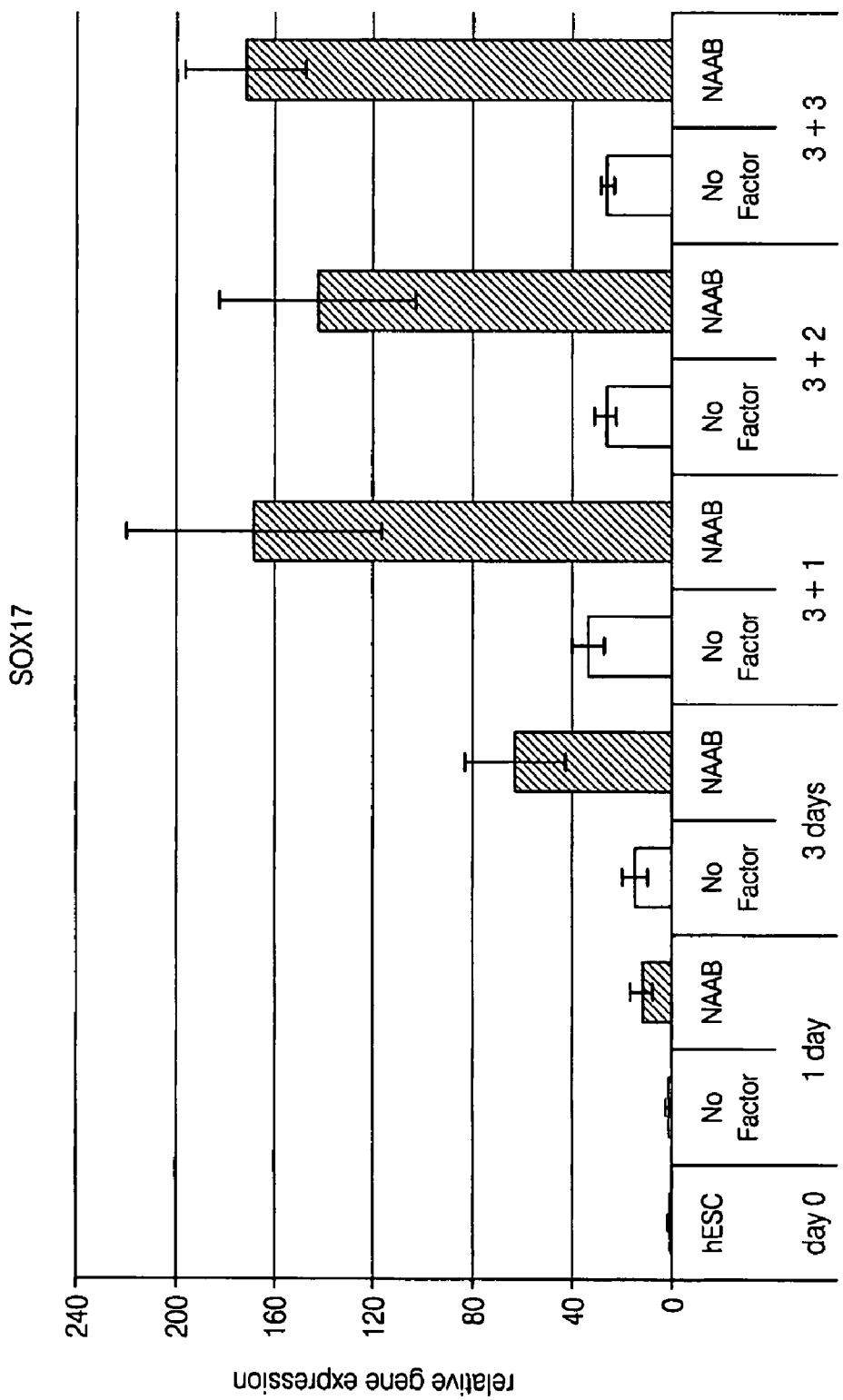
FIG. 21 is a bar chart showing induction of SOX17 expression over time as a result of treatment with combinations of TGFβ factors.
Figure 22:
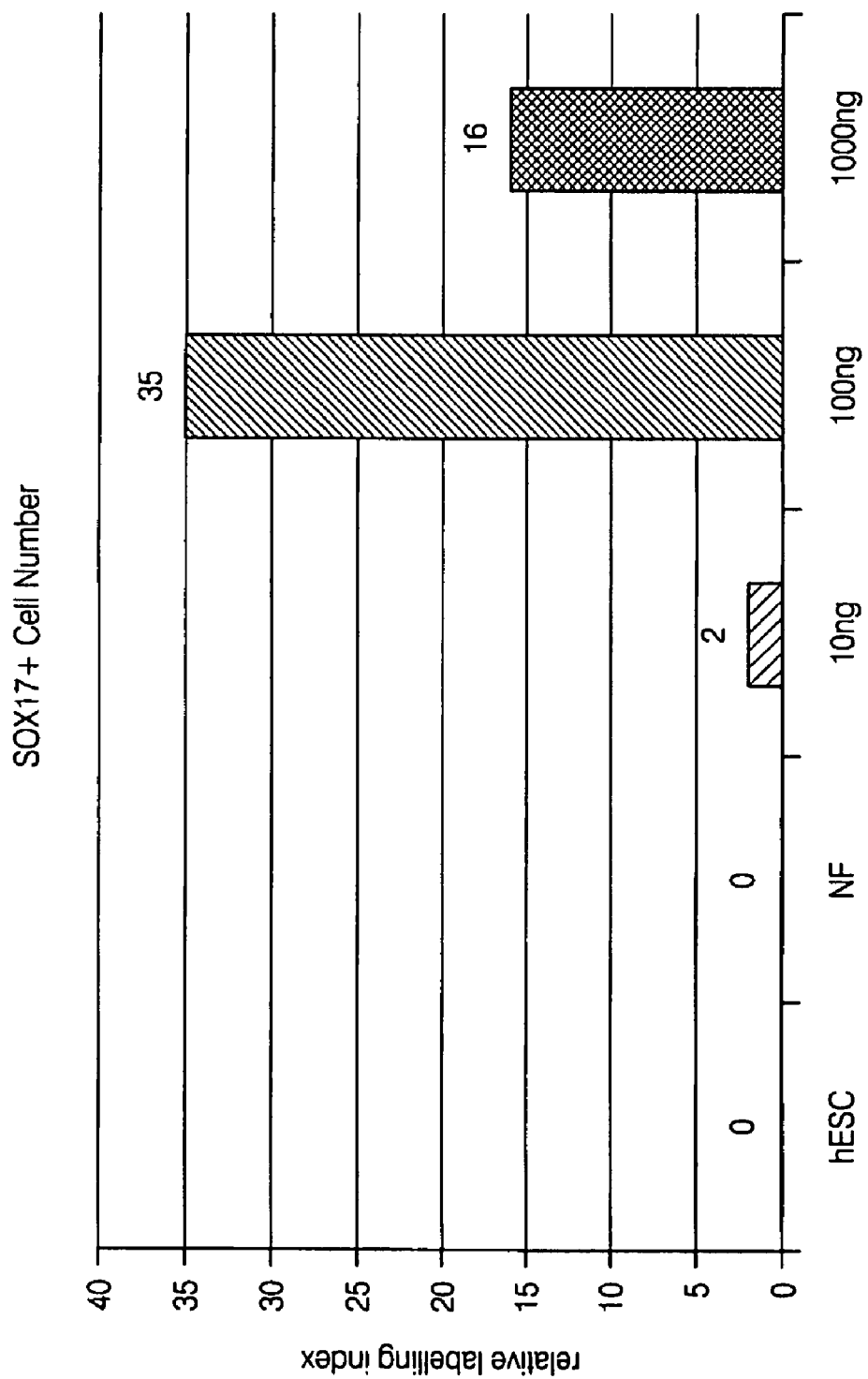
FIG. 22 is a bar chart showing that activin A induces a dose-dependent increase in SOX17$^+$ cell number.

To determine the effect of TGFβ factor treatment at the individual cell level, a time course of TGFβ factor addition was examined using SOX17 antibody labeling. As previously shown in FIGS. 10A-F, there was a dramatic increase in the relative number of SOX17 labeled cells over time. The relative quantification (FIG. 20) shows more than a 20-fold increase in SOX17-labeled cells. This result indicates that both the numbers of cells as well SOX17 gene expression level are increasing with time of TGFβ factor exposure. As shown in FIG. 21, after four days of exposure to Nodal, activin A, activin B and BMP4, the level of SOX17 induction reached 168-fold over undifferentiated hESCs. FIG. 22 shows that the relative number of SOX17-positive cells was also dose responsive. activin A doses of 100 ng/ml or more were capable of potently inducing SOX17 gene expression and cell number.

Figure 23:
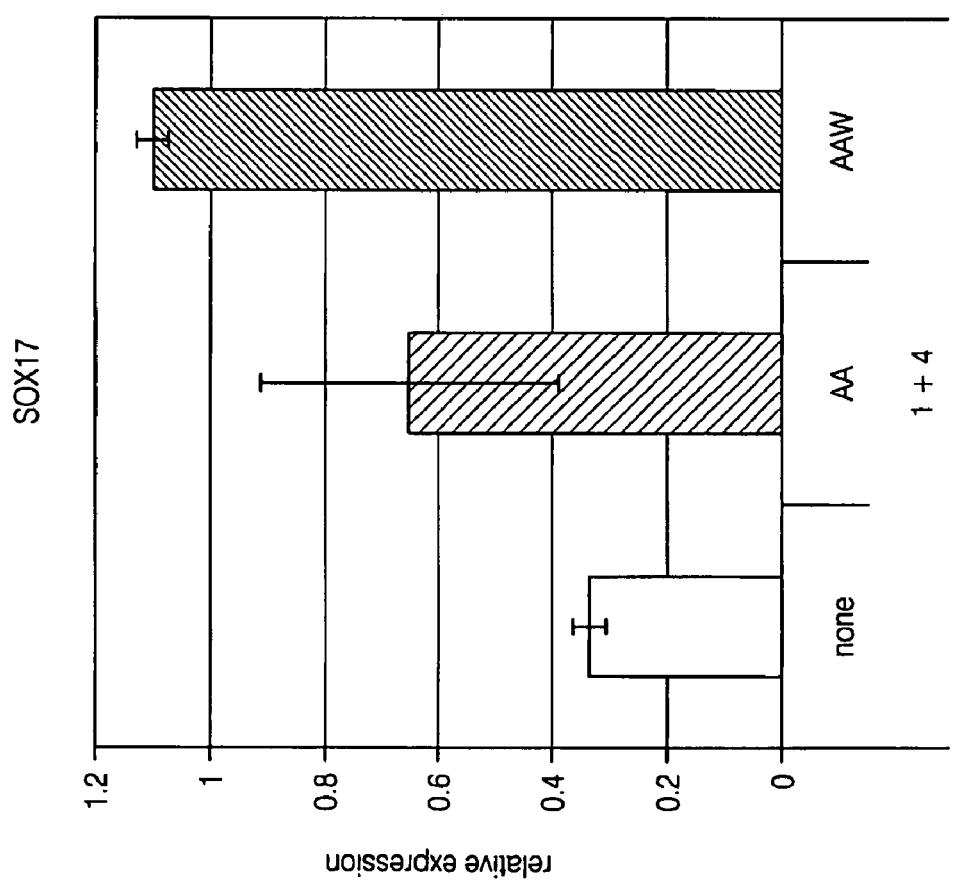
FIG. 23 is a bar chart showing that addition of Wnt3a to activin A and activin B treated cultures increases SOX17 expression above the levels induced by activin A and activin B alone.

In addition to the TGFβ family members, the Wnt family of molecules may play a role in specification and/or maintenance of definitive endoderm. The use of Wnt molecules was also beneficial for the differentiation of hESCs to definitive endoderm as indicated by the increased SOX17 gene expression in samples that were treated with activins plus Wnt3a over that of activins alone (FIG. 23).

Figure 24A:
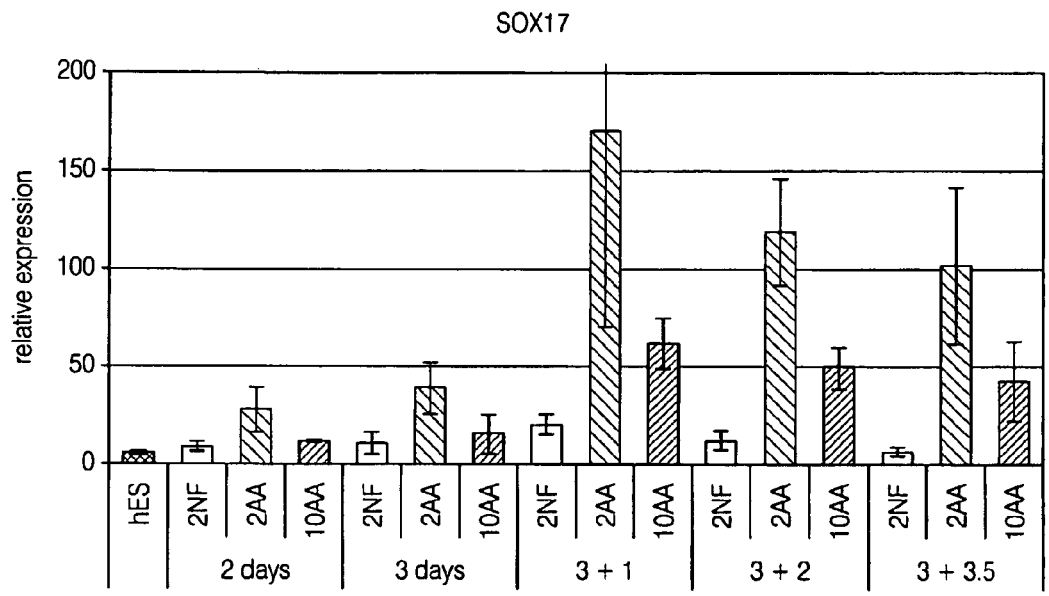
FIGS. 24A-C are bar charts showing differentiation to definitive endoderm is enhanced in low FBS conditions. Treatment of hESCs with activins A and B in media containing 2% FBS (2AA) yields a 2-3 times greater level of SOX17 expression as compared to the same treatment in 10% FBS media (10AA) (panel A). Induction of the definitive endoderm marker MIXL1 (panel B) is also affected in the same way and the suppression of AFP (visceral endoderm) (panel C) is greater in 2% FBS than in 10% FBS conditions.
Figure 24B:
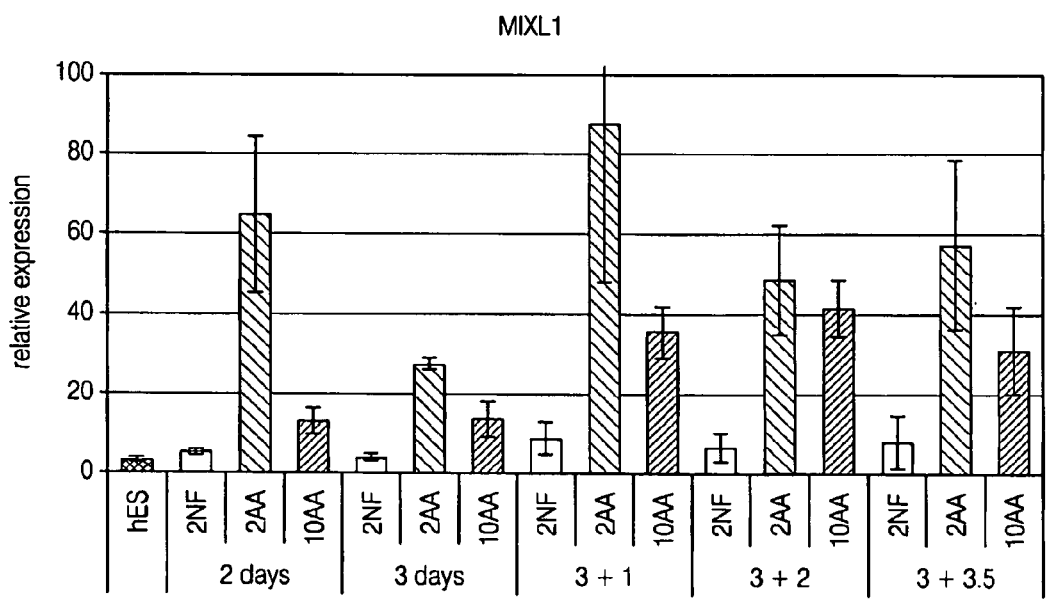
Figure 24C:
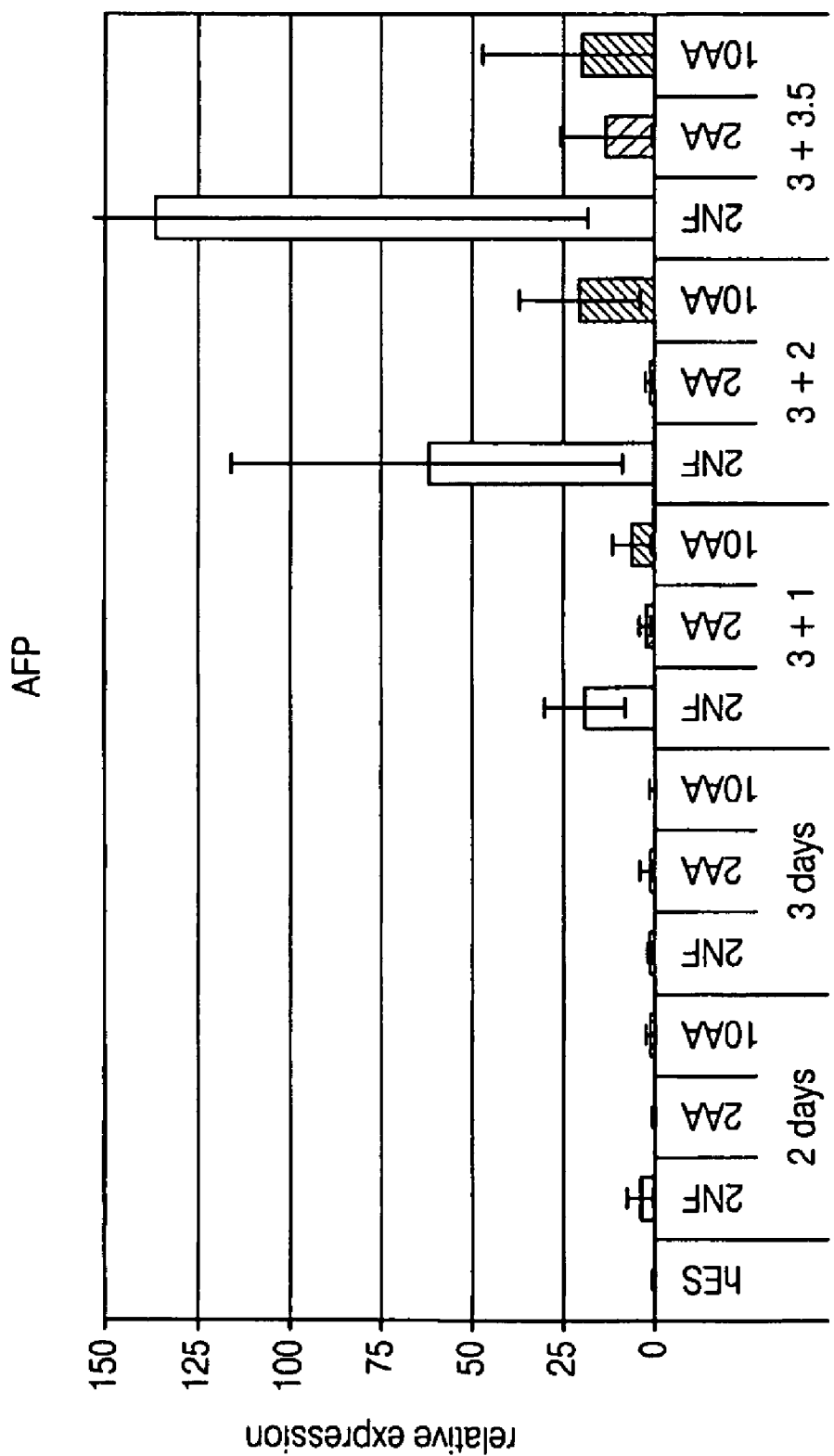
Figure 25:
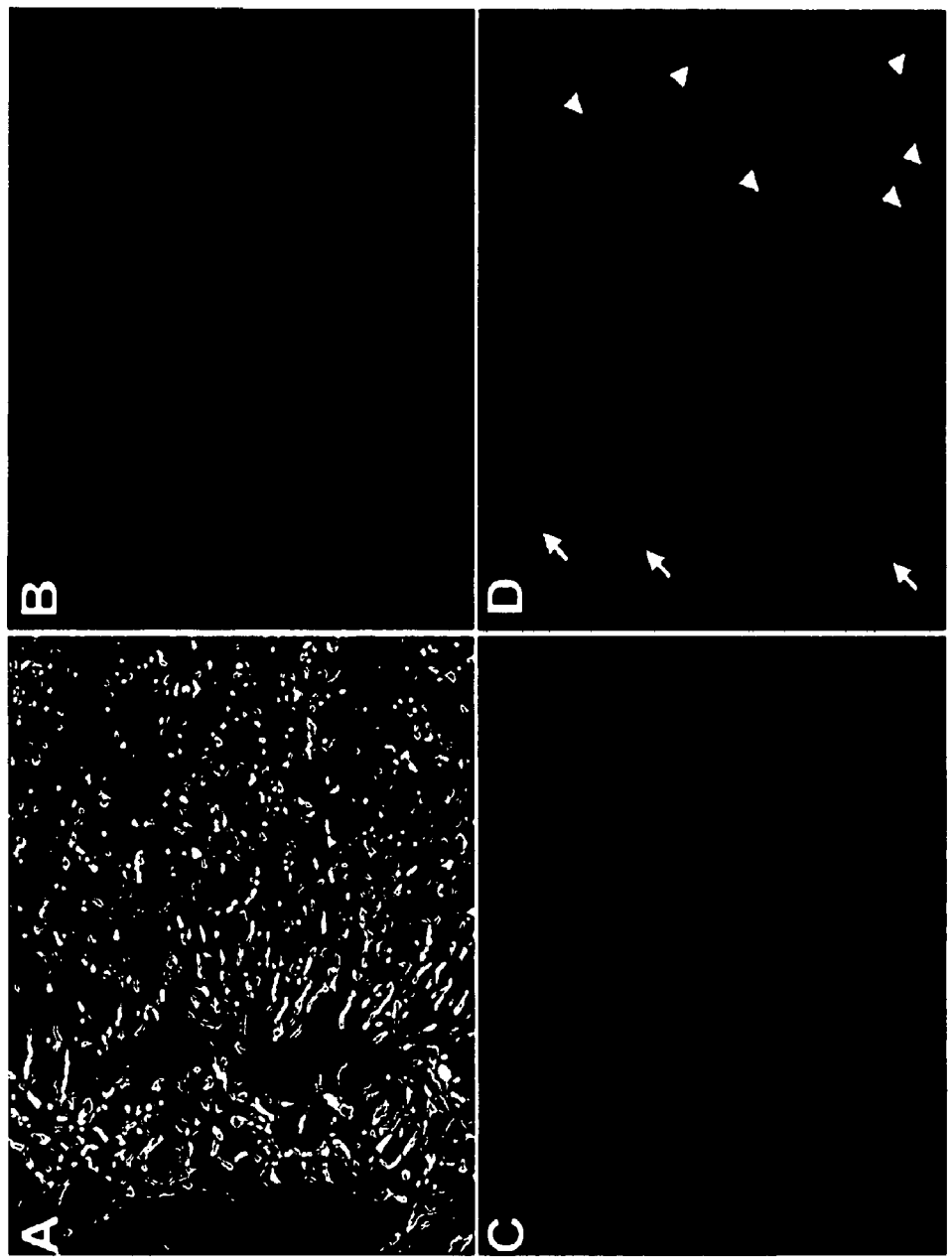
FIGS. 25A-D are micrographs which show SOX17$^+$ cells are dividing in culture. SOX17 immunoreactive cells are present at the differentiating edge of an hESC colony (C, D) and are labeled with proliferating cell nuclear antigen (PCNA) (panel B) yet are not co-labeled with OCT4 (panel C). In addition, clear mitotic figures can be seen by DAPI labeling of nuclei in both SOX17$^+$ cells (arrows) as well as OCT4$^+$, undifferentiated hESCs (arrowheads) (D).

All of the experiments described above were performed using a tissue culture medium containing 10% serum with added factors. Surprisingly, we discovered that the concentration of serum had an effect on the level of SOX17 expression in the presence of added activins as shown in FIGS. 24A-C. When serum levels were reduced from 10% to 2%, SOX17 expression tripled in the presence of activins A and B.

Finally, we demonstrated that activin induced SOX17$^+$ cells divide in culture as depicted in FIGS. 25A-D. The arrows show cells labeled with SOX17/PCNA/DAPI that are in mitosis as evidenced by the PCNA/DAPI-labeled mitotic plate pattern and the phase contrast mitotic profile.

Example 7

Chemokine Receptor 4 (CXCR4) Expression Correlates with Markers for Definitive Endoderm and not Markers for Mesoderm, Ectoderm or Visceral Endoderm As described above, hESCs can be induced to differentiate to the definitive endoderm germ layer by the application of cytokines of the TGFβ family and more specifically of the activin/nodal subfamily. Additionally, we have shown that the proportion of fetal bovine serum (FBS) in the differentiation culture medium effects the efficiency of definitive endoderm differentiation from hESCs. This effect is such that at a given concentration of activin A in the medium, higher levels of FBS will inhibit maximal differentiation to definitive endoderm. In the absence of exogenous activin A, differentiation of hESCs to the definitive endoderm lineage is very inefficient and the FBS concentration has much milder effects on the differentiation process of hESCs.

In these experiments, hESCs were differentiated by growing in RPMI medium (Invitrogen, Carlsbad, Calif.; cat# 61870-036) supplemented with 0.5%, 2.0% or 10% FBS and either with or without 100 ng/ml activin A for 6 days. In addition, a gradient of FBS ranging from 0.5% to 2.0% over the first three days of differentiation was also used in conjunction with 100 ng/ml of activin A. After the 6 days, replicate samples were collected from each culture condition and analyzed for relative gene expression by real-time quantitative PCR. The remaining cells were fixed for immunofluorescent detection of SOX17 protein.

Figure 26:
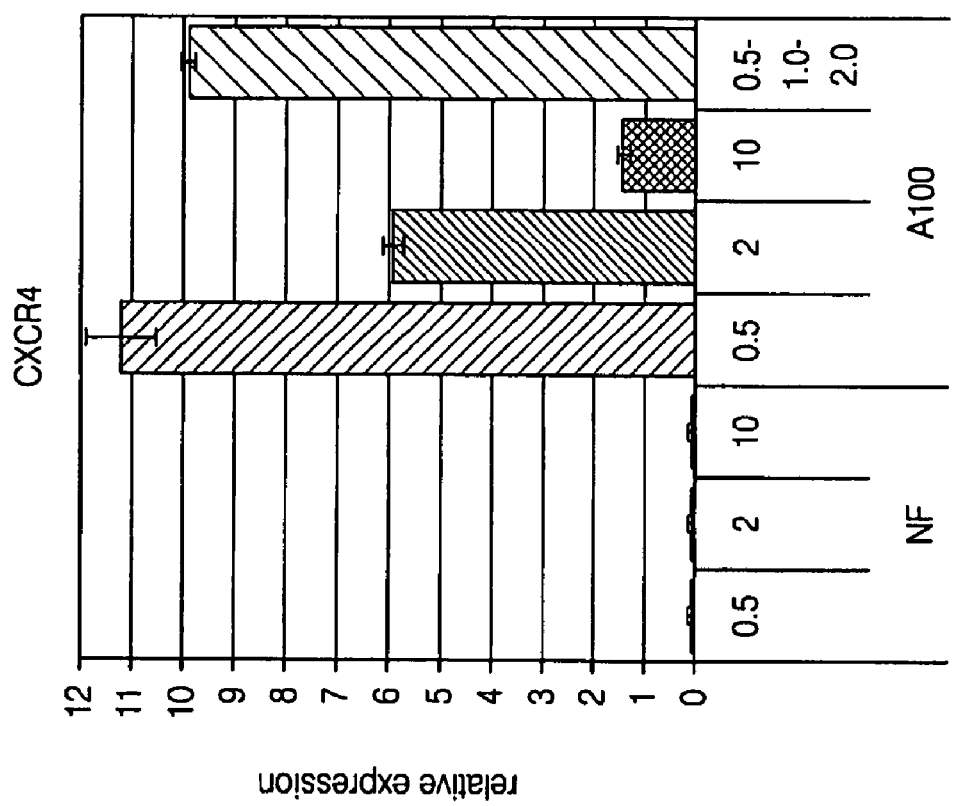
FIG. 26 is a bar chart showing the relative expression level of CXCR4 in differentiating hESCs under various media conditions.
Figure 27B:
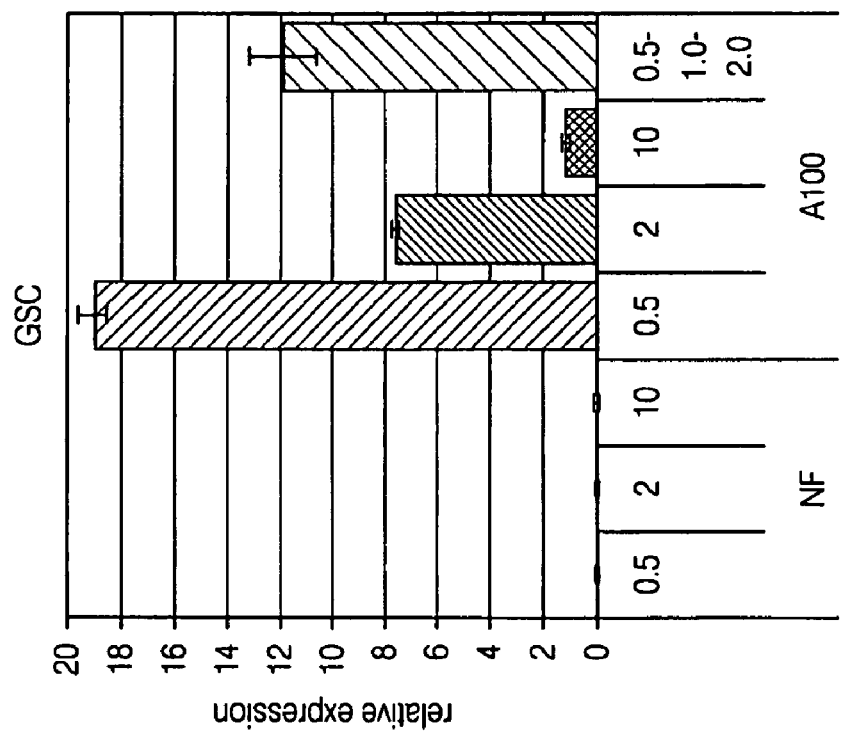
Figure 27A:
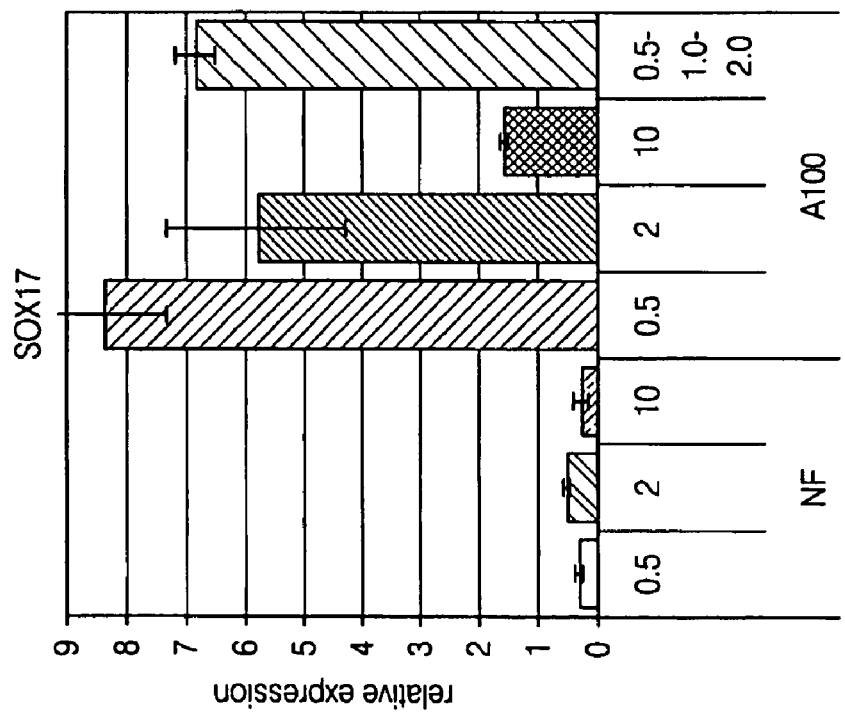

The expression levels of CXCR4 varied dramatically across the 7 culture conditions used (FIG. 26). In general, CXCR4 expression was high in activin A treated cultures (A100) and low in those which did not receive exogenous activin A (NF). In addition, among the A100 treated cultures, CXCR4 expression was highest when FBS concentration was lowest. There was a remarkable decrease in CXCR4 level in the 10% FBS condition such that the relative expression was more in line with the conditions that did not receive activin A (NF).

As described above, expression of the SOX17, GSC, MIXL1, and HNF3β genes is consistent with the characterization of a cell as definitive endoderm. The relative expression of these four genes across the 7 differentiation conditions mirrors that of CXCR4 (FIGS. 27A-D). This demonstrates that CXCR4 is also a marker of definitive endoderm.

Ectoderm and mesoderm lineages can be distinguished from definitive endoderm by their expression of various markers. Early mesoderm expresses the genes Brachyury and MOX1 while nascent neuro-ectoderm expresses SOX1 and ZIC1. FIGS. 28A-D demonstrate that the cultures which did not receive exogenous activin A were preferentially enriched for mesoderm and ectoderm gene expression and that among the activin A treated cultures, the 10% FBS condition also had increased levels of mesoderm and ectoderm marker expression. These patterns of expression were inverse to that of CXCR4 and indicated that CXCR4 was not highly expressed in mesoderm or ectoderm derived from hESCs at this developmental time period.

Figure 28B:
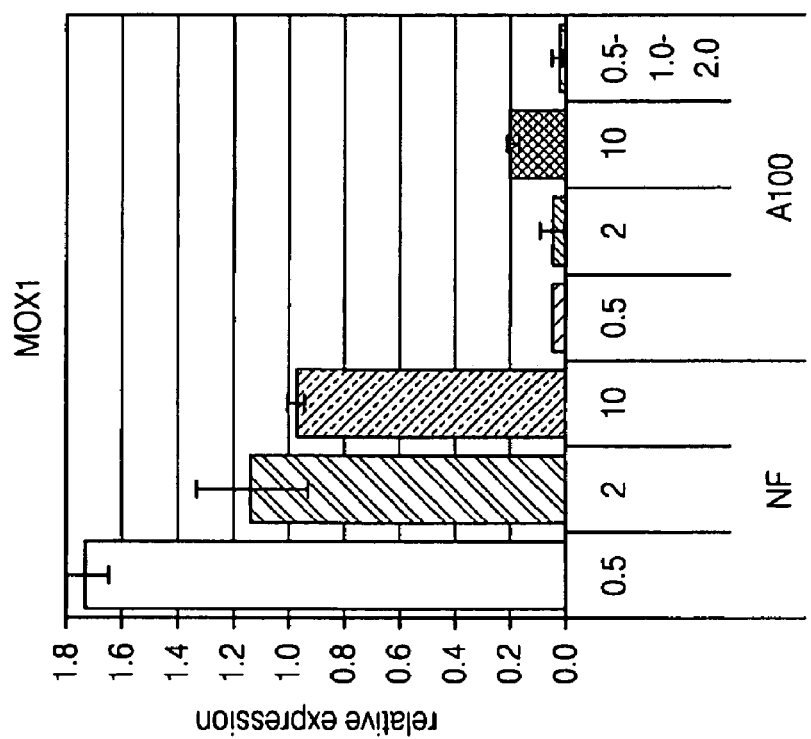
FIGS. 28A-E are bar charts showing how markers for mesoderm (BRACHYURY, MOX1), ectoderm (SOX1, ZIC1) and visceral endoderm (SOX7) exhibit an inverse relationship to CXCR4 expression across the same treatments displayed in FIG. 26.
Figure 28A:
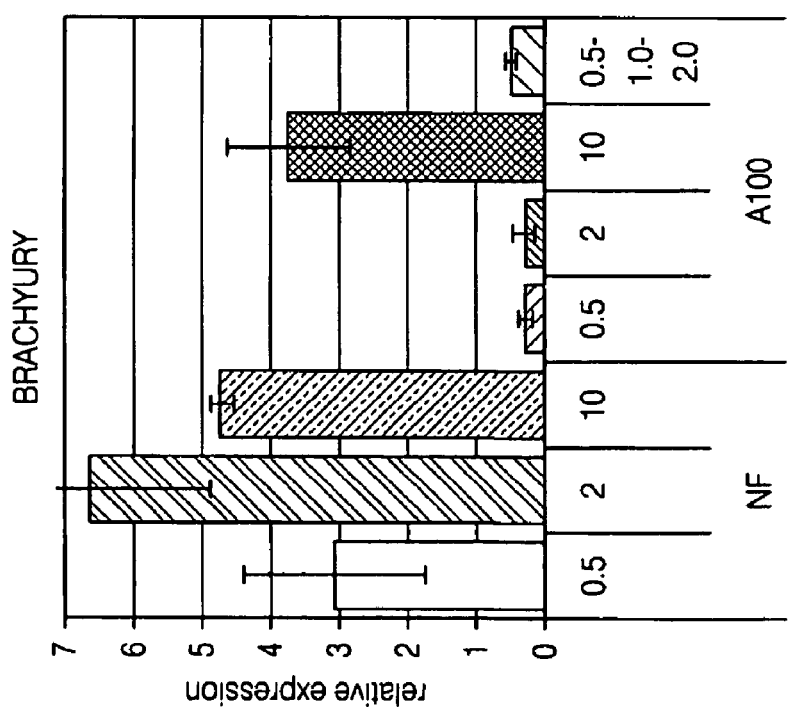
Figure 28D:
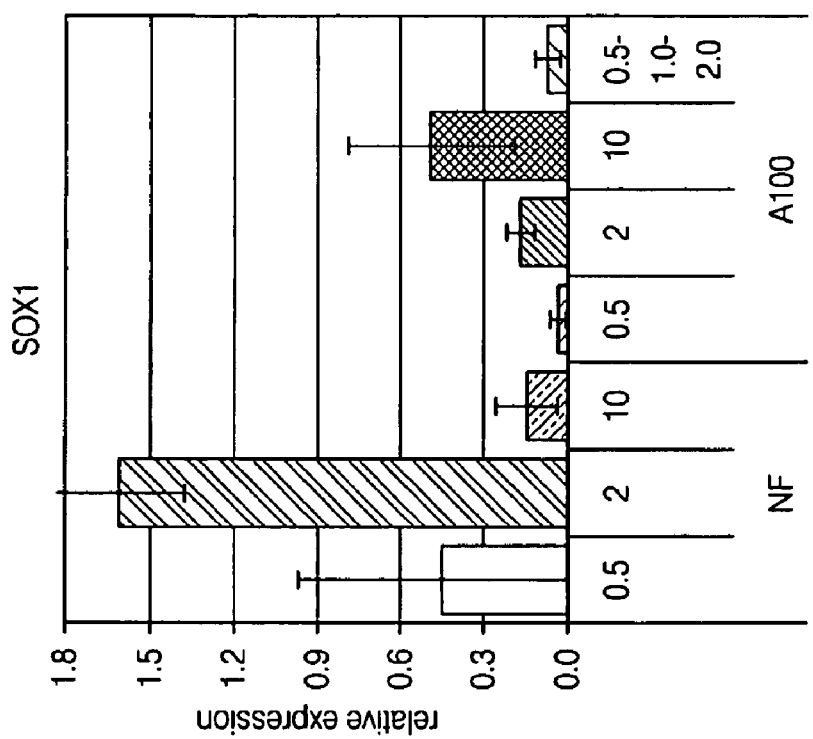
Figure 28C:
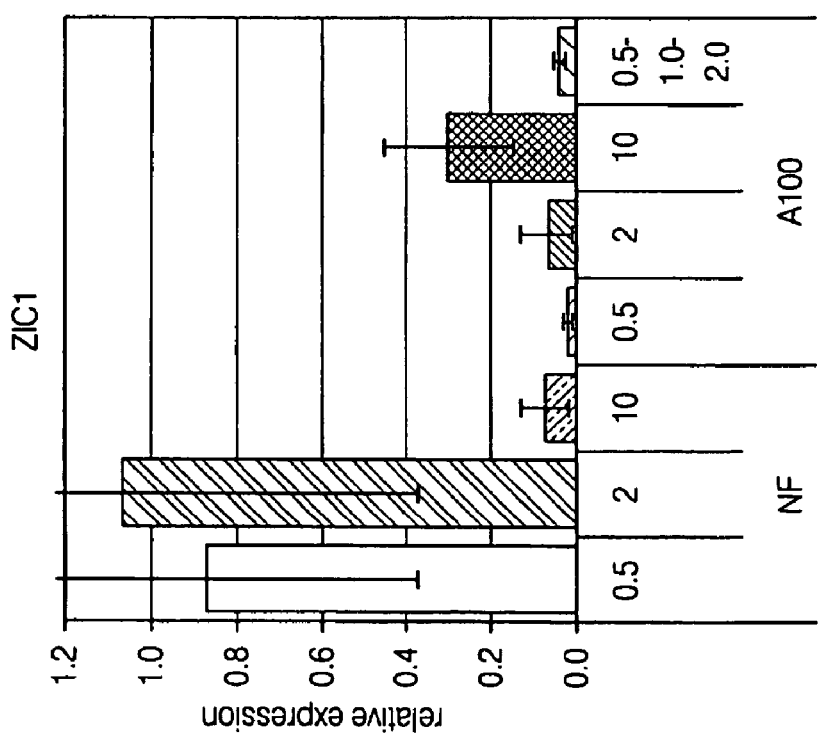
Figure 28E:
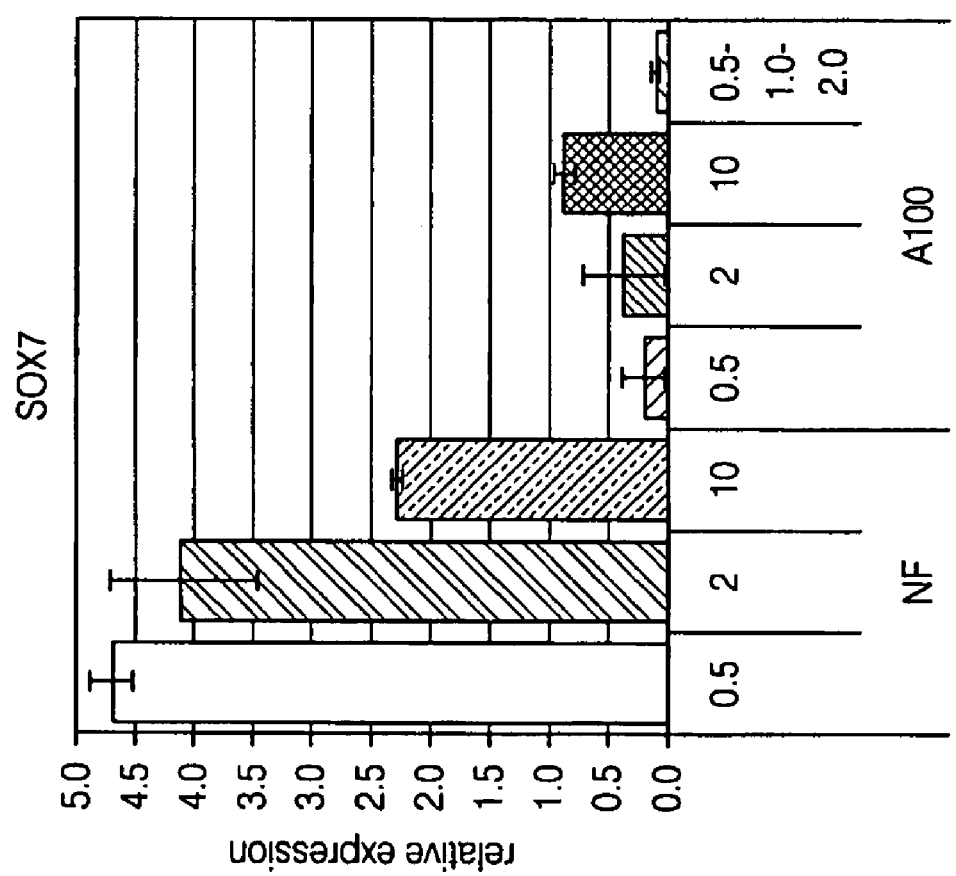

Early during mammalian development, differentiation to extra-embryonic lineages also occurs. Of particular relevance here is the differentiation of visceral endoderm that shares the expression of many genes in common with definitive endoderm, including SOX17. To distinguish definitive endoderm from extra-embryonic visceral endoderm one should examine a marker that is distinct between these two. SOX7 represents a marker that is expressed in the visceral endoderm but not in the definitive endoderm lineage. Thus, culture conditions that exhibit robust SOX17 gene expression in the absence of SOX7 expression are likely to contain definitive and not visceral endoderm. It is shown in FIG. 28E that SOX7 was highly expressed in cultures that did not receive activin A, SOX7 also exhibited increased expression even in the presence of activin A when FBS was included at 10%. This pattern is the inverse of the CXCR4 expression pattern and suggests that CXCR4 is not highly expressed in visceral endoderm.

Figure 29:
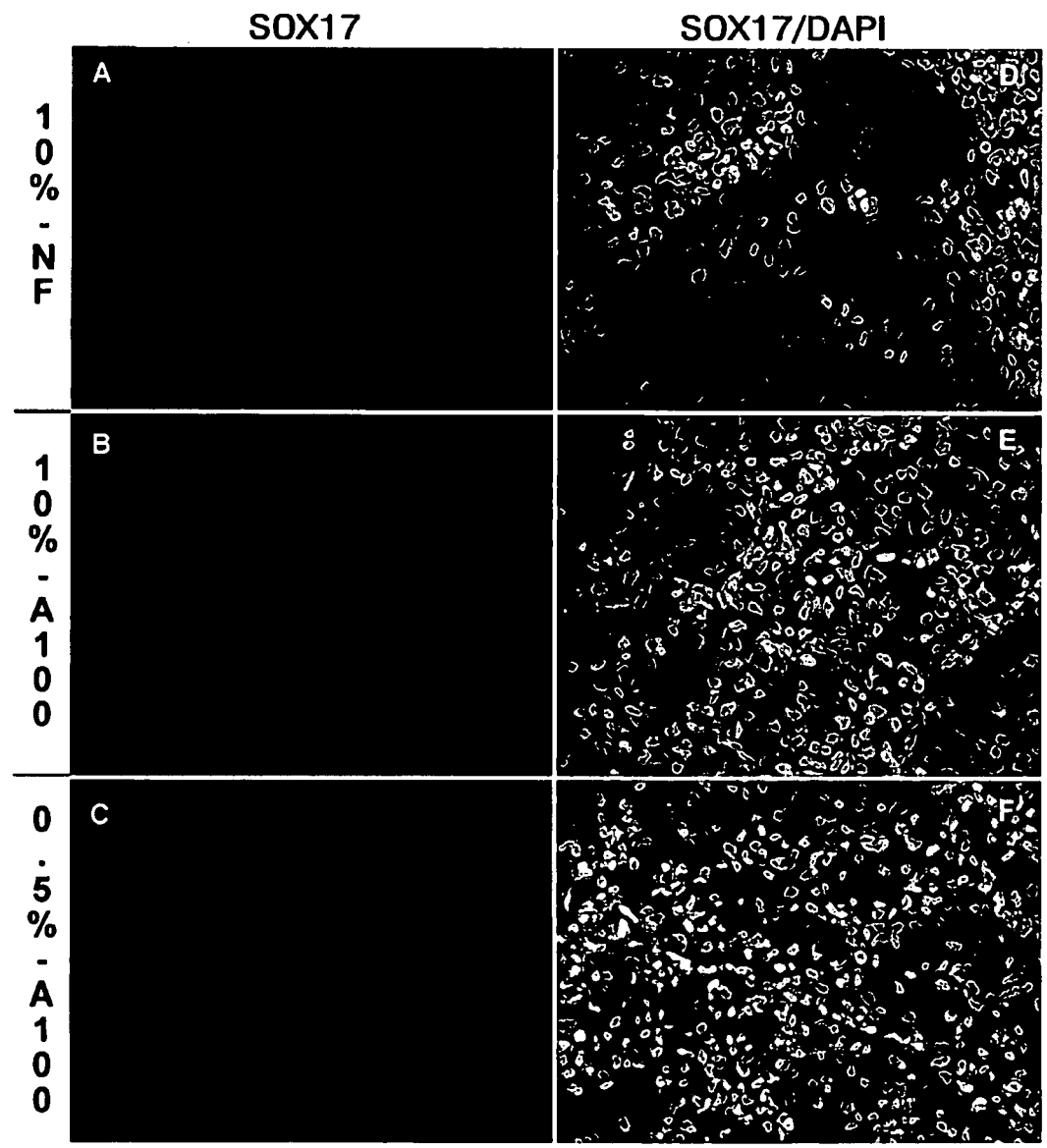
FIGS. 29A-F are micrographs that show the relative difference in SOX17 immunoreactive cells across three of the media conditions displayed in FIGS. 26-28.

The relative number of SOX17 immunoreactive (SOX17$^+$) cells present in each of the differentiation conditions mentioned above was also determined. When hESCs were differentiated in the presence of high dose activin A and low FBS concentration (0.5%-2.0%) SOX17$^+$ cells were ubiquitously distributed throughout the culture. When high dose activin A was used but FBS was included at 10% (v/v), the SOX17$^+$ cells appeared at much lower frequency and always appeared in isolated clusters rather than evenly distributed throughout the culture (FIGS. 29A and C as well as B and E). A further decrease in SOX17$^+$ cells was seen when no exogenous activin A was used. Under these conditions the SOX17$^+$ cells also appeared in clusters and these clusters were smaller and much more rare than those found in the high activin A, low FBS treatment (FIGS. 29 C and F). These results demonstrate that the CXCR4 expression patterns not only correspond to definitive endoderm gene expression but also to the number of definitive endoderm cells in each condition.

Example 8

Differentiation Conditions that Enrich for Definitive Endoderm Increase the Proportion of CXCR4 Positive Cells The dose of activin A also effects the efficiency at which definitive endoderm can be derived from hESCs. This example demonstrates that increasing the dose of activin A increases the proportion of CXCR4$^+$ cells in the culture.

hESCs were differentiated in RPMI media supplemented with 0.5%-2% FBS (increased from 0.5% to 1.0% to 2.0% over the first 3 days of differentiation) and either 0, 10, or 100 ng/ml of activin A. After 7 days of differentiation the cells were dissociated in PBS without Ca$^{2+}$/Mg$^{2+}$ containing 2% FBS and 2 mM (EDTA) for 5 minutes at room temperature. The cells were filtered through 35 µm nylon filters, counted and pelleted. Pellets were resuspended in a small volume of 50% human serum/50% normal donkey serum and incubated for 2 minutes on ice to block non-specific antibody binding sites. To this, 1 µl of mouse anti-CXCR4 antibody (Abcam, cat# ab10403-100) was added per 50 µl (containing approximately 10$^5$ cells) and labeling proceeded for 45 minutes on ice. Cells were washed by adding 5 ml of PBS containing 2% human serum (buffer) and pelleted. A second wash with 5 ml of buffer was completed then cells were resuspended in 50 µl buffer per 10$^5$ cells. Secondary antibody (FITC conjugated donkey anti-mouse; Jackson ImmunoResearch, cat# 715-096-151) was added at 5 µg/ml final concentration and allowed to label for 30 minutes followed by two washes in buffer as above. Cells were resuspended at 5×10$^6$ cells/ml in buffer and analyzed and sorted using a FACS Vantage (Beckton Dickenson) by the staff at the flow cytometry core facility (The Scripps Research Institute). Cells were collected directly into RLT lysis buffer (Qiagen) for subsequent isolation of total RNA for gene expression analysis by real-time quantitative PCR.

Figure 30:
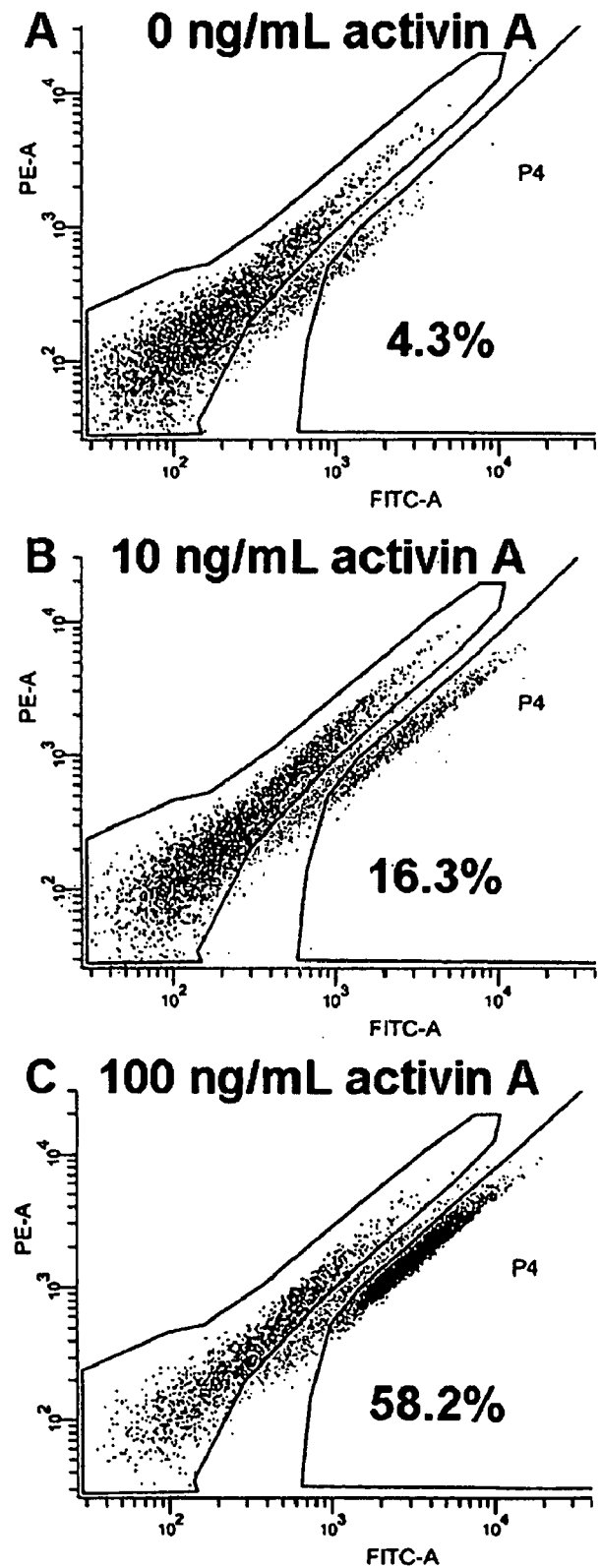
FIGS. 30A-C are flow cytometry dot plots that demonstrate the increase in CXCR4$^+$ cell number with increasing concentration of activin A added to the differentiation media.
Figure 31B:
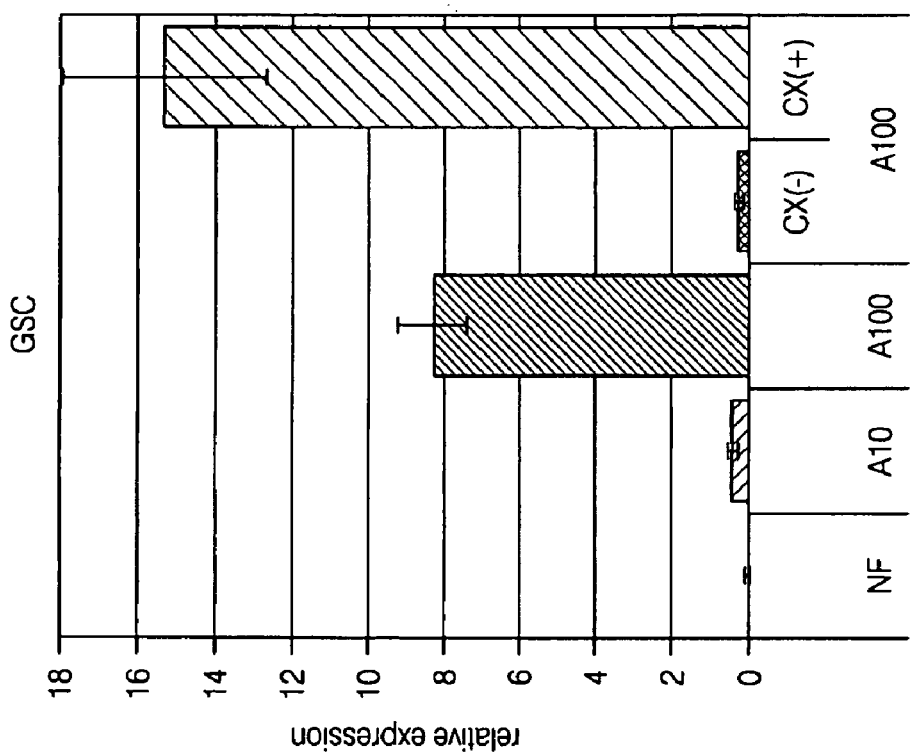
FIGS. 31A-D are bar charts that show the CXCR4$^+$ cells isolated from the high dose activin A treatment (A100-CX+) are even further enriched for definitive endoderm markers than the parent population (A100).
Figure 31A:
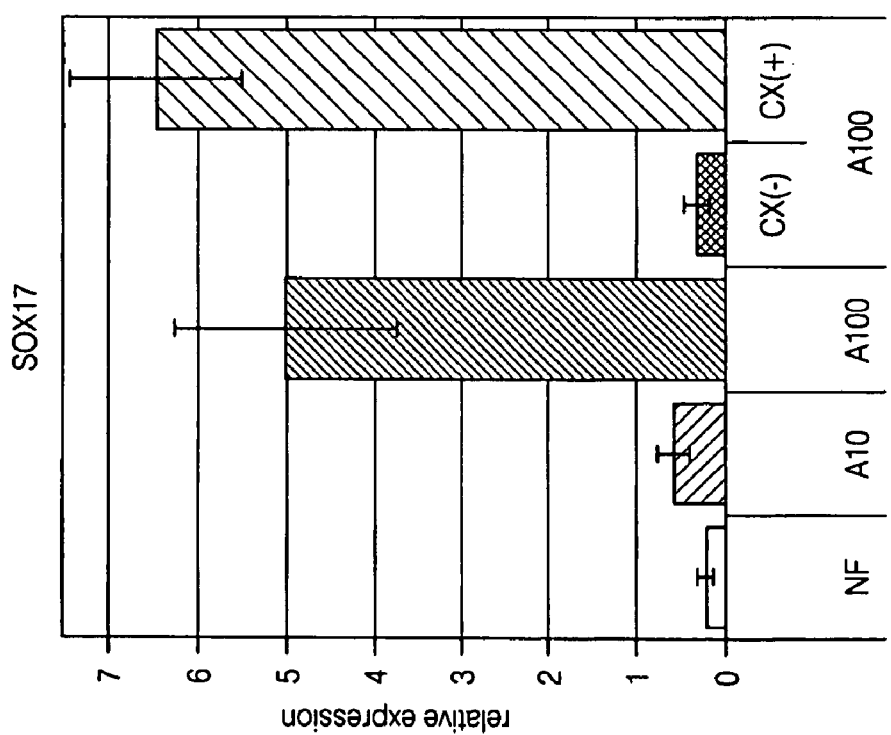
Figure 31D:
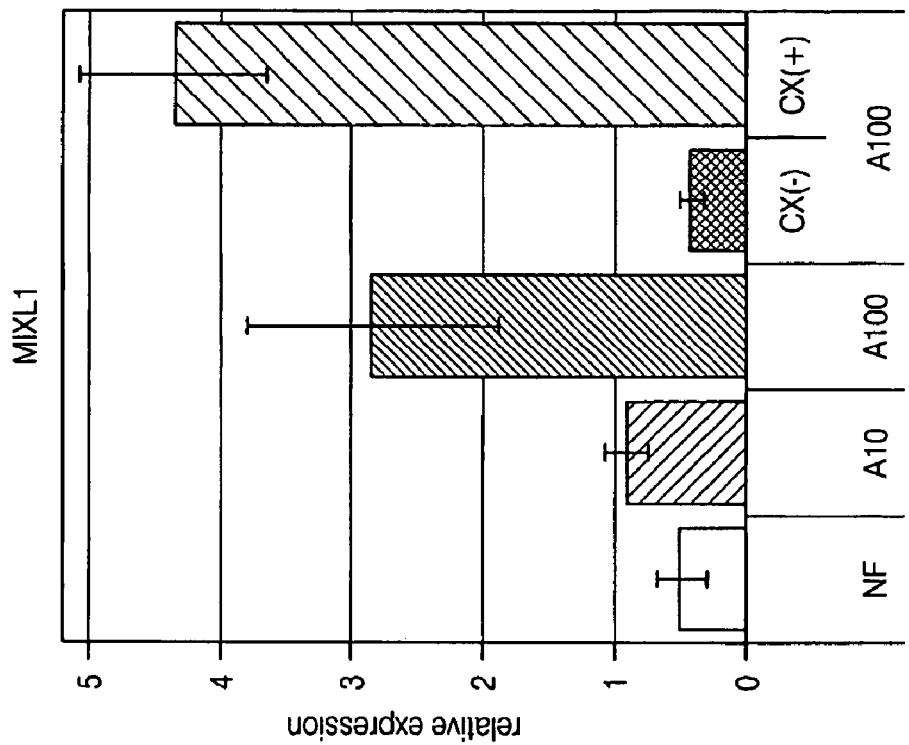
Figure 31C:
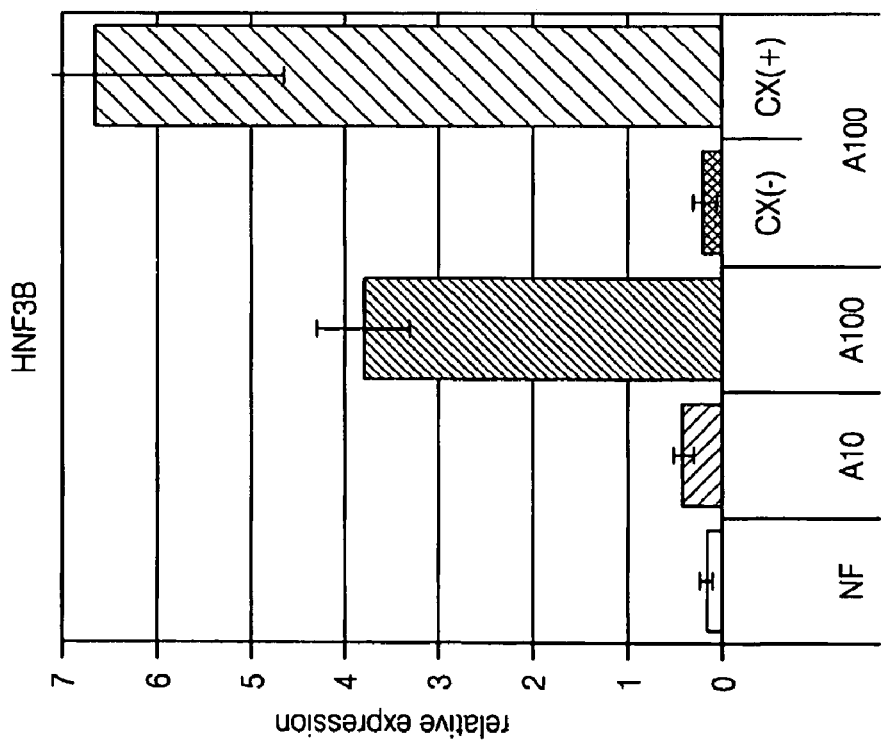

The number of CXCR4$^+$ cells as determined by flow cytometry were observed to increase dramatically as the dose of activin A was increased in the differentiation culture media (FIGS. 30A-C). The CXCR4$^+$ cells were those falling within the R4 gate and this gate was set using a secondary antibody-only control for which 0.2% of events were located in the R4 gate. The dramatically increased numbers of CXCR4$^+$ cells correlates with a robust increase in definitive endoderm gene expression as activin A dose is increased (FIGS. 31A-D).

Example 9

Isolation of CXCR4 Positive Cells Enriches for Definitive Endoderm Gene Expression and Depletes Cells Expressing Markers of Mesoderm, Ectoderm and Visceral Endoderm The CXCR4$^+$ and CXCR4$^-$ cells identified in Example 8 above were collected and analyzed for relative gene expression and the gene expression of the parent populations was determined simultaneously.

Figure 32:
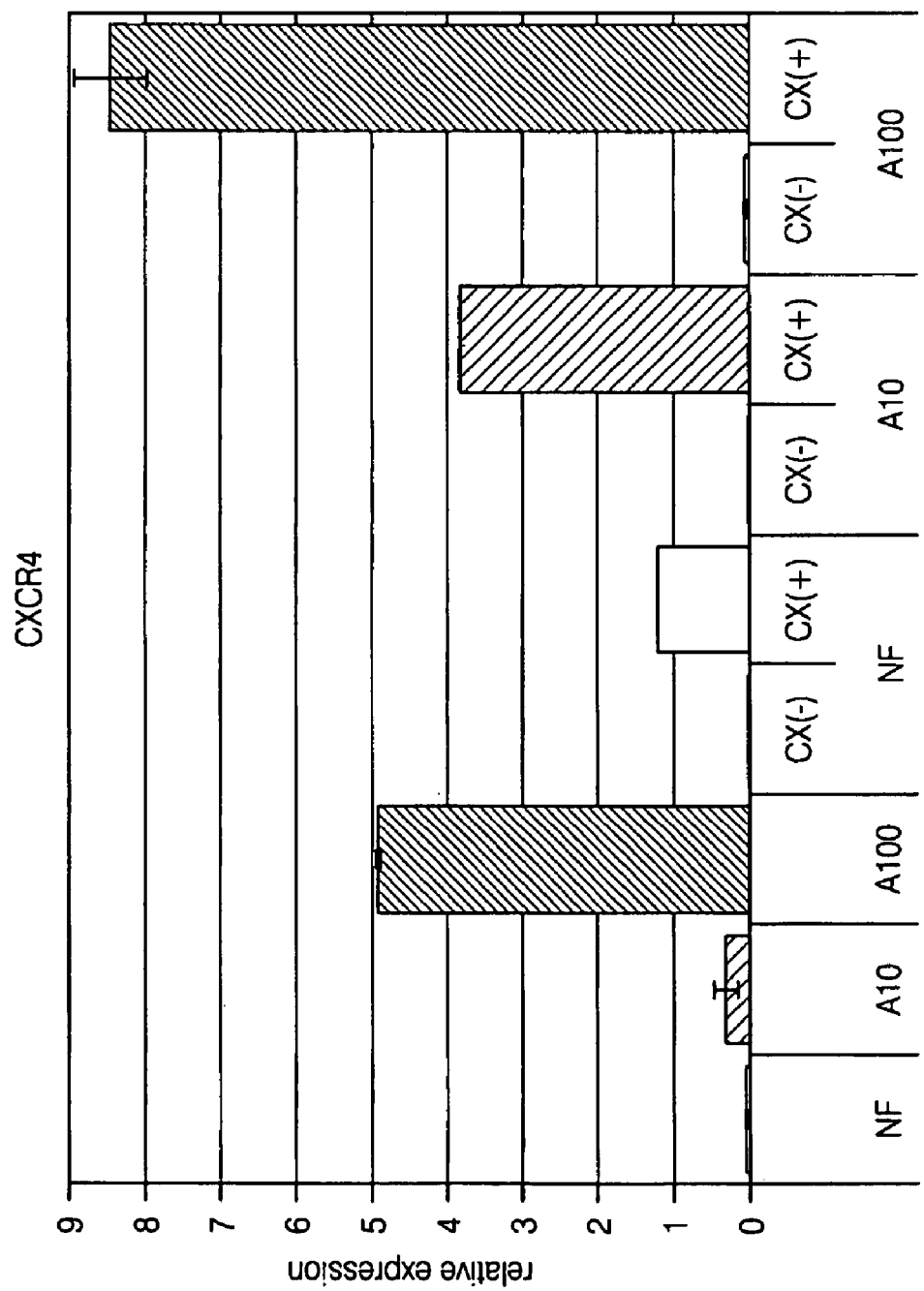
FIG. 32 is a bar chart showing gene expression from CXCR4$^+$ and CXCR4$^-$ cells isolated using fluorescence-activated cell sorting (FACS) as well as gene expression in the parent populations. This demonstrates that the CXCR4$^+$ cells contain essentially all the CXCR4 gene expression present in each parent population and the CXCR4$^-$ populations contain very little or no CXCR4 gene expression.
Figure 33B:
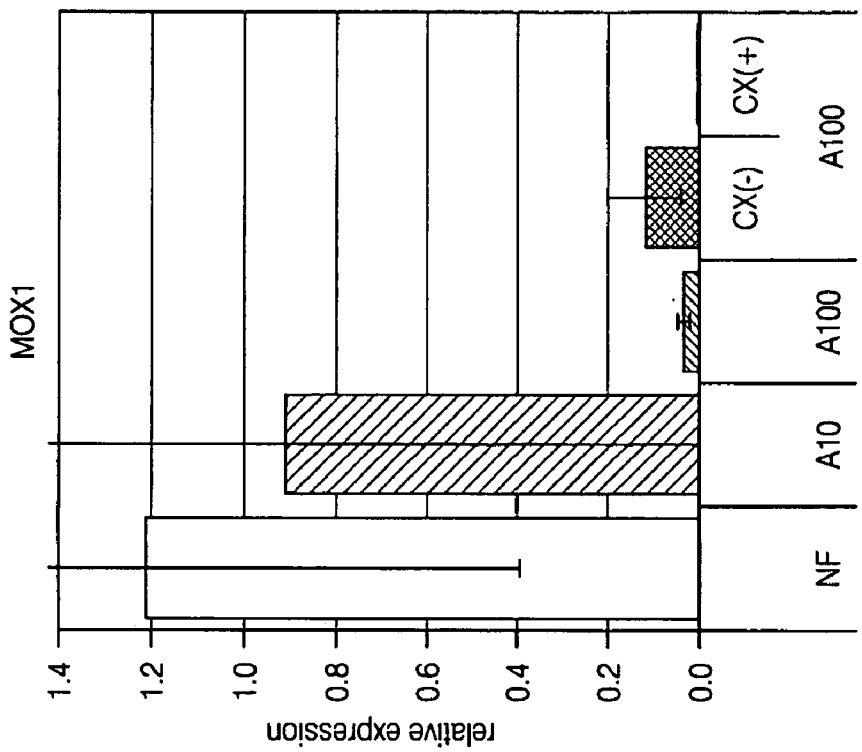
FIGS. 33A-D are bar charts that demonstrate the depletion of mesoderm (BRACHYURY, MOX1), ectoderm (ZIC1) and visceral endoderm (SOX7) gene expression in the CXCR4+ cells isolated from the high dose activin A treatment which is already suppressed in expression of these non-definitive endoderm markers.
Figure 33A:
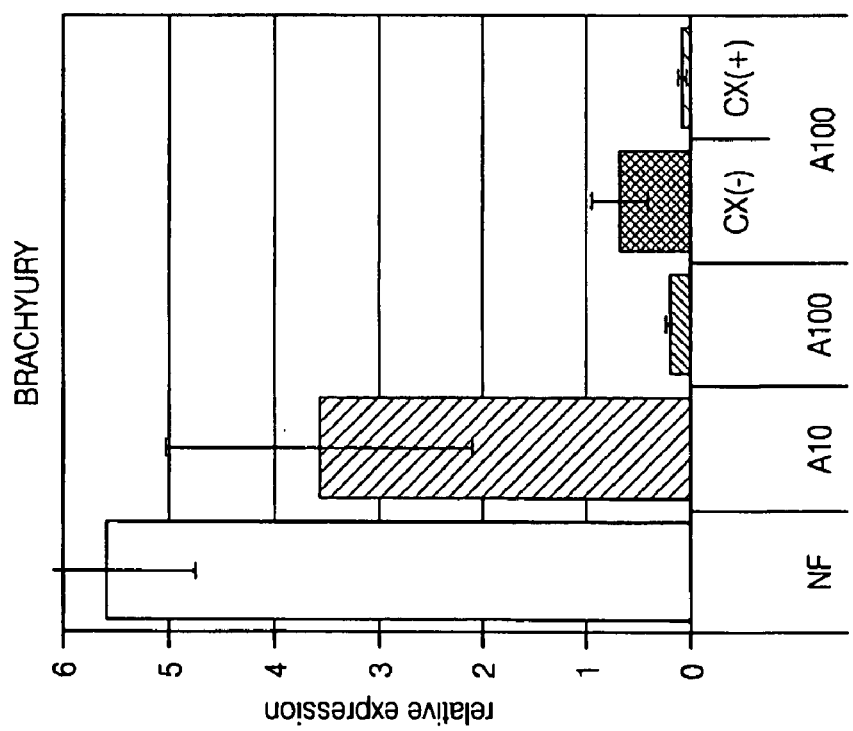
Figure 33D:
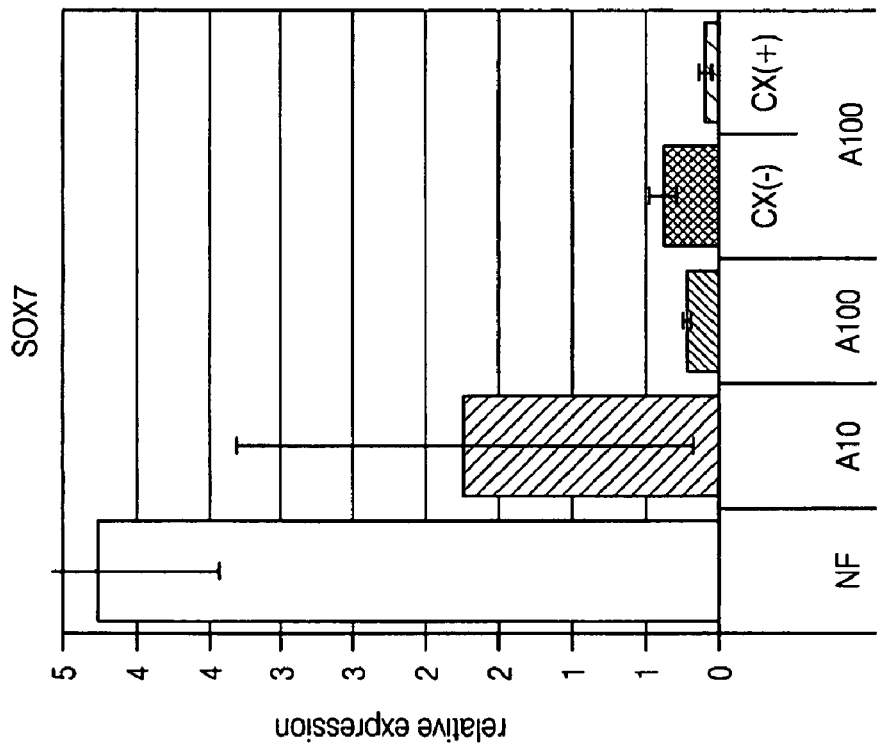
Figure 33C:
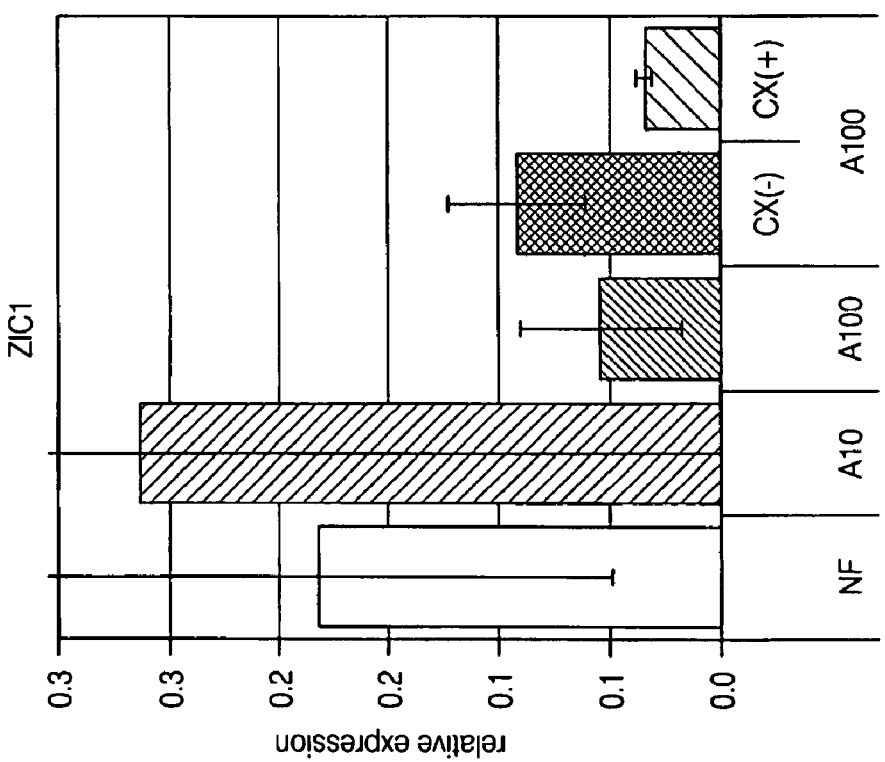

The relative levels of CXCR4 gene expression was dramatically increased with increasing dose of activin A (FIG. 32). This correlated very well with the activin A dose-dependent increase of CXCR4$^+$ cells (FIGS. 30A-C). It is also clear that isolation of the CXCR4$^+$ cells from each population accounted for nearly all of the CXCR4 gene expression in that population. This demonstrates the efficiency of the FACS method for collecting these cells.

Gene expression analysis revealed that the CXCR4$^+$ cells contain not only the majority of the CXCR4 gene expression, but they also contained gene expression for other markers of definitive endoderm. As shown in FIGS. 31A-D, the CXCR4$^+$ cells were further enriched over the parent A100 population for SOX17, GSC, HNF3B, and MIXL1. In addition, the CXCR4$^-$ fraction contained very little gene expression for these definitive endoderm markers. Moreover, the CXCR4$^+$ and CXCR4$^-$ populations displayed the inverse pattern of gene expression for markers of mesoderm, ectoderm and extra-embryonic endoderm. FIGS. 33A-D shows that the CXCR4$^+$ cells were depleted for gene expression of Brachyury, MOX1, ZIC1, and SOX7 relative to the A100 parent population This A100 parent population was already low in expression of these markers relative to the low dose or no activin A conditions. These results show that the isolation of CXCR4$^+$ cells from hESCs differentiated in the presence of high activin A yields a population that is highly enriched for and substantially pure definitive endoderm.

Example 10

Quantitation of Definitive Endoderm Cells in a Cell Population Using CXCR4

To confirm the quantitation of the proportion of definitive endoderm cells present in a cell culture or cell population as determined previously herein and as determined in U.S. Provisional Patent Application No. 60/532,004, entitled DEFINITIVE ENDODERM, filed Dec. 23, 2003, the disclosure of which is incorporated herein by reference in its entirety, cells expressing CXCR4 and other markers of definitive endoderm were analyzed by FACS.

Using the methods such as those described in the above Examples, hESCs were differentiated to produce definitive endoderm. In particular, to increase the yield and purity in differentiating cell cultures, the serum concentration of the medium was controlled as follows: 0.2% FBS on day 1, 1.0%

FBS on day 2 and 2.0% FBS on days 3-6. Differentiated cultures were sorted by FACS using three cell surface epitopes, E-Cadherin, CXCR4, and Thrombomodulin. Sorted cell populations were then analyzed by Q-PCR to determine relative expression levels of markers for definitive and extraembryonic-endoderm as well as other cell types. CXCR4 sorted cells taken from optimally differentiated cultures resulted in the isolation of definitive endoderm cells that were >98% pure.

Table 2 shows the results of a marker analysis for a definitive endoderm culture that was differentiated from hESCs using the methods described herein.

TABLE 2

Composition of Definitive Endoderm Cultures

| Marker(s) | Percent of culture | Percent Definitive Endoderm | Percent Extraembryonic endoderm | Percent hES cells |
|---|---|---|---|---|
| SOX17 | 70-80 | 100 | | |
| Thrombomodulin | <2 | 0 | 75 | |
| AFP | <1 | 0 | 25 | |
| CXCR4 | 70-80 | 100 | 0 | |
| ECAD | 10 | 0 | | 100 |
| other (ECAD neg.) | 10-20 | | | |
| Total | 100 | 100 | 100 | 100 |

In particular, Table 2 indicates that CXCR4 and SOX17 positive cells (endoderm) comprised from 70%-80% of the cells in the cell culture. Of these SOX17-expressing cells, less than 2% expressed TM (parietal endoderm) and less than 1% expressed AFP (visceral endoderm). After subtracting the proportion of TM-positive and AFP-positive cells (combined parietal and visceral endoderm; 3% total) from the proportion of SOX17/CXCR4 positive cells, it can be seen that about 67% to about 77% of the cell culture was definitive endoderm. Approximately 10% of the cells were positive for E-Cadherin (ECAD), which is a marker for hESCs, and about 10-20% of the cells were of other cell types.

We have discovered that the purity of definitive endoderm in the differentiating cell cultures that are obtained prior to FACS separation can be improved as compared to the above-described low serum procedure by maintaining the FBS concentration at ≦0.5% throughout the 5-6 day differentiation procedure. However, maintaining the cell culture at ≦0.5% throughout the 5-6 day differentiation procedure also results in a reduced number of total definitive endoderm cells that are produced.

Definitive endoderm cells produced by methods described herein have been maintained and expanded in culture in the presence of activin for greater than 50 days without appreciable differentiation. In such cases, SOX17, CXCR4, MIXL1, GATA4, HNF3β expression is maintained over the culture period. Additionally, TM, SPARC, OCT4, AFP, SOX7, ZIC1 and BRACH were not detected in these cultures. It is likely that such cells can be maintained and expanded in culture for substantially longer than 50 days without appreciable differentiation.

Example 11

Additional Markers of Definitive Endoderm Cells

In the following experiment, RNA was isolated from purified definitive endoderm and human embryonic stem cell populations. Gene expression was then analyzed by gene chip analysis of the RNA from each purified population. Q-PCR was also performed to further investigate the potential of genes expressed in definitive endoderm, but not in embryonic stem cells, as a marker for definitive endoderm.

Human embryonic stem cells (hESCs) were maintained in DMEM/F12 media supplemented with 20% KnockOut Serum Replacement, 4 ng/ml recombinant human basic fibroblast growth factor (bFGF), 0.1 mM 2-mercaptoethanol, L-glutamine, non-essential amino acids and penicillin/streptomycin. hESCs were differentiated to definitive endoderm by culturing for 5 days in RPMI media supplemented with 100 ng/ml of recombinant human activin A, fetal bovine serum (FBS), and penicillin/streptomycin. The concentration of FBS was varied each day as follows: 0.1% (first day), 0.2% (second day), 2% (days 3-5).

Cells were isolated by fluorescence activated cell sorting (FACS) in order to obtain purified populations of hESCs and definitive endoderm for gene expression analysis. Immunopurification was achieved for hESCs using SSEA4 antigen (R&D Systems, cat# FAB1435P) and for definitive endoderm using CXCR4 (R&D Systems, cat# FAB170P). Cells were dissociated using trypsin/EDTA (Invitrogen, cat# 25300-054), washed in phosphate buffered saline (PBS) containing 2% human serum and resuspended in 100% human serum on ice for 10 minutes to block non-specific binding. Staining was carried out for 30 minutes on ice by adding 200 μl of phycoerythrin-conjugated antibody to $5 \times 10^6$ cells in 800 μl human serum. Cells were washed twice with 8 ml of PBS buffer and resuspended in 1 ml of the same. FACS isolation was carried out by the core facility of The Scripps Research Institute using a FACSVantage (BD Biosciences). Cells were collected directly into RLT lysis buffer and RNA was isolated by RNeasy according to the manufacturers instructions (Qiagen).

Purified RNA was submitted in duplicate to Expression Analysis (Durham, N.C.) for generation of the expression profile data using the Affymetrix platform and U133 Plus 2.0 high-density oligonucleotide arrays. Data presented is a group comparison that identifies genes differentially expressed between the two populations, hESCs and definitive endoderm. Genes that exhibited a robust upward change in expression level over that found in hESCs were selected as new candidate markers that are highly characteristic of definitive endoderm. Select genes were assayed by Q-PCR, as described above, to verify the gene expression changes found on the gene chip and also to investigate the expression pattern of these genes during a time course of hESC differentiation.

Figures 34A, 34B:
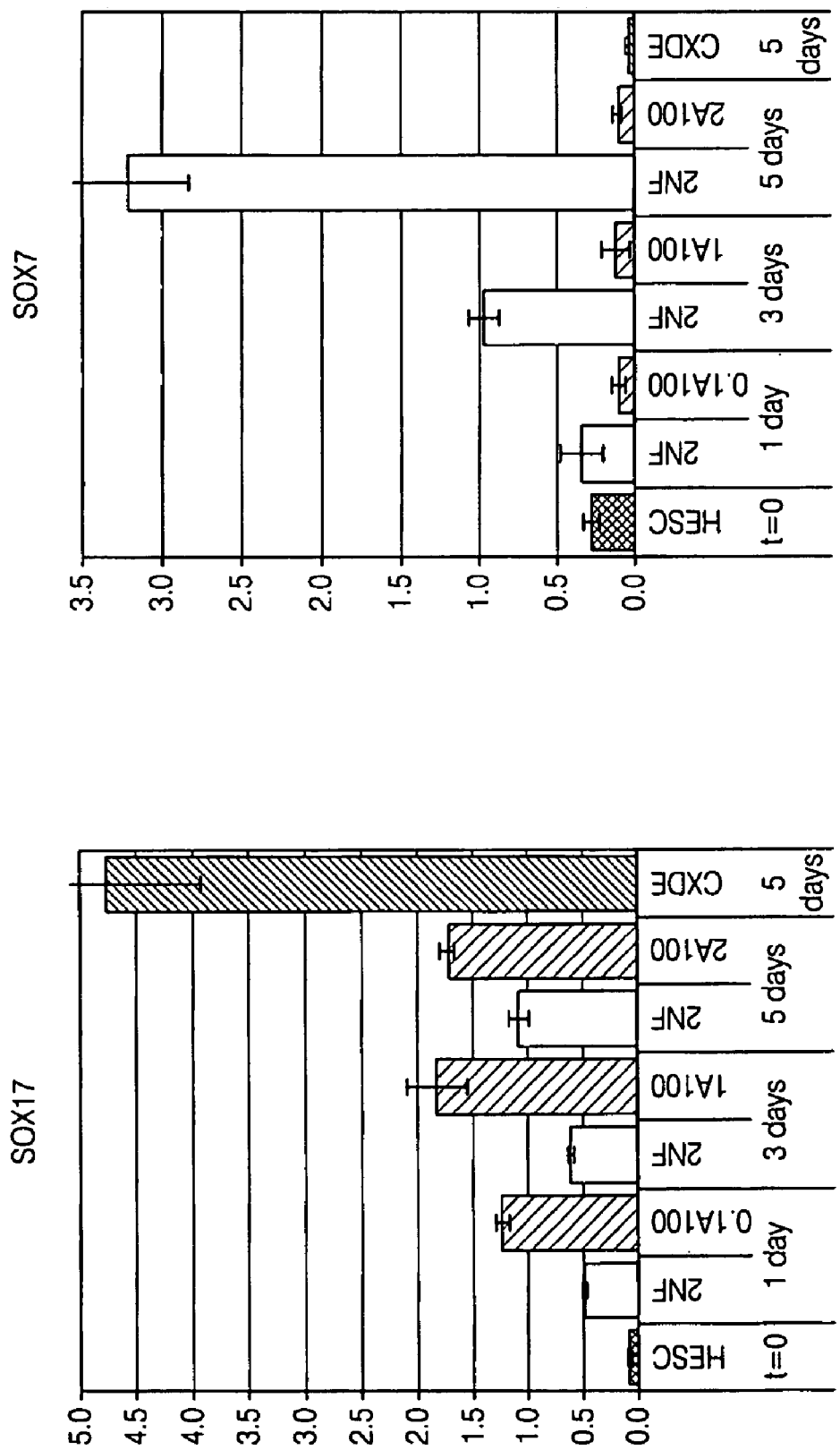
FIGS. 34A-M are bar charts showing the expression patterns of marker genes that can be used to identify definitive endoderm cells. The expression analysis of definitive endoderm markers, FGF17, VWF, CALCR, FOXQ1, CMKOR1 and CRIP1 is shown in panels G-L, respectively. The expression analysis of previously described lineage marking genes, SOX17, SOX7, SOX17/SOX7, TM, ZIC1, and MOX1 is shown in panels A-F, respectively. Panel M shows the expression analysis of CXCR4. With respect to each of panels A-M, the column labeled hESC indicates gene expression from purified human embryonic stem cells; 2NF indicates cells treated with 2% FBS, no activin addition; 0.1A100 indicates cells treated with 0.1% FBS, 100 ng/ml activin A; 1A100 indicates cells treated with 1% FBS, 100 ng/ml activin A; and 2A100 indicates cells treated with 2% FBS, 100 ng/ml activin A.
Figure 34D:
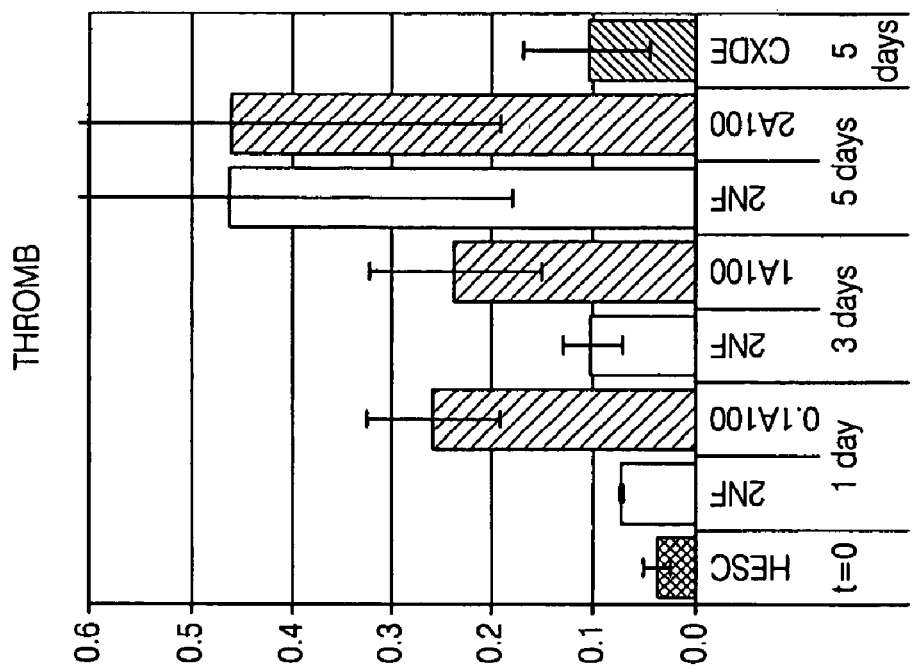
Figure 34C:
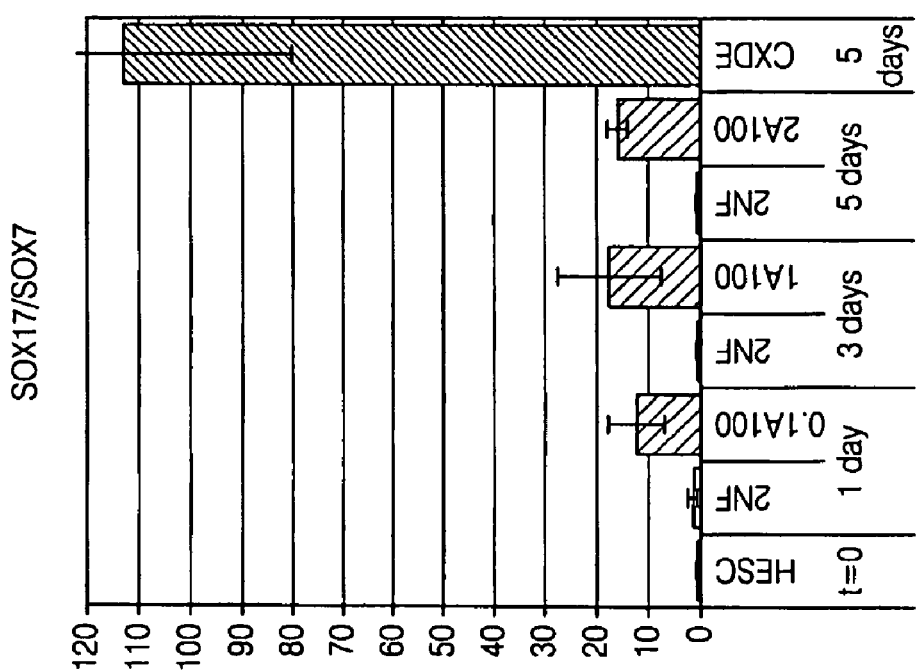
Figure 34F:
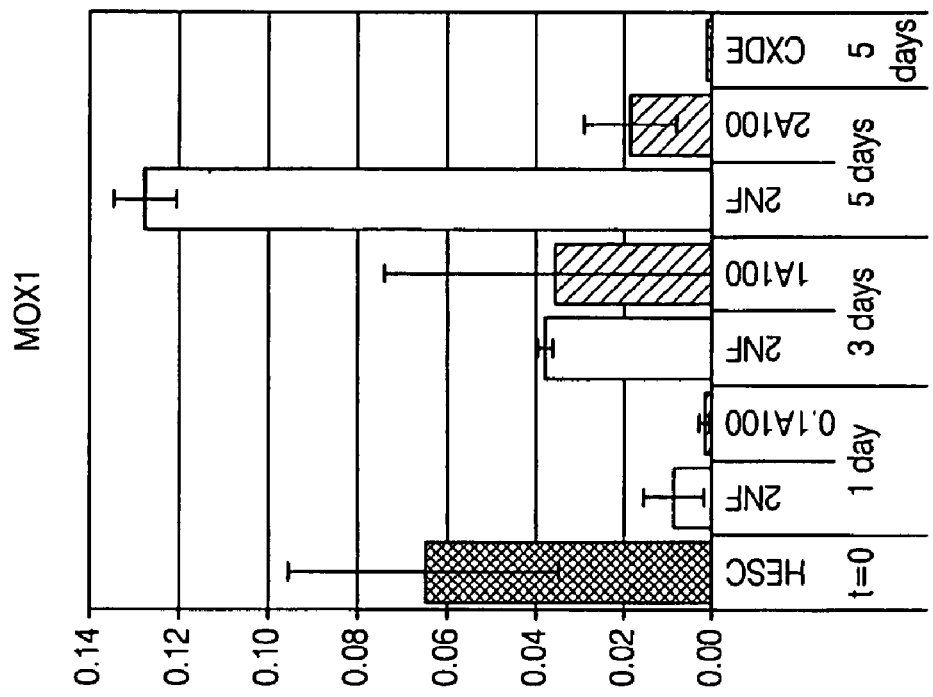
Figure 34E:
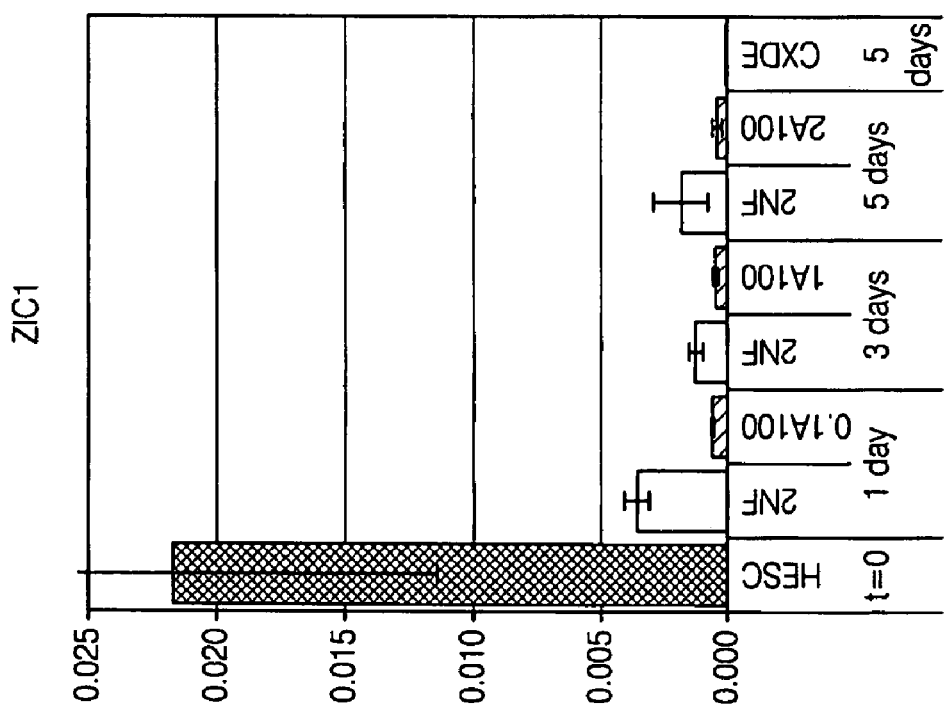
Figure 34G:
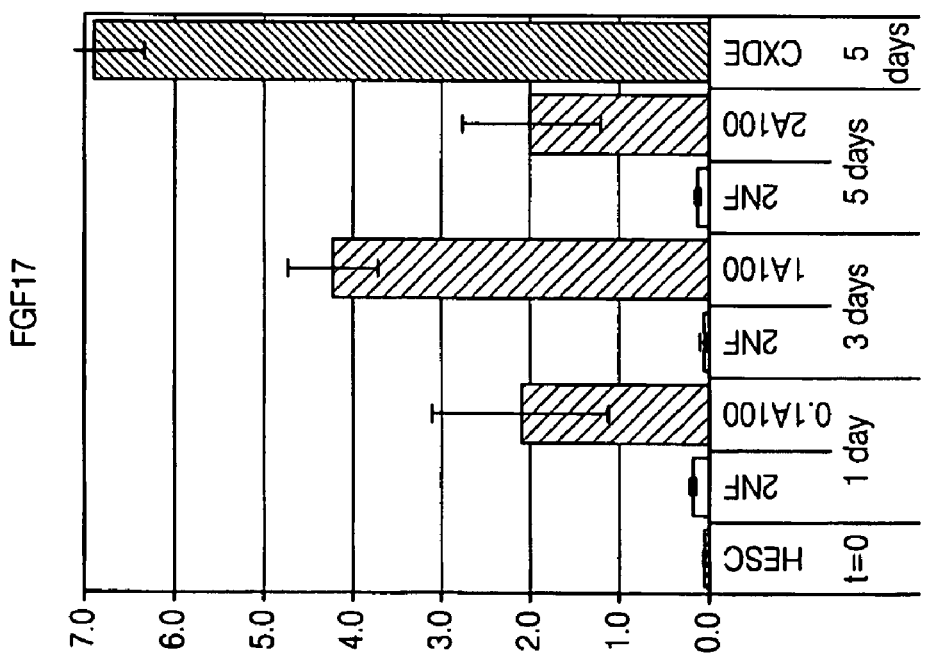
Figure 34H:
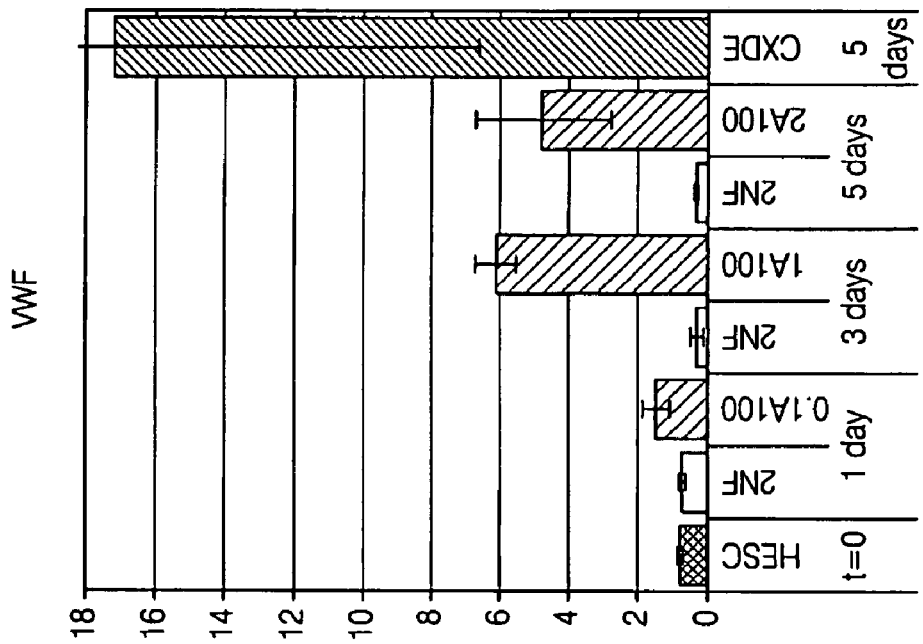
Figure 34J:
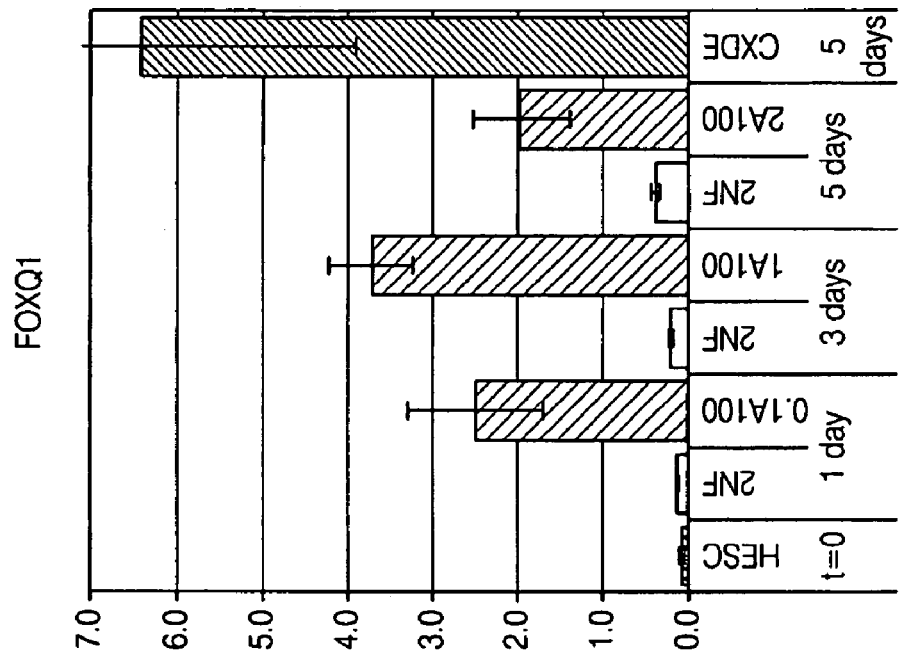
Figure 34I:
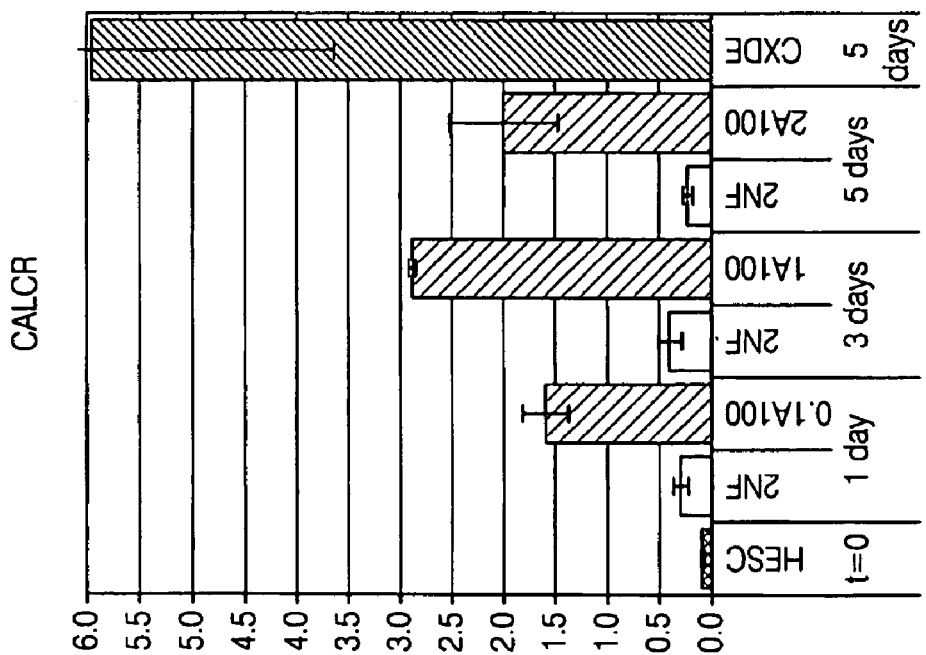
Figure 34L:
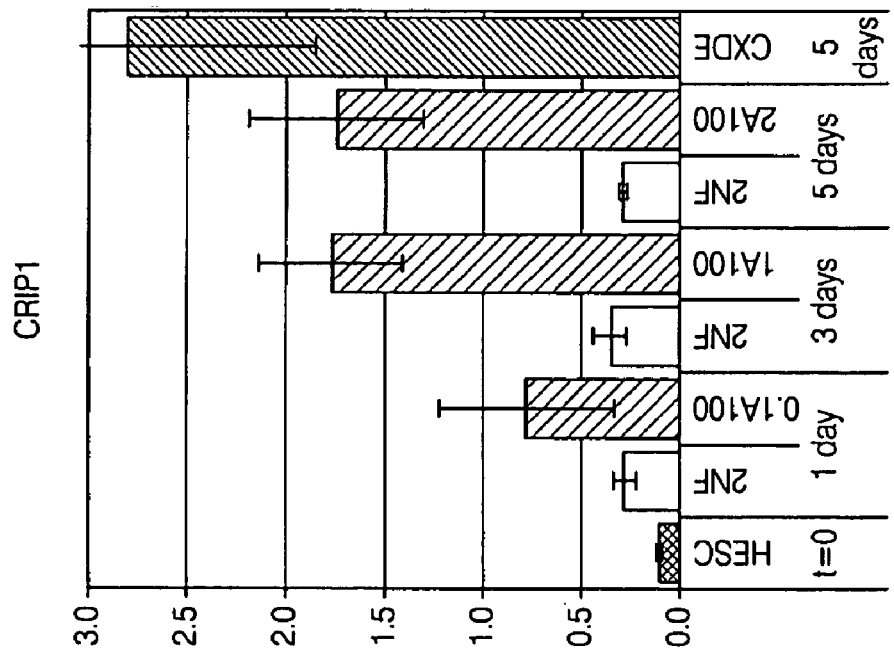
Figure 34K:
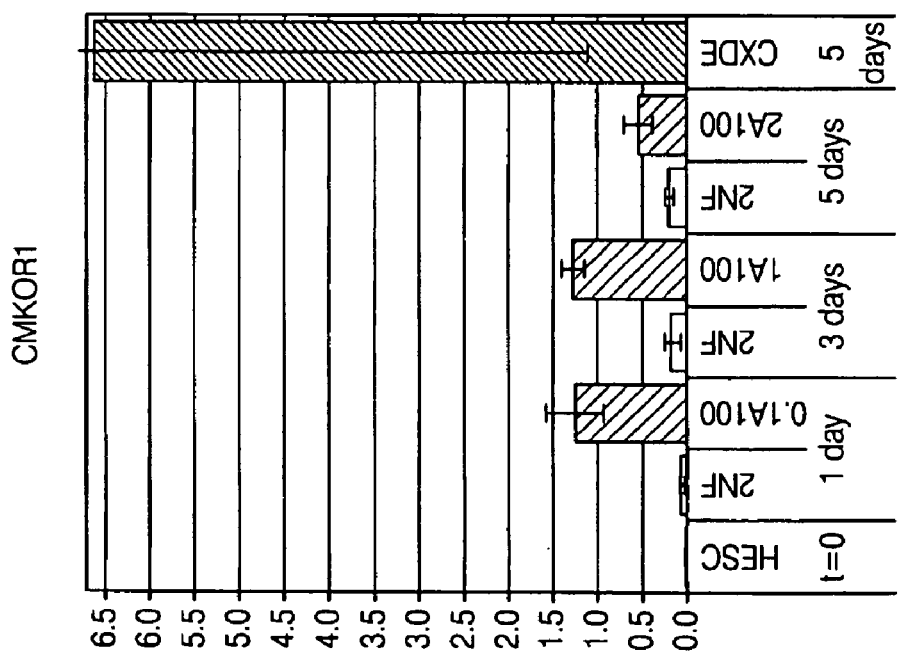
Figure 34M:
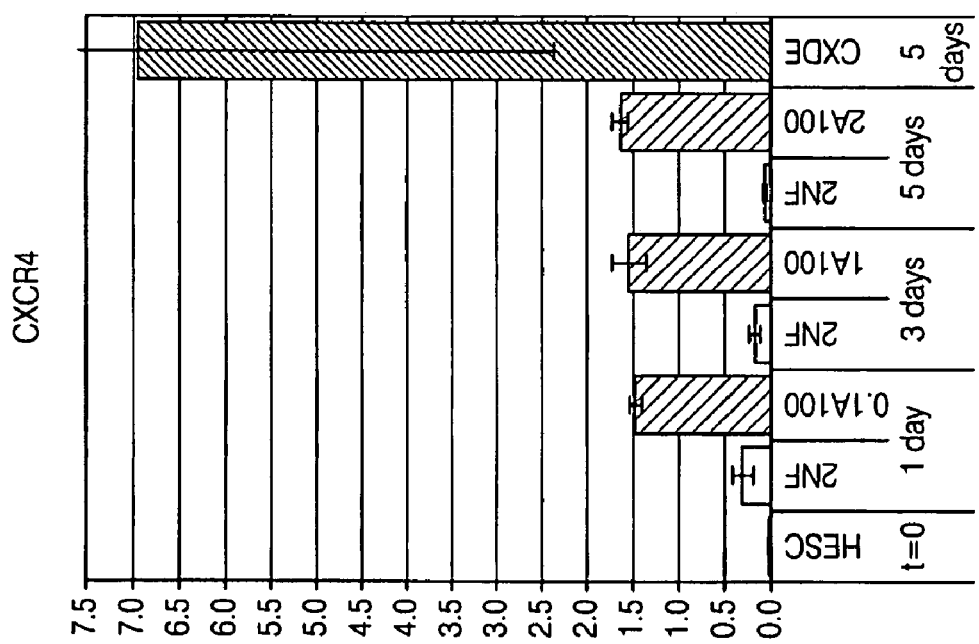

FIGS. 34A-M show the gene expression results for certain markers. Results are displayed for cell cultures analyzed 1, 3 and 5 days after the addition of 100 ng/ml activin A, CXCR4-expressing definitive endoderm cells purified at the end of the five day differentiation procedure (CXDE), and in purified hESCs. A comparison of FIGS. 34C and G-M demonstrates that the six marker genes, FGF17, VWF, CALCR, FOXQ1, CMKOR1 and CRIP1, exhibit an expression pattern that is almost identical to each other and which is also identical to the pattern of expression of CXCR4 and the ratio of SOX17/SOX7. As described previously, SOX17 is expressed in both the definitive endoderm as well as in the SOX7-expressing extra-embryonic endoderm. Since SOX7 is not expressed in the definitive endoderm, the ratio of SOX17/SOX7 provides a reliable estimate of definitive endoderm contribution to the SOX17 expression witnessed in the population as a whole. The similarity of panels G-L and M to panel C indicates that FGF17, VWF, CALCR, FOXQ1, CMKOR1 and CRIP1 are likely markers of definitive endoderm and that they are not significantly expressed in extra-embryonic endoderm cells.

It will be appreciated that the Q-PCR results described herein can be further confirmed by ICC.

Example 12

Differentiation and Purification of Liver Precursor Cells

The ability to differentiate definitive endoderm into liver precursor cells and hepatocyte cells and to purify those cells was also studied. Previous reports have suggested that the DPP4 marker is present on all epithelia cells of the liver including both oval cells and SHPCs. (Menthena, A., et al., *Stem Cells,* 22, 1049-1061), which represent each of the cell types that reportedly can regenerate the liver. (Gordon, G., et al., (2000) *Am. J Pathol.* 157(3) 771-786). The inventors have now surprisingly discovered that DPP4 is expressed in liver precursor cells. The following example describes a method for producing DPP4$^+$ liver precursor cells from hESCs and further methods for enriching, isolating and/or purifying DPP4$^+$ liver precursor cells at various stages of development.

hESCs were differentiated to definitive endoderm by culturing for three days in RPMI media supplemented with 100 ng/ml of recombinant human activin A, concentrations of 0% FBS (first day), 0.2% FBS (second day), and 2% FBS (third day). On day three, BMP was added at 3 ng/ml and FGF10 was added at 50 ng/ml. After day three, the culture media was changed, and cells were cultured in RPMI media supplemented with 2% FBS, 3 ng/ml BMP, and 50 ng/ml FGF10. On day five, the culture media was changed to Connaught Medical Research Labs (CMRL) medium (Invitrogen, Carlsbad, Calif.) (see, Parker R. C., et al 1957 *N.Y. Acad. Sci.* 5:303, the disclosure of which is hereby expressly incorporated by reference in its entirety) supplemented with B27 (1 part B27 to 200 parts medium by volume—(1:200)) (Invitrogen, Carlsbad, Calif.), 3 ng/ml BMP, and 50 ng/ml FGF10.

On days 0, 3, 5, and 8, cell cultures were sorted by FACS using an anti-CD26 (DPP4) antibody. FIGS. 35A-L show the results of the FACS analysis. The percentage of DPP4$^+$ cells increased throughout the differentiation protocol described above. Only 3.4% of undifferentiated hESCs expressed the DPP4 marker, whereas 57.3% of cells on day 6 of the above differentiation protocol expressed DPP4, and 66.7% of cells on day 8 of the differentiation protocol expressed DPP4.

Figure 35:
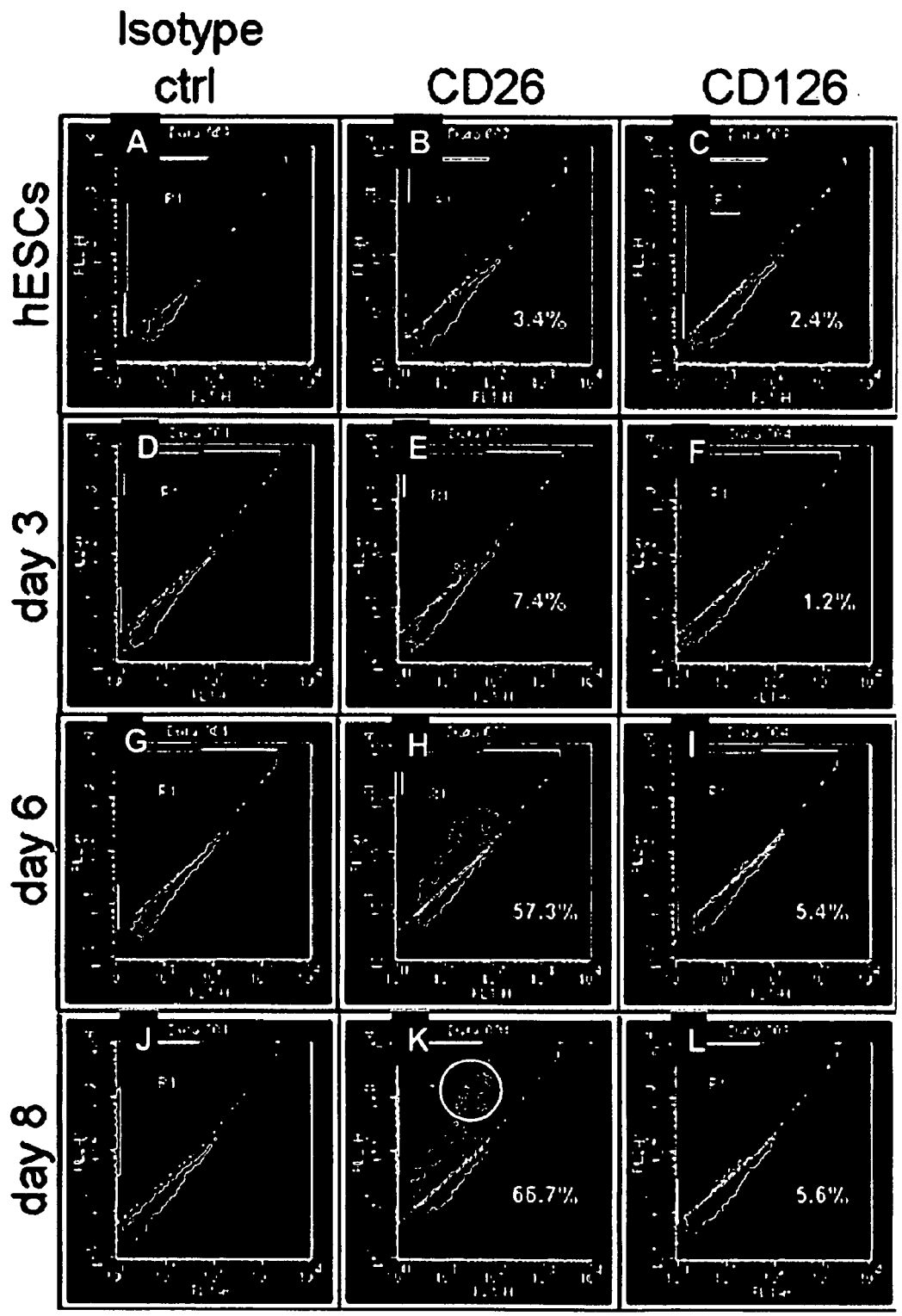
FIGS. 35A-L are flow cytometry dot plots that demonstrate the increase in DPP4$^+$ cell number over time when hESCs are treated with activin A added to the differentiation media for 3 days, followed by treatment with BMP4 and FGF10 until the cells were analyzed using fluorescence activated cell sorting (FACS) at the indicated times (i.e., 3 days, 6, days, 8 days). The circle demarks the cells that were collected for the gene expression analysis in FIG. 36.

To examine the gene expression pattern in differentiated cells, gene expression in DPP4$^+$ cells was compared to gene expression in DPP4$^-$ cells using Q-PCR as described in Example 5. Briefly, DPP4$^+$ cells were collected on day 8, (FIG. 35K, circle). A sample of differentiated cells that had not been sorted (parent), and a sample of cells that did not express DPP4 (DPP4$^-$, or CD26$^-$) cells were harvested. RNA was purified from the three cell samples using the RNeasy kit (Qiagen, Valencia, Calif.) according to the manufacturer's instructions. Quantification of mRNAs of the following markers was tested in each sample using Q-PCR: APOA1, APOA2, HNF4α, OCT4, PDX1 and CDX2. The gene expression results are presented in FIGS. 36A-F.

Figure 36C:
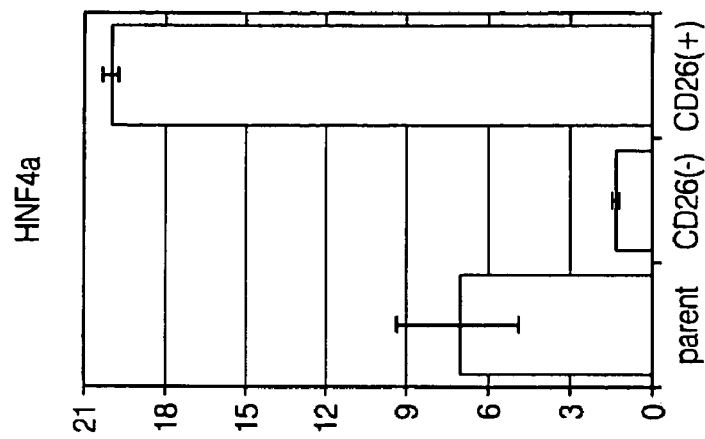
FIGS. 36A-F are bar charts depicting gene expression patterns from DPP4$^+$ and DPP4$^-$ cells isolated using FACS shown in FIG. 35, as well as gene expression in the parent populations.
Figure 36B:
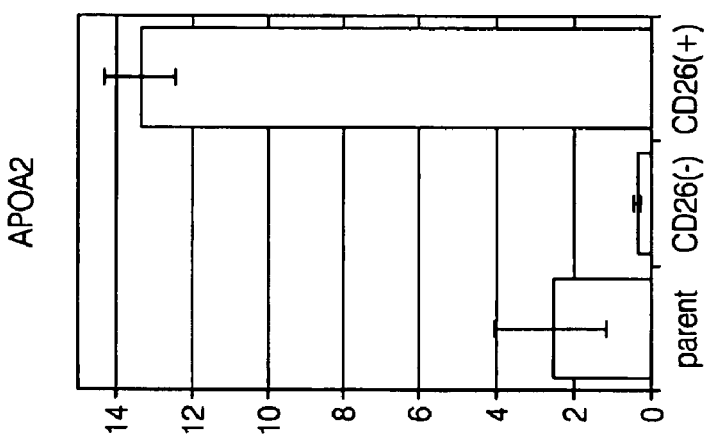
Figure 36A:
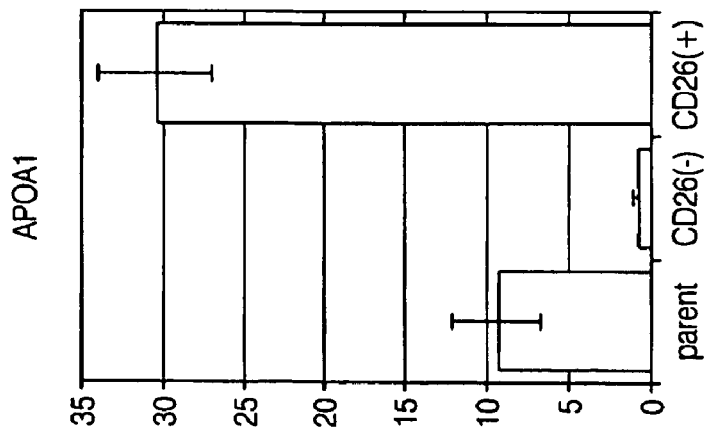
Figure 36F:
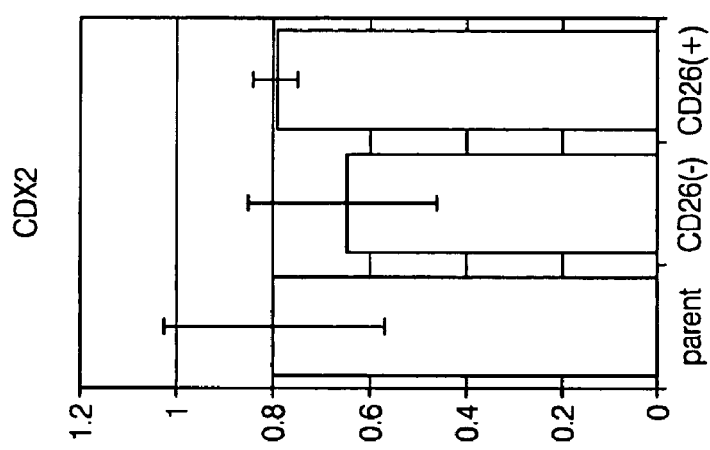
Figure 36E:
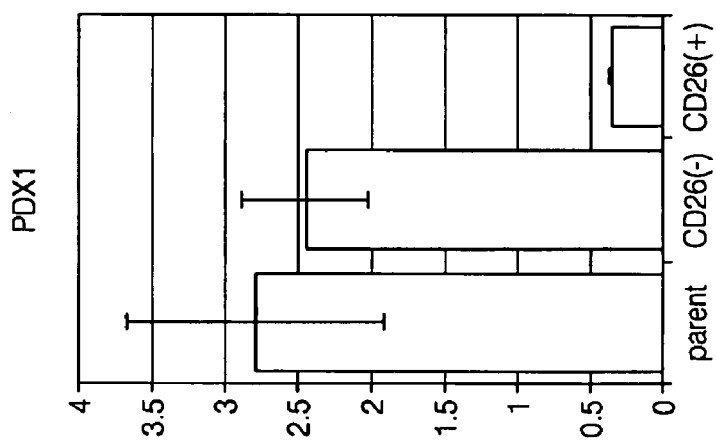
Figure 36D:
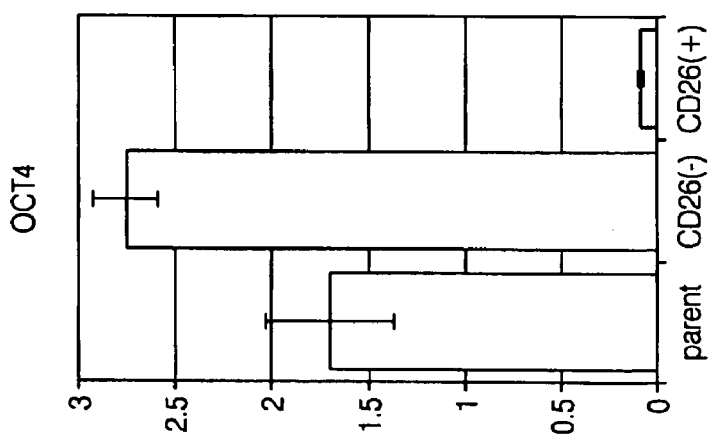

Known liver markers APOA1 (panel A), APOA2 (panel B) and HNF4α (panel C) markers were significantly enriched in the DPP4$^+$ cell sample compared to the DPP4$^-$ or parent cell samples. As discussed in Example 2, OCT4 is a marker of undifferentiated hESCs. Consistent with the data demonstrating that hESCs differentiate into liver precursor cells and/or hepatocyte cells expressing DPP4$^+$, OCT4 expression is significantly decreased in the DPP4$^+$ cell population. FIG. 36D. Similarly, PDX1 which is a foregut endoderm-specific marker. (See, e.g., U.S. Patent Application No. 60/730,917 entitled PDX-1 EXPRESSING DORSAL AND VENTRAL FOREGUT ENDODERM, the disclosure of which is hereby expressly incorporated in its entirety), was not significantly expressed in DPP4$^+$ cells, which is consistent with DPP4$^+$ cells representing liver precursor and/or hepatocyte cells. FIG. 36E. Furthermore, CDX2 which is a marker for intestinal precursors was not significantly expressed in DPP4$^+$ as compared to parent or DPP4$^-$ cells, which is consistent with DPP4$^+$ cells representing liver precursor or hepatocyte cells. FIG. 36F.

To determine if the above methods could be used to isolate liver precursor cells, hESCs were cultured in the conditions described above. On day 7, the culture was sorted by FACS using the anti-CD26 (DPP4) antibody described above. Total RNA was isolated from DPP4+, DPP4−, and parent cells as described above. Quantification of mRNAs of the following markers was tested in the various cell samples: PROX1, AFP, and Albumin. The results of the experiments are shown in FIGS. 36A-C.

PROX1, AFP, and albumin are known early liver markers. Burke, Z., et al., (2002) *Mech Dev.;* 118(1-2):147-55, Gordon, G., et al. (2000), *Am. J. Pathol.* 157(3):771-786, the disclosures of which are hereby expressly incorporated by reference in their entireties. DPP4$^+$ cells were enriched for PROX1, AFP and Albumin, compared to DPP4$^-$ cells. FIGS. 36A-C. DPP4$^+$ cells were also significantly enriched for AFP and Albumin compared to parent cells. FIGS. 36A-C. In view of the inventors' discovery that DPP4 is expressed by liver precursor cells, these data demonstrate that during differentiation of liver tissue from hESC-generated definitive endoderm, DPP4 is useful in the purification of liver precursor cells throughout their development into mature hepatocytes.

Example 13

Markers for Purification and Isolation of Mature Hepatocytes from Liver Precursor Cells The following experiments were done to analyze gene expression in order to uncover novel markers that are expressed in both liver precursor cells and mature hepatocyte cells, but that are not substantially expressed in non-liver precursor cells or non-hepatocyte cells. Such markers are useful, for example, as tools for isolating liver precursor cells or hepatocytes generated from hESCs in vitro.

Ventral or dorsal definitive endoderm cells were produced from undifferentiated hESCs using a 3 (ventral differentiation) or 5 day (dorsal differentiation) protocol, respectively, in which activin A is provided to the culture medium at a concentration of 100 ng/mL each day. Cells were cultured in the following medium: Day 1, RPMI+0% FBS, Day 2, RPMI+0.2% FBS, Day 3, RPMI+2.0% FBS, Day 4 RPMI+2.0% FBS and Day 5, RPMI+2.0% FBS. For the ventral differentiation (F), cells were cultured for 3 days in activin A at 100 ng/ml. Cells were then cultured in RPMI media supplemented with BMP at 3 ng/ml and FGF10 at 50 ng/ml and 2% FBS for the first 2 days (i.e., days 4 and 5) and then subsequently in CMRL media containing B27 supplement (1:200), as described in Example 11. For the dorsal differentiation (R) procedure, hESCs were cultured for 5 days in medium supplemented with activin A at 100 ng/mL. Subsequently, cells were grown in CMRL media activin A at 25 ng/ml containing B27 supplement (1:200, v/v) and retinoic acid (RA) at a final concentration of 2 μM and in CMRL media.

As demonstrated in Example 11, the ventral differentiation protocol described above results in robust differentiation of hESCs down the liver lineages in the BMP4/FGF10 treated condition.

On days 0, 3, 5, 7, 9, and 11, mRNA was isolated from cells cultured using the ventral differentiation protocol described above (0d, 5d, 7dF, 9dF, 11dF). On day 7, mRNA was isolated from cells cultured using the dorsal differentiation protocol described above (7dR). Purified RNA was submitted in duplicate to Expression Analysis (Durham, N.C.) for generation of the expression profile data using the Affymetrix platform and U133 Plus 2.0 high-density oligonucleotide arrays.

Figure 39A:
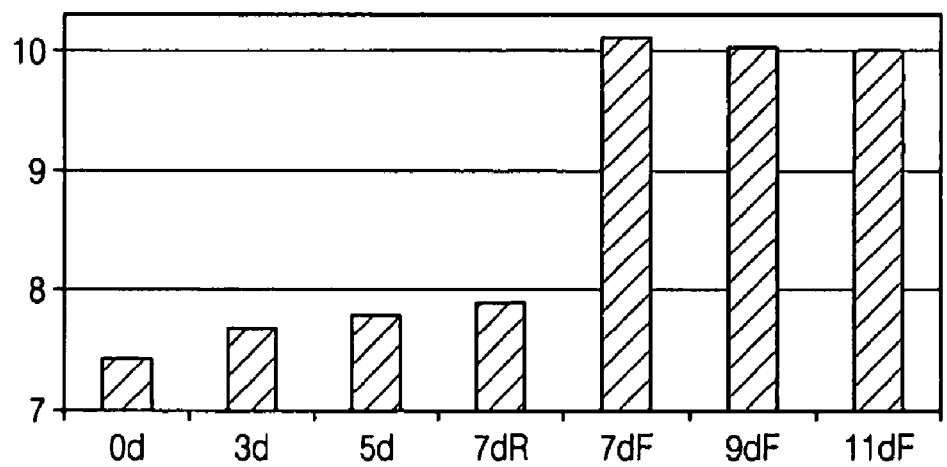
FIGS. 39A-CC are a series of bar charts depicting gene expression patterns of DOK4 (panel A), SLC35D1 (panel B), HPX (panel C), PCDH17 (panel D), LOC440450 (panel E), LOC286167 (panel F), C3orf15 (panel G), FN1 (panel H), GLUD1//GLUD2 (panel I), LOC286167 (panel J), GSN (panel K), EVI1 (panel L), SP8 (panel M), GLUD1 (panel N), ALDH2 panel O), Hs571099 (panel P), HLA-B//HLA-C (panel Q), PLA2G12B (panel R), STYL5 (panel S), LOC130576 (panel T), FKBP7 (panel U), MUSTN1 (panel V), CYP4X1 (panel W), EPHA6 (panel X), PP1057 (panel Y), PFTK1 (panel Z), CUBN (panel AA), NOSTRIN (panel BB) and DGKB (panel CC), from hESCs cultured under ventral or dorsal differentiation conditions for 0, 3, 5, 7, 9, or 11 days as indicated in the bar charts and as described in Example 13. These figures demonstrate that DOK4, SLC35D1, HPX, PCDH17, LOC440450, LOC286167, C3orf15, FN1, GLUD1//GLUD2, LOC286167, GSN, EVI1, SP8, GLUD1, ALDH2, Hs571099, HLA-B//HLA-C, PLA2G12B, STYL5, LOC130576, FKBP7, MUSTN1, CYP4X1, EPHA6, PP1057, PFTK1, CUBN, NOSTRIN and DGKB, expression is enhanced in liver precursor cells (day 7F) (panels A-CC), compared to days 0, 3, and 5, and compared to hESCs cultured under dorsal differentiation conditions (day 7R).
Figure 39B:
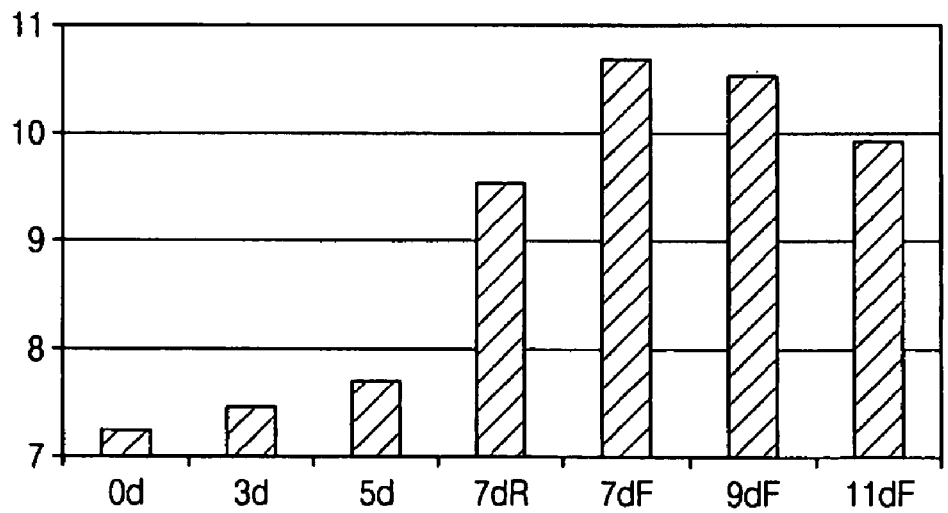
Figure 39C:
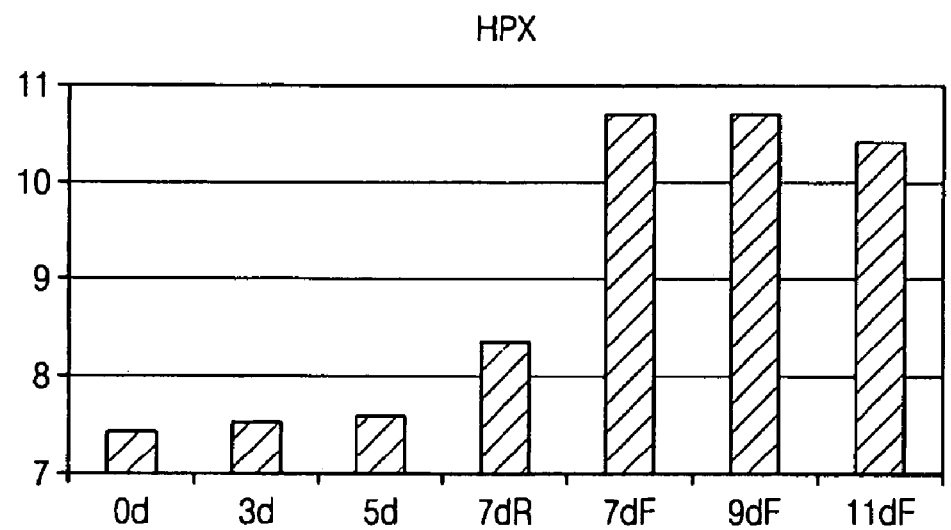
Figure 39D:
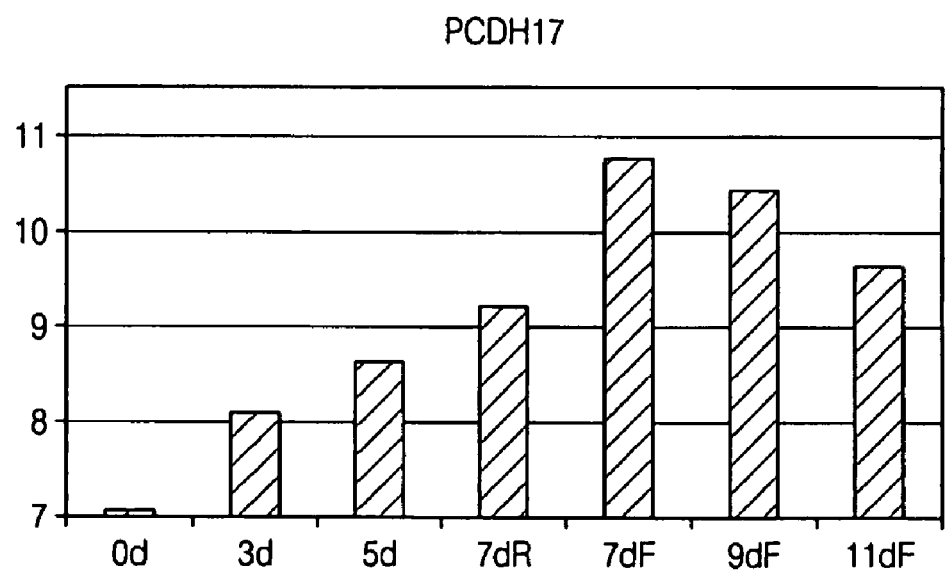
Figure 39E:
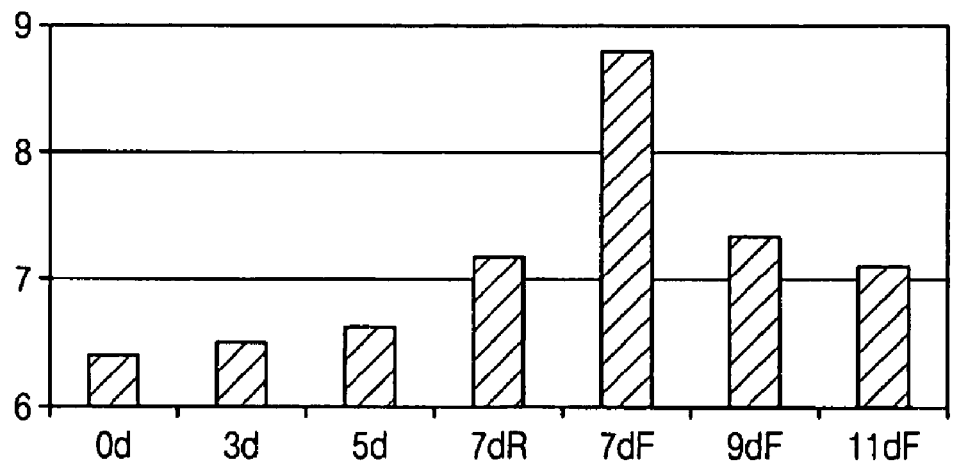
Figure 39F:
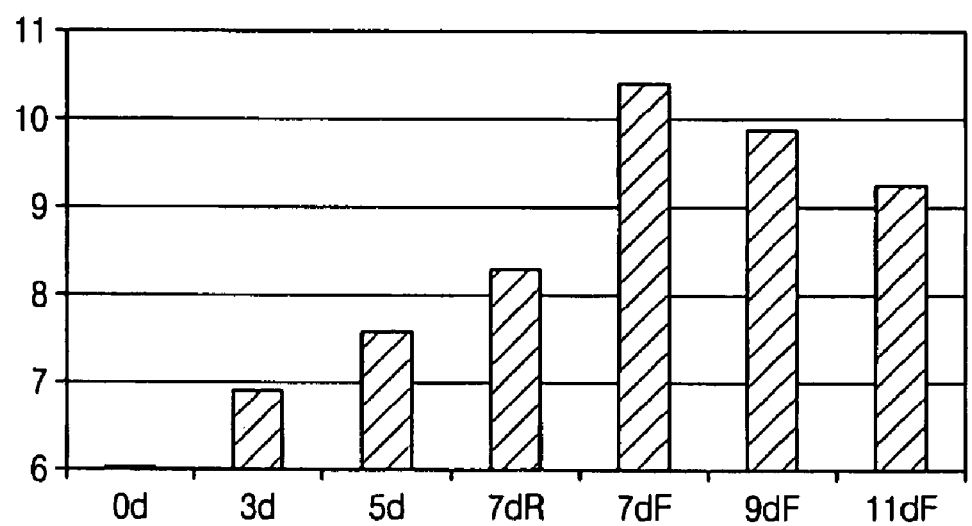
Figure 39G:
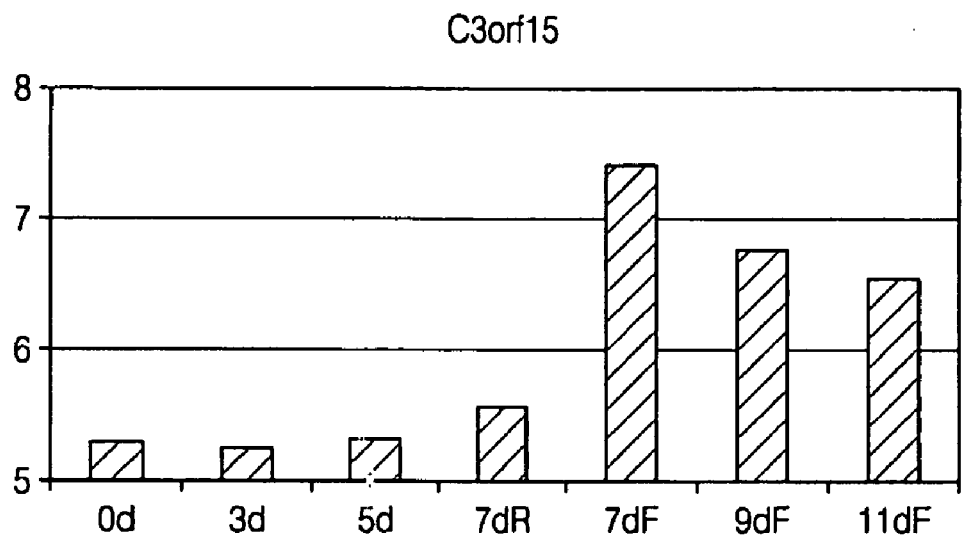
Figure 39H:
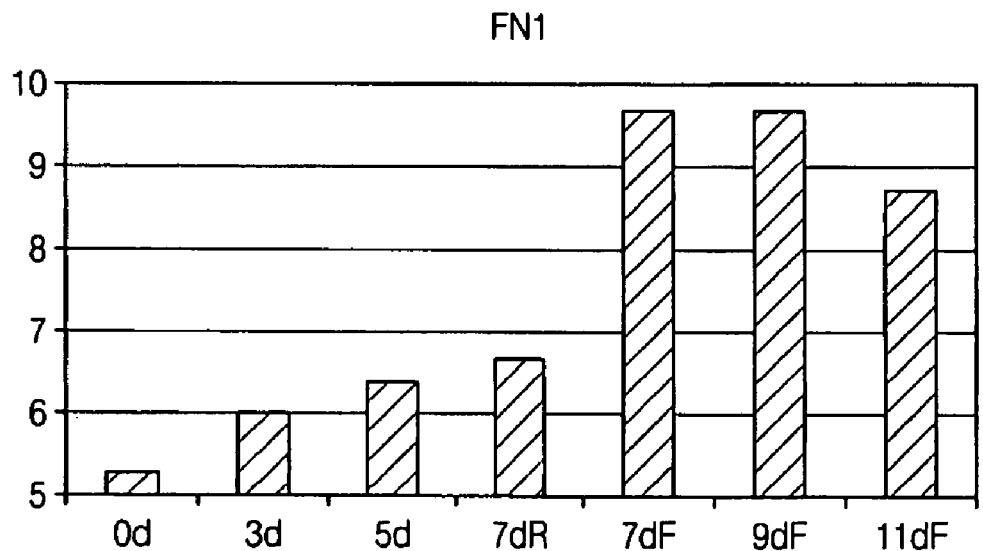
Figure 39I:
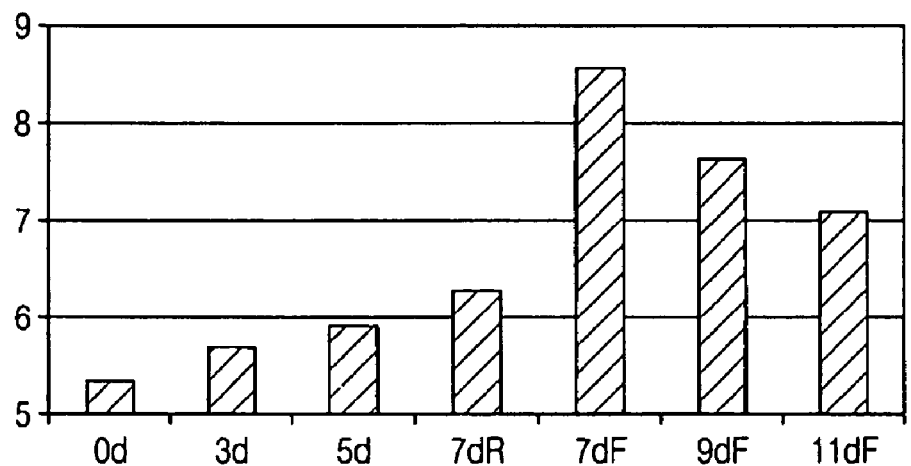
Figure 39J:
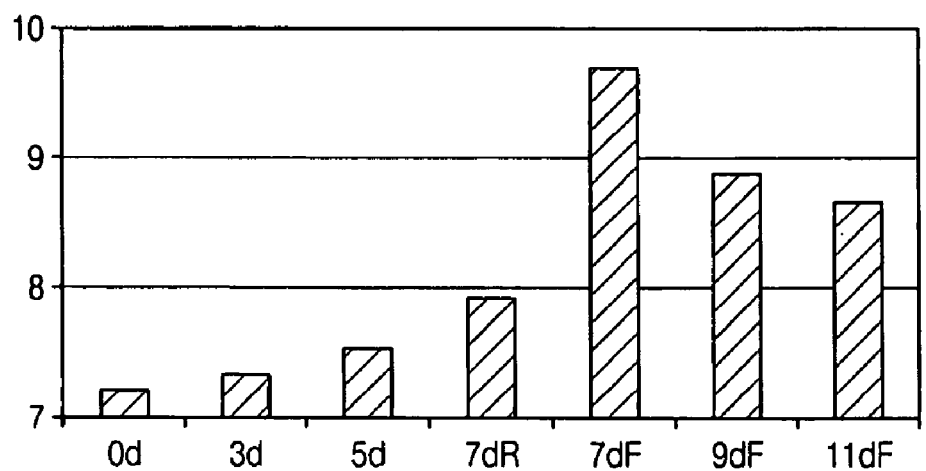
Figure 39K:
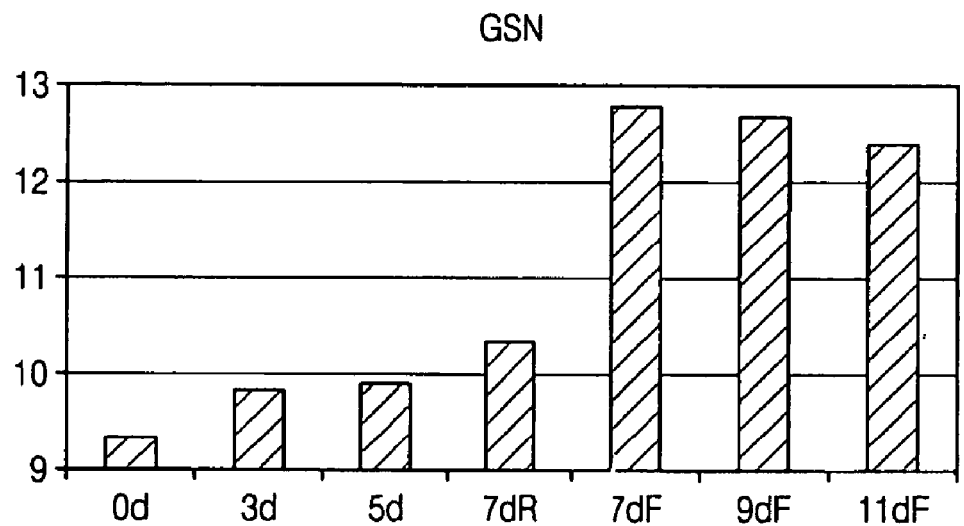
Figure 39L:
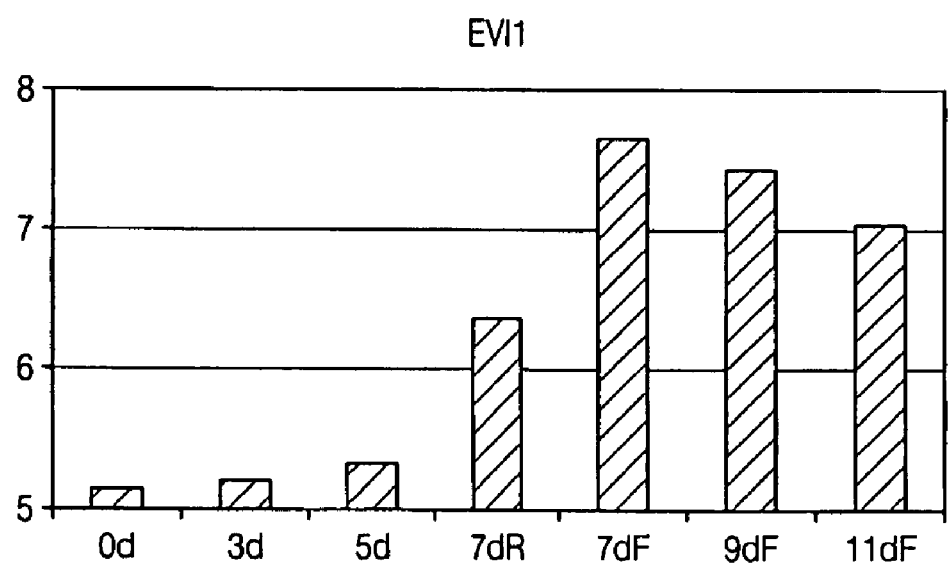
Figure 39M:
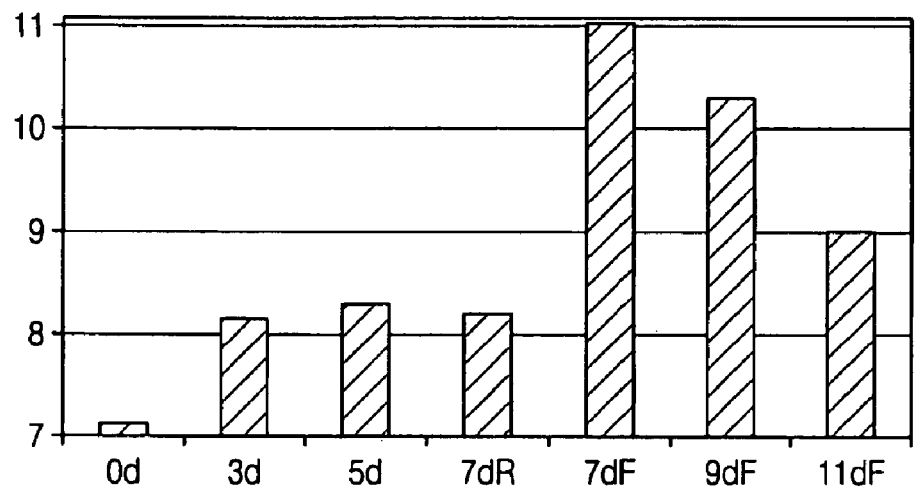
Figure 39N:
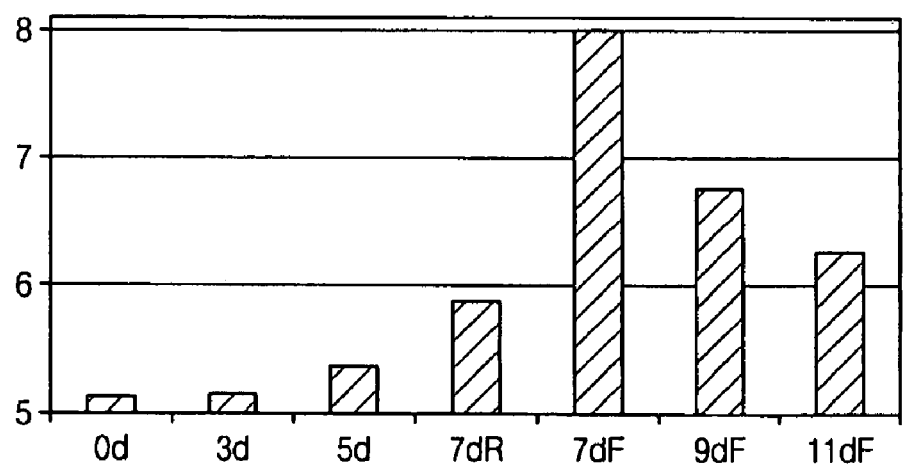
Figure 39O:
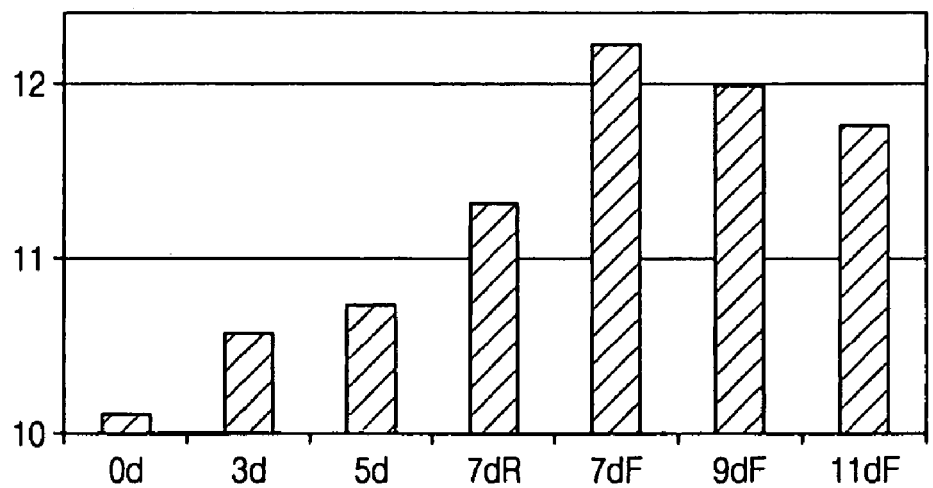
Figure 39P:
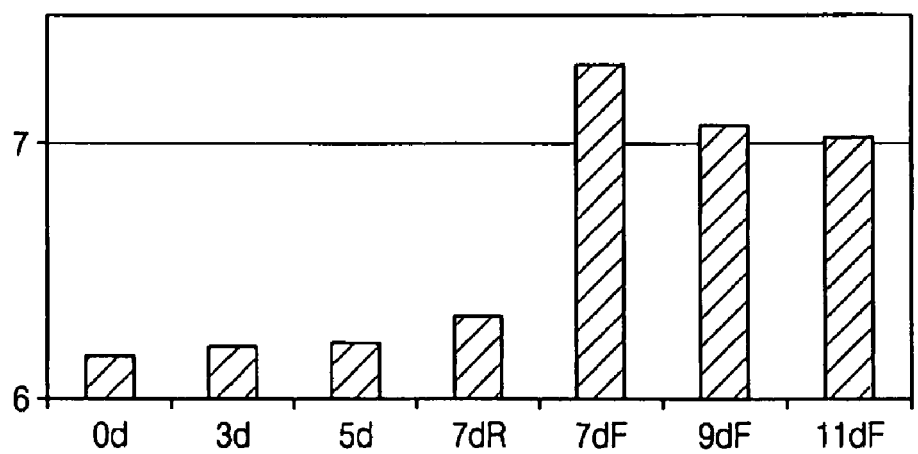
Figure 39Q:
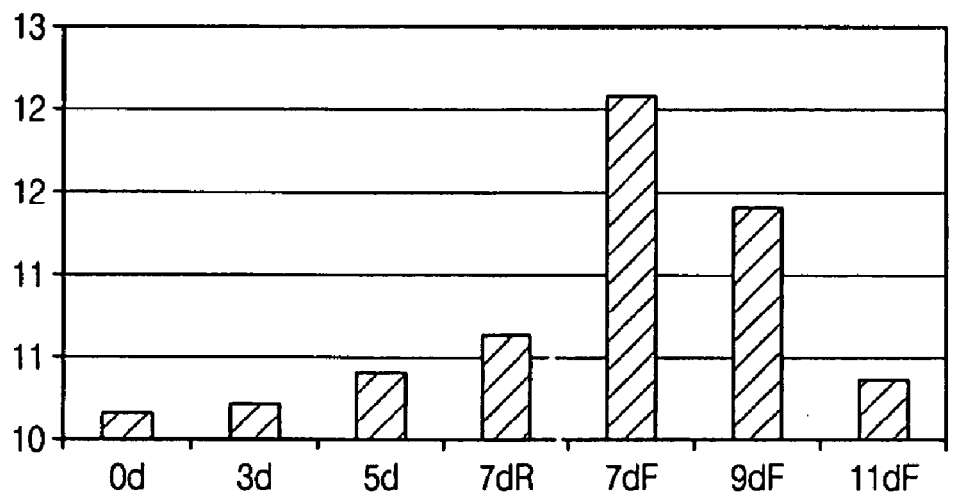
Figure 39R:
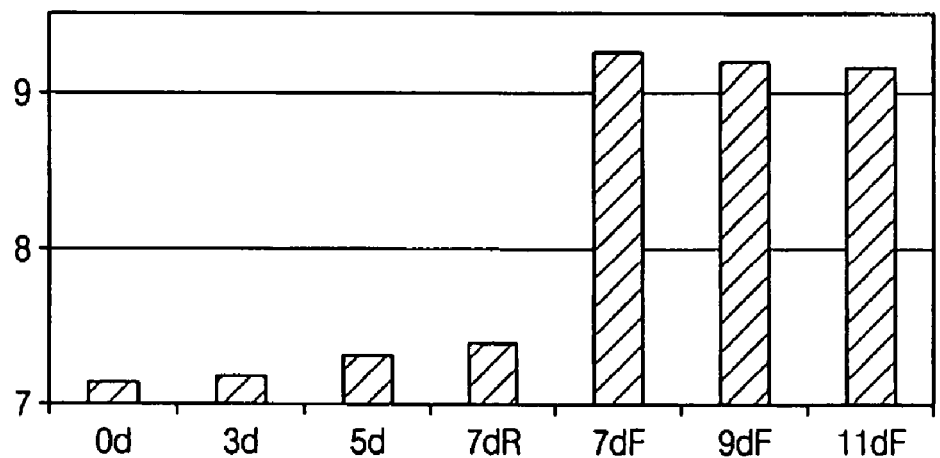
Figure 39S:
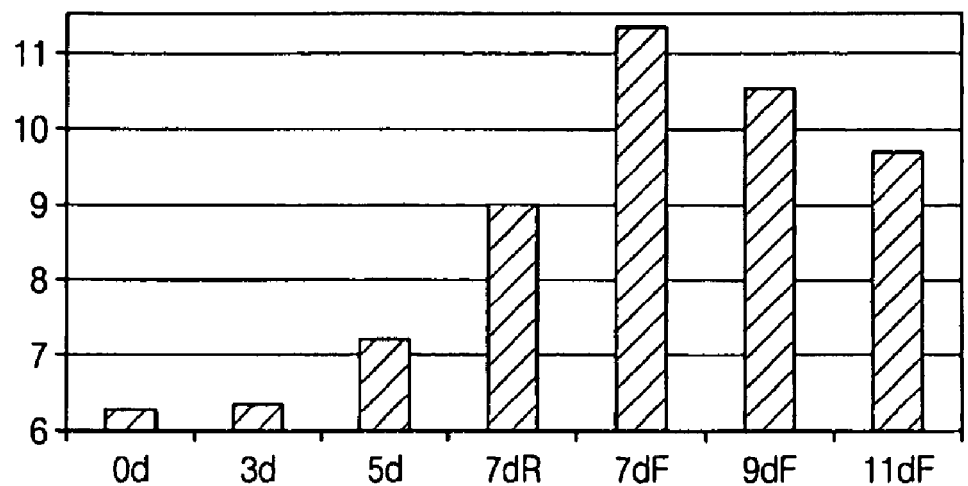
Figure 39T:
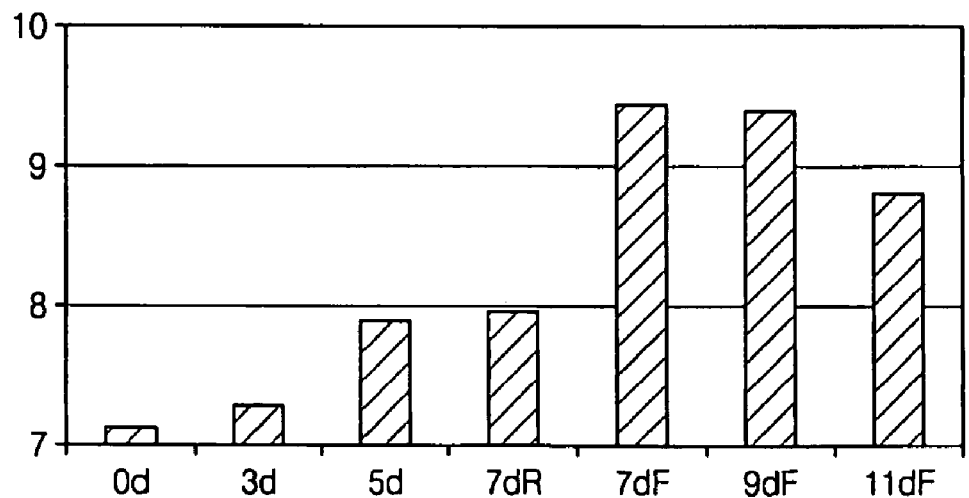
Figure 39U:
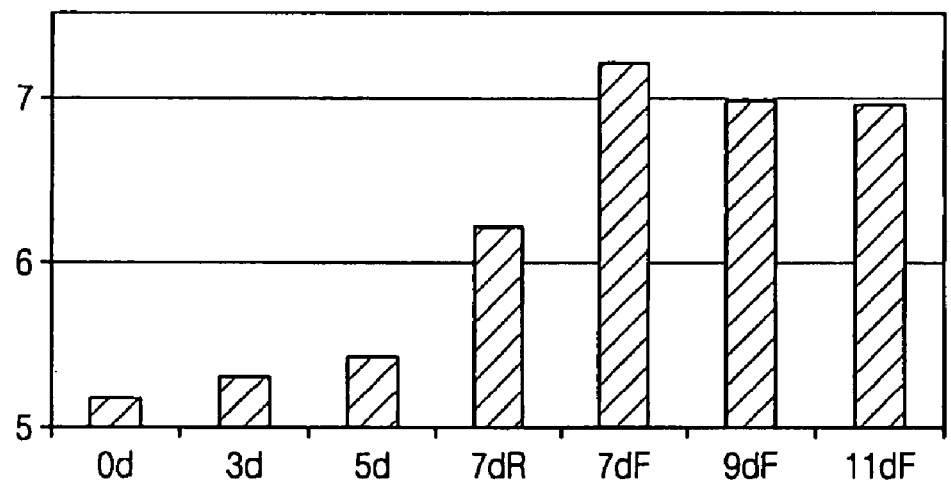
Figure 39V:
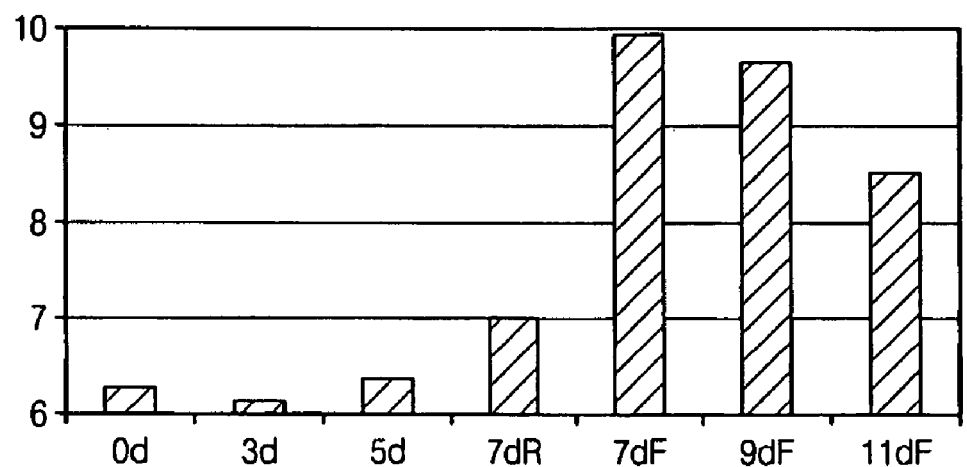
Figure 39W:
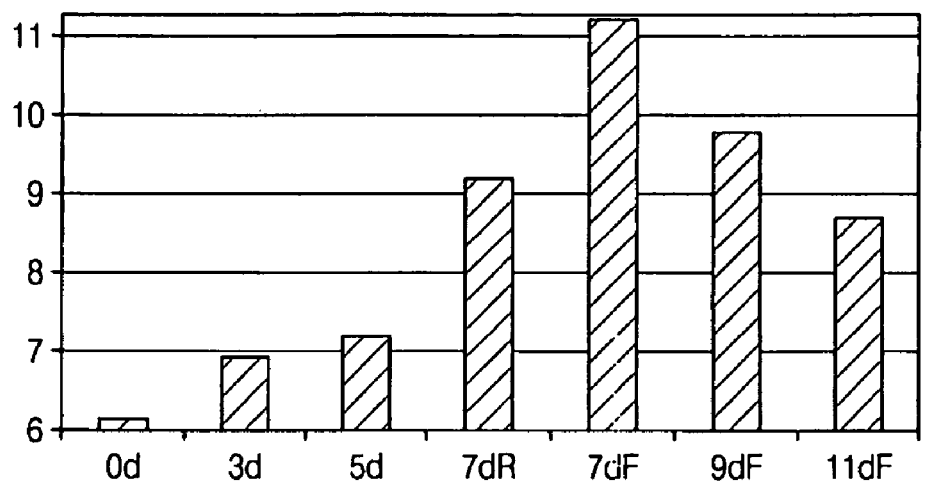
Figure 39X:
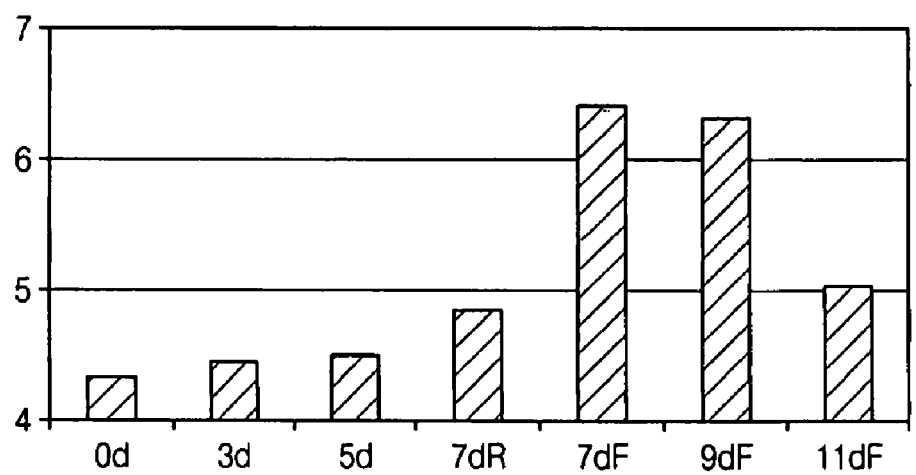
Figure 39Y:
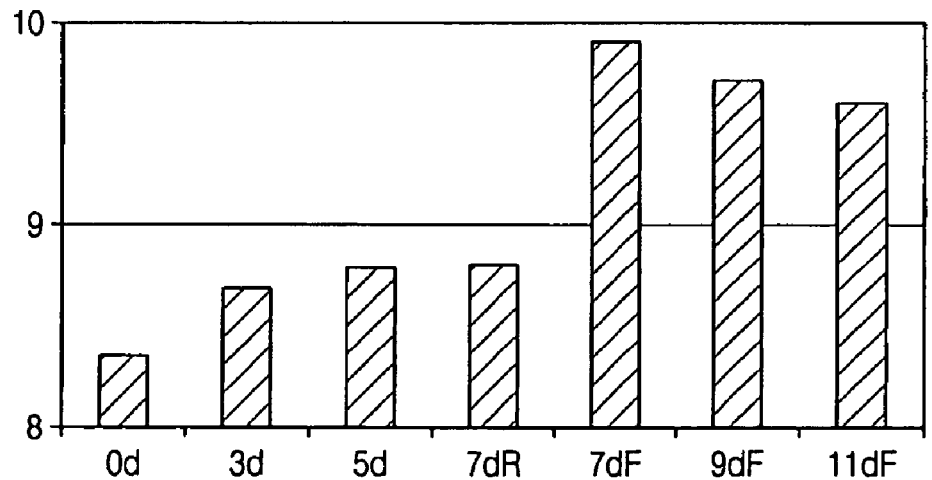
Figure 39Z:
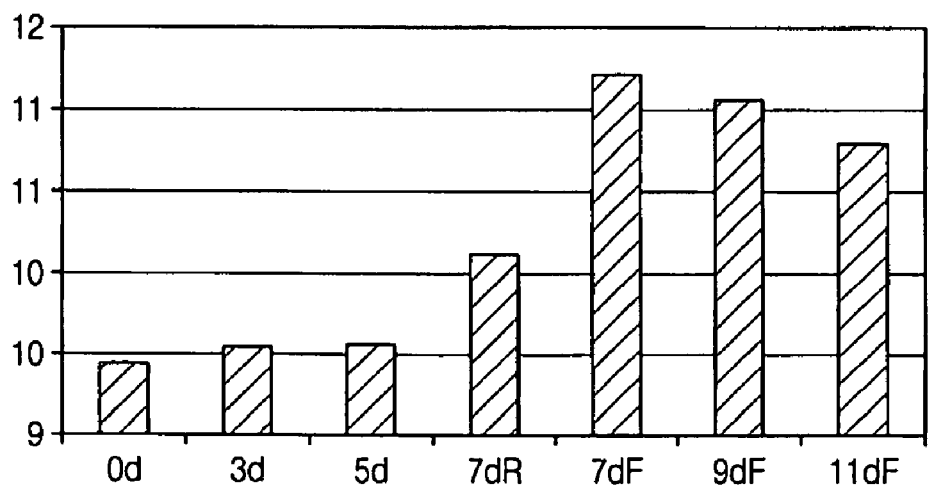
Figure 39A:
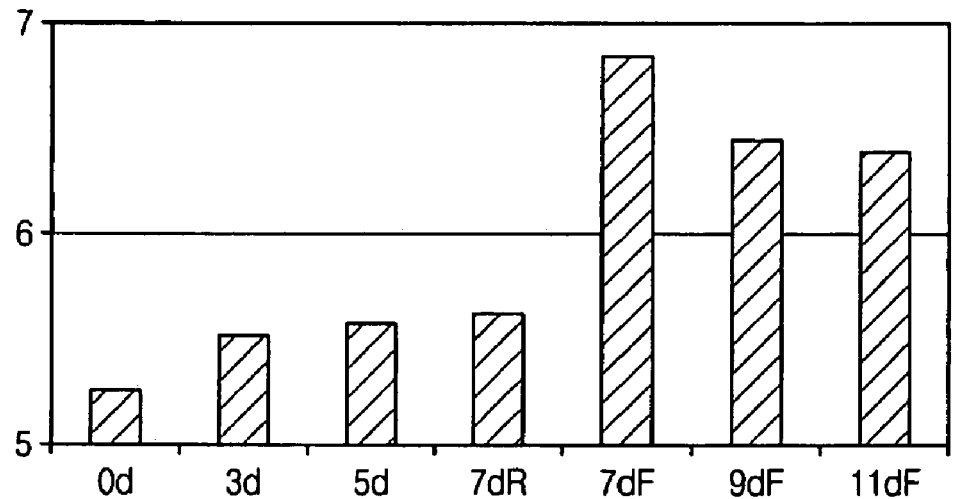
Figure 39B:
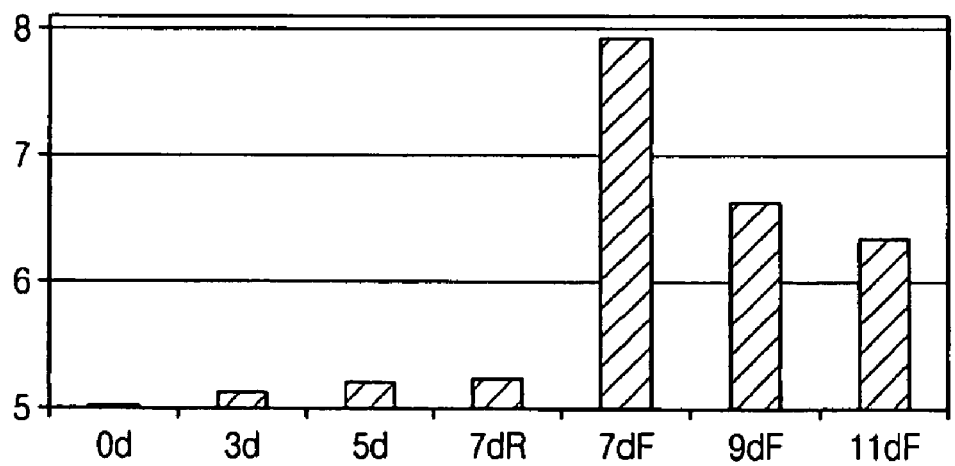
Figure 39C:
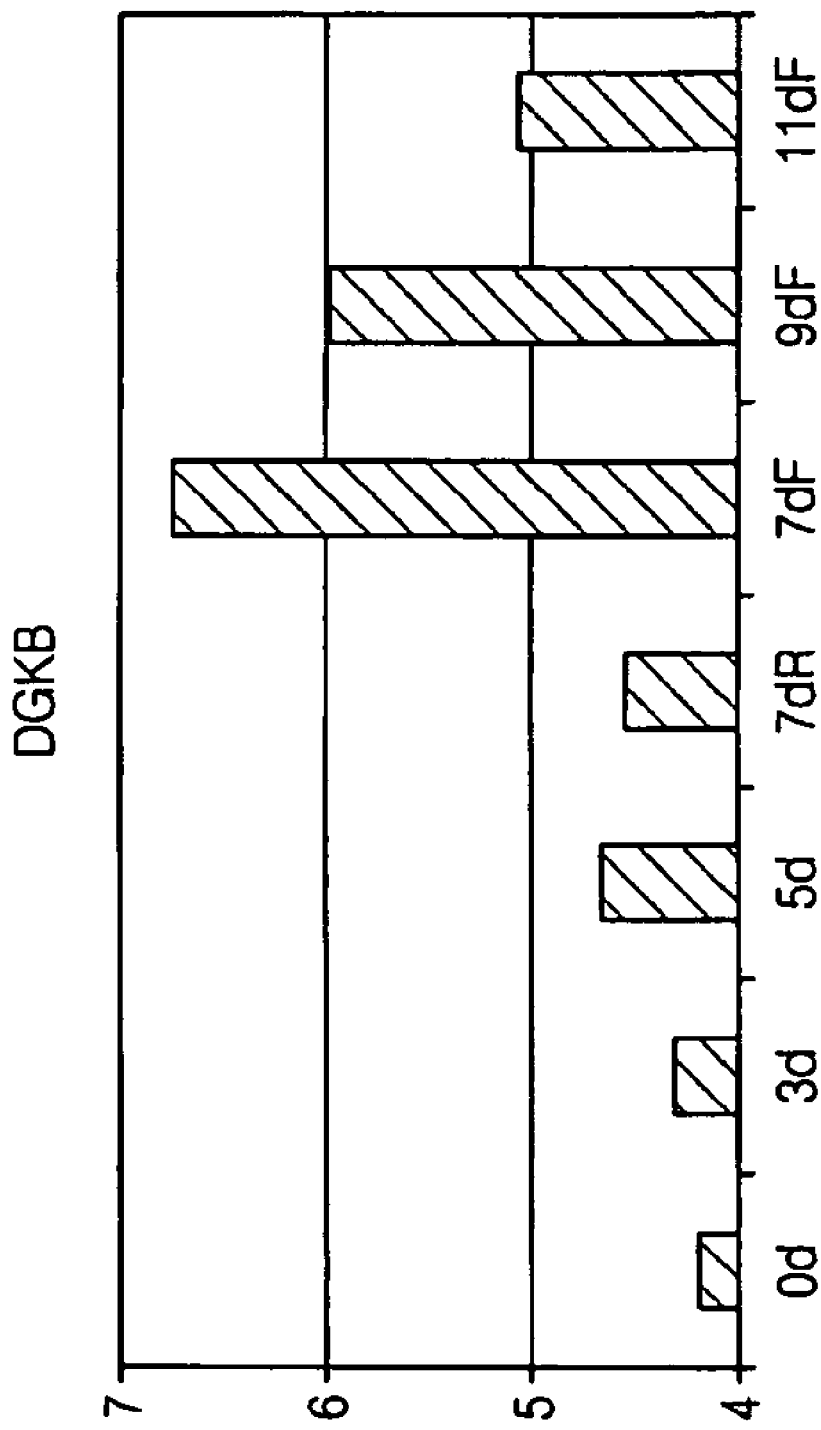

FIGS. 39A-CC show the relative gene expression of DOK4, SLC35D1, HPX, PCDH17, LOC440450, LOC286167, C3orf15, FN1, GLUD1/GLUD2, LOC286167, GSN, EVI1, SP8, GLUD1, ALDH2, Hs571099, HLA-B// HLA-C, PLA2G12B, STYL5, LOC130576, FKBP7, MUSTN1, CYP4X1, EPHA6, PP1057, PFTK1, CUBN, NOSTRIN and DGKB in cells cultured as indicated above. FIGS. 39A-CC demonstrate that expression of DOK4, SLC35D1, HPX, PCDH17, LOC440450, LOC286167, C3orf15, FN1, GLUD1//GLUD2, LOC286167, GSN, EVI1, SP8, GLUD1, ALDH2, Hs571099, HLA-B//HLA-C, PLA2G12B, STYL5, LOC130576, FKBP7, MUSTN1, CYP4X1, EPHA6, PP1057, PFTK1, CUBN, NOSTRIN and DGKB is enhanced in liver precursor cells as compared to hESCs (day 0, day 3), or cells undergoing a ventral differentiation pathway (day 7R). FIGS. 39A-CC, day 7F. These expression data demonstrate the usefulness of DOK4, SLC35D1, HPX, PCDH17, LOC440450, LOC286167, C3orf15, FN1, GLUD1//GLUD2, LOC286167, GSN, EVI1, SP8, GLUD1, ALDH2, Hs571099, HLA-B//HLA-C, PLA2G12B, STYL5, LOC130576, FKBP7, MUSTN1, CYP4X1, EPHA6, PP1057, PFTK1, CUBN, NOSTRIN and DGKB as tools for the identification, purification and/or isolation of liver precursor cells.

Figure 40A:
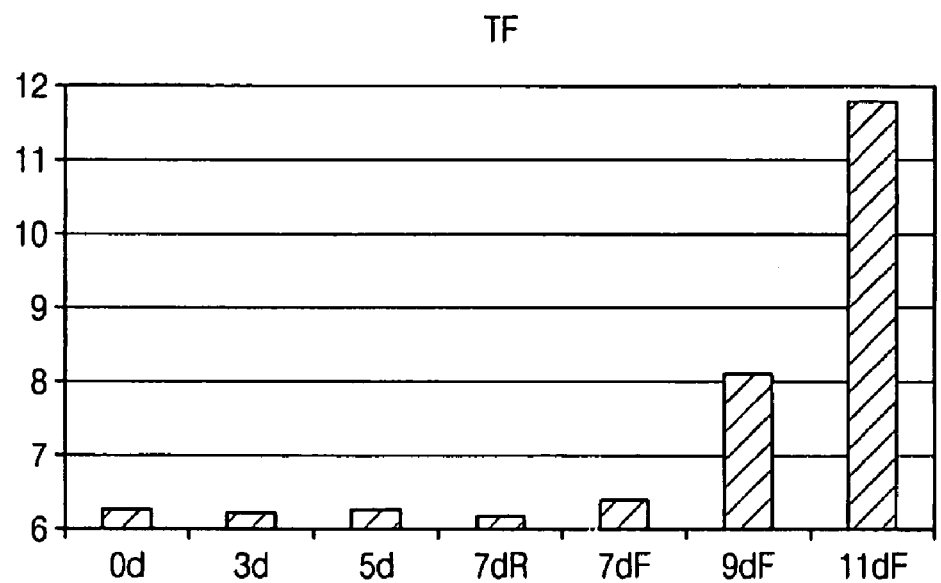
FIGS. 40A-W are a series of bar charts depicting gene expression patterns of TF (panel A), ADH6 (panel B), HBG2 (panel C), CYP3A7 (panel D), SLC2A2 (panel E), CYP3A5 (panel F), CYP3A4 (panel G), MUSK (panel H), CYP2A9 (panel I), OLR1 (panel J), SLC5A12 (panel K), TM4SF4 (panel L), TM4SF4 (panel M), SLC38A4 (panel N), MEP1A (panel O), SMP3 (panel P), UBD (panel Q), KNG1 (panel R), ORM1///ORM2 (panel S), HAL (panel T), SLC10A1 (panel U), NR1H4 (panel V), SERPINA7 (panel W) from hESCs cultured under ventral or dorsal differentiation conditions for 0, 3, 5, 7, 9, or 11 days as indicated in the bar charts and described in Example 13. These figures demonstrate that TF, ADH6, HBG2, CYP3A7, SLC2A2, CYP3A5, CYP3A4, MUSK, CYP2A9, OLR1, SLC5A12, TM4SF4, TM4SF4, SLC38A4, MEP1A, SMP3, UBD, KNG1, ORM1///ORM2, HAL, SLC10A1, NR1H4, SERPINA7 expression is enhanced in hepatocyte cells (day 11F) (panels A-W), compared to liver precursor cells (day 7F) and compared to hESCs cultured under dorsal differentiation conditions (day 7R).
Figure 40B:
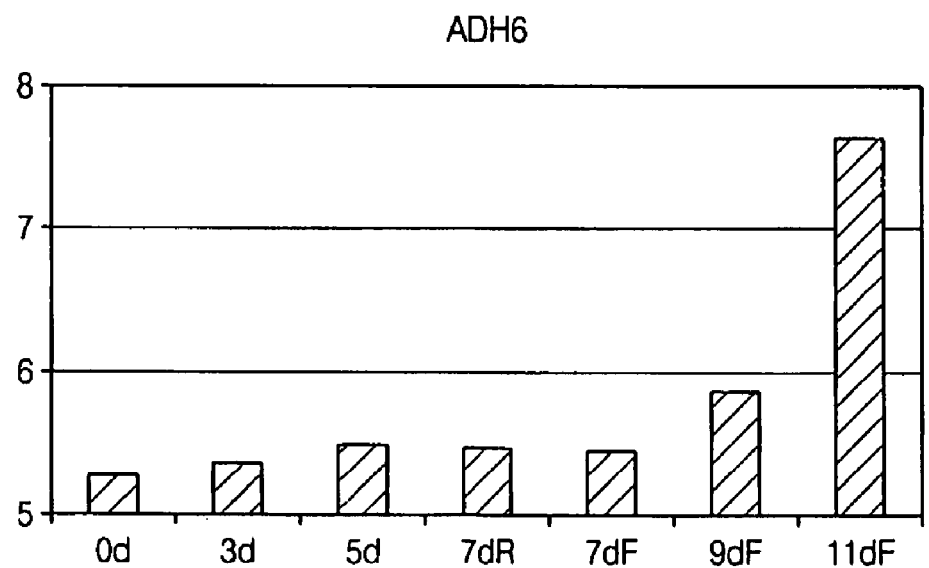
Figure 40C:
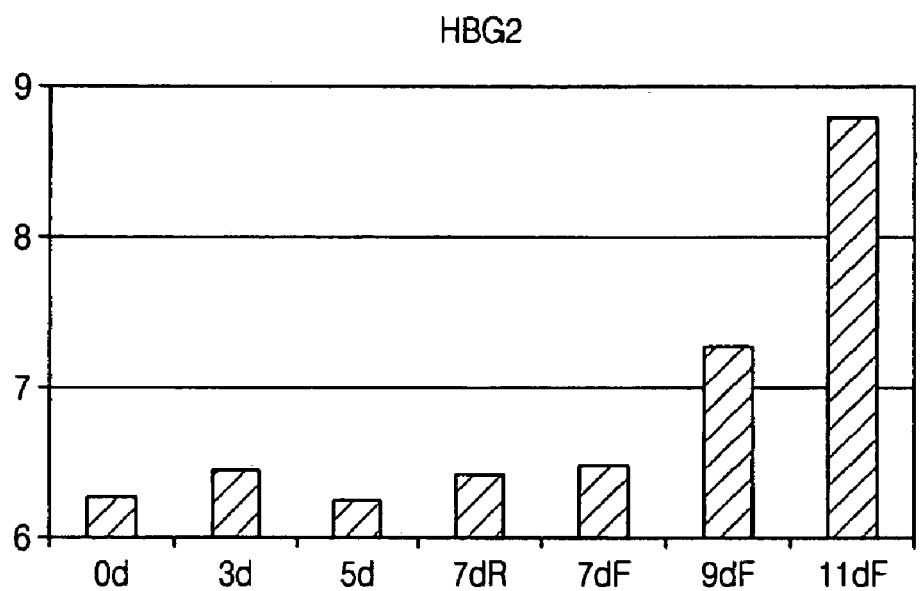
Figure 40D:
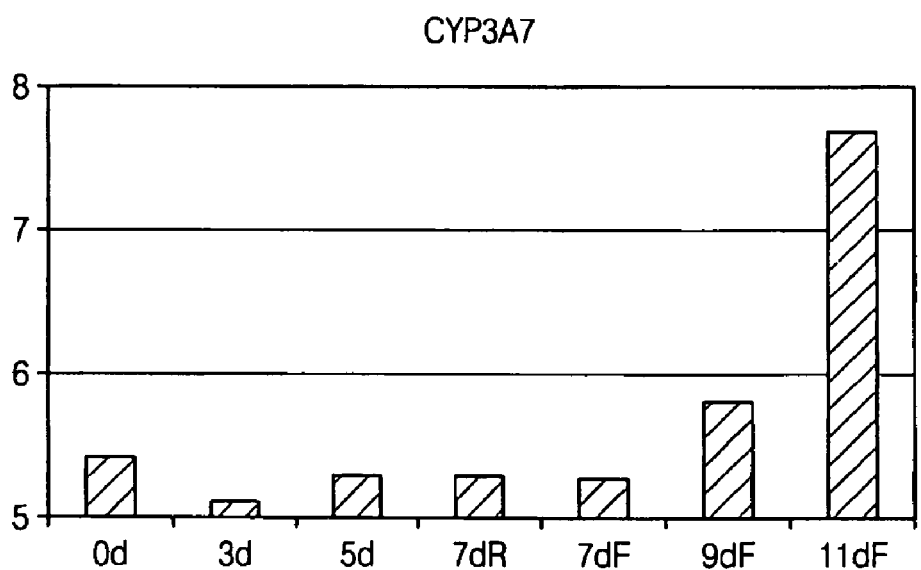
Figure 40E:
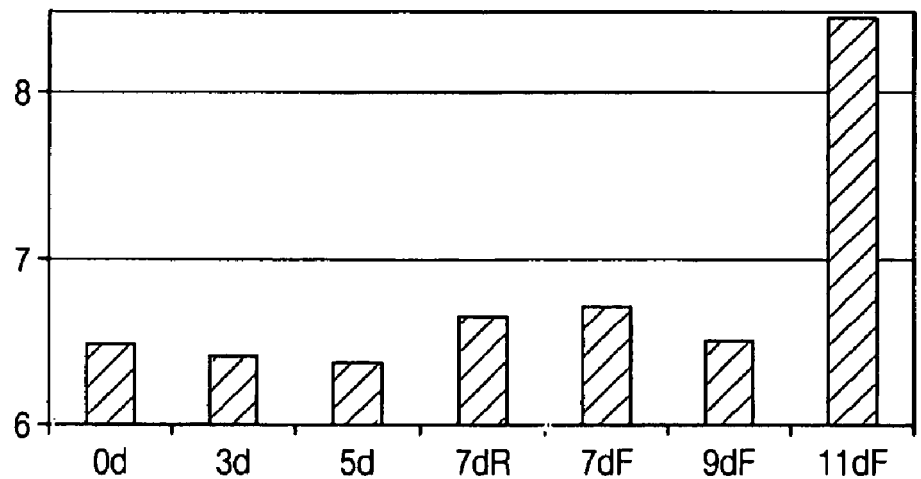
Figure 40F:
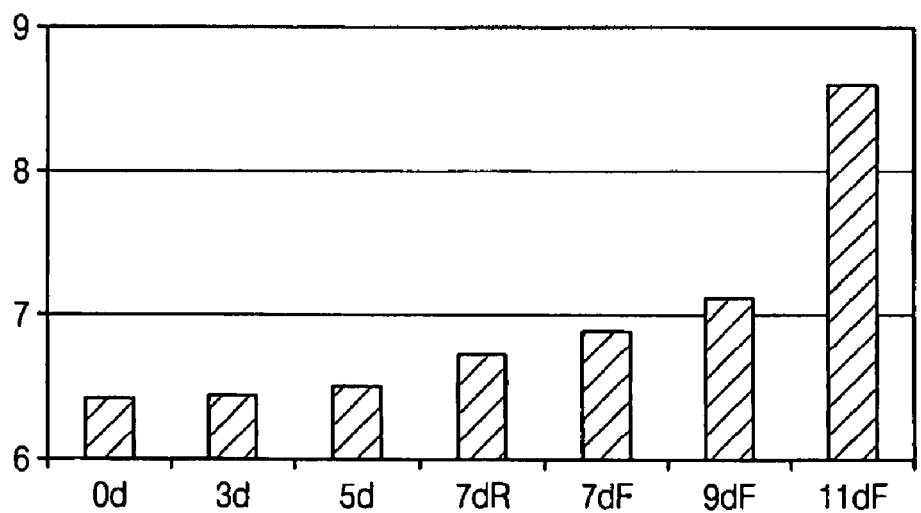
Figure 40G:
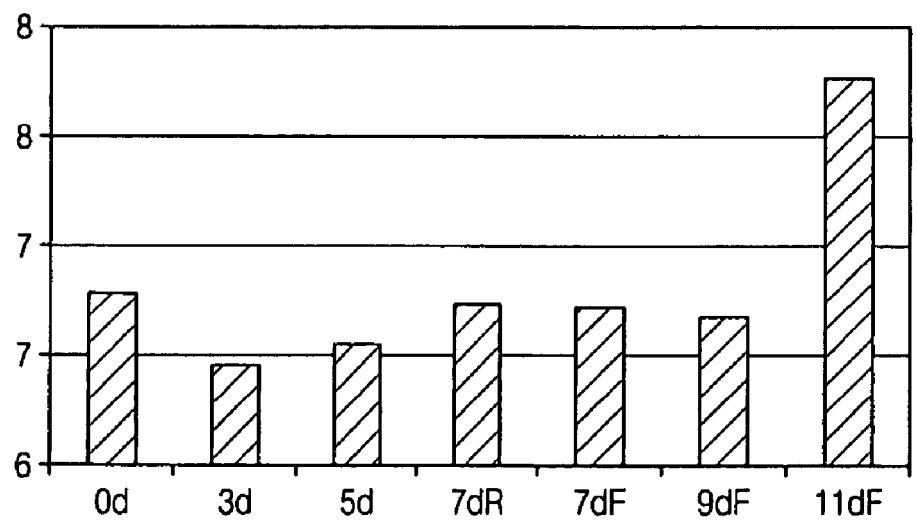
Figure 40H:
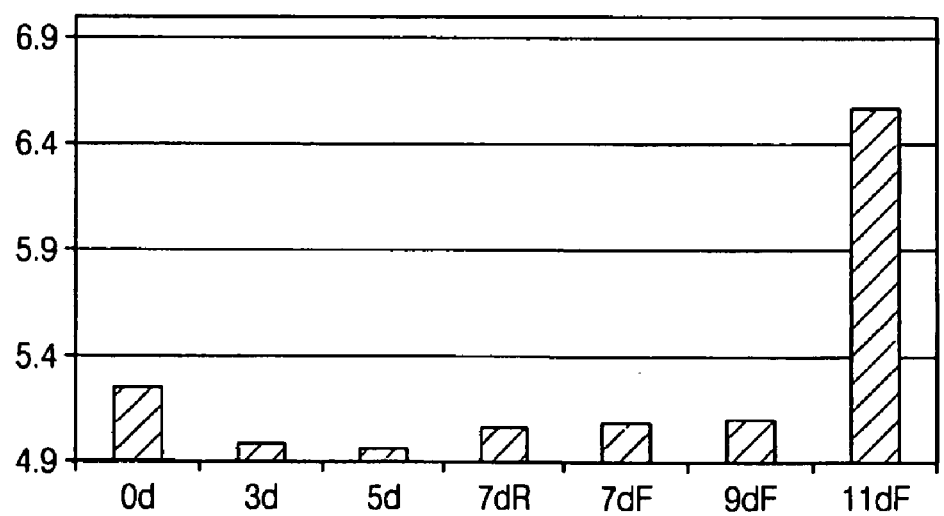
Figure 40I:
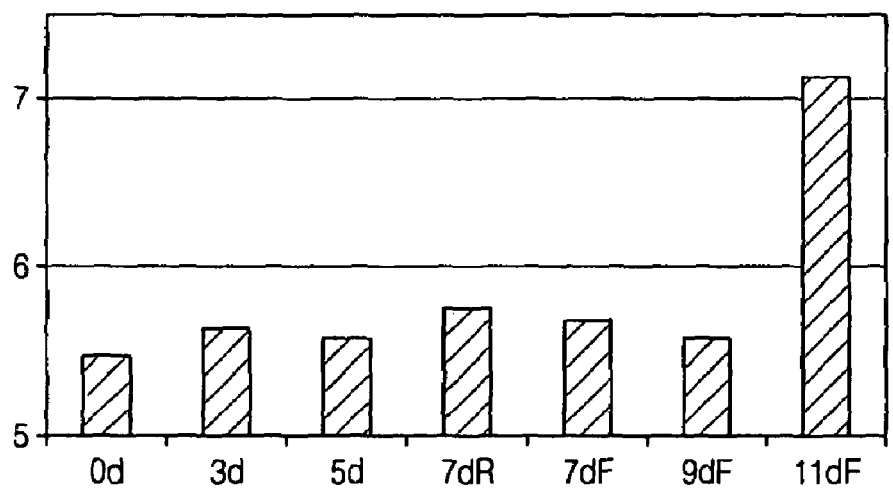
Figure 40J:
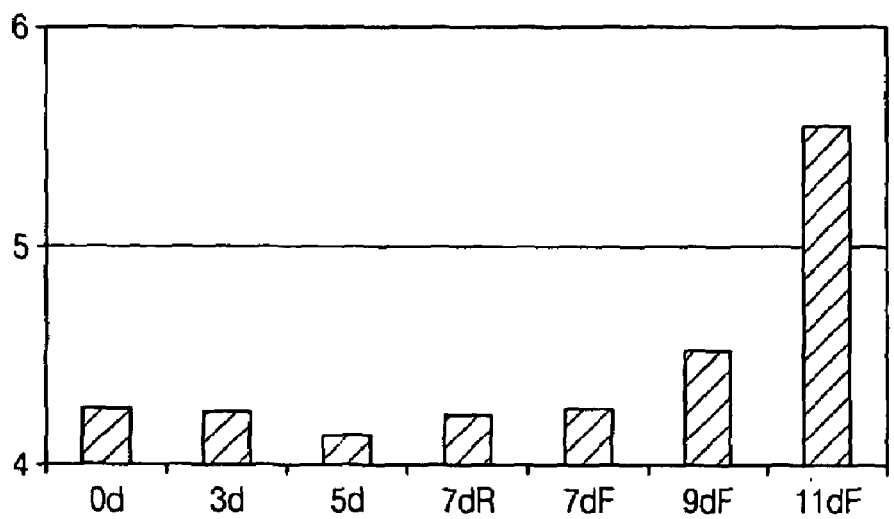
Figure 40K:
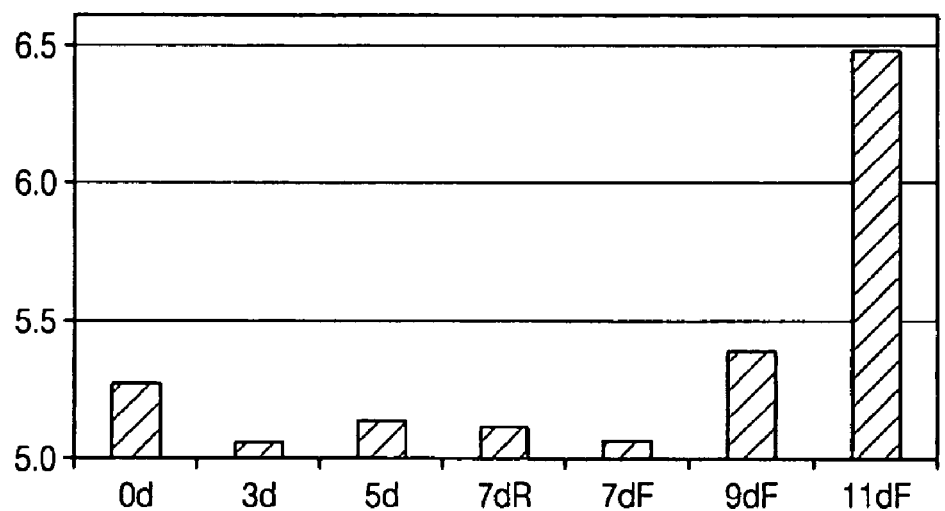
Figure 40L:
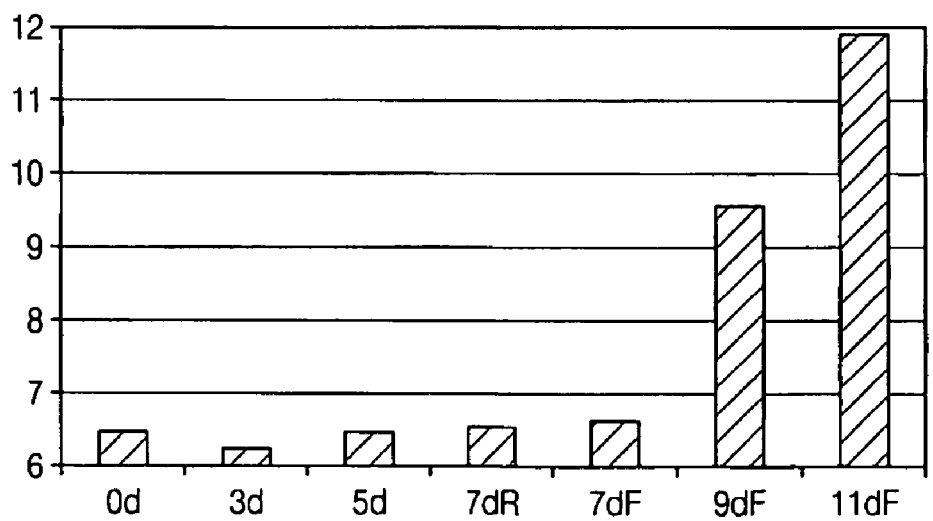
Figure 40M:
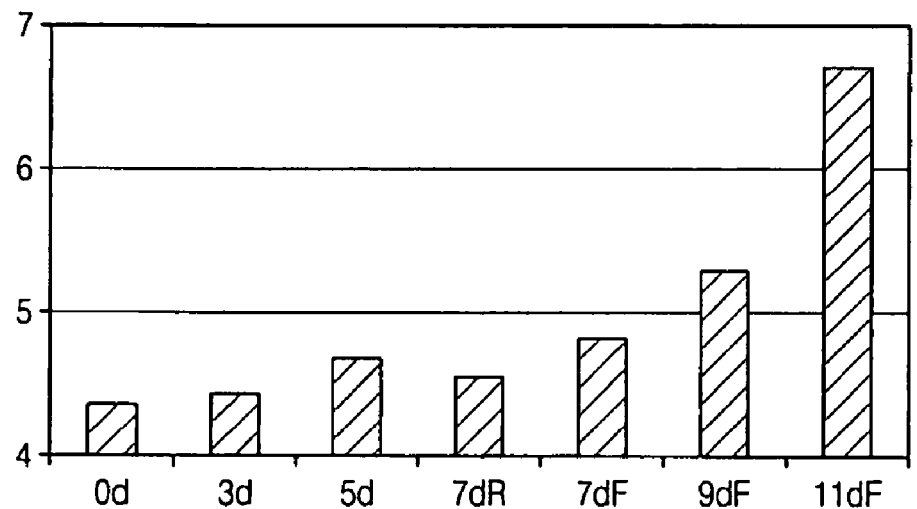
Figure 40N:
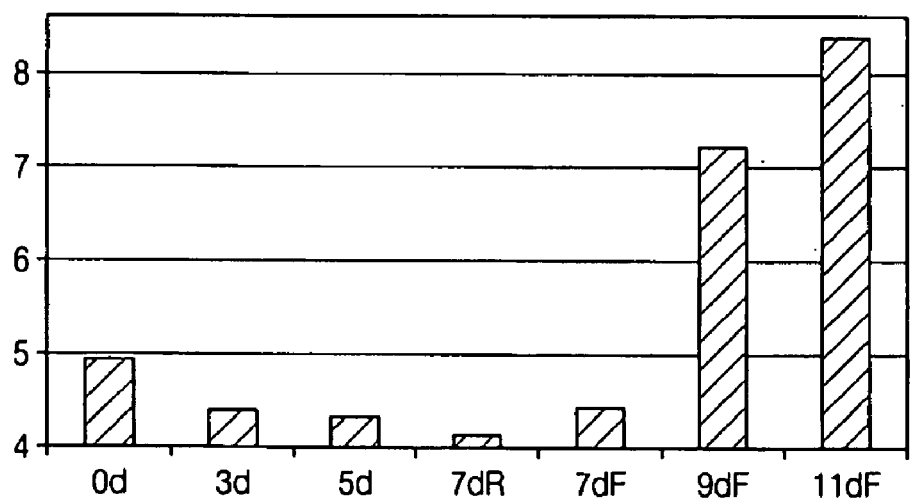
Figure 40O:
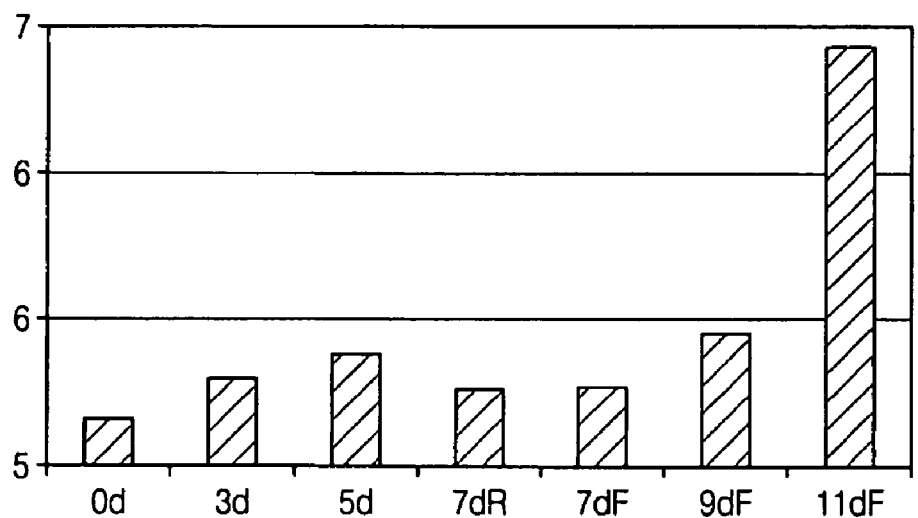
Figure 40P:
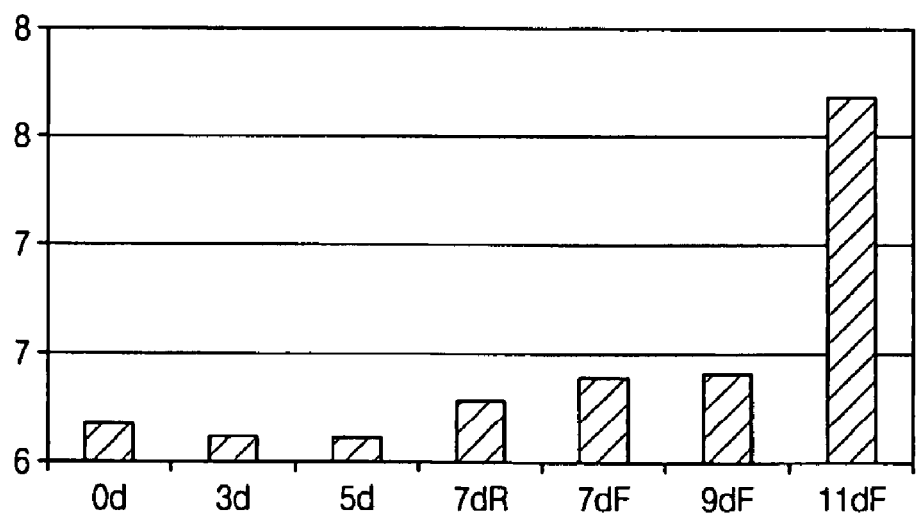
Figure 40Q:
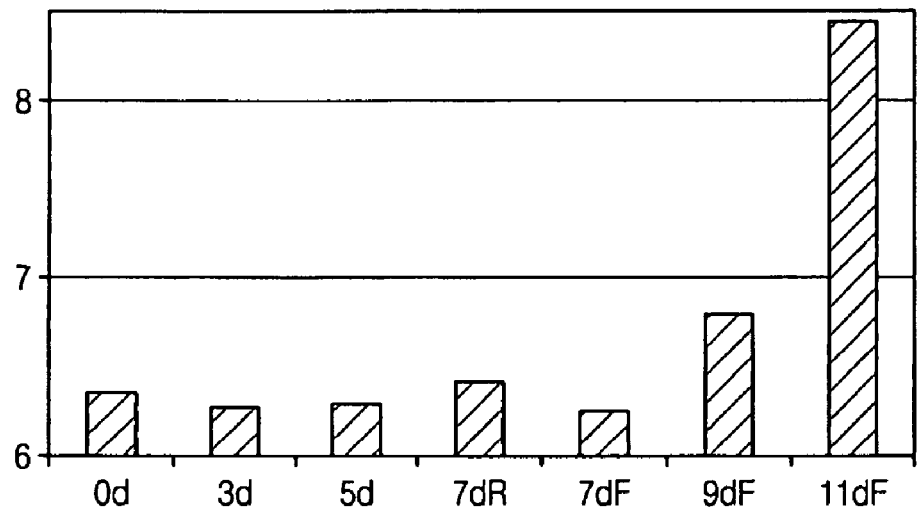
Figure 40R:
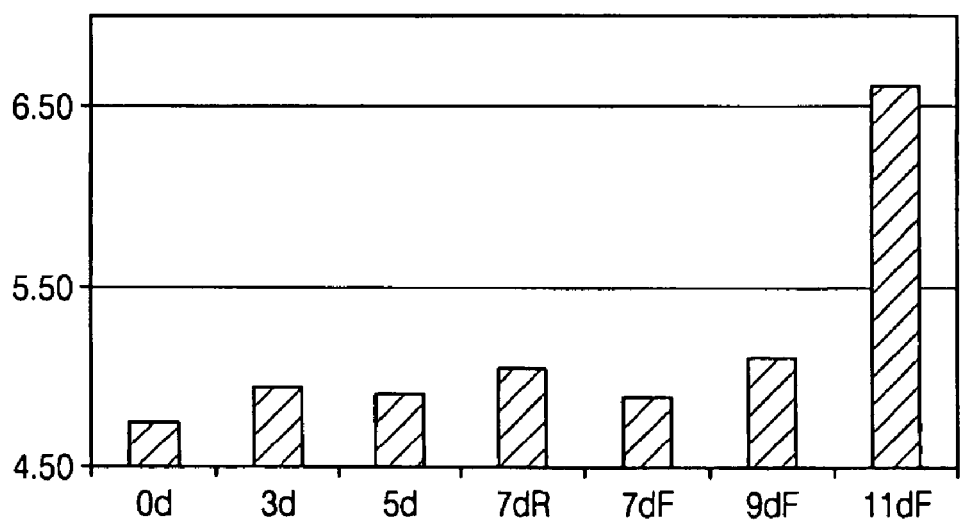
Figure 40S:
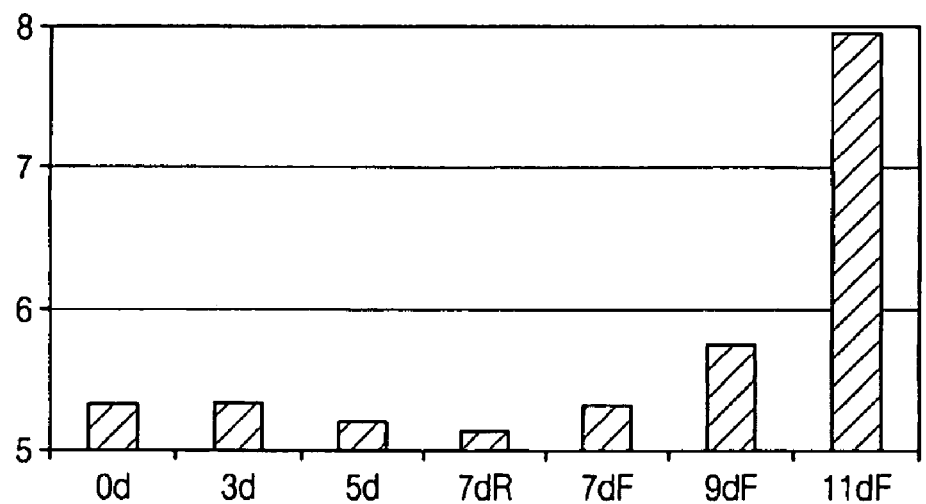
Figure 40T:
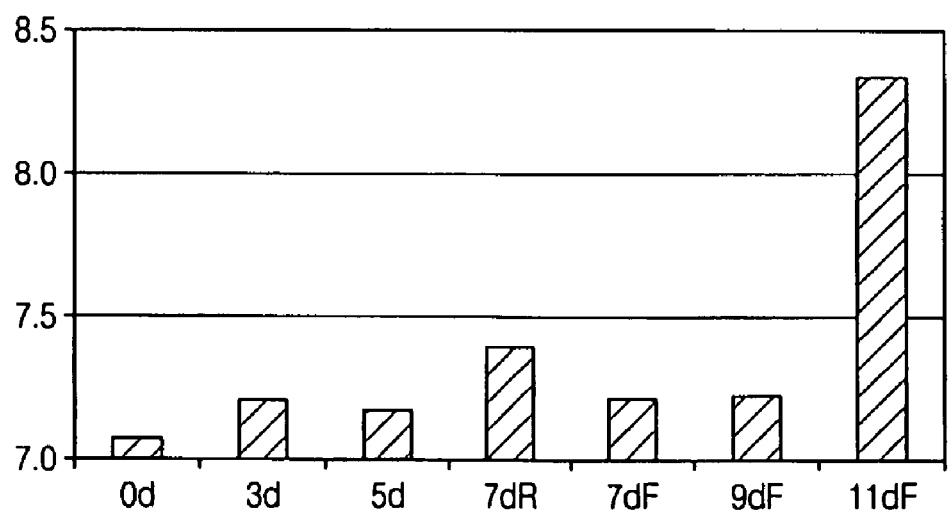
Figure 40U:
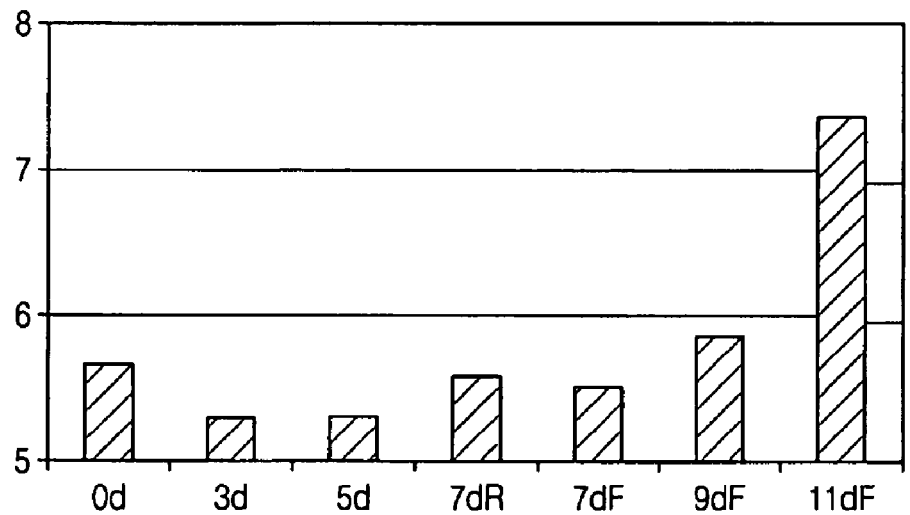
Figure 40V:
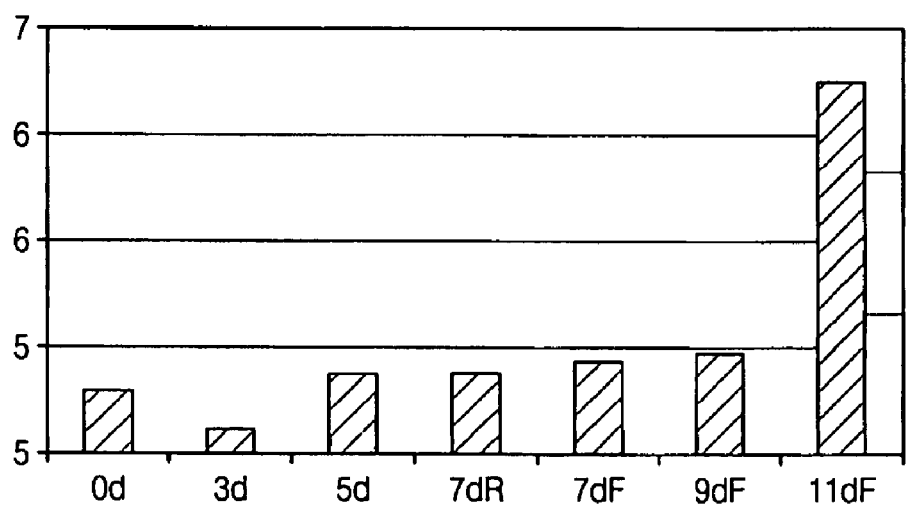
Figure 40W:
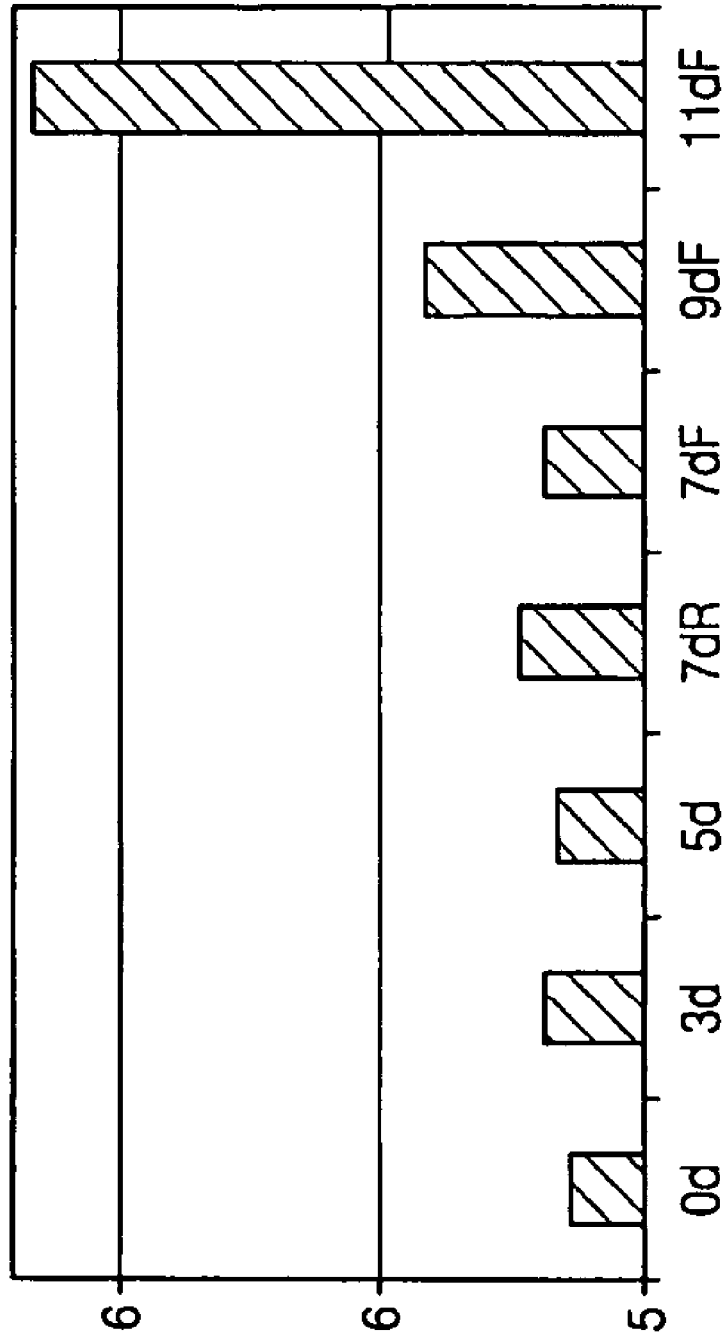

FIGS. 40A-W show the relative gene expression of TF, ADH6, HBG2, CYP3A7, SLC2A2, CYP3A5, CYP3A4, MUSK, CYP2A9, OLR1, SLC5A12, TM4SF4, TM4SF4, SLC38A4, MEP1A, SMP3, UBD, KNG1, ORM1///ORM2, HAL, SLC10A1, NR1H4, SERPINA7 in cells cultured as indicated above. FIGS. 40A-W demonstrate that expression of TF, ADH6, HBG2, CYP3A7, SLC2A2, CYP3A5, CYP3A4, MUSK, CYP2A9, OLR1, SLC5A12, TM4SF4, TM4SF4, SLC38A4, MEP1A, SMP3, UBD, KNG1, ORM1///ORM2, HAL, SLC10A1, NR1H4, SERPINA7 is enhanced in hepatocyte cells (see, FIGS. 40A-W, day 11F) as compared to hESCs (FIGS. 40A-W, day 0, day 3) liver precursor cells (FIGS. 40A-W, day 7F), or non-hepatocyte cells (FIGS. 40A-W, day 7R). These expression data demonstrate the usefulness of TF, ADH6, HBG2, CYP3A7, SLC2A2, CYP3A5, CYP3A4, MUSK, CYP2A9, OLR1, SLC5A12, TM4SP4, TM4SF4, SLC38A4, MEP1A, SMP3, UBD, KNG1, ORM1///ORM2, HAL, SLC10A1, NR1H4, SERPINA7 in cells cultured as indicated above. FIGS. 40A-W demonstrate that expression of TF, ADH6, HBG2, CYP3A7, SLC2A2, CYP3A5, CYP3A4, MUSK, CYP2A9, OLR1, SLC5A12, TM4SF4, TM4SF4, SLC38A4, MEP1A, SMP3, UBD, KNG1, ORM1///ORM2, HAL, SLC10A1, NR1H4, SERPINA7 as tools for the identification, purification and/or isolation of hepatocyte cells.

Example 14

Validation of Markers for Purification and Isolation of Mature Hepatocytes from Liver Precursor Cells The following experiments were done to further analyze gene expression of several genes identified in Example 13 as liver precursor or hepatocyte cell markers.

Serum glycoproteins containing terminal galactose and N-acetylgalactosamine residues are rapidly bound and internalized by the hepatocyte-specific asialoglycoprotein receptor (ASGPR), thus removing them from the circulation. This oligomeric receptor is highly expressed in liver and consists of a major subunit (42 kDa) and a highly homologous minor subunit (with alternatively glycosylated species of 45 and 51 kDa), designated either ASGR1 or MHL1 (mouse hepatic lectin 1) and ASGR2 or MHL2/3 (mouse hepatic lectin 2 and 3), respectively Lodish, H. F., (1991) *Trends Biochem. Sci.* 16:374-377.

The regulation of ASGR1 expression has a number of intriguing features. Although ASGR1 was originally described as a hepatic-specific gene, subsequent analysis has shown that ASGR1 is expressed, albeit at much lower levels, in a wide variety of non-hepatic tissues (Mu and Pacifico). For example, ASGR1 is expressed at substantial levels in the testes, and has a 5' RNA end that is quite different from those that have been described for the hepatic RNA (Monroe and Monroe).

Ventral or dorsal definitive endoderm cells were produced from undifferentiated hESCs using the same 3 (ventral differentiation) or 5 day (dorsal differentiation) protocols described in Example 13.

Figure 38A:
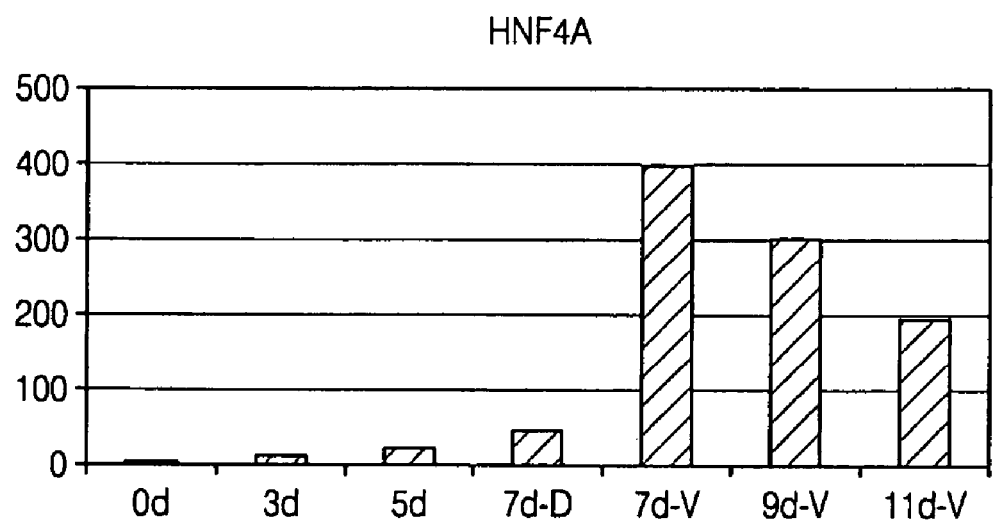
FIGS. 38A-J are a series of bar charts depicting gene expression patterns of HNF4α (panel A), CYP3A7 (panel B), DPP4 (panel C), Transferrin (panel D), AFP (panel E), HBGZ (panel F), ASGR1 (panel G), SLC17A8 (panel H), PCDHGB7 (panel I), and SLC10A1 (panel J) from hESCs cultured under either ventral or dorsal differentiation conditions for 0, 3, 5, 7, 9, or 11 days as indicated in the bar charts and as described in Example 13. These figures demonstrate that HNF4α (panel A), DPP4 (panel C), AFP (panel C) expression is enhanced in liver precursor cells (day 7). Further, the data demonstrate that the expression of ASGR1 (panel G), SLC17A8 (panel H), PCDHGB7 (panel I), and SLC10A1 (panel J) coincides with the expression of CYP3A7 (panel B), Transferrin (panel D), and HBGZ (panel F).
Figure 38B:
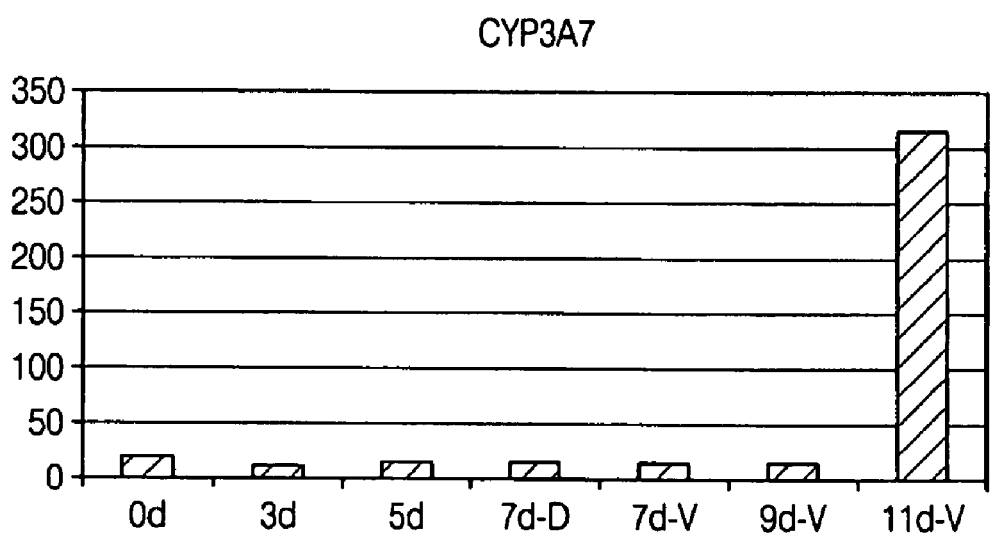
Figure 38C:
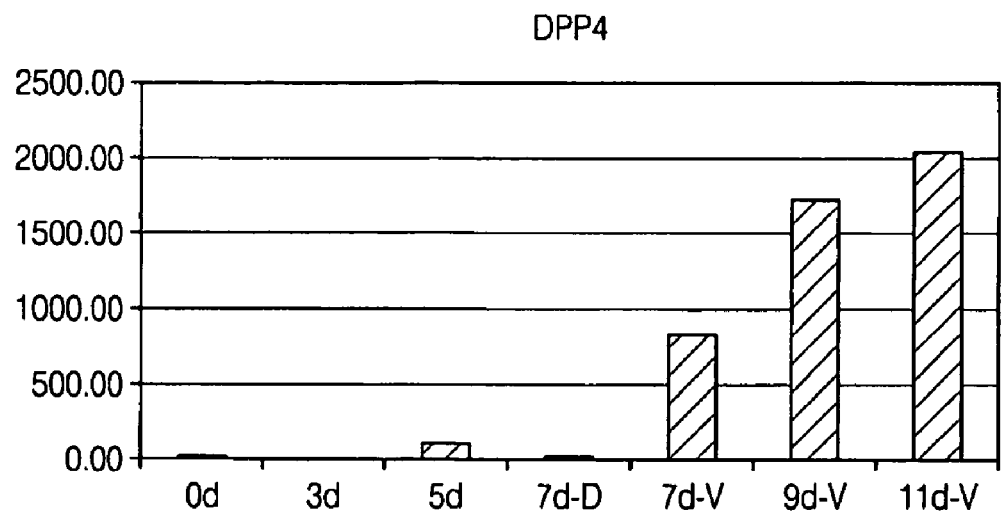
Figure 38D:
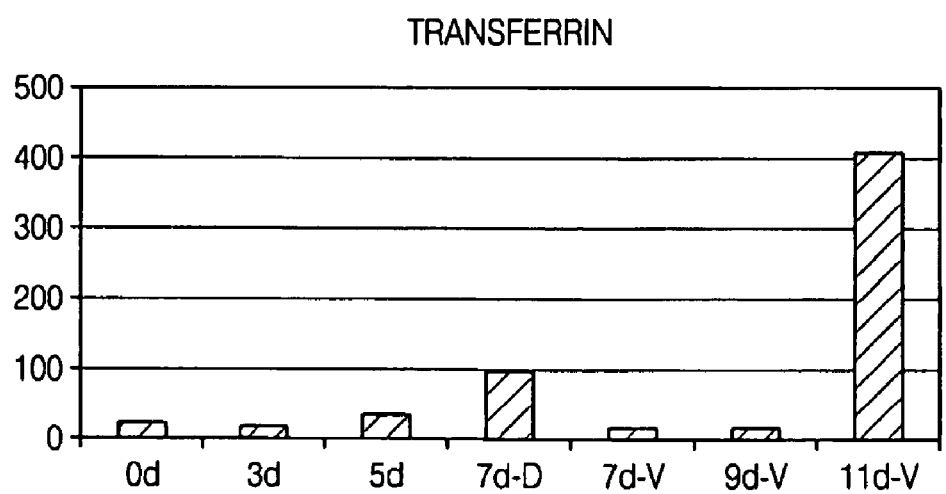
Figure 38E:
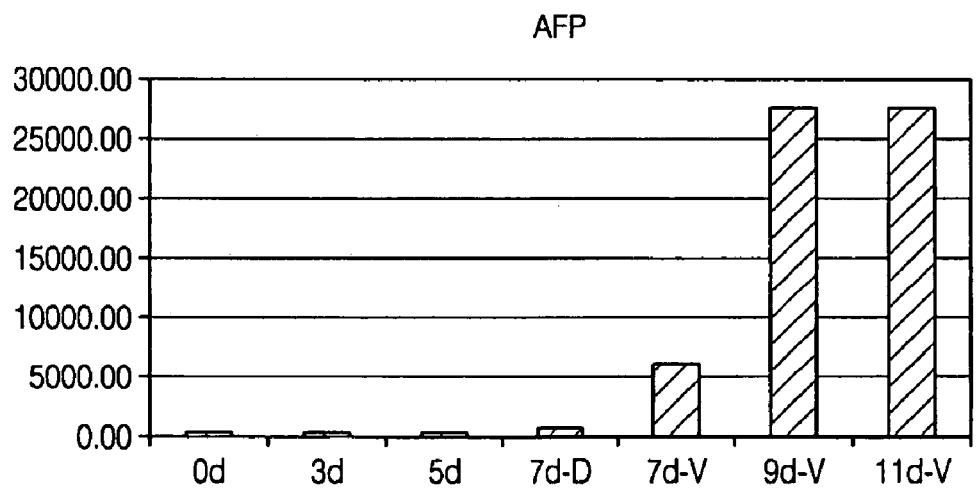
Figure 38F:
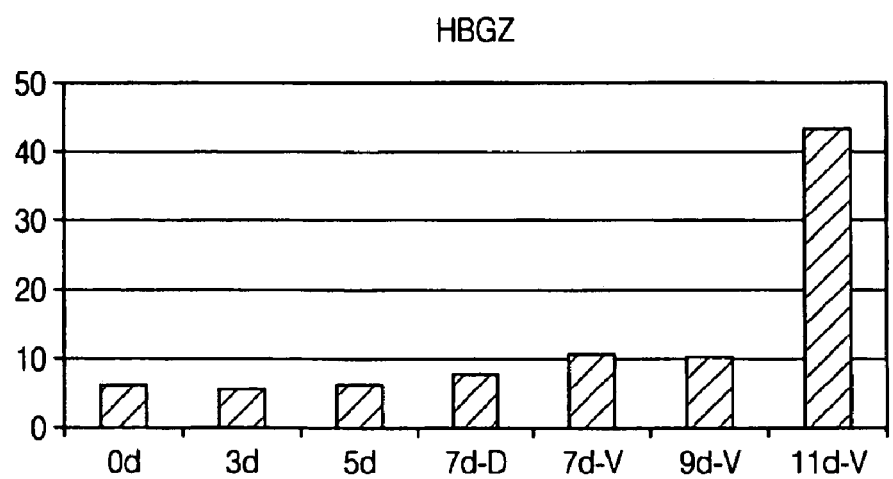
Figure 38G:
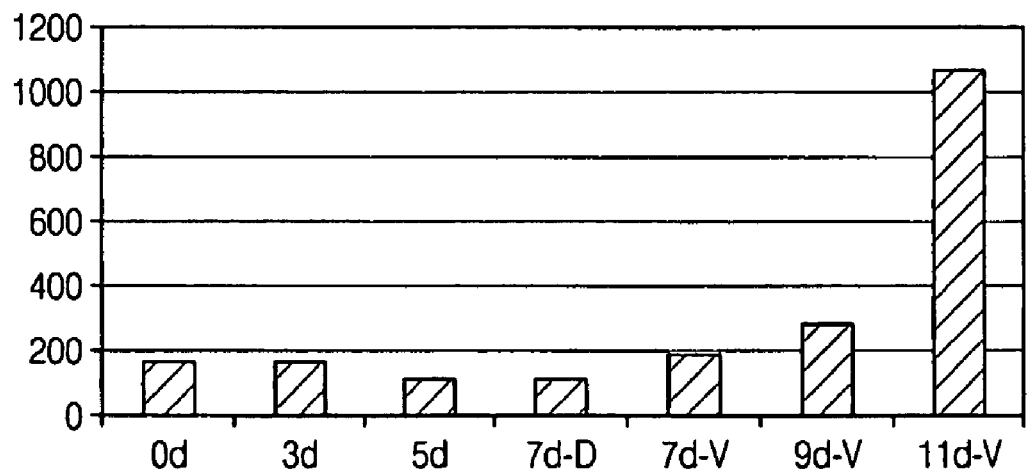
Figure 38H:
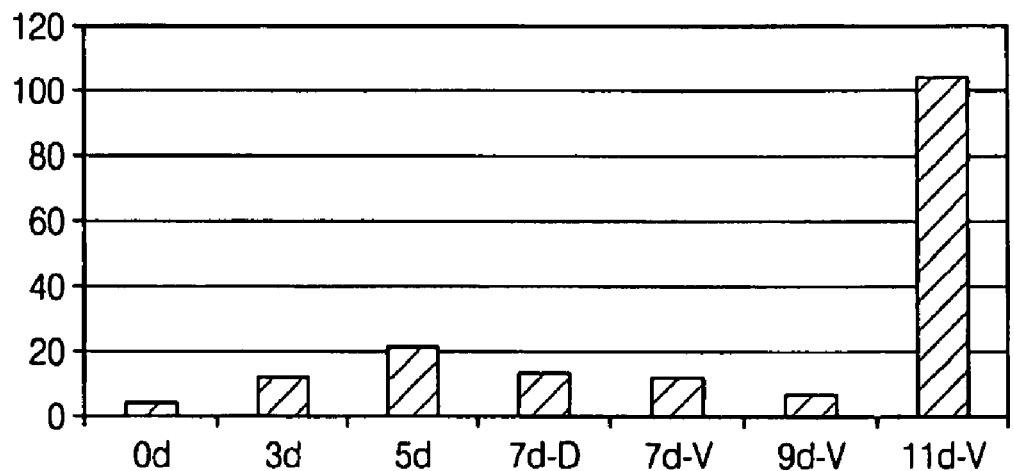
Figure 38I:
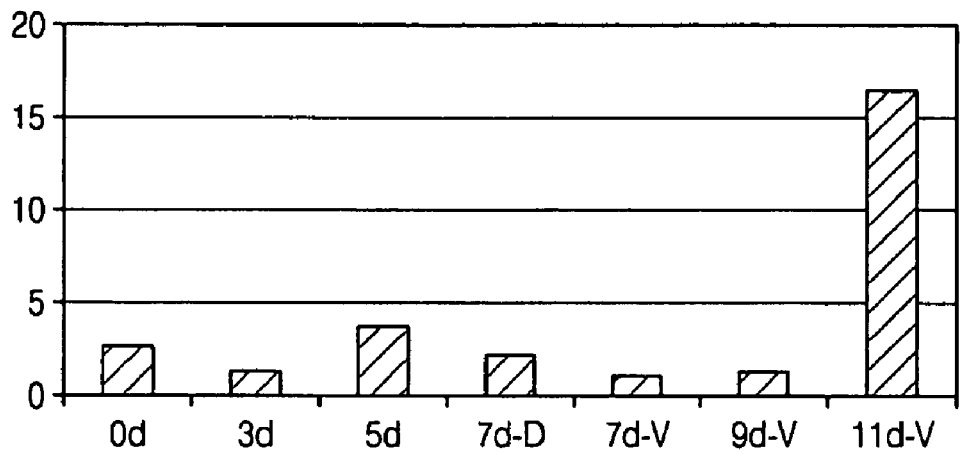
Figure 38J:
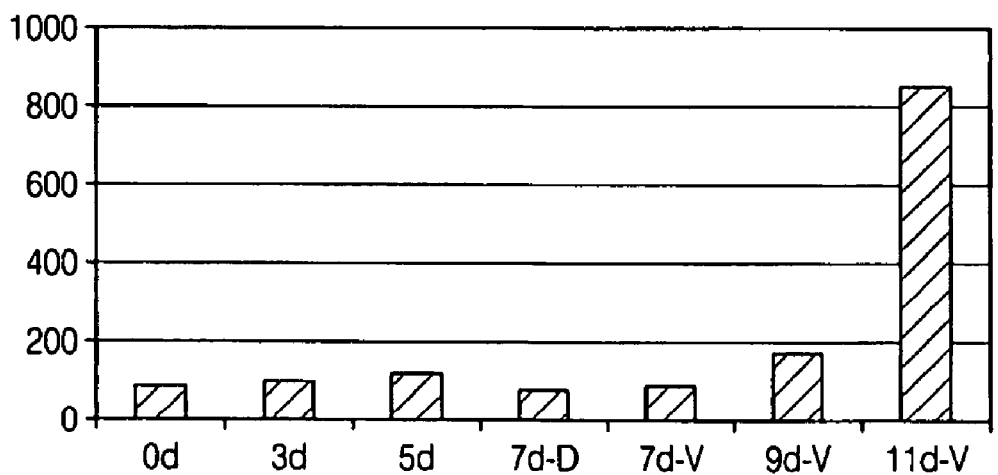

On days 0, 3, 5, 7, 9, and 11, mRNA was isolated from cells cultured using the ventral differentiation protocol described above. Similarly, on day 7 mRNA was isolated from cells treated with the dorsal differentiation procedure described above. Quantification of mRNAs of the following markers was tested in each sample using Q-PCR: HNF4α, DPP4, AFP, ASGR1, PCDHGB7, CYP3A7, Transferrin, HBGZ, SLC17A8, and SLC10A1. The gene expression results are presented in FIG. 37A-J. Differentiation to liver precursor cells is evident beginning at 7 days (HNF4α, DPP4, and AFP) (see FIGS. 38A, 38C, 38E) and culminating with more mature hepatocyte markers by 11 days (CYP3A7, Transferrin, Hemoglobin zeta) (see FIGS. 38B, 38D, 38F). The expression pattern of ASGR1 in differentiating hESCs shows that it is expressed in similar fashion to mature hepatocyte markers and not similar to markers of liver precursor cells. FIG. 38G. This is also true for the other surface proteins, solute carrier family 10 (sodium/bile acid cotransporter family, member 1 (SLC10A1)) (FIG. 38J), solute carrier family 17 (sodium-dependent inorganic phosphate cotransporter), member 8 (SLC17A8) (FIG. 38H), and protocadherin gamma subfamily B, 7 (PCDHGB7) (FIG. 38I). These expression data confirm the usefulness of ASGR1, SLC10A1, SLC17A8 and PCDHGB7 as tools to identify, purify and/or isolate mature hepatocytes.

Example 15

Hepatocyte Formation in Aggregate Cultures with Wnt3a

The following experiments were performed to compare hepatocyte differentiation conditions to pancreatic cell differentiation conditions in aggregate culture.

Undifferentiated hESCs were differentiated to foregut endoderm employing the following 6-day differentiation protocol. The initial medium used for differentiation was RPMI. During the six day protocol, the FBS concentrations in the RPMI medium changed from 0% for the first 24 hours followed by 0.2% for the next 48 hrs and then to 2% for the remaining 3 days. One day one, the medium contained both 100 ng/ml activin A and 25 ng/ml Wnt3a. On days two and three, Wnt3a was removed and on days four, five and six, activin A was replaced with 25 ng/ml KGF (FGF7).

On day 6, the foregut endoderm was dissociated to a single cell suspension using Accutase. About 5 million to 20 million cells were plated per well on an ultra-low adhesion Costar 6 well plate. The 6-well plate was rotated at 75-100 RPM to allow specific aggregation of the foregut endoderm cells during the differentiation process described below. To enhance hepatocyte-specific differentiation, the foregut cells were incubated in DMEM containing 100 ng/ml noggin; 0.2 µM retinoic acid; 50 ng/ml FGF10; 25 ng/ml Wnt3a and B27 at 1 part per hundred. Parallel cultures were incubated in the same medium lacking Wnt3a. After 9 days of rotation culture, all aggregated samples were incubated in DMEM+B27 (1/100) for 3 days followed by CMRL+B27 (1/100) out to 27 days. Duplicate samples of the differentiated aggregates were removed at various time points for QPCR analysis.

Figure 41A:
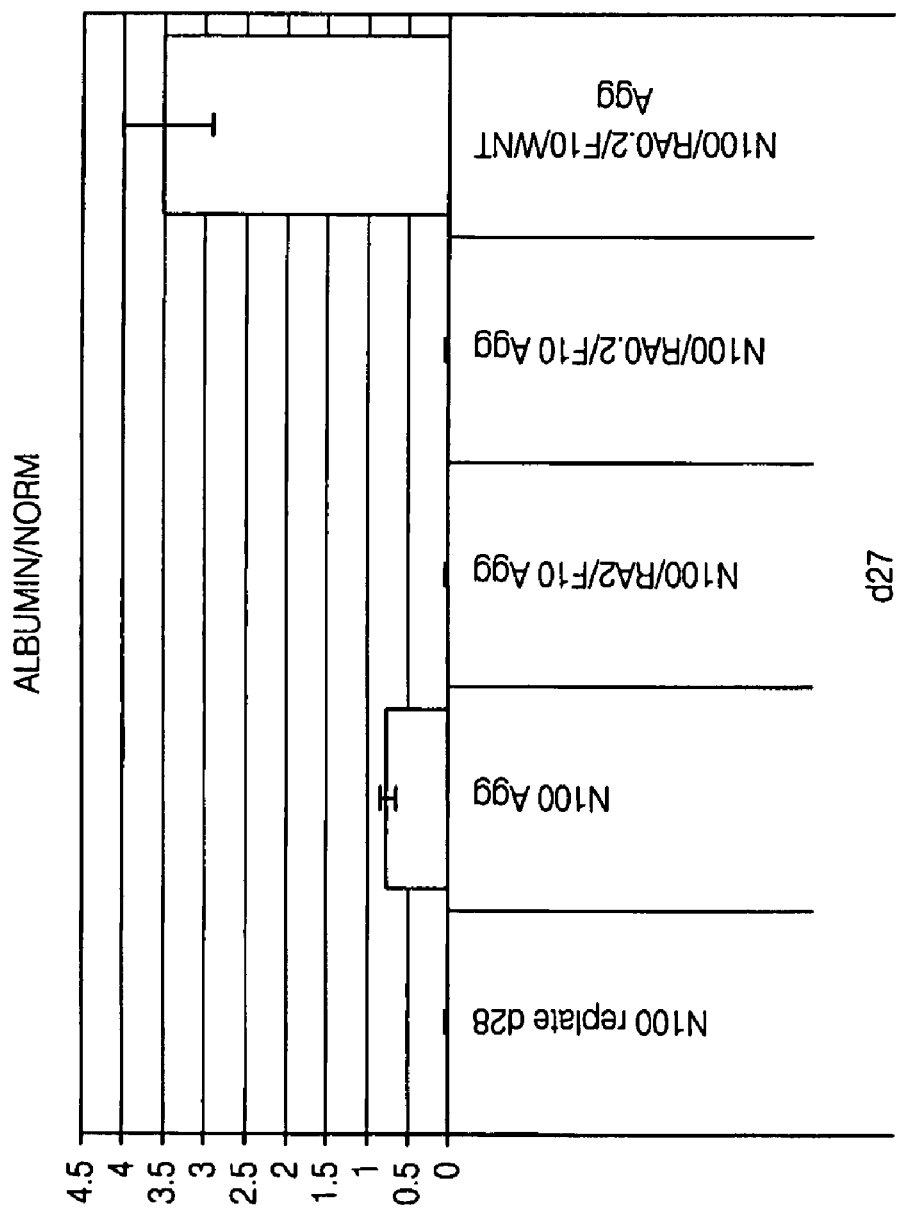
FIGS. 41A-B are bar charts showing expression of albumin transcript (panel A) and alpha-fetoprotein (AFP) transcript (panel B) as measured at day 27 of culture, or in the case of the column labeled "NL100 replate d28," at day 28. N100-100 ng/ml noggin; RA2-2 µM retinoic acid; RA0.2-0.2 µM retinoic acid; F10-50 ng/ml FGF10; WNT-25 ng/ml Wnt3a; Agg—aggregated.
Figure 41B:
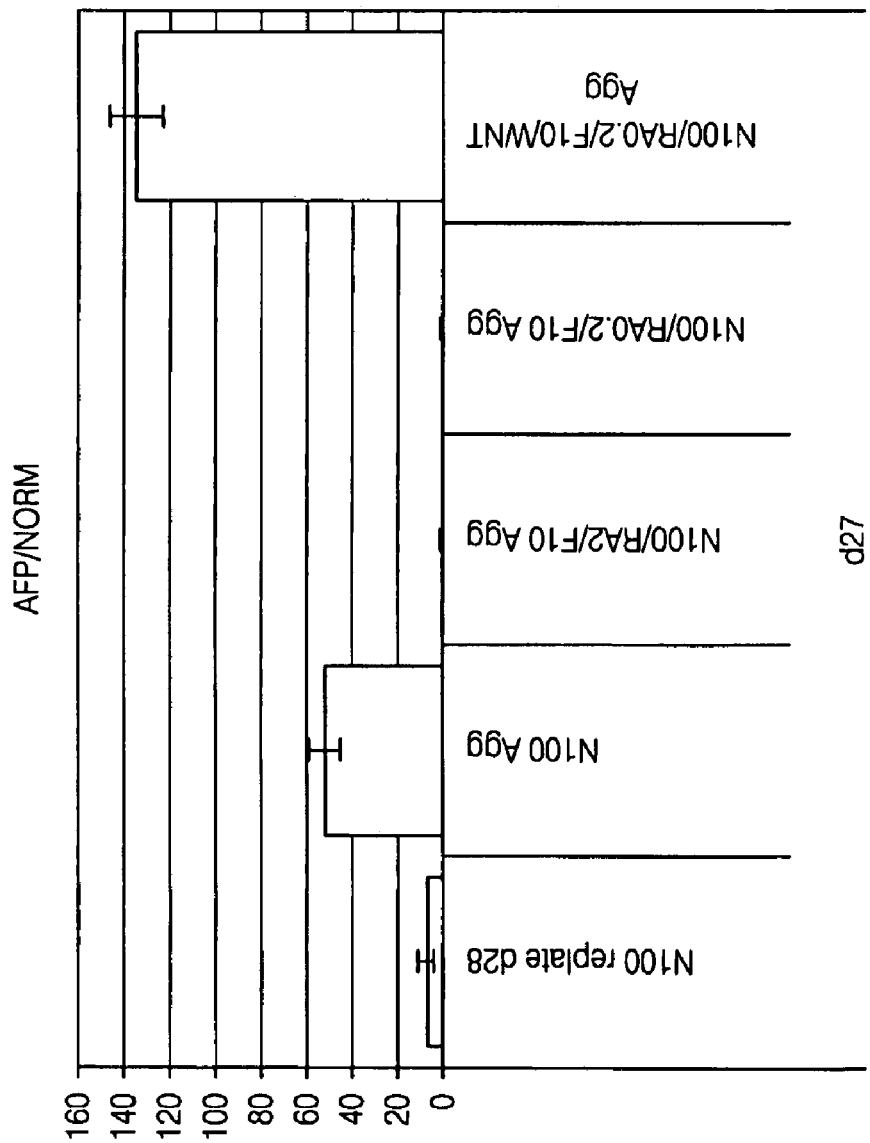

As shown in FIG. 41, a dramatic increase in the expression of liver markers, albumin (FIG. 41A) and AFP (FIG. 41B), was observed in cell aggregates that were contacted with Wnt3a. No appreciable marker expression was observed in cell aggregates that were not contacted with this factor. The difference in albumin transcript expression between aggregates contacted with Wnt3a and those not contacted with this factor is about 2676-fold. The difference in AFP transcript expression between aggregates contacted with Wnt3a and those not contacted with this factor is about 574-fold.

While the addition of Wnt3a during differentiation resulted in robust early liver gene upregulation as determined by the expression of albumin and AFP transcript, there was a reciprocal loss of pancreatic gene expression. Insulin gene expression was reduced by about 80-fold and GCG gene expression by about 79-fold. All major pancreatic transcription factors were significantly reduced in gene expression including PDX1(2.25×), PTF1a(9.4×), NKX6.1(13.7×), NKX2.2 (71×), PAX4(356×), and ISL1(27×).

The methods, compositions, and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure. Accordingly, it will be apparent to one skilled in the art that varying substitutions and modifications may be made to the invention disclosed herein without departing from the scope and spirit of the invention.

As used in the claims below and throughout this disclosure, by the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Marker Cross Reference

Table 3 lists the full gene name and accession number for each HUGO gene symbol and/or alias that is used to describe markers in this application.

TABLE 3

| HUGO Gene Symbol/Alias | Gene Full Name | Genbank Accession No. |
| --- | --- | --- |
| ADH6 | alcohol dehydrogenase 6 (class V) | NM_000672 |
| ALB | Albumin | NM_000477 |
| AFP | alpha-fetoprotein | NM_001134 |
| ALDH2 | aldehyde dehydrogenase 2 family (mitochondrial) | NM_000690 |
| APOA1 | apolipoprotein A-I | NM_000039 |
| APOA2 | apolipoprotein A-II | NM_001643 |
| ASGR1 | asialoglycoprotein receptor 1 | NM_001671 |
| BMP | bone morphogenetic protein | — |
| C3orf15 | chromosome 3 open reading frame 15 | NM_033364 |
| CUBN | cubilin (intrinsic factor-cobalamin receptor) | NM_001081 |
| CYP2C9 | cytochrome P450, family 2, subfamily C, polypeptide 9 | NM_000771 |
| CYP3A4 | cytochrome P450, family 3, subfamily A, polypeptide 4 | AF280107 |
| CYP3A5 | cytochrome P450, family 3, subfamily A, polypeptide 5 | L26985 |
| CYP3A7 | cytochrome P450, family 3, subfamily A, polypeptide 7 | NM_000765 |
| CYP4X1 | cytochrome P450, family 4, subfamily X, polypeptide 1 | NM_178033 |
| DGKB | diacylglycerol kinase, beta 90 kDa | NM_004080 |
| DOK4 | docking protein 4 | BC003541 |
| DPP4 | dipeptidyl-peptidase 4 (CD26, adenosine deaminase complexing protein 2) | M74777 |
| EPHA6 | EPH receptor A6 | XM_114973 |
| EVI1 | ecotropic viral integration site 1 | NM_005241 |
| FGF10 | fibroblast growth factor 10 | NM_004465 |
| FKBP7 | FK506 binding protein 7 | AF092137 |
| FN1 | fibronectin 1 | NM_002026 |
| GLUD1 | glutamate dehydrogenase 1 | NM_005271 |
| GLUD2 | glutamate dehydrogenase 2 | NM_012084 |
| GSN | gelsolin (amyloidosis, Finnish type) | X04412 |
| N/A | Histidine ammonia lyase (HAL) | P42357 |
| HBZ/HBGZ | hemoglobin, zeta | M24173 |
| HLA-B | major histocompatibility complex, class I, B | NM_005514 |
| HLA-C | major histocompatibility complex, class I, C | NM_002117 |
| HNF4α | hepatocyte nuclear factor 4, alpha | X76930 |
| HPX | hemopexin | NM_000613 |
| N/A | Hs.570199 | DW426910 |

TABLE 3-continued

| HUGO Gene Symbol/Alias | Gene Full Name | Genbank Accession No. |
|---|---|---|
| KNG1 | kininogen 1 | NM_000893 |
| N/A | hypothetical protein LOC130576 | NM_177964.3 |
| N/A | hypothetical protein LOC286167 | BC063665 |
| N/A | LOC440450 | XM_498676.1 |
| MEP1A | meprin A, alpha (PABA peptide hydrolase) | NM_005588 |
| MUSK | muscle, skeletal, receptor tyrosine kinase | AF006464 |
| MUSTN1 | musculoskeletal, embryonic nuclear protein 1 | XM_371644 |
| NOSTRIN | nitric oxide synthase trafficker | NM_052946 |
| NR1H4 | nuclear receptor subfamily 1, group H, member 4 | U68233 |
| OLR1 | oxidised low density lipoprotein (lectin-like) receptor 1 | D89050 |
| ORM1 | orosomucoid 1 | NM_000607 |
| ORM2 | orosomucoid 2 | NM_000608 |
| POU5F1/OCT4 | POU domain, class 5, transcription factor 1 | Z11898 |
| PCDH17 | protocadherin 17 | AF029343 |
| PCDHGB7 | protocadherin gamma subfamily B, 7 | AF152523 |
| PDHX/PDX1 | pyruvate dehydrogenase complex, component X | U82328 |
| PFTK1 | PFTAIRE protein kinase 1 | NM_012395 |
| PLA2G12B | phospholipase A2, group XIIB | NM_032562 |
| N/A | hypothetical protein PP1057 | PP1057 |
| PROX1 | prospero-related homeobox 1 | NM_002763 |
| TF | Transferrin | NM_001063 |
| TFGβ | transforming growth factor, beta | — |
| SERPINA7 | serpin peptidase inhibitor, clade A (alpha-1 antiproteinase, antitrypsin), member 7 | M14091 |
| SLC5A12 | solute carrier family 5 (sodium/glucose cotransporter), member 12 | NM_178498 |
| SLC10A1 | solute carrier family 10 (sodium/bile acid cotransporter family), member 1 | L21893 |
| SLC17A8 | solute carrier family 17 (sodium-dependent inorganic phosphate cotransporter), member 8 | NM_139319 |
| SLC35D1 | solute carrier family 35 (UDP-glucuronic acid/UDP-N-acetylgalactosamine dual transporter), member D1 | NM_015139 |
| SLC38A4 | solute carrier family 38, member 4 | AF193836 |
| SLC2A2 | solute carrier family 2 (facilitated glucose transporter), member 2 | NM_000340 |
| PIGZ/SMP3 | phosphatidylinositol glycan, class Z | NM_025163 |
| SP8 | Sp8 transcription factor | NM_198956 |
| SYTL5 | synaptotagmin-like 5 | NM_138780 |
| TM4SF1 | transmembrane 4 L six family member 1 | M90657 |
| TM4SF4 | transmembrane 4 L six family member 4 | NM_004617 |
| UBD | ubiquitin D | Y12653 |

N/A means not available

REFERENCES

Numerous literature and patent references have been cited in the present patent application. Each and every reference that is cited in this patent application is incorporated by reference herein in its entirety.

For some references, the complete citation is in the body of the text. For other references the citation in the body of the text is by author and year, the complete citation being as follows:

United States Patent Application Publication No. 2006/0019387, filed Jan. 19, 2005.

Alexander, J., Rothenberg, M., Henry, G. L., and Stainier, D. Y. (1999). Casanova plays an early and essential role in endoderm formation in zebrafish. Dev Biol 215, 343-357.

Alexander, J., and Stainier, D. Y. (1999). A molecular pathway leading to endoderm formation in zebrafish. Curr Biol 9, 1147-1157.

Aoki, T. O., Mathieu, J., Saint-Etienne, L., Rebagliati, M. R., Peyrieras, N., and Rosa, F. M. (2002). Regulation of nodal signalling and mesendoderm formation by TARAM-A, a TGFbeta-related type I receptor. Dev Biol 241, 273-288.

Ausubel et al., (1997), Current Protocols of Molecular Biology, John Wiley and Sons, Hoboken, N.J.

Beck, S., Le Good, J. A., Guzman, M., Ben Haim, N., Roy, K., Beermann, F., and Constam, D. B. (2002). Extra-embryonic proteases regulate Nodal signalling during gastrulation. Nat Cell Biol 4, 981-985.

Beddington, R. S., Rashbass, P., and Wilson, V. (1992). Brachyury—a gene affecting mouse gastrulation and early organogenesis. Dev Suppl, 157-165.

Bongso, A., Fong, C. Y., Ng, S. C., and Ratnam, S. (1994). Isolation and culture of inner cell mass cells from human blastocysts. Hum Reprod 9, 2110-2117.

Chang, H., Brown, C. W., and Matzuk, M. M. (2002). Genetic analysis of the mammalian transforming growth factor-beta superfamily. Endocr Rev 23, 787-823.

Collins, J. C., Stockert, R. J. and Morell, A. G., 1984. Asialoglycoprotein receptor expression in murine pregnancy development. *Hepatology* 1:80-83.

Conlon, F. L., Lyons, K. M., Takaesu, N., Barth, K. S., Kispert, A., Herrmann, B., and Robertson, E. J. (1994). A primary requirement for nodal in the formation and maintenance of the primitive streak in the mouse. Development 120, 1919-1928.

Dougan, S. T., Warga, R. M., Kane, D. A., Schier, A. F., and Talbot, W. S. (2003). The role of the zebrafish nodal-related genes squint and cyclops in patterning of mesendoderm. Development 130, 1837-1851.

Feldman, B., Gates, M. A., Egan, E. S., Dougan, S. T., Rennebeck, G., Sirotkin, H. I., Schier, A. F., and Talbot, W. S. (1998). Zebrafish organizer development and germ-layer formation require nodal-related signals. Nature 395, 181-185.

Feng, Y., Broder, C. C., Kennedy, P. E., and Berger, E. A. (1996). HIV-1 entry cofactor: functional cDNA cloning of a seven-transmembrane, G protein-coupled receptor. Science 272, 872-877.

Futaki, S., Hayashi, Y., Yamashita, M., Yagi, K., Bono, H., Hayashizaki, Y., Okazaki, Y., and Sekiguchi, K. (2003). Molecular basis of constitutive production of basement membrane components: Gene expression profiles of engelbreth-holm-swarm tumor and F9 embryonal carcinoma cells. J Biol Chem.

Grapin-Botton, A., and Melton, D. A. (2000). Endoderm development: from patterning to organogenesis. Trends Genet 16, 124-130.

Harris, T. M., and Childs, G. (2002). Global gene expression patterns during differentiation of F9 embryonal carcinoma cells into parietal endoderm. Funct Integr Genomics 2, 105-119.

Hogan, B. L. (1996). Bone morphogenetic proteins in development. Curr Opin Genet Dev 6, 432-438.

Hogan, B. L. (1997). Pluripotent embryonic cells and methods of making same (U.S.A., Vanderbilt University).

Howe, C. C., Overton, G. C., Sawicki, J., Solter, D., Stein, P., and Strickland, S. (1988). Expression of SPARC/osteonectin transcript in murine embryos and gonads. Differentiation 37, 20-25.

Hudson, C., Clements, D., Friday, R. V., Stott, D., and Woodland, H. R. (1997). Xsox17alpha and -beta mediate endoderm formation in Xenopus. Cell 91, 397-405.

Imada, M., Imada, S., Iwasaki, H., Kume, A., Yamaguchi, H., and Moore, E. E. (1987). Fetomodulin: marker surface protein of fetal development which is modulatable by cyclic AMP. Dev Biol 122, 483-491.

Ise H, Sugihara N, Negishi N, Nikaido T, Akaike T: 2001. Low asialoglycoprotein receptor expression as markers for highly proliferative potential hepatocytes. *Biochem Biophys Res Commun* 285:172-182.

Kanai-Azuma, M., Kanai, Y., Gad, J. M., Tajima, Y., Taya, C., Kurohmaru, M., Sanai, Y., Yonekawa, H., Yazaki, K., Tam, P. P., and Hayashi, Y. (2002). Depletion of definitive gut endoderm in Sox17-null mutant mice. Development 129, 2367-2379.

Katoh, M. (2002). Expression of human SOX7 in normal tissues and tumors. Int J Mol Med 9, 363-368.

Kikuchi, Y., Agathon, A., Alexander, J., Thisse, C., Waldron, S., Yelon, D., Thisse, B., and Stainier, D. Y. (2001). casanova encodes a novel Sox-related protein necessary and sufficient for early endoderm formation in zebrafish. Genes Dev 15, 1493-1505.

Kim, C. H., and Broxmeyer, H. E. (1999). Chemokines: signal lamps for trafficking of T and B cells for development and effector function. J Leukoc Biol 65, 6-15.

Kimelman, D., and Griffin, K. J. (2000). Vertebrate mesendoderm induction and patterning. Curr Opin Genet Dev 10, 350-356.

Kubo A, Shinozaki K, Shannon J M, Kouskoff V, Kennedy M, Woo S, Fehling H J, Keller G. (2004) Development of definitive endoderm from embryonic stem cells in culture. Development. 131, 1651-62.

Kumar, A., Novoselov, V., Celeste, A. J., Wolfman, N. M., ten Dijke, P., and Kuehn, M. R. (2001). Nodal signaling uses activin and transforming growth factor-beta receptor-regulated Smads. J Biol Chem 276, 656-661.

Labosky, P. A., Barlow, D. P., and Hogan, B. L. (1994a). Embryonic germ cell lines and their derivation from mouse primordial germ cells. Ciba Found Symp 182, 157-168; discussion 168-178.

Labosky, P. A., Barlow, D. P., and Hogan, B. L. (1994b). Mouse embryonic germ (EG) cell lines: transmission through the germline and differences in the methylation imprint of insulin-like growth factor 2 receptor (Igf2r) gene compared with embryonic stem (ES) cell lines. Development 120, 3197-3204.

Lickert, H., Kutsch, S., Kanzler, B., Tamai, Y., Taketo, M. M., and Kemler, R. (2002). Formation of multiple hearts in mice following deletion of beta-catenin in the embryonic endoderm. Dev Cell 3, 171-181.

Lodish, H. F., 1991. Recognition of complex oligosaccharides by the multi-subunit asialoglycoprotein receptor. *Trends Biochem. Sci.* 16:374-377.

Lu, C. C., Brennan, J., and Robertson, E. J. (2001). From fertilization to gastrulation: axis formation in the mouse embryo. Curr Opin Genet Dev 11, 384-392.

Ma, Q., Jones, D., and Springer, T. A. (1999). The chemokine receptor CXCR4 is required for the retention of B lineage and granulocytic precursors within the bone marrow microenvironment. Immunity 10, 463-471.

Malik V and Lillehoj E (ed.), (1994), Antibody Techniques, Academic Press, Inc. Burlington, Mass.

McGrath K E, Koniski A D, Maltby K M, McGann J K, Palis J. (1999) Embryonic expression and function of the chemokine SDF-1 and its receptor, CXCR4. Dev Biol. 213, 442-56.

Miyazono, K., Kusanagi, K., and Inoue, H. (2001). Divergence and convergence of TGF-beta/BMP signaling. J Cell Physiol 187, 265-276.

Monroe, R. S. and Huber, B. E., 1994. The major form of the murine asialoglycoprotein receptor: cDNA sequence and expression in liver, testes and epididymis. *Gene* 148:237-244.

Mu, J. Z., Tang, L. H. and Alpers, D. H., 1993. Asialoglycoprotein receptor mRNAs are expressed in most extrahepatic rat tissues during development. *Am. J. Physiol.* 264: G752-G762.

Nagasawa, T., Hirota, S., Tachibana, K., Takakura, N., Nishikawa, S., Kitamura, Y., Yoshida, N., Kikutani, H., and Kishimoto, T. (1996). Defects of B-cell lymphopoiesis and bone-marrow myelopoiesis in mice lacking the CXC chemokine PBSF/SDF-1. Nature 382, 635-638.

Niwa, H. (2001). Molecular mechanism to maintain stem cell renewal of ES cells. Cell Struct Funct 26, 137-148.

Ogura, H., Aruga, J., and Mikoshiba, K. (2001). Behavioral abnormalities of Zic1 and Zic2 mutant mice: implications as models for human neurological disorders. Behav Genet 31, 317-324.

Pacifico, F., Laviola, L., Ulianich, L., Porcellini, A., Ventra, C., Consiglio, E. and Avvedimento, V. E., 1995. Differential expression of the asyaloglycoprotein receptor in discrete brain areas, in kidney and thyroid. *Biochem. Biophys. Res. Commun.* 210:138-144.

Reubinoff, B. E., Pera, M. F., Fong, C. Y., Trounson, A., and Bongso, A. (2000). Embryonic stem cell lines from human blastocysts: somatic differentiation in vitro. Nat Biotechnol 18, 399-404.

Rodaway, A., and Patient, R. (2001). Mesendoderm. an ancient germ layer? Cell 105, 169-172.

Rodaway, A., Takeda, H., Koshida, S., Broadbent, J., Price, B., Smith, J. C., Patient, R., and Holder, N. (1999). Induction of the mesendoderm in the zebrafish germ ring by yolk cell-derived TGF-beta family signals and discrimination of mesoderm and endoderm by FGF. Development 126, 3067-3078.

Rohr, K. B., Schulte-Merker, S., and Tautz, D. (1999). Zebrafish zic1 expression in brain and somites is affected by BMP and hedgehog signalling. Mech Dev 85, 147-159.

Schier, A. F. (2003). Nodal signaling in vertebrate development. Annu Rev Cell Dev Biol 19, 589-621.

Schoenwolf, G. C., and Smith, J. L. (2000). Gastrulation and early mesodermal patterning in vertebrates. Methods Mol Biol 135, 113-125.

Shamblott, M. J., Axelman, J., Wang, S., Bugg, E. M., Littlefield, J. W., Donovan, P. J., Blumenthal, P. D., Huggins, G. R., and Gearhart, J. D. (1998). Derivation of pluripotent stem cells from cultured human primordial germ cells. Proc Natl Acad Sci USA 95, 13726-13731.

Shapiro, A. M., Lakey, J. R., Ryan, E. A., Korbutt, G. S., Toth, E., Warnock, G. L., Kneteman, N. M., and Rajotte, R. V. (2000). Islet transplantation in seven patients with type 1 diabetes mellitus using a glucocorticoid-free immunosuppressive regimen. N Engl J Med 343, 230-238.

Shapiro, A. M., Ryan, E. A., and Lakey, J. R. (2001a). Pancreatic islet transplantation in the treatment of diabetes mellitus. Best Pract Res Clin Endocrinol Metab 15, 241-264.

Shapiro, J., Ryan, E., Warnock, G. L., Kneteman, N. M., Lakey, J., Korbutt, G. S., and Rajotte, R. V. (2001b). Could fewer islet cells be transplanted in type 1 diabetes? Insulin independence should be dominant force in islet transplantation. Bmj 322, 861.

Shiozawa, M., Hiraoka, Y., Komatsu, N., Ogawa, M., Sakai, Y., and Aiso, S. (1996). Cloning and characterization of Xenopus laevis xSox7 cDNA. Biochim Biophys Acta 1309, 73-76.

Smith, J. (1997). Brachyury and the T-box genes. Curr Opin Genet Dev 7, 474-480.

Smith, J. C., Armes, N. A., Conlon, F. L., Tada, M., Umbhauer, M., and Weston, K. M. (1997). Upstream and downstream from Brachyury, a gene required for vertebrate mesoderm formation. Cold Spring Harb Symp Quant Biol 62, 337-346.

Takash, W., Canizares, J., Bonneaud, N., Poulat, F., Mattei, M. G., Jay, P., and Berta, P. (2001). SOX7 transcription factor: sequence, chromosomal localisation, expression, transactivation and interference with Wnt signalling. Nucleic Acids Res 29, 4274-4283.

Taniguchi, K., Hiraoka, Y., Ogawa, M., Sakai, Y., Kido, S., and Aiso, S. (1999). Isolation and characterization of a mouse SRY-related cDNA, mSox7. Biochim Biophys Acta 1445, 225-231.

Technau, U. (2001). Brachyury, the blastopore and the evolution of the mesoderm. Bioessays 23, 788-794.

Thomson, J. A., Itskovitz-Eldor, J., Shapiro, S. S., Waknitz, M. A., Swiergiel, J. J., Marshall, V. S., and Jones, J. M. (1998). Embryonic stem cell lines derived from human blastocysts. Science 282, 1145-1147.

Tremblay, K. D., Hoodless, P. A., Bikoff, E. K., and Robertson, E. J. (2000). Formation of the definitive endoderm in mouse is a Smad2-dependent process. Development 127, 3079-3090.

Vandesompele, J., De Preter, K., Pattyn, F., Poppe, B., Van Roy, N., De Paepe, A., and Speleman, F. (2002). Accurate normalization of real-time quantitative RT-PCR data by geometric averaging of multiple internal control genes. Genome Biol 3, RESEARCH0034.

Varlet, I., Collignon, J., and Robertson, E. J. (1997). nodal expression in the primitive endoderm is required for specification of the anterior axis during mouse gastrulation. Development 124, 1033-1044.

Vincent, S. D., Dunn, N. R., Hayashi, S., Norris, D. P., and Robertson, E. J. (2003), Cell fate decisions within the mouse organizer are governed by graded Nodal signals. Genes Dev 17, 1646-1662.

Weiler-Guettler, H., Aird, W. C., Rayburn, H., Husain, M., and Rosenberg, R. D. (1996). Developmentally regulated gene expression of thrombomodulin in postimplantation mouse embryos. Development 122, 2271-2281.

Weiler-Guettler, H., Yu, K., Soff, G., Gudas, L. J., and Rosenberg, R. D. (1992). Thrombomodulin gene regulation by cAMP and retinoic acid in F9 embryonal carcinoma cells. Proceedings Of The National Academy Of Sciences Of The United States Of America 89, 2155-2159.

Wells, J. M., and Melton, D. A. (1999). Vertebrate endoderm development. Annu Rev Cell Dev Biol 15, 393-410.

Wells, J. M., and Melton, D. A. (2000). Early mouse endoderm is patterned by soluble factors from adjacent germ layers. Development 127, 1563-1572.

Willison, K. (1990). The mouse Brachyury gene and mesoderm formation. Trends Genet 6, 104-105.

Zhao, G. Q. (2003). Consequences of knocking out BMP signaling in the mouse. Genesis 35, 43-56.

Zhou, X., Sasaki, H., Lowe, L., Hogan, B. L., and Kuehn, M. R. (1993). Nodal is a novel TGF-beta-like gene expressed in the mouse node during gastrulation. Nature 361, 543-547.

What is claimed is:

1. An in vitro method for producing human liver precursor cells, said method comprising contacting a cell population comprising human definitive endoderm cells with BMP4 and FGF10 for a time sufficient to allow the differentiation of human liver precursor cells from said human definitive endoderm cells.

2. The method of claim 1, wherein said BMP4 is provided to said cell population for about 1 day to about 8 days.

3. The method of claim 1, wherein said BMP4 is provided to said cell population for about 1 day to about 5 days.

4. The method of claim 1, wherein said BMP4 is provided to said cell population for about 1 day to about 3 days.

5. The method of claim 1, wherein said FGF10 is provided to said cell population for about 1 day to about 8 days.

6. The method of claim 1, wherein said FGF10 is provided to said cell population for about 1 day to about 5 days.

7. The method of claim 1, wherein said FGF10 is provided to said cell population for about 1 day to about 3 days.

8. The method of claim 1, wherein said FGF10 is provided to said cell population for about 1 day to about 2 days.

9. The method of claim 1, wherein BMP4 is provided to said cell population at a concentration ranging from about 0.1 ng/ml to about 100 ng/ml.

10. The method of claim 1, wherein BMP4 is provided to said cell population at a concentration ranging from about 1 ng/ml to about 5 ng/ml.

11. The method of claim 1, wherein BMP4 is provided to said cell population at a concentration of about 3 ng/ml.

12. The method of claim 1, wherein FGF10 is provided to said cell population at a concentration ranging from about 1 ng/ml to about 1000 ng/ml.

13. The method of claim 1, wherein FGF10 is provided to said cell population at a concentration ranging from about 5 ng/ml to about 500 ng/ml.

14. The method of claim 1, wherein said FGF10 is provided to said cell population at a concentration ranging from about 20 ng/ml to about 200 ng/ml.

15. The method of claim 1, wherein FGF10 is provided to said cell population at a concentration of about 50 ng/ml.

16. The method of claim 1 further comprising providing B27 to said cell population.

17. The method of claim 16, wherein said B27 is provided to said cell population at a concentration ranging from about 0.1% to about 20% of the total medium.

18. The method of claim 16, wherein said B27 is provided to said cell population at a concentration ranging from about 0.2% to about 2% of the total medium.

19. The method of claim 16, wherein said B27 is provided to said cell population at a concentration of about 0.5% of the total medium.

20. The method of claim 16, wherein said B27 is provided to said cell population for about 1 day to about 8 days.

21. The method of claim 16, wherein said B27 is provided to said cell population for about 2 days to about 6 days.

22. The method of claim 16, wherein said B27 is provided to said cell population for about 5 days.

23. The method of claim 1, wherein activin A is present in said cell population.

24. The method of claim 1, wherein activin A is not substantially present in said cell population.

25. The method of claim 1, wherein said human definitive endoderm cells are differentiated in vitro from human embryonic stem cells (hESCs).

26. The method of claim 25, wherein the differentiation of said hESCs to definitive endoderm cells comprises providing said hESCs with activin A.

27. The method of claim 26, wherein said hESCs are provided with activin A for about 1 day to about 8 days.

28. The method of claim 26, wherein said hESCs are provided with activin A for about 1 day to about 6 days.

29. The method of claim 26, wherein said hESCs are provided with activin A for about 1 day to about 5 days.

30. The method of claim 26, wherein said hESCs are provided with activin A for about 3 days.

31. The method of claim 26, wherein activin A is provided to said hESCs at a concentration ranging from about 0.1 ng/ml to about 1000 ng/ml.

32. The method of claim 26, wherein activin A is provided to said hESCs at a concentration ranging from about 1 ng/ml to about 500 ng/ml.

33. The method of claim 26, wherein activin A is provided to said hESCs at a concentration ranging from about 20 ng/ml to about 200 ng/ml.

34. The method of claim 26, wherein activin A is provided to said hESCs at a concentration of about 100 ng/ml.

35. The method of claim 1, wherein said cell population comprises at least about 10% human definitive endoderm cells.

36. The method of claim 1, wherein said cell population comprises at least about 25% human definitive endoderm cells.

37. The method of claim 1, wherein said cell population comprises at least about 50% human definitive endoderm cells.

38. The method of claim 1, wherein said cell population comprises at least about 75% human definitive endoderm cells.

39. The method of claim 1, wherein said cell population comprises at least about 90% human definitive endoderm cells.

* * * * *

UNITED STATES PATENT AND TRADEMARK OFFICE
CERTIFICATE OF CORRECTION

PATENT NO.        : 7,989,204 B2
APPLICATION NO.   : 12/298898
DATED             : August 2, 2011
INVENTOR(S)       : D'Amour et al.

It is certified that error appears in the above-identified patent and that said Letters Patent is hereby corrected as shown below:

On Column 4, Line 35, please change "APP," to --AFP,--;

On Column 16, Line 44, please change "panel" to --(panel--;

On Column 17, Line 10, please change "panel" to --(panel--;

On Column 17, Line 50, please change ""NL100" to --"N100--;

On Column 20, Line 32, please change "fitters" to --filters--;

On Column 20, Line 44, please change "RNAS)," to --RNAs),--;

On Column 29, Line 38, please change "PFTK1" to --PFTK1,--;

On Column 39, Line 60, please change "herein" to --herein.--;

On Column 44, Line 34, please change "cells)" to --cells,--;

On Column 50, Line 57, please change "Techniques" to --Techniques:--;

On Column 68, Line 46 (Approx.), please change "TBP)," to --(TBP),--;

On Column 69, Line 20 (Approx.), please change "endoderm," to --endoderm.--;

On Column 70, Line 60, after "in" please insert --in--;

On Column 74, Line 43, please change "population" to --population.--;

On Column 79, Line 14, please change "GLUD1/GLUD2," to --GLUD1//GLUD2,--;

On Column 79, Line 50 (Approx.), please change "TM4SP4," to --TM4SF4,--.

Signed and Sealed this
Thirty-first Day of July, 2012

David J. Kappos
*Director of the United States Patent and Trademark Office*

SEQUENCE LISTING

```
<160> NUMBER OF SEQ ID NOS: 2

<210> SEQ ID NO 1
<211> LENGTH: 1245
<212> TYPE: DNA
<213> ORGANISM: Homo sapiens

<400> SEQUENCE: 1
atgagcagcc cggatgcggg atacgccagt gacgaccaga gccagaccca gagcgcgctg      60
cccgcggtga tggccgggct gggcccctgc ccctgggccg agtcgctgag ccccatcggg     120
gacatgaagg tgaagggcga ggcgccggcg aacagcggag caccggccgg ggccgcgggc     180
cgagccaagg gcgagtcccg tatccggcgg ccgatgaacg ctttcatggt gtgggctaag     240
gacgagcgca agcggctggc gcagcagaat ccagacctgc acaacgccga gttgagcaag     300
atgctgggca agtcgtggaa ggcgctgacg ctggcggaga agcggccctt cgtggaggag     360
```

-continued

```
gcagagcggc tgcgcgtgca gcacatgcag gaccacccca actacaagta ccggccgcgg      420
cggcgcaagc aggtgaagcg gctgaagcgg gtggagggcg gcttcctgca cggcctggct      480
gagccgcagg cggccgcgct gggccccgag ggcggccgcg tggccatgga cggcctgggc      540
ctccagttcc ccgagcaggg cttccccgcc ggcccgccgc tgctgcctcc gcacatgggc      600
ggccactacc gcgactgcca gagtctgggc gcgcctccgc tcgacggcta cccgttgccc      660
acgcccgaca cgtccccgct ggacggcgtg gaccccgacc cggctttctt cgccgccccg      720
atgcccgggg actgcccggc ggccggcacc tacagctacg cgcaggtctc ggactacgct      780
ggccccccgg agcctcccgc cggtcccatg cacccccgac tcggcccaga gcccgcgggt      840
ccctcgattc cgggcctcct ggcgccaccc agcgcccttc acgtgtacta cggcgcgatg      900
ggctcgcccg ggcgggcgg cgggcgcggc ttccagatgc agccgcaaca ccagcaccag      960
caccagcacc agcaccaccc ccgggcccc ggacagccgt cgcccctcc ggaggcactg      1020 ccctgccggg acgcacgga ccccagtcag cccgccgagc tcctcgggga ggtggaccgc      1080
acggaatttg aacagtatct gcacttcgtg tgcaagcctg agatgggcct cccctaccag      1140
gggcatgact ccggtgtgaa tctccccgac agccacgggg ccatttcctc ggtggtgtcc      1200
gacgccagct ccgcggtata ttactgcaac tatcctgacg tgtga                     1245
```

<210> SEQ ID NO 2
<211> LENGTH: 414
<212> TYPE: PRT
<213> ORGANISM: Homo sapiens

<400> SEQUENCE: 2

```
Met Ser Ser Pro Asp Ala Gly Tyr Ala Ser Asp Asp Gln Ser Gln Thr
 1               5                  10                  15

Gln Ser Ala Leu Pro Ala Val Met Ala Gly Leu Gly Pro Cys Pro Trp
            20                  25                  30

Ala Glu Ser Leu Ser Pro Ile Gly Asp Met Lys Val Lys Gly Glu Ala
        35                  40                  45

Pro Ala Asn Ser Gly Ala Pro Ala Gly Ala Ala Gly Arg Ala Lys Gly
    50                  55                  60

Glu Ser Arg Ile Arg Arg Pro Met Asn Ala Phe Met Val Trp Ala Lys
65                  70                  75                  80

Asp Glu Arg Lys Arg Leu Ala Gln Gln Asn Pro Asp Leu His Asn Ala
                85                  90                  95

Glu Leu Ser Lys Met Leu Gly Lys Ser Trp Lys Ala Leu Thr Leu Ala
            100                 105                 110

Glu Lys Arg Pro Phe Val Glu Glu Ala Glu Arg Leu Arg Val Gln His
        115                 120                 125

Met Gln Asp His Pro Asn Tyr Lys Tyr Arg Pro Arg Arg Arg Lys Gln
    130                 135                 140

Val Lys Arg Leu Lys Arg Val Glu Gly Gly Phe Leu His Gly Leu Ala
145                 150                 155                 160

Glu Pro Gln Ala Ala Leu Gly Pro Glu Gly Gly Arg Val Ala Met Asp
                165                 170                 175

Asp Gly Leu Gly Leu Gln Phe Pro Glu Gln Gly Phe Pro Ala Gly Pro
            180                 185                 190

Pro Leu Leu Pro Pro His Met Gly Gly His Tyr Arg Asp Cys Gln Ser
        195                 200                 205

Leu Gly Ala Pro Pro Leu Asp Gly Tyr Pro Leu Pro Thr Pro Asp Thr
    210                 215                 220
```

-continued

```
Ser Pro Leu Asp Gly Val Asp Pro Asp Pro Ala Phe Phe Ala Ala Pro
225                 230                 235                 240

Met Pro Gly Asp Cys Pro Ala Ala Gly Thr Tyr Ser Tyr Ala Gln Val
            245                 250                 255

Ser Asp Tyr Ala Gly Pro Pro Glu Pro Pro Ala Gly Pro Met His Pro
            260                 265                 270

Arg Leu Gly Pro Glu Pro Ala Gly Pro Ser Ile Pro Gly Leu Leu Ala
            275                 280                 285

Pro Pro Ser Ala Leu His Val Tyr Tyr Gly Ala Met Gly Ser Pro Gly
            290                 295                 300

Ala Gly Gly Gly Arg Gly Phe Gln Met Gln Pro Gln His Gln His Gln
305                 310                 315                 320

His Gln His Gln His His Pro Pro Gly Pro Gly Gln Pro Ser Pro Pro
            325                 330                 335

Pro Glu Ala Leu Pro Cys Arg Asp Gly Thr Asp Pro Ser Gln Pro Ala
            340                 345                 350

Glu Leu Leu Gly Glu Val Asp Arg Thr Glu Phe Glu Gln Tyr Leu His
            355                 360                 365

Phe Val Cys Lys Pro Glu Met Gly Leu Pro Tyr Gln Gly His Asp Ser
            370                 375                 380

Gly Val Asn Leu Pro Asp Ser His Gly Ala Ile Ser Ser Val Val Ser
385                 390                 395                 400

Asp Ala Ser Ser Ala Val Tyr Tyr Cys Asn Tyr Pro Asp Val
                405                 410
```